(12) United States Patent
Xie et al.

(10) Patent No.: US 8,691,841 B2
(45) Date of Patent: Apr. 8, 2014

(54) INDAZOLES, BENZOTHIAZOLES, BENZOISOTHIAZOLES, BENZISOXAZOLES, AND PREPARATION AND USE THEREOF

(71) Applicant: Memory Pharmaceuticals Corporation, Montvale, NJ (US)

(72) Inventors: Wenge Xie, Mahwah, NJ (US); Brian Herbert, Stockholm, NJ (US); Richard Schumacher, Monroe, NY (US); Truc Nguyen, New York, NY (US); Jianguo Ma, Montvale, NJ (US); Carla Gauss, New York, NY (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 0 days.

(21) Appl. No.: 13/838,088

(22) Filed: Mar. 15, 2013

(65) Prior Publication Data

US 2013/0217683 A1    Aug. 22, 2013

Related U.S. Application Data

(60) Division of application No. 13/165,370, filed on Jun. 21, 2011, which is a continuation of application No. 12/631,435, filed on Dec. 4, 2009, now Pat. No. 8,263,619, which is a continuation of application No. 11/089,533, filed on Mar. 25, 2005, now abandoned.

(60) Provisional application No. 60/555,951, filed on Mar. 25, 2004, provisional application No. 60/616,033, filed on Oct. 6, 2004.

(51) Int. Cl.
  *A01N 43/90*    (2006.01)
  *A61K 31/44*    (2006.01)

(52) U.S. Cl.
  USPC ........................................................ 514/305

(58) Field of Classification Search
  USPC ........................................................ 514/305
  See application file for complete search history.

(56) References Cited

U.S. PATENT DOCUMENTS

| | | | |
|---|---|---|---|
| 4,605,652 A | 8/1986 | Welstead |
| 4,775,668 A | 10/1988 | Jefson |
| 4,789,673 A | 12/1988 | Donatsch |
| 4,798,829 A | 1/1989 | King |
| 4,845,092 A | 7/1989 | Sanger |
| 4,886,808 A | 12/1989 | King |
| 4,895,943 A | 1/1990 | Friedman |
| 4,910,193 A | 3/1990 | Buchheit |
| 4,910,207 A | 3/1990 | Donatsch |
| 4,937,247 A | 6/1990 | King |
| 4,942,160 A | 7/1990 | Sanger |
| 4,975,436 A | 12/1990 | Tyers |
| 4,985,424 A | 1/1991 | Van Wijngaarden |
| 5,017,582 A | 5/1991 | Donatsch |
| 5,034,398 A | 7/1991 | King |
| 5,063,231 A | 11/1991 | Sanger |
| 5,098,889 A | 3/1992 | Costall |
| 5,098,909 A | 3/1992 | Williams |
| 5,192,770 A | 3/1993 | Clark |
| 5,204,356 A | 4/1993 | Tyers |
| 5,223,625 A | 6/1993 | Van Wijingaarden |
| 5,272,154 A | 12/1993 | Dixon |
| 5,273,972 A | 12/1993 | Jagdmann |
| 5,446,050 A | 8/1995 | Rosen |
| 5,543,426 A | 8/1996 | Dixon |
| 5,561,149 A | 10/1996 | Azria |
| 5,641,802 A | 6/1997 | Arcamone |
| 5,679,673 A | 10/1997 | Bowen |
| 5,714,946 A | 2/1998 | Gottshall |
| 5,773,436 A | 6/1998 | Muller |
| 5,985,866 A | 11/1999 | Muller |
| 6,492,385 B2 | 12/2002 | Myers |
| 6,500,840 B2 | 12/2002 | Myers |
| 6,599,916 B2 | 7/2003 | Myers |
| 6,624,173 B1 | 9/2003 | Crooks |
| 6,780,861 B2 | 8/2004 | Nozulak |
| 6,828,330 B2 | 12/2004 | Walker |
| 6,849,620 B2 | 2/2005 | Walker |
| 6,911,543 B2 | 6/2005 | Walker |

(Continued)

FOREIGN PATENT DOCUMENTS

| | | |
|---|---|---|
| CA | 2 361 437 | 3/1988 |
| DE | 101 56 719 | 5/2003 |
| DE | 103 05 922 | 3/2004 |
| EP | 0 013 138 | 7/1980 |
| EP | 0 200 444 | 11/1986 |
| EP | 0 214 772 | 3/1987 |
| EP | 0 279 512 | 8/1988 |
| EP | 0 377 238 | 7/1990 |
| EP | 0 498 466 | 8/1992 |
| EP | 1 079 828 | 3/2001 |
| EP | 1 217 001 | 6/2002 |
| EP | 1 219 622 | 7/2002 |
| EP | 1 235 826 | 9/2002 |
| EP | 0 261 964 | 8/2008 |
| FR | 2 548 666 | 1/1985 |

(Continued)

OTHER PUBLICATIONS

Toyohara et al., The open Medicinal Chemistry Journal, 2010, 4, 37-56.*

(Continued)

*Primary Examiner* — Niloofar Rahmani
(74) *Attorney, Agent, or Firm* — Millen, White, Zelano & Branigan, P.C.

(57) ABSTRACT

The present invention relates generally to the field of ligands for nicotinic acetylcholine receptors (nACh receptors), activation of nACh receptors, and the treatment of disease conditions associated with defective or malfunctioning nicotinic acetylcholine receptors, especially of the brain. Further, this invention relates to novel compounds (e.g., indazoles and benzothiazoles), which act as ligands for the α7 nACh receptor subtype, methods of preparing such compounds, compositions containing such compounds, and methods of use thereof.

28 Claims, No Drawings

(56) References Cited

U.S. PATENT DOCUMENTS

| | | |
|---|---|---|
| 7,001,900 B2 | 2/2006 | Jacobsen |
| 2002/0086871 A1 | 7/2002 | O'Neill |
| 2002/0119972 A1 | 8/2002 | Leftheris |
| 2003/0073707 A1 | 4/2003 | Walker |
| 2003/0236270 A1 | 12/2003 | Jacobsen |
| 2004/0002513 A1 | 1/2004 | Mazurov |
| 2004/0132790 A1 | 7/2004 | Xie |
| 2004/0138286 A1 | 7/2004 | Imazaki |
| 2004/0224977 A1 | 11/2004 | Walker |
| 2005/0182062 A1 | 8/2005 | Galli |
| 2005/0209236 A1 | 9/2005 | Hendrix |
| 2006/0014750 A1 | 1/2006 | O'Donnell |
| 2006/0019984 A1 | 1/2006 | Groppi |
| 2006/0160877 A1 | 7/2006 | Luithle |
| 2007/0078147 A1 | 4/2007 | Schumacher |

FOREIGN PATENT DOCUMENTS

| | | |
|---|---|---|
| GB | 2 125 398 | 3/1984 |
| GB | 2 145 416 | 3/1985 |
| JP | 2002-30084 | 1/2002 |
| WO | WO 84/00166 | 1/1984 |
| WO | WO 85/01048 | 3/1985 |
| WO | WO 90/14347 | 11/1990 |
| WO | WO 91/09593 | 7/1991 |
| WO | WO 92/12149 | 7/1992 |
| WO | WO 93/08185 | 4/1993 |
| WO | WO 94/14805 | 7/1994 |
| WO | WO 97/30998 | 8/1997 |
| WO | WO 00/45846 | 8/2000 |
| WO | WO 00/58311 | 10/2000 |
| WO | WO 01/58869 | 8/2001 |
| WO | WO 01/90109 | 11/2001 |
| WO | WO 01/92260 | 12/2001 |
| WO | WO 02/17358 | 2/2002 |
| WO | WO 02/36114 | 5/2002 |
| WO | WO 02/085901 | 10/2002 |
| WO | WO 02/096911 | 12/2002 |
| WO | WO 02/100833 | 12/2002 |
| WO | WO 02/100857 | 12/2002 |
| WO | WO 02/100858 | 12/2002 |
| WO | WO 03/022856 | 3/2003 |
| WO | WO 03/029252 | 4/2003 |
| WO | WO 03/037896 | 5/2003 |
| WO | WO 03/042210 | 5/2003 |
| WO | WO 03/051874 | 6/2003 |
| WO | WO 03/070731 | 8/2003 |
| WO | WO 03/072578 | 9/2003 |
| WO | WO 03/078431 | 9/2003 |
| WO | WO 03/080606 | 10/2003 |
| WO | WO 03/094830 | 11/2003 |
| WO | WO 03/101987 | 11/2003 |
| WO | WO 2004/014864 | 2/2004 |
| WO | WO 2004/014922 | 2/2004 |
| WO | WO 2004/016616 | 2/2004 |
| WO | WO 2004/016617 | 2/2004 |
| WO | WO 2004/029050 | 4/2004 |
| WO | WO 2004 033456 | 4/2004 |
| WO | WO 2004052348 | 6/2004 |
| WO | WO 2004052461 | 6/2004 |
| WO | WO 2005/001299 | 2/2005 |

OTHER PUBLICATIONS

Wu et al., International Journal of Alzheimer's disease, vol. 10 (2010), pp. 1-11.*
McGranahan et al., The journal of Neuroscience, (2011), 31(30), pp. 10891-10902.*
Kazuo et al., International congress series, 1290(2006), pp. 144-149.*
Davies et al., Neurosci Biobehav Rev. (2008); 32(4), pp. 693-706.*
Pohanka et al., International Journal of Molecular Sciences (2012), 13, 2219-2238.*
Austrian Search Report and Written Opinion for Application No. 200606539-5 mailed Oct. 3, 2008.
Search report for European Patent Application No. EP 05 75 5169 dated Apr. 3, 2008.
Int'l Partial Search Report and Invitation to Pay Additional Fees, issued Sep. 1, 2005 in PCT/US2005/010120.
Evans, S.M. et al., "Probing the 5-$HT_3$ Receptor Site Using Novel Indole-3-Glyoxylic Acid Derivatives", Med. Chem. Res. (1993), 3:386-406.
Flammia, D. "Lobeline: Structure-Affinity Investigation of Nicotinic Acetylcholinergic Receptor Binding", J. Med. Chem., 42:3726-2731 (1999).
Azuma R., et al. "Metabolism and Disposition of GTS-21, a Novel Drug for Alzheimer's Disease", Xenobiotica, 29(7):747-762 (1999).
Stevens, K. E. et al., "Selective $\alpha_7$-nicotinic agonists normalize inhibition of auditory response in DBA mice", Psychopharmacology, 136:320-327 (1998).
Azuma, R. et al., "The effect of repeat administration of GTS-21 on mixed-function oxidase activities in rat", Elsevier Science Ireland Ltd., Toxicology Letters 110, pp. 137-144 (1999).
Decker, M. et al., "Neuronal Nicotinic Acetylcholine Receptors: Novel Targets for CNS Therapeutics", pp. 1-14 (2000).
Holladay, M.W. et al., "Neuronal Nicotinic Acetylcholine Receptors as Targets for Drug Discovery", Journal of Medicinal Chemistry, 40(26):4169-4194 (1997).
Astles et al., Current Drug Targets—CNS Neurological Disorders, 1, pp. 337-348 (2002).
Mazurov et al., Biorg. & Med. Chem. Lett., No. 1, 15, pp. 2073-2077 (2005).
Nurhrich et al., Eur. J. Med. Chem., No. 31, pp. 957-964 (1996).
Bermudez et al., J. Med. Chem., 33, 1924-1929 (1990).
Japan Patent Abstract No. 2002-030084; Publication date of Application: Jan. 29, 2002; Application No. 2000-217709; Date of Filing Jul. 18, 2000; Applicant: Mitsubishi Pharma Corp. (http://www.19.ipdl.inpit.go.jp/PA1/).

* cited by examiner

INDAZOLES, BENZOTHIAZOLES, BENZOISOTHIAZOLES, BENZISOXAZOLES, AND PREPARATION AND USE THEREOF

This application is a divisional of Ser. No. 13/165,370, filed Jun. 21, 2011, which is a continuation of Ser. No. 12/631,435, filed Dec. 4, 2009, which is a continuation of application Ser. No. 11/089,533, filed Mar. 25, 2005, now abandoned, and this application claims the benefit of U.S. Provisional application Ser. No. 60/555,951, filed Mar. 25, 2004, and U.S. Provisional application Ser. No. 60/616,033, filed Oct. 6, 2004, the entire disclosures of which are hereby incorporated by reference.

This application is also related to U.S. patent application Ser. No. 10/669,645, filed Sep. 25, 2003, which claims the benefit of U.S. Provisional application Ser. No. 60/413,151, filed Sep. 25, 2002, and U.S. Provisional application Ser. No. 60/448,469, filed Feb. 21, 2003, the entire disclosures of which are hereby incorporated by reference.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds, which act as ligands for the α7 nAChR subtype, methods of preparing such compounds, compositions comprising such compounds, and methods of use thereof.

BACKGROUND OF THE INVENTION

There are two types of receptors for the neurotransmitter, acetylcholine:muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7nACh receptor subtype, for the treatment of disease conditions associated with defective or malfunctioning nicotinic acetylcholine receptors.

SUMMARY OF THE INVENTION

This invention relates to novel compounds, which act as ligands for the α7 nACh receptor subtype, methods of preparing such compounds, compositions comprising such compounds, and methods of use thereof.

DETAILED DESCRIPTION OF THE INVENTION

The present invention includes compounds of Formulas I, II, III, or IV:

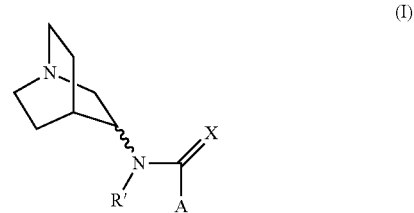
(I)

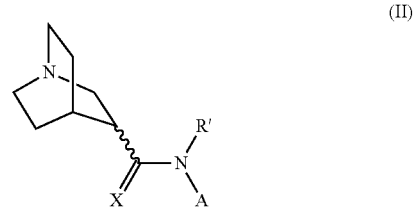
(II)

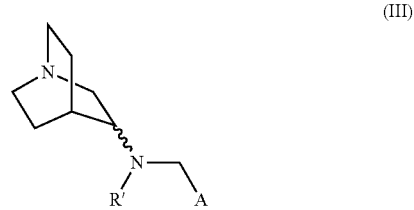
(III)

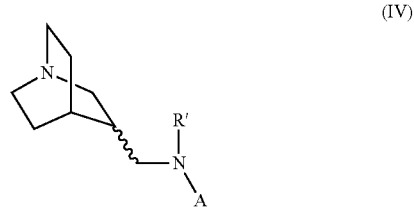
(IV)

wherein
A is

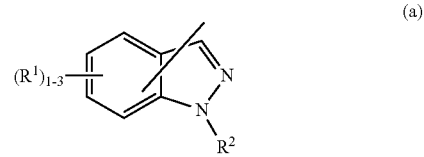
(a)

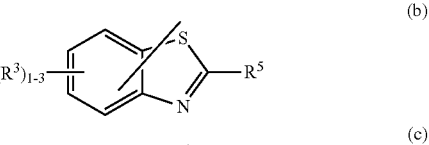
(b)

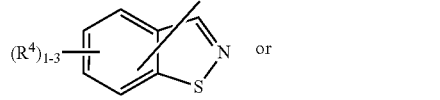
(c)

or

-continued

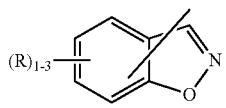
(d)

X is O or S;

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

R is H, F, Cl, Br, I, OH, CN, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2,-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het—$C_{1-6}$-alkyl-O—, Het-CO-Het-, Het—$C_{1-6}$-alkyl-$NR^2$—, or Ar—$C_{1-6}$-alkyl-Het-O—, with the proviso that R is not $NH_2$; or R is of one of the following formulas

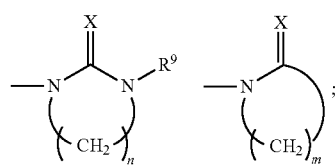

n is 2 to 4;

m is 3 to 5; or two R can together form a 5-membered fused ring structure containing at least one N atom;

$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2,-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het—$C_{1-6}$-alkyl-O—, Het-CO-Het-, Het—$C_{1-6}$-alkyl-$NR^2$—, or Ar—$C_{1-6}$-alkyl-Het-O—; or $R^1$ is of one of the following formulas

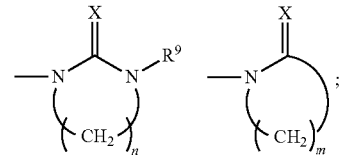

or two $R^1$ can together form a 5-membered fused ring structure containing at least one N atom;

$R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl- (e.g., $CH_2CH_2$—O—$CH_3$), or Ar—$C_{1-4}$-alkyl-NH—CO—;

$R^3$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2,-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^3$ is of one of the following formulas

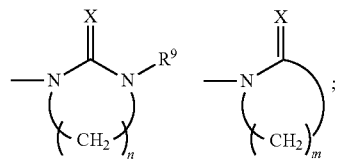

or two $R^3$ can together form a 5-membered fused ring structure containing at least one N atom;

$R^4$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—($C_{1-6}$-alkyl-O)$_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2,-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^4$ is of one of the following formulas

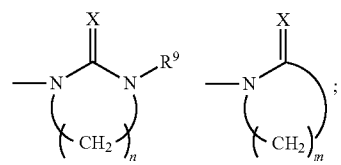

or two $R^4$ can together form a 5-membered fused ring structure containing at least one N atom;

$R^5$ is H, F, Cl, Br, I, OH, CN, nitro, $NH_2$, carboxy, $CONR^6R^7$, $NR^2COR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2,-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, or OHet;

$R^6$ and $R^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom (e.g., piperidinyl, pyrrolidinyl);

$R^8$ is H, alkyl having 1 to 4 carbon atoms, fluorinated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

$R^9$ is Ar, Ar-alkyl wherein the alkyl portion has 1 to 4 carbon atoms, or Het;

$R^{10}$ is alkyl having 1 to 4 carbon atoms, fluorinated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, fluorinated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;

Ar is an aryl group containing 6 to 10 carbon atoms which is unsubstituted or substituted one or more times by alkyl having 1 to 8 C atoms, alkoxy having 1 to 8 C atoms, halogen (F, Cl, Br, or I, preferably F or Cl), dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms (e.g., phenyl, naphthyl, biphenyl) and is optionally substituted, arylthio wherein the aryl portion contains 6 to 10 carbon atoms (e.g., phenyl, naphthyl, biphenyl) and is optionally substituted, cycloalkyloxy wherein the cycloalkyl group has 3 to 7 C atoms and is optionally substituted, sulfo, sulfonylamino, acylamido (e.g., acetamido), acyloxy (e.g., acetoxy) or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) which is optionally substituted, alkyl having 1 to 8 C atoms, alkoxy having 1 to 8 C atoms, cycloalkyl having 3 to 7 carbon atoms, cyano, trifluoromethyl, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, —$CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 C atoms, alkoxy having 1 to 8 C atoms, hydroxy, nitro, cyano, oxo, or combinations thereof (e.g., indanyl, tetrahydronaphthenyl, etc.); and $R^{11}$ is alkyl having 1 to 4 carbon atoms, halogenated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, halogenated alkyl, alkenyl, or alkynyl groups are in each unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar; and pharmaceutically acceptable salts thereof, wherein said compound is optionally in the form of an N-oxide.

In Formula I, when A is an indazolyl group of subformula (a), it is preferably attached to the remainder of the compound via its 3, 4 or 7 position, particularly via the 3-position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position, particularly via the 3-position. When A is a benzisoxazolyl group of subformula (d), it is preferably attached to the remainder of the compound via its 3, 4 or 7 position, particularly via the 3-position.

Similarly, in Formula II, when A is an indazolyl group of subformula (a), it is preferably attached to the remainder of the compound via its 3, 4 or 7 position, particularly via the 3-position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position, particularly via the 3-position. When A is a benzisoxazolyl group of subformula (d), it is preferably attached to the remainder of the compound via its 3, 4 or 7 position, particularly via the 3-position.

Also, in Formula III, when A is an indazolyl group of subformula (a), it is preferably attached to the remainder of the compound via its 3, 4 or 7 position, particularly via the 3-position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position, particularly via the 3-position. When A is a benzisoxazolyl group of subformula (d), it is preferably attached to the remainder of the compound via its 3, 4 or 7 position, particularly via the 3-position.

Further, in Formula IV, when A is an indazolyl group of subformula (a), it is preferably attached to the remainder of the compound via its 3, 4 or 7 position, particularly via the 3-position. When A is a benzothiazolyl group of subformula (b), it is preferably attached to the remainder of the compound via its 4 or 7 position. When A is a benzoisothiazolyl group of subformula (c), it is preferably attached to the remainder of the compound via its 3, 4 or 7 position, particularly via the 3-position. When A is a benzisoxazolyl group of subformula (d), it is preferably attached to the remainder of the compound via its 3, 4 or 7 position, particularly via the 3-position.

In Formulas I-IV, the indazolyl, benzothiazolyl, benzoisothiazolyl, and benzisoxazolyl groups of A can be attached to the remainder of the structure via any suitable attachment point. The following subformulas illustrate some of the preferred attachments between the indazole, benzothiazole, benzoisothiazole, and benzisoxazole groups and the remainder of the structure.

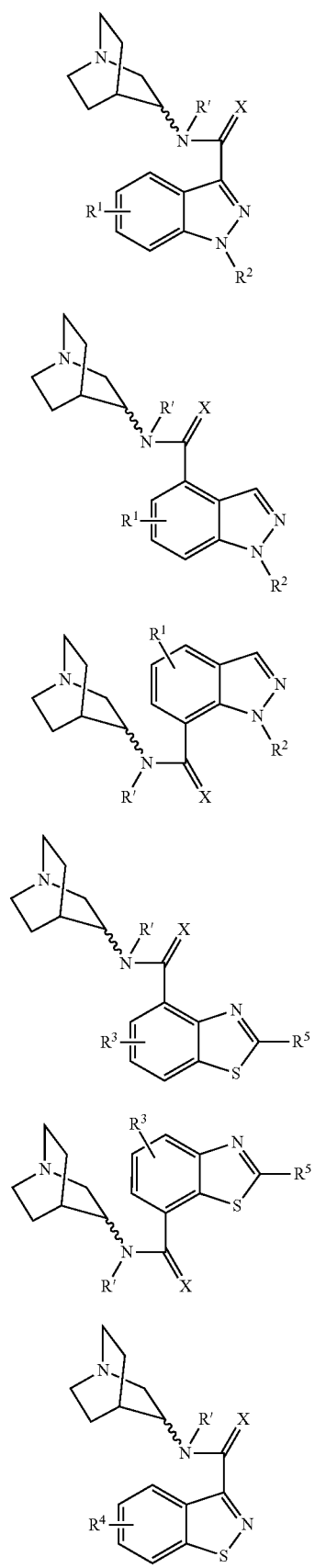
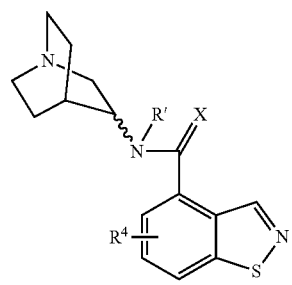
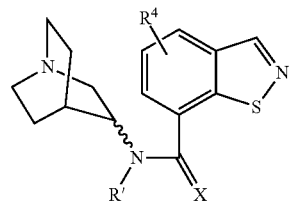
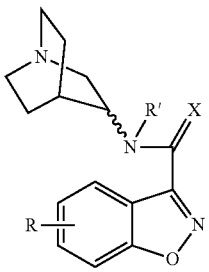
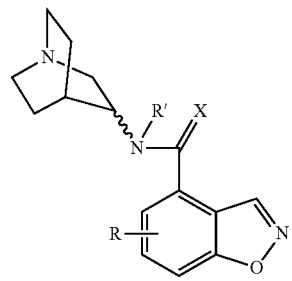
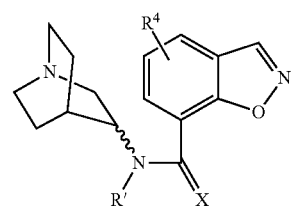
The following subformulas further illustrate some of the preferred attachments between the indazolyl, benzothiazolyl, benzoisothiazolyl and benzisoxazolyl groups and the remainder of the structure.

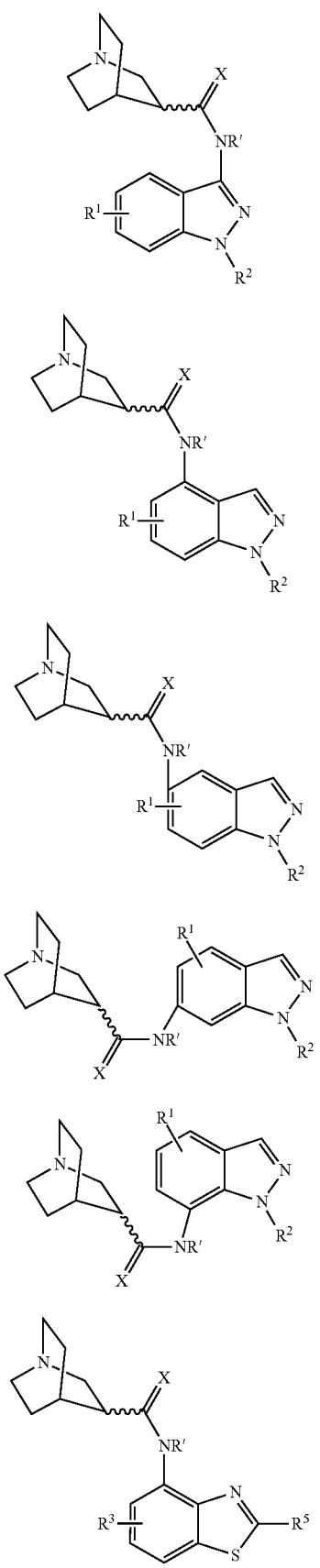
(IIa)
(IIb)
(IIc)
(IId)
(IIe)
(IIf)
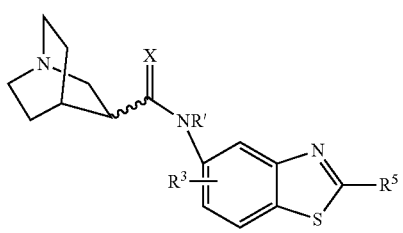
(IIg)
(IIh)
(IIi)
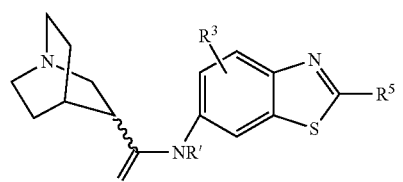
(IIj)
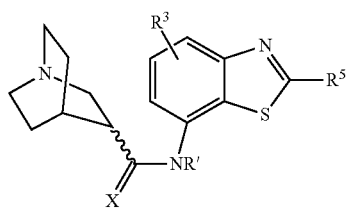
(IIk)
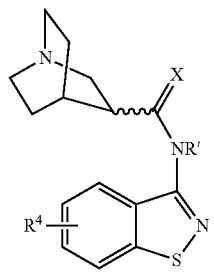
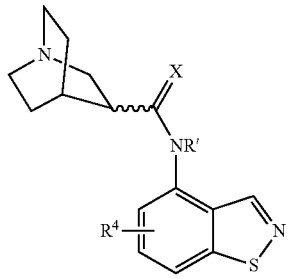
(IIm)
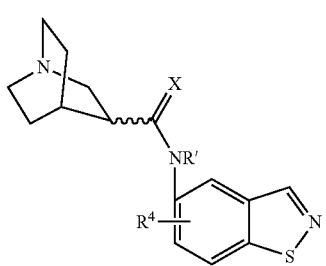

(IIn) 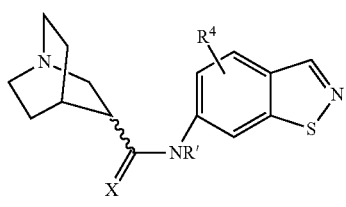
(IIo) 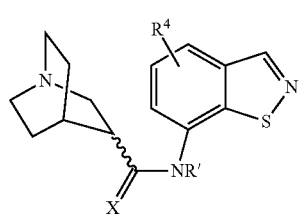
(IIp) 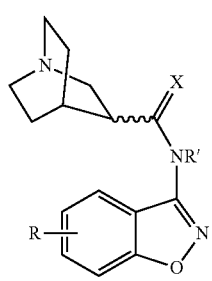
(IIq) 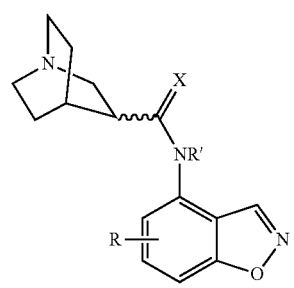
(IIr) 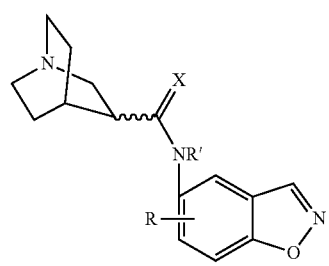
(IIs) 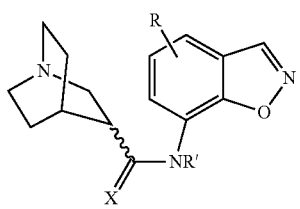
(IIt) 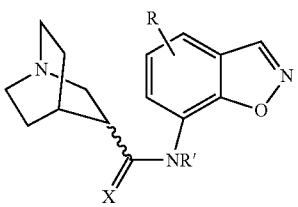
The following subformulas further illustrate some of the preferred attachments between the indazolyl, benzothiazolyl, benzoisothiazolyl and benzisoxazolyl groups and the remainder of the structure.
(IIIa) 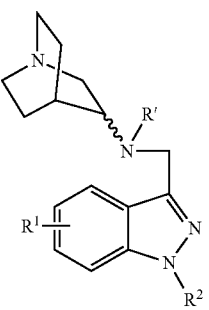
(IIIb) 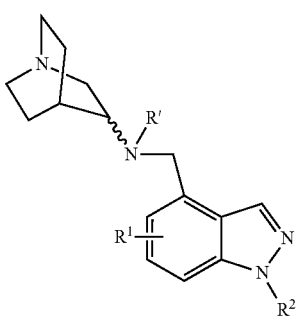
(IIIc) 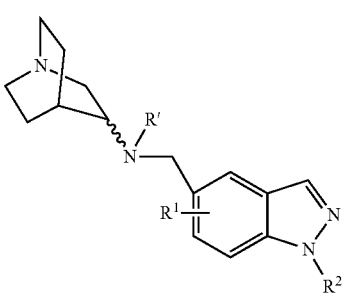
(IIId) 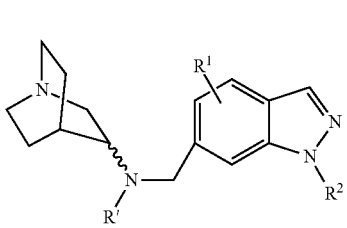

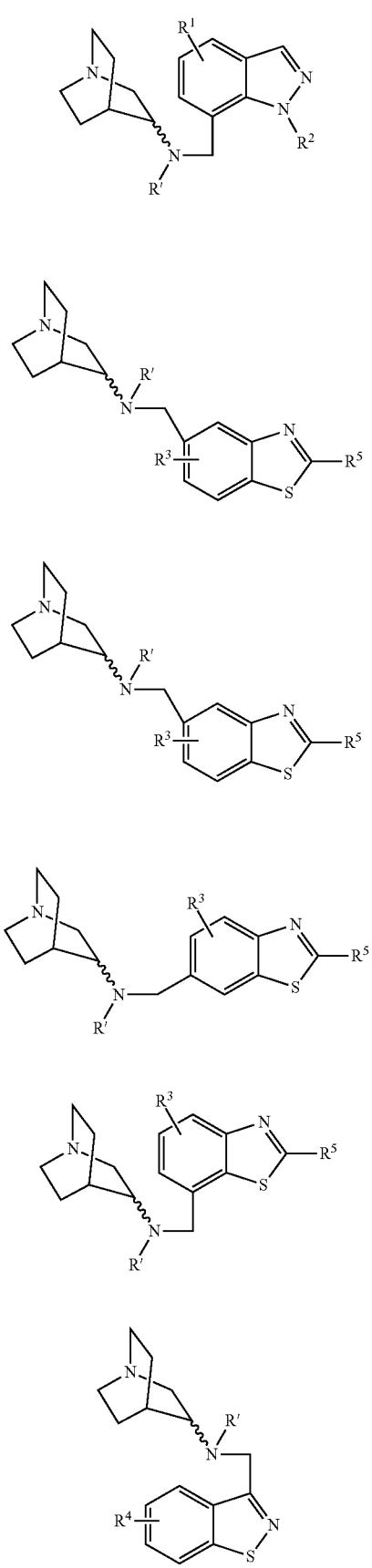
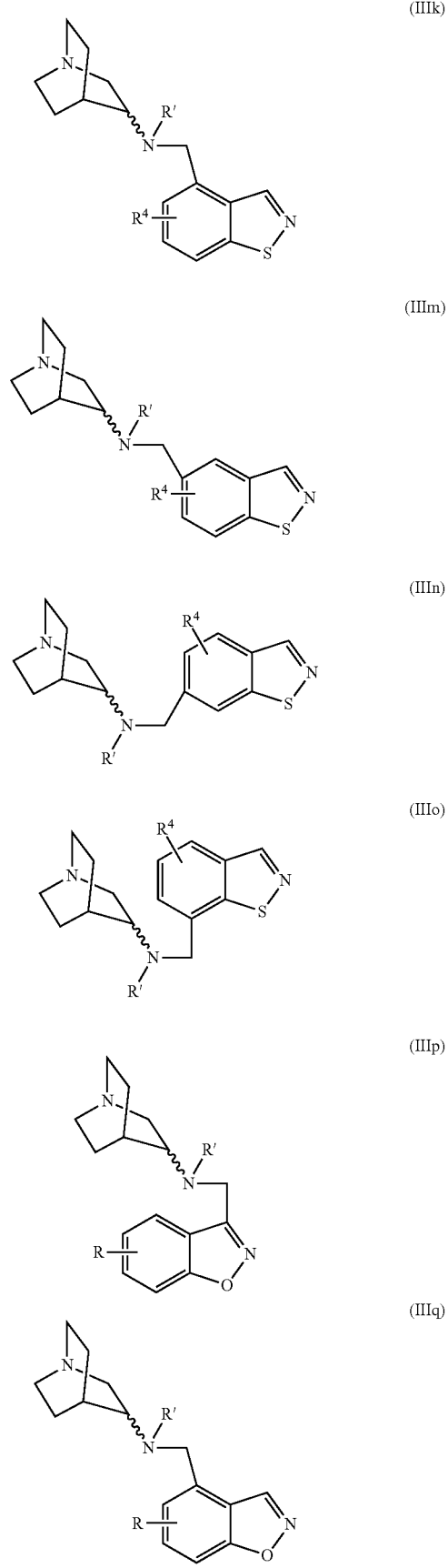

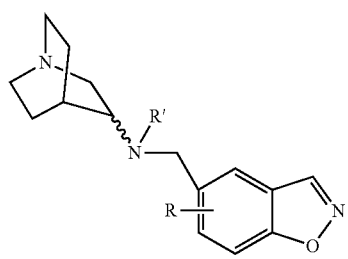
(IIIr)
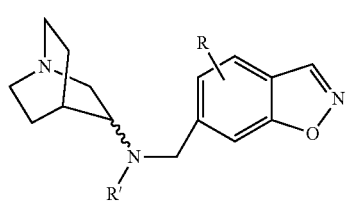
(IIIs)
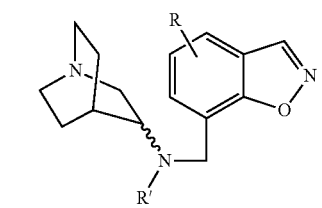
(IIIt)
The following subformulas further illustrate some of the preferred attachments between the indazolyl, benzothiazolyl, benzoisothiazolyl and benzisoxazolyl groups and the remainder of the structure.
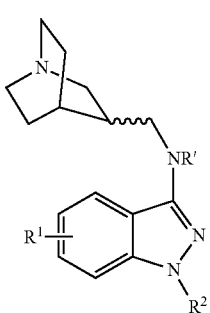
(IVa)
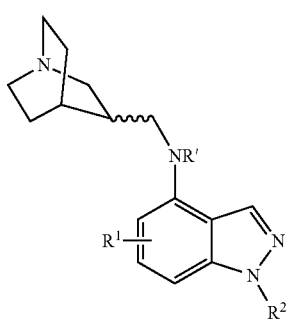
(IVb)
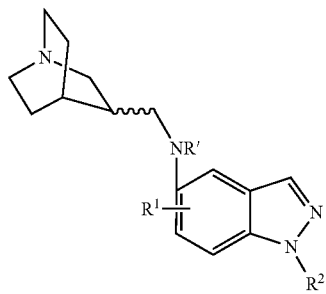
(IVc)
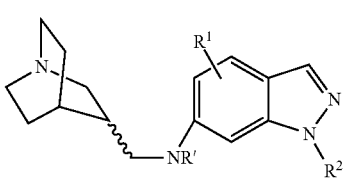
(IVd)
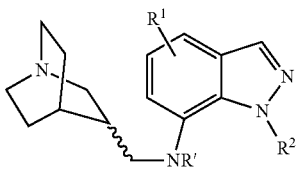
(IVe)
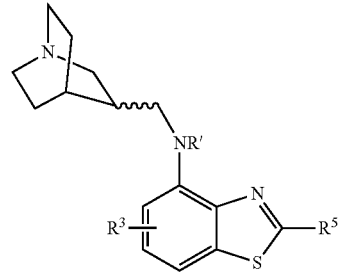
(IVf)
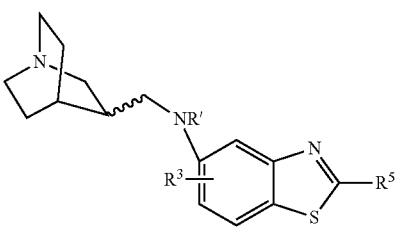
(IVg)
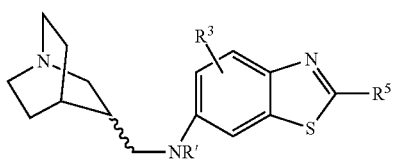
(IVh)
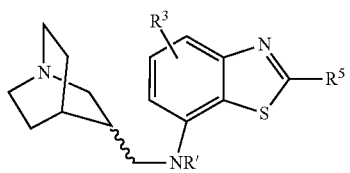
(IVi)

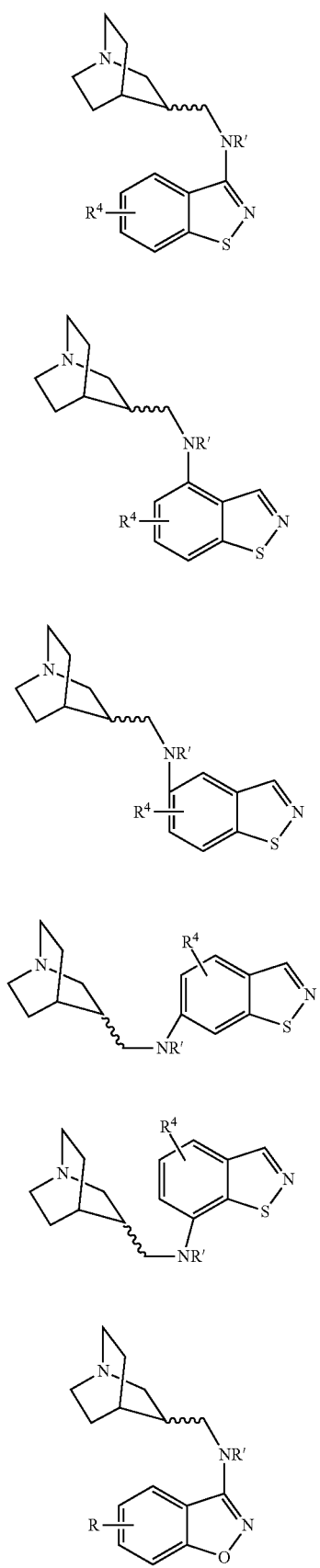
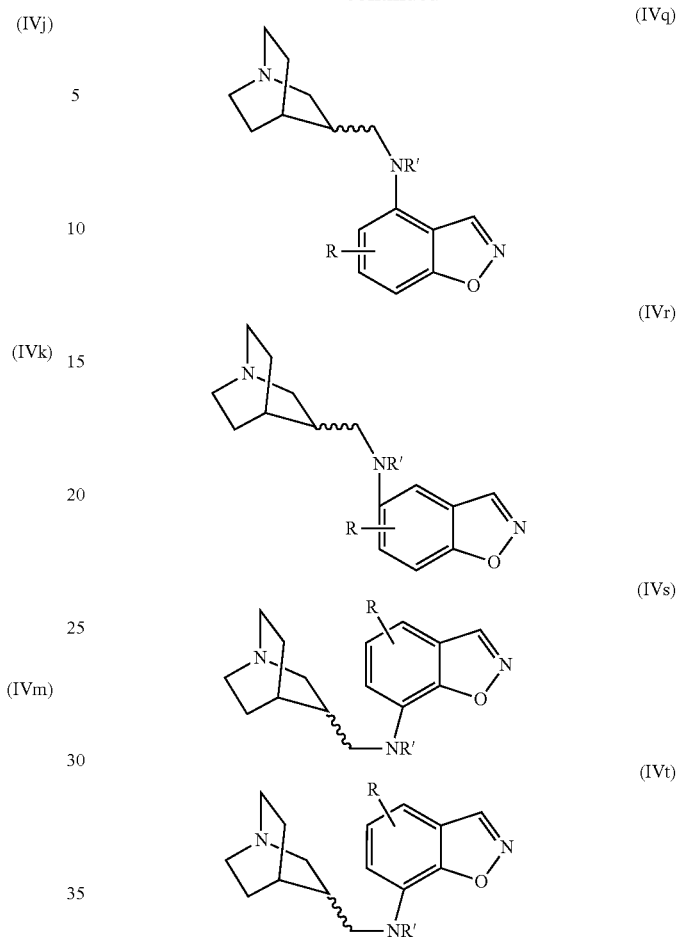

X is preferably O.

R' is preferably H or CH$_3$, particularly H.

Alkyl throughout means a straight-chain or branched-chain aliphatic hydrocarbon radical having preferably 1 to 4 carbon atoms. Suitable alkyl groups include but are not limited to methyl, ethyl, propyl, isopropyl, butyl, sec-butyl, and tert-butyl.

Alkenyl throughout means a straight-chain or branched-chain aliphatic hydrocarbon radical having preferably 2 to 6 carbon atoms. Suitable alkenyl groups include but are not limited to ethenyl, propenyl, butenyl, and pentenyl.

Alkynyl throughout means a straight-chain or branched-chain aliphatic hydrocarbon radical having preferably 2 to 6 carbon atoms. Suitable alkynyl groups include but are not limited to ethyne, propyne, butyne, etc.

Alkoxy means alkyl-O— groups in which the alkyl portion preferably has 1 to 4 carbon atoms. Suitable alkoxy groups include but are not limited to methoxy, ethoxy, propoxy, isopropoxy, isobutoxy, and sec-butoxy.

Alkylthio means alkyl-S— groups in which the alkyl portion preferably has 1 to 4 carbon atoms. Suitable alkylthio groups include but are not limited to methylthio and ethylthio.

Cycloalkyl means a cyclic, bicyclic or tricyclic saturated hydrocarbon radical having 3 to 7 carbon atoms. Suitable cycloalkyl groups include but are not limited to cyclopropyl, cyclobutyl, cyclopentyl, and cyclohexyl. Other suitable cycloalkyl groups include but are not limited to spiropentyl, bicyclo[2.1.0]pentyl, and bicyclo[3.1.0]hexyl.

Cycloalkoxy means cycloalkyl-O— groups in which the cycloalkyl portion preferably is a cyclic, bicyclic or tricyclic saturated hydrocarbon radical having 3 to 7 carbon atoms.

Cycloalkylalkyl groups contain 4 to 7 carbon atoms. Suitable cycloalkylalkyl groups include but are not limited to, for example, cyclopropylmethyl, cyclopropylethyl, cyclobutylmethyl, and cyclopentylmethyl.

Cycloalkylalkoxy groups contain 4 to 7 carbon atoms. Suitable cycloalkylalkoxy groups include but are not limited to, for example, cyclo-propylmethyloxy, cyclopropylethyloxy, cyclobutylmethyloxy, and cyclo-pentylmethyloxy.

The cycloalkyl and cycloalkylalkyl groups can be substituted by $C_{1-4}$-alkyl, $C_{1-4}$-alkoxy, hydroxyl, amino, monoalkylamino having 1 to 4 carbon atoms, and/or dialkylamino in which each alkyl group has 1 to 4 carbon atoms.

Aryl, as a group or substituent per se or as part of a group or substituent, refers to an aromatic carbocyclic radical containing 6 to 10 carbon atoms, unless indicated otherwise. Suitable aryl groups include but are not limited to phenyl, napthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Heterocyclic groups refer to saturated, partially saturated and fully unsaturated heterocyclic groups having one, two or three rings and a total number of 5 to 10 ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to dihydropyranyl, tetrahydropyranyl, tetrahydrofuranyl, tetrahydrothienyl, pyrrolidinyl, piperidinyl, piperazinyl, morpholinyl, isoxazolinyl and the like. Suitable heteroaryl groups include but are not limited to furyl, thienyl, thiazolyl, oxazolyl, pyrrolyl, pyrazolyl, imidazolyl, pyridyl, pyrimidinyl, indolyl, quinolinyl, isoquinolinyl, naphthyridinyl and the like. Other examples of suitable heterocyclic groups, are 2-furyl, 3-furyl, 2-quinolinyl, 1,3-benzodioxyl, 2-thienyl, 3-thienyl, 1,3-thiazoly-2-yl, 1,3-oxazol-2-yl, pyrrolidin-1-yl, piperidin-1-yl, morpholin-4-yl, 2-benzofuranyl, 2-benzothiophenyl, 3-thienyl, 2,3-dihydro-5-benzofuranyl, 4-indolyl, 4-pyridyl, 3-quinolinyl, 4-quinolinyl, 1,4-benzodioxan-6-yl, 3-indoyl, 2-pyrrolyl, tetrahydro-2H-pyran-4-yl, 3,6-dihydro-2H-pyran-4-yl, 5-indolyl, 1,5-benzoxepin-8-yl, 3-pyridyl, 6-coumarinyl, 5-benzofuranyl, 2-isoimidazol-4-yl, 3-pyrazolyl, and 3-carbazolyl.

Substituted heterocyclic groups refer to the heterocyclic groups described above, which are substituted in one or more places by, for example, halogen, aryl, alkyl, alkoxy, cyano, trifluoromethyl, nitro, oxo, amino, alkylamino, and dialkylamino.

Radicals that are substituted one or more times preferably have 1 to 3 substituents, especially 1 or 2 substituents of the exemplified substituents. Halogenated radicals such as halogenated alkyls are preferably fluorinated and include but are not limited to perhalo radicals such as trifluoromethyl.

According to a further aspect of the invention, in the compounds of Formulas I-IV, when R is $NR^6R^7$, at least one of $R^6$ and $R^7$ is alkyl having 2 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom.

According to a further aspect of the invention, in the compounds of Formulas I-IV, R is not $NR^6R^7$.

According to a further aspect of the invention, in the compounds of Formulas I-IV, A is a radical according to formulas (a), (b) or (c), and at least one of $R^1$, $R^3$, or $R^4$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, or OHet; or is of one of the following formulas

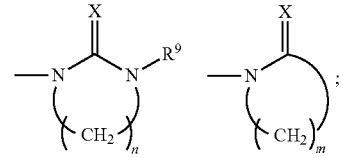

and/or $R^2$ is H, alkyl having 1 to 4 carbon atoms, fluorinated alkyl having 1 to 4 carbon atoms, cycloalkyl having 3 to 7 carbon atoms, or cycloalkylalkyl having 4 to 7 carbon atoms; and/or Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms and is optionally substituted, alkyl having 1 to 8 C atoms, alkoxy having 1 to 8 C atoms, cyano, trifluoromethyl, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, —$CXR^{11}$, piperidinylethyl or combinations thereof.

According to a further aspect of the invention, in the compounds of Formulas I-IV, at least one of $R^1$, $R^3$, or $R^4$ is COH, $NR^6R^7$ wherein at least one of $R^6$ and $R^7$ is other than alkyl, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkyl having 1 to 4 carbon atoms which is substituted by Ar or Het, fluorinated alkyl having 1 to 4 carbon atoms which is substituted by Ar or Het, alkenyl having 2 to 6 carbon atoms which is optionally substituted by Ar or Het, alkynyl having 2 to 6 carbon atoms which is optionally substituted by Ar or Het, cycloalkenyl having 5 to 8 carbon atoms, cycloalkenylalkyl having 6 to 9 carbon atoms, fluorinated hydroxyalkyl having 1 to 4 carbon atoms, alkoxycarbonyl having 2 to 6 carbon atoms, OAr, OHet, or Het which is substituted by $SO_2R^{11}$ or $—CXR^{11}$, or is selected from the following formulas

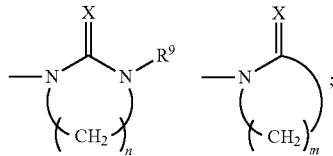

and/or $R^5$ is carboxy, alkoxycarbonyl having 2 to 6 carbon atoms, $CONR^6R^7$, $NR^2COR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkenyl having 2 to 6 carbon atoms, alkynyl having 2 to 6 carbon atoms (e.g., ethynyl, propynyl), alkyl substituted by Ar or Het, alkenyl substituted by Ar or Het, alkynyl substituted by Ar or Het (e.g., phenylacetylene), cycloalkenyl having 5 to 8 carbon atoms, cycloalkenylalkyl having 6 to 9 carbon atoms, fluorinated hydroxyalkyl having 1 to 4 carbon atoms (e.g., 2,2,2,-trifluoro-1-hydroxyl-1-(trifluoromethyl)ethyl), fluorinated hydroxyalkoxy having 2 to 4 carbon atoms, OAr, OHet, or Het which is substituted by $SO_2R^{11}$ or $—CXR^{11}$.

According to a further aspect of the invention, in the compounds of Formulas I-IV, at least one of $R^1$, $R^3$, $R^4$, and $R^5$ is carboxy, alkoxycarbonyl having 2 to 6 carbon atoms, $CONR^6R^7$, $NR^2COR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkenyl having 2 to 6 carbon atoms, alkynyl having 2 to 6 carbon atoms (e.g., ethynyl, propynyl), alkyl substituted by Ar or Het, alkenyl substituted by Ar or Het, alkynyl substituted by Ar or Het (e.g., phenylacetylene), cycloalkenyl having 5 to 8 carbon atoms, cycloalkenylalkyl having 6 to 9 carbon atoms, fluorinated hydroxyalkyl having 1 to 4 carbon atoms (e.g., 2,2,2,-trifluoro-1-hydroxyl-1-(trifluoromethyl)ethyl), fluorinated hydroxyalkoxy having 2 to 4 carbon atoms, OAr, OHet, or Het which is substituted by $SO_2R^{11}$ or $—CXR^{11}$ (Preferably, at least one of $R^1$, $R^3$, $R^4$, and $R^5$ is alkynyl having 2 to 6 carbon atoms, fluorinated hydroxyalkyl having 1 to 4 carbon atoms, or Ar-alkynyl (e.g., phenylacetylene), especially $R^1$ or $R^4$.);

$R^6$ and Rare each, independently, H, alkyl having 1 to 4 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom;

$R^9$ is Ar or Het; and

Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) and is optionally substituted, alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, $SO_2R^{11}$, $—CXR^{11}$, or combinations thereof.

According to a further aspect of the invention, the compounds are selected from formula I in which A is of formulae (a) or (c), X is O, $R^2$ is H or alkyl (e.g., $CH_3$), and $R^1$ and $R^4$ are each F, Cl, CN, $NO_2$, $NH_2$, fluorinated alkyl (e.g., $CF_3$), alkoxy (e.g., $OCH_3$), fluorinated alkoxy (e.g., $OCF_3$), fluorinated hydroxyalkyl (e.g., 2,2,2,-trifluoro-1-hydroxyl-1-(trifluoromethyl)ethyl), alkynyl (e.g., ethynyl, propynyl), cycloalkyl, cycloalkylalkoxy, Ar, Ar-alkynyl (e.g., phenylacetylene), or Het. For example, $R^1$ and $R^4$ are each selected from F, Cl, CN, $NO_2$, $NH_2$, $CF_3$, $OCH_3$, $OC_2H_5$, $OCF_3$, 2,2,2,-trifluoro-1-hydroxyl-1-(trifluoromethyl)ethyl, ethynyl, propynyl, pentynyl, cyclopentyl, cyclohexyl, cyclopropylmethoxy, phenyl, phenylethynyl, dihydropyranyl (e.g., 3,6-dihydro-2H-pyran-4-yl), thiazolyl (e.g., 1,3-thiazol-2-yl), oxazolyl (e.g., 1,3-oxazol-2-yl), pyrrolidinyl (e.g., pyrrolidin-1-yl), piperidinyl (e.g. piperidin-1-yl), or morpholinyl (e.g. morpholin-4-yl). $R^4$ can also be selected from CN, alkoxy, fluorinated alkoxy, and cycloalkylalkoxy, such as CN, $OCH_3$, $OC_2H_5$, $OCF_3$, and cyclopropylmethoxy.

According to a further aspect of the invention, the compounds are selected from formulae Ia or Ij wherein $R^2$ is H or alkyl (e.g., $CH_3$), and $R^1$ and $R^4$ are each F, Cl, CN, $NO_2$, $NH_2$, fluorinated alkyl (e.g., $CF_3$), alkoxy (e.g., $OCH_3$), fluorinated alkoxy (e.g., $OCF_3$), fluorinated hydroxyalkyl (e.g., 2,2,2,-trifluoro-1-hydroxyl-1-(trifluoromethyl)ethyl), alkynyl (e.g., ethynyl, propynyl), cycloalkyl, cycloalkylalkoxy, Ar, Ar-alkynyl (e.g., phenylacetylene), or Het. For example, $R^1$ and $R^4$ are each selected from F, Cl, CN, $NO_2$, $NH_2$, $CF_3$, $OCH_3$, $OC_2H_5$, $OCF_3$, 2,2,2,-trifluoro-1-hydroxyl-1-(trifluoromethyl)ethyl, ethynyl, propynyl, pentynyl, cyclopentyl, cyclohexyl, cyclopropylmethoxy, phenyl, phenylethynyl, dihydropyranyl (e.g., 3,6-dihydro-2H-pyran-4-yl), thiazolyl (e.g., 1,3-thiazol-2-yl), oxazolyl (e.g., 1,3-oxazol-2-yl), pyrrolidinyl (e.g., pyrrolidin-1-yl), piperidinyl (e.g. piperidin-1-yl), or morpholinyl (e.g. morpholin-4-yl). $R^4$ can also be selected from CN, alkoxy, fluorinated alkoxy, and cycloalkylalkoxy, such as CN, $OCH_3$, $OC_2H_5$, $OCF_3$, and cyclopropylmethoxy.

According to a further aspect of the invention, in the compounds of Formulas I-IV, at least one $R^1$, $R^3$ or $R^4$ is COH, $NR^6R^7$ wherein at least one of $R^6$ and $R^7$ is other than alkyl, or $NR^2COOR^8$.

According to a further aspect of the invention, in the compounds of Formulas I-IV, at least one $R^1$, $R^3$ or $R^4$ is selected from the following formulas

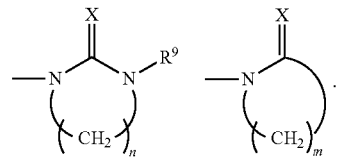

According to a further aspect of the invention, the compounds of Formulas I-IV, exhibit 2-3 of substituents $R^1$, $R^3$, or $R^4$.

According to a further aspect of the invention, in the compounds of Formulas I-IV, $R^2$ is fluorinated alkyl having 1 to 4 carbon atoms.

According to a further aspect of the invention, in the compounds of Formulas I-IV, at least one $R^6$ and $R^7$ is alkoxyalkyl having 2 to 8 carbon atoms.

According to a further aspect of the invention, in the compounds of Formulas I-IV, the compound exhibits at least one $R^9$ group that is Ar-alkyl wherein the alkyl portion has 1 to 4 carbon atoms.

According to a further aspect of the invention, in the compounds of Formulas I-IV, the compound exhibits at least one Het that is a heterocyclic group, which is fully saturated, partially saturated or fully unsaturated, having 5 to 10 ring atoms in which at least 1 ring atom is a N, O or S atom, and which is substituted by at least one substituent selected from OH, alkoxycarbonylalkyl having 3 to 8 carbon atoms, and piperidinylethyl.

According to a further compound and/or method aspect of the invention, the compound of formulas I-IV is selected from (wherein compounds in their salt forms can also be in their non-salt forms):

3-{[(3R)-1-Azabicyclo[2.2.2]oct-3-ylamino]carbonyl}-1H-indazole-6-carboxylic acid hydroformate,
3-{[(3R)-1-Azabicyclo[2.2.2]oct-3-ylamino]carbonyl}-1H-indazole-6-carboxylic acid,
6-Amino-N-[(3S)-1-azabicyclo[2.2.2]oct-3-yl]-1H-indazole-3-carboxamide,
N-[(3R)-1-Azabicyclo[2.2.2]oct-3-yl]-5-(1,3-oxazol-2-yl)-1H-indazole-3-carboxamide,
N-[(3R)-1-Azabicyclo[2.2.2]oct-3-yl]-5-(1,3-thiazol-2-yl)-1H-indazole-3-carboxamide hydroformate,
N-[(3R)-1-Azabicyclo[2.2.2]oct-3-yl]-5-(1,3-thiazol-2-yl)-1H-indazole-3-carboxamide,
N-[(3R)-1-Azabicyclo[2.2.2]oct-3-yl]-5-(cyclohex-1-en-1-yl)-1H-indazole-3-carboxamide hydroformate,
N-[(3R)-1-Azabicyclo[2.2.2]oct-3-yl]-5-(cyclohex-1-en-1-yl)-1H-indazole-3-carboxamide,
N-[(3R)-1-Azabicyclo[2.2.2]oct-3-yl]-5-(tetrahydro-2H-pyran-4-yl)-1H-indazole-3-carboxamide,
N-[(3R)-1-Azabicyclo[2.2.2]oct-3-yl]-5-(tetrahydro-2H-pyran-4-yl)-1H-indazole-3-carboxamide,
N-[(3R)-1-Azabicyclo[2.2.2]oct-3-yl]-5-(trifluoromethoxy)-1H-indazole-3-carboxamide hydroformate,
N-[(3R)-1-Azabicyclo[2.2.2]oct-3-yl]-5-(trifluoromethoxy)-1H-indazole-3-carboxamide,
N-[(3R)-1-Azabicyclo[2.2.2]oct-3-yl]-5-chloro-1H-indazole-3-carboxamide hydroformate,
N-[(3R)-1-Azabicyclo[2.2.2]oct-3-yl]-5-chloro-1H-indazole-3-carboxamide,
N-[(3R)-1-Azabicyclo[2.2.2]oct-3-yl]-5-cyano-1H-indazole-3-carboxamide hydroformate,
N-[(3R)-1-Azabicyclo[2.2.2]oct-3-yl]-5-cyano-1H-indazole-3-carboxamide,
N-[(3R)-1-Azabicyclo[2.2.2]oct-3-yl]-5-cyclopentyl-1H-indazole-3-carboxamide,
N-[(3R)-1-Azabicyclo[2.2.2]oct-3-yl]-5-ethynyl-1H-indazole-3-carboxamide hydrochloride,
N-[(3R)-1-Azabicyclo[2.2.2]oct-3-yl]-5-ethynyl-1H-indazole-3-carboxamide hydroformate,
N-[(3R)-1-Azabicyclo[2.2.2]oct-3-yl]-5-ethynyl-1H-indazole-3-carboxamide hydroformate,
N-[(3R)-1-Azabicyclo[2.2.2]oct-3-yl]-5-fluoro-1H-indazole-3-carboxamide hydroformate,
N-[(3R)-1-Azabicyclo[2.2.2]oct-3-yl]-5-fluoro-1H-indazole-3-carboxamide,
N-[(3R)-1-azabicyclo[2.2.2]oct-3-yl]-5-hydroxy-1H-indazole-3-carboxamide hydroformate,
N-[(3R)-1-azabicyclo[2.2.2]oct-3-yl]-5-hydroxy-1H-indazole-3-carboxamide,
N-[(3R)-1-Azabicyclo[2.2.2]oct-3-yl]-5-methoxy-1H-indazole-3-carboxamide hydroformate,
N-[(3R)-1-Azabicyclo[2.2.2]oct-3-yl]-5-methoxy-1H-indazole-3-carboxamide,
N-[(3R)-1-Azabicyclo[2.2.2]oct-3-yl]-5-phenoxy-1H-indazole-3-carboxamide hydroformate,
N-[(3R)-1-Azabicyclo[2.2.2]oct-3-yl]-5-phenoxy-1H-indazole-3-carboxamide,
N-[(3R)-1-Azabicyclo[2.2.2]oct-3-yl]-5-piperidin-1-yl-1H-indazole-3-carboxamide hydroformate,
N-[(3R)-1-Azabicyclo[2.2.2]oct-3-yl]-5-piperidin-1-yl-1H-indazole-3-carboxamide,
N-[(3R)-1-Azabicyclo[2.2.2]oct-3-yl]-5-pyrrolidin-1-yl-1H-indazole-3-carboxamide,
N-[(3R)-1-Azabicyclo[2.2.2]oct-3-yl]-6-(1,3-oxazol-2-yl)-1H-indazole-3-carboxamide,
N-[(3R)-1-Azabicyclo[2.2.2]oct-3-yl]-6-(1,3-thiazol-2-yl)-1H-indazole-3-carboxamide hydrochloride,
N-[(3R)-1-Azabicyclo[2.2.2]oct-3-yl]-6-(1,3-thiazol-2-yl)-1H-indazole-3-carboxamide hydroformate,
N-[(3R)-1-Azabicyclo[2.2.2]oct-3-yl]-6-(1,3-thiazol-2-yl)-1H-indazole-3-carboxamide,
N-[(3R)-1-Azabicyclo[2.2.2]oct-3-yl]-6-(1-methyl-1H-imidazol-2-yl)-1H-indazole-3-carboxamide hydroformate,
N-[(3R)-1-Azabicyclo[2.2.2]oct-3-yl]-6-(1-methyl-1H-imidazol-2-yl)-1H-indazole-3-carboxamide,
N-[(3R)-1-Azabicyclo[2.2.2]oct-3-yl]-6-(3,6-dihydro-2H-pyran-4-yl)-1H-indazole-3-carboxamide hydroformate,
N-[(3R)-1-Azabicyclo[2.2.2]oct-3-yl]-6-(3,6-dihydro-2H-pyran-4-yl)-1H-indazole-3-carboxamide,
N-[(3R)-1-Azabicyclo[2.2.2]oct-3-yl]-6-(cyclopropylmethoxy)-1,2-benzisothiazole-3-carboxamide,
N-[(3R)-1-Azabicyclo[2.2.2]oct-3-yl]-6-(pent-1-yn-1-yl)-1H-indazole-3-carboxamide hydroformate,
N-[(3R)-1-Azabicyclo[2.2.2]oct-3-yl]-6-(pent-1-yn-1-yl)-1H-indazole-3-carboxamide,
N-[(3R)-1-Azabicyclo[2.2.2]oct-3-yl]-6-(phenylethynyl)-1H-indazole-3-carboxamide hydroformate,
N-[(3R)-1-Azabicyclo[2.2.2]oct-3-yl]-6-(phenylethynyl)-1H-indazole-3-carboxamide,
N-[(3R)-1-Azabicyclo[2.2.2]oct-3-yl]-6-(trifluoromethoxy)-1,2-benzisothiazole-3-carboxamide hydroformate,
N-[(3R)-1-Azabicyclo[2.2.2]oct-3-yl]-6-(trifluoromethoxy)-1,2-benzisothiazole-3-carboxamide,
N-[(3R)-1-Azabicyclo[2.2.2]oct-3-yl]-6-(trifluoromethyl)-1H-indazole-3-carboxamide,
N-[(3R)-1-Azabicyclo[2.2.2]oct-3-yl]-6-cyano-1,2-benzisothiazole-3-carboxamide hydroformate,
N-[(3R)-1-Azabicyclo[2.2.2]oct-3-yl]-6-cyano-1,2-benzisothiazole-3-carboxamide hydrotrifluoroacetate,
N-[(3R)-1-Azabicyclo[2.2.2]oct-3-yl]-6-cyano-1,2-benzisothiazole-3-carboxamide,
N-[(3R)-1-Azabicyclo[2.2.2]oct-3-yl]-6-cyano-1H-indazole-3-carboxamide hydroformate,
N-[(3R)-1-Azabicyclo[2.2.2]oct-3-yl]-6-cyano-1H-indazole-3-carboxamide,
N-[(3R)-1-Azabicyclo[2.2.2]oct-3-yl]-6-cyclohexyl-1H-indazole-3-carboxamide hydroformate,
N-[(3R)-1-Azabicyclo[2.2.2]oct-3-yl]-6-cyclohexyl-1H-indazole-3-carboxamide,
N-[(3R)-1-Azabicyclo[2.2.2]oct-3-yl]-6-cyclopentyl-1H-indazole-3-carboxamide,
N-[(3R)-1-Azabicyclo[2.2.2]oct-3-yl]-6-ethoxy-1,2-benzisothiazole-3-carboxamide hydroformate,
N-[(3R)-1-Azabicyclo[2.2.2]oct-3-yl]-6-ethoxy-1,2-benzisothiazole-3-carboxamide,
N-[(3R)-1-Azabicyclo[2.2.2]oct-3-yl]-6-ethynyl-1H-indazole-3-carboxamide hydroformate,
N-[(3R)-1-Azabicyclo[2.2.2]oct-3-yl]-6-ethynyl-1H-indazole-3-carboxamide,
N-[(3R)-1-Azabicyclo[2.2.2]oct-3-yl]-6-fluoro-1H-indazole-3-carboxamide,
N-[(3R)-1-Azabicyclo[2.2.2]oct-3-yl]-6-hydroxy-1H-indazole-3-carboxamide hydroformate, N-[(3R)-1-Azabicyclo[2.2.2]oct-3-yl]-6-hydroxy-1H-indazole-3-carboxamide,
N-[(3R)-1-Azabicyclo[2.2.2]oct-3-yl]-6-methoxy-1H-indazole-3-carboxamide hydrochloride,
N-[(3R)-1-Azabicyclo[2.2.2]oct-3-yl]-6-methoxy-1H-indazole-3-carboxamide,
N-[(3R)-1-Azabicyclo[2.2.2]oct-3-yl]-6-morpholin-4-yl-1H-indazole-3-carboxamide,
N-[(3R)-1-Azabicyclo[2.2.2]oct-3-yl]-6-piperidin-1-yl-1H-indazole-3-carboxamide hydrotrifluoroacetate,
N-[(3R)-1-Azabicyclo[2.2.2]oct-3-yl]-6-piperidin-1-yl-1H-indazole-3-carboxamide,
N-[(3R)-1-Azabicyclo[2.2.2]oct-3-yl]-6-pyrrolidin-1-yl-1H-indazole-3-carboxamide,
N-[(3S)-1-Azabicyclo[2.2.2]oct-3-yl]-5-(1,3-oxazol-2-yl)-1H-indazole-3-carboxamide,
N-[(3S)-1-Azabicyclo[2.2.2]oct-3-yl]-5-(1,3-thiazol-2-yl)-1H-indazole-3-carboxamide hydroformate,
N-[(3S)-1-Azabicyclo[2.2.2]oct-3-yl]-5-(1,3-thiazol-2-yl)-1H-indazole-3-carboxamide,
N-[(3S)-1-Azabicyclo[2.2.2]oct-3-yl]-5-(tetrahydro-2H-pyran-4-yl)-1H-indazole-3-carboxamide,
N-[(3S)-1-Azabicyclo[2.2.2]oct-3-yl]-5-(trifluoromethoxy)-1H-indazole-3-carboxamide hydrochloride,
N-[(3S)-1-Azabicyclo[2.2.2]oct-3-yl]-5-(trifluoromethoxy)-1H-indazole-3-carboxamide hydroformate,
N-[(3S)-1-Azabicyclo[2.2.2]oct-3-yl]-5-(trifluoromethoxy)-1H-indazole-3-carboxamide,
N-[(3S)-1-Azabicyclo[2.2.2]oct-3-yl]-5-chloro-1H-indazole-3-carboxamide hydroformate,
N-[(3S)-1-Azabicyclo[2.2.2]oct-3-yl]-5-chloro-1H-indazole-3-carboxamide,
N-[(3S)-1-Azabicyclo[2.2.2]oct-3-yl]-5-cyano-1H-indazole-3-carboxamide hydroformate,
N-[(3S)-1-Azabicyclo[2.2.2]oct-3-yl]-5-cyano-1H-indazole-3-carboxamide,
N-[(3S)-1-Azabicyclo[2.2.2]oct-3-yl]-5-cyclopentyl-1H-indazole-3-carboxamide,
N-[(3S)-1-Azabicyclo[2.2.2]oct-3-yl]-5-ethynyl-1H-indazole-3-carboxamide hydroformate,
N-[(3S)-1-Azabicyclo[2.2.2]oct-3-yl]-5-ethynyl-1H-indazole-3-carboxamide,
N-[(3S)-1-Azabicyclo[2.2.2]oct-3-yl]-5-fluoro-1H-indazole-3-carboxamide hydroformate,
N-[(3S)-1-Azabicyclo[2.2.2]oct-3-yl]-5-fluoro-1H-indazole-3-carboxamide,
N-[(3S)-1-Azabicyclo[2.2.2]oct-3-yl]-5-methoxy-1H-indazole-3-carboxamide hydroformate,
N-[(3S)-1-Azabicyclo[2.2.2]oct-3-yl]-5-methoxy-1H-indazole-3-carboxamide,
N-[(3S)-1-Azabicyclo[2.2.2]oct-3-yl]-5-nitro-1H-indazole-3-carboxamide,
N-[(3S)-1-Azabicyclo[2.2.2]oct-3-yl]-6-(1,3-oxazol-2-yl)-1H-indazole-3-carboxamide,
N-[(3S)-1-Azabicyclo[2.2.2]oct-3-yl]-6-(1,3-thiazol-2-yl)-1H-indazole-3-carboxamide hydrochloride,
N-[(3S)-1-Azabicyclo[2.2.2]oct-3-yl]-6-(1,3-thiazol-2-yl)-1H-indazole-3-carboxamide hydroformate,
N-[(3S)-1-Azabicyclo[2.2.2]oct-3-yl]-6-(1,3-thiazol-2-yl)-1H-indazole-3-carboxamide,
N-[(3S)-1-Azabicyclo[2.2.2]oct-3-yl]-6-(1-methyl-1H-imidazol-2-yl)-1H-indazole-3-carboxamide hydroformate,
N-[(3S)-1-Azabicyclo[2.2.2]oct-3-yl]-6-(1-methyl-1H-imidazol-2-yl)-1H-indazole-3-carboxamide,
N-[(3S)-1-Azabicyclo[2.2.2]oct-3-yl]-6-(3,6-dihydro-2H-pyran-4-yl)-1H-indazole-3-carboxamide hydroformate,
N-[(3S)-1-Azabicyclo[2.2.2]oct-3-yl]-6-(3,6-dihydro-2H-pyran-4-yl)-1H-indazole-3-carboxamide,
N-[(3S)-1-Azabicyclo[2.2.2]oct-3-yl]-6-(cyclopropylmethoxy)-1,2-benzisothiazole-3-carboxamide,
N-[(3S)-1-Azabicyclo[2.2.2]oct-3-yl]-6-(morpholin-4-yl)-1H-indazole-3-carboxamide,
N-[(3S)-1-Azabicyclo[2.2.2]oct-3-yl]-6-(prop-1-yn-1-yl)-1H-indazole-3-carboxamide hydroformate,
N-[(3S)-1-Azabicyclo[2.2.2]oct-3-yl]-6-(prop-1-yn-1-yl)-1H-indazole-3-carboxamide,
N-[(3S)-1-Azabicyclo[2.2.2]oct-3-yl]-6-(trifluoromethoxy)-1,2-benzisothiazole-3-carboxamide hydroformate,
N-[(3S)-1-Azabicyclo[2.2.2]oct-3-yl]-6-(trifluoromethoxy)-1,2-benzisothiazole-3-carboxamide,
N-[(3S)-1-Azabicyclo[2.2.2]oct-3-yl]-6-(trifluoromethyl)-1H-indazole-3-carboxamide,
N-[(3S)-1-Azabicyclo[2.2.2]oct-3-yl]-6-[2,2,2-trifluoro-1-hydroxy-1-(trifluoromethyl)ethyl]-1H-indazole-3-carboxamide,
N-[(3S)-1-Azabicyclo[2.2.2]oct-3-yl]-6-cyano-1,2-benzisothiazole-3-carboxamide hydroformate,
N-[(3S)-1-Azabicyclo[2.2.2]oct-3-yl]-6-cyano-1,2-benzisothiazole-3-carboxamide,
N-[(3S)-1-Azabicyclo[2.2.2]oct-3-yl]-6-cyano-1,2-benzisothiazole-3-carboxamide,
N-[(3S)-1-Azabicyclo[2.2.2]oct-3-yl]-6-cyano-1H-indazole-3-carboxamide hydroformate,
N-[(3S)-1-Azabicyclo[2.2.2]oct-3-yl]-6-cyano-1H-indazole-3-carboxamide,
N-[(3S)-1-Azabicyclo[2.2.2]oct-3-yl]-6-cyclohexyl-1H-indazole-3-carboxamide hydroformate,
N-[(3S)-1-Azabicyclo[2.2.2]oct-3-yl]-6-cyclohexyl-1H-indazole-3-carboxamide,
N-[(3S)-1-Azabicyclo[2.2.2]oct-3-yl]-6-cyclohexyl-1H-indazole-3-carboxamide,
N-[(3S)-1-Azabicyclo[2.2.2]oct-3-yl]-6-cyclopentyl-1H-indazole-3-carboxamide,
N-[(3S)-1-Azabicyclo[2.2.2]oct-3-yl]-6-ethoxy-1,2-benzisothiazole-3-carboxamide hydroformate,
N-[(3S)-1-Azabicyclo[2.2.2]oct-3-yl]-6-ethoxy-1,2-benzisothiazole-3-carboxamide,
N-[(3S)-1-Azabicyclo[2.2.2]oct-3-yl]-6-ethynyl-1H-indazole-3-carboxamide hydroformate,
N-[(3S)-1-Azabicyclo[2.2.2]oct-3-yl]-6-ethynyl-1H-indazole-3-carboxamide,
N-[(3S)-1-Azabicyclo[2.2.2]oct-3-yl]-6-fluoro-1H-indazole-3-carboxamide,
N-[(3S)-1-Azabicyclo[2.2.2]oct-3-yl]-6-methoxy-1H-indazole-3-carboxamide,
N-[(3S)-1-Azabicyclo[2.2.2]oct-3-yl]-6-nitro-1H-indazole-3-carboxamide,
and physiologically acceptable salts thereof.

According to a further compound and/or method aspect of the invention, the compound of formulas I-IV is selected from (wherein compounds in their salt forms can also be in their non-salt forms):
N-[(3S)-1-Azabicyclo[2.2.2]oct-3-yl]-5-methoxy-1-methyl-1H-indazole-3-carboxamide,
N-[(3S)-1-Azabicyclo[2.2.2]oct-3-yl]-5-methoxy-1-ethyl-1H-indazole-3-carboxamide,
N-[(3S)-1-Azabicyclo[2.2.2]oct-3-yl]-5-methoxy-1-cyclopentyl-1H-indazole-3-carboxamide,
N-[(3R)-1-Azabicyclo[2.2.2]oct-3-yl]-5-(nitro)-1H-indazole-3-carboxamide,
N-[(3R)-1-Azabicyclo[2.2.2]oct-3-yl]-6-(4-hydroxytetrahydro-2H-pyran-4-yl)-1H-indazole-3-carboxamide, N-[(3S)-1-Azabicyclo[2.2.2]oct-3-yl]-6-(4-hydroxytetrahydro-2H-pyran-4-yl)-1H-indazole-3-carboxamide,
N-[(3S)-1-Azabicyclo[2.2.2]oct-3-yl]-6-(trifluoromethoxy)-1H-indazole-3-carboxamide hydroformate,
N-[(3R)-1-Azabicyclo[2.2.2]oct-3-yl]-6-(trifluoromethoxy)-1H-indazole-3-carboxamide hydroformate,
N-[(3R)-1-Azabicyclo[2.2.2]oct-3-yl]-7-(trifluoromethoxy)-1H-indazole-3-carboxamide hydroformate,
N-[(3S)-1-Azabicyclo[2.2.2]oct-3-yl]-7-(trifluoromethoxy)-1H-indazole-3-carboxamide hydroformate,
N-[(3S)-1-Azabicyclo[2.2.2]oct-3-yl]-6-(hydroxy)-1H-indazole-3-carboxamide,
N-[(3S)-1-Azabicyclo[2.2.2]oct-3-yl]-5-(hydroxy)-1H-indazole-3-carboxamide,
N-[(3S)-1-Azabicyclo[2.2.2]oct-3-yl]-7-(nitro)-1H-indazole-3-carboxamide,
N-[(3S)-1-Azabicyclo[2.2.2]oct-3-yl]-5-(3,6-dihydro-2H-pyran-4-yl)-1H-indazole-3-carboxamide hydroformate,
N-[(3R)-1-Azabicyclo[2.2.2]oct-3-yl]-5-(3,6-dihydro-2H-pyran-4-yl)-1H-indazole-3-carboxamide,
N-[(3R)-1-Azabicyclo[2.2.2]oct-3-yl]-4-bromo-5-methoxy-1H-indazole-3-carboxamide hydroformate,
N-[(3S)-1-Azabicyclo[2.2.2]oct-3-yl]-4-bromo-5-methoxy-1H-indazole-3-carboxamide hydroformate,
N-[(3S)-1-Azabicyclo[2.2.2]oct-3-yl]-5-bromo-4-nitro-1H-indazole-3-carboxamide,
N-[(3S)-1-Azabicyclo[2.2.2]oct-3-yl]-5-(nitro)-1H-indazole-3-carboxamide,
N-[(3R)-1-Azabicyclo[2.2.2]oct-3-yl]-5-(nitro)-1H-indazole-3-carboxamide,
N-[(3S)-1-Azabicyclo[2.2.2]oct-3-yl]-6-(hydroxy)-1,2-benzisothiazole-3-carboxamide,
N-[(3S)-1-azabicyclo[2.2.2]oct-3-yl]-5-(formyl)-1H-indazole-3-carboxamide hydroformate,
N-[(3S)-1-Azabicyclo[2.2.2]oct-3-yl]-6-(tetrahydro-2H-pyran-4-yl)-1H-indazole-3-carboxamide,
N-[(3R)-1-Azabicyclo[2.2.2]oct-3-yl]-6-(tetrahydro-2H-pyran-4-yl)-1H-indazole-3-carboxamide,
N-[(3S)-1-Azabicyclo[2.2.2]oct-3-yl]-5-(3,6-dihydro-2H-pyran-4-yl)-1H-indazole-3-carboxamide hydroformate,
N-[(3S)-1-Azabicyclo[2.2.2]oct-3-yl]-5-methoxy-1-(2,2,2-trifluoroethyl)-1H-indazole-3-carboxamide,
N-[(3S)-1-Azabicyclo[2.2.2]oct-3-yl]-5-(hydroxymethyl)-1H-indazole-3-carboxamide,
N-[(3S)-1-Azabicyclo[2.2.2]oct-3-yl]-5-(cyclopentylamino)-1H-indazole-3-carboxamide,
N-[(3S)-1-Azabicyclo[2.2.2]oct-3-yl]-5-methoxy-4-(3-thienyl)-1H-indazole-3-carboxamide hydroformate,
N-[(3S)-1-Azabicyclo[2.2.2]oct-3-yl]-5-methoxy-4-(2-thienyl)-1H-indazole-3-carboxamide hydroformate,
N-[(3R)-1-Azabicyclo[2.2.2]oct-3-yl]-5-methoxy-4-(2-thienyl)-1H-indazole-3-carboxamide hydroformate,
N-[(3S)-1-Azabicyclo[2.2.2]oct-3-yl]-6-(propyl)-1H-indazole-3-carboxamide hydroformate,
N-[(3S)-1-Azabicyclo[2.2.2]oct-3-yl]-6-(1,3-thiazol-2-yl)-1,2-benzisothiazole-3-carboxamide hydroformate,
N-[(3R)-1-Azabicyclo[2.2.2]oct-3-yl]-6-(1,3-thiazol-2-yl)-1,2-benzisothiazole-3-carboxamide hydroformate,
N-[(3S)-1-Azabicyclo[2.2.2]oct-3-yl]-5-(ethyl)-1H-indazole-3-carboxamide hydroformate,
N-[(3S)-1-Azabicyclo[2.2.2]oct-3-yl]-6-(4-methyl-1,3-thiazol-2-yl)-1H-indazole-3-carboxamide,
N-[(3S)-1-Azabicyclo[2.2.2]oct-3-yl]-6-(5-methyl-1,3-thiazol-2-yl)-1H-indazole-3-carboxamide,
N-[(3R)-1-Azabicyclo[2.2.2]oct-3-yl]-6-(5-methyl-1,3-thiazol-2-yl)-1H-indazole-3-carboxamide,
N-[(3R)-1-Azabicyclo[2.2.2]oct-3-yl]-6-(4-methyl-1,3-thiazol-2-yl)-1H-indazole-3-carboxamide,
N-[(3S)-1-Azabicyclo[2.2.2]oct-3-yl]-5-(butyl)-1H-indazole-3-carboxamide hydroformate,
N-[(3S)-1-Azabicyclo[2.2.2]oct-3-yl]-4-cyclopropyl-5-methoxy-1H-indazole-3-carboxamide hydroformate,
N-[(3S)-1-Azabicyclo[2.2.2]oct-3-yl]-4-ethyl-5-methoxy-1H-indazole-3-carboxamide hydroformate,
N-[(3S)-1-Azabicyclo[2.2.2]oct-3-yl]-6-(4-methyl-1,3-thiazol-2-yl)-1H-indazole-3-carboxamide hydroformate,
N-[(3S)-1-Azabicyclo[2.2.2]oct-3-yl]-5-(methyl)-1H-indazole-3-carboxamide hydroformate,
N-[(3S)-1-Azabicyclo[2.2.2]oct-3-yl]-6-ethynyl-1,2-benzisothiazole-3-carboxamide hydroformate,
N-[(3R)-1-Azabicyclo[2.2.2]oct-3-yl]-6-ethynyl-1,2-benzisothiazole-3-carboxamide hydroformate,
N-[(3S)-1-Azabicyclo[2.2.2]oct-3-yl]-6-(tetrahydrofuran-3-yl)-1H-indazole-3-carboxamide hydroformate,
N-[(3S)-1-Azabicyclo[2.2.2]oct-3-yl]-6-(cyclopropylmethoxy)-1,2-benzisothiazole-3-carboxamide hydroformate,
N-[(3R)-1-Azabicyclo[2.2.2]oct-3-yl]-5-[(2-methoxyethyl)amino]-1H-indazole-3-carboxamide hydroformate,
N-[(3S)-1-Azabicyclo[2.2.2]oct-3-yl]-5-(2,5-dimethyl-1H-pyrrol-1-yl)-1H-indazole-3-carboxamide,
N-[(3S)-1-Azabicyclo[2.2.2]oct-3-yl]-5-(1H-pyrrol-1-yl)-1H-indazole-3-carboxamide,
N-[(3R)-1-Azabicyclo[2.2.2]oct-3-yl]-5-(1H-pyrrol-1-yl)-1H-indazole-3-carboxamide,
5-Amino-N-[(3R)-1-azabicyclo[2.2.2]oct-3-yl]-1H-indazole-3-carboxamide,
5-Amino-N-[(3S)-1-azabicyclo[2.2.2]oct-3-yl]-1H-indazole-3-carboxamide,
4-Amino-N-[(3S)-1-azabicyclo[2.2.2]oct-3-yl]-1H-indazole-3-carboxamide,
6-Amino-N-[(3S)-1-azabicyclo[2.2.2]oct-3-yl]-1,2-benzisothiazole-3-carboxamide,
6-Amino-N-[(3R)-1-azabicyclo[2.2.2]oct-3-yl]-1,2-benzisothiazole-3-carboxamide,
7-Amino-N-[(3S)-1-azabicyclo[2.2.2]oct-3-yl]-1H-indazole-3-carboxamide,
N-[(3S)-1-Azabicyclo[2.2.2]oct-3-yl]-5-[(cyclopropylmethyl)amino]-1H-indazole-3-carboxamide hydroformate,
N-[(3S)-1-Azabicyclo[2.2.2]oct-3-yl]-5-{[(4-methoxyphenyl)acetyl]amino}-1H-indazole-3-carboxamide hydroformate,
N-[(3S)-1-Azabicyclo[2.2.2]oct-3-yl]-5-[(trifluoroacetyl)amino]-1H-indazole-3-carboxamide hydroformate,
N-[(3S)-1-Azabicyclo[2.2.2]oct-3-yl]-5-[(cyclopropylcarbonyl)amino]-1H-indazole-3-carboxamide hydroformate,
N-[(3R)-1-Azabicyclo[2.2.2]oct-3-yl]-5-[(ethylsulfonyl)amino]-1H-indazole-3-carboxamide hydroformate,
N-[(3S)-1-Azabicyclo[2.2.2]oct-3-yl]-5-[(methylsulfonyl)amino]-1H-indazole-3-carboxamide hydroformate,
N-[(3S)-1-Azabicyclo[2.2.2]oct-3-yl]-5-[(ethylsulfonyl)amino]-1H-indazole-3-carboxamide hydroformate,
N-[(3R)-1-Azabicyclo[2.2.2]oct-3-yl]-6-[(ethylsulfonyl)amino]-1,2-benzisothiazole-3-carboxamide,
N-[(3S)-1-Azabicyclo[2.2.2]oct-3-yl]-6-[(ethylsulfonyl)amino]-1,2-benzisothiazole-3-carboxamide,
N-[(3R)-1-Azabicyclo[2.2.2]oct-3-yl]-6-[(methylsulfonyl)amino]-1,2-benzisothiazole-3-carboxamide,
N-[(3S)-1-Azabicyclo[2.2.2]oct-3-yl]-6-[(methylsulfonyl)amino]-1,2-benzisothiazole-3-carboxamide,
N-[(3S)-1-Azabicyclo[2.2.2]oct-3-yl]-4-[(methylsulfonyl)amino]-1H-indazole-3-carboxamide, N-[(3S)-1-Azabicyclo[2.2.2]oct-3-yl]-5-[(benzylsulfonyl)
amino]-1H-indazole-3-carboxamide hydroformate,
N-[(3S)-1-Azabicyclo[2.2.2]oct-3-yl]-6-[({[2-(2,6-dichlorophenyl)ethyl]amino}carbonyl)amino]-1,2-benzisothiazole-3-carboxamide,
N-[(3S)-1-Azabicyclo[2.2.2]oct-3-yl]-6-({[(3-cyanophenyl)amino]carbonyl}amino)-1,2-benzisothiazole-3-carboxamide,
N-[(3R)-1-Azabicyclo[2.2.2]oct-3-yl]-6-[({[2-(4-fluorophenyl)ethyl]amino}carbonyl)amino]-1,2-benzisothiazole-3-carboxamide,
N-[(3R)-1-Azabicyclo[2.2.2]oct-3-yl]-6-({[(3,4-dimethylphenyl)amino]carbonyl}amino)-1,2-benzisothiazole-3-carboxamide,
N-[(3R)-1-Azabicyclo[2.2.2]oct-3-yl]-6-({[(2,5-dimethylphenyl)amino]carbonyl}amino)-1,2-benzisothiazole-3-carboxamide,
N-[(3R)-1-Azabicyclo[2.2.2]oct-3-yl]-6-({[(4-methylbenzyl)amino]carbonyl}amino)-1,2-benzisothiazole-3-carboxamide,
N-[(3S)-1-Azabicyclo[2.2.2]oct-3-yl]-6-[({[2-(4-methylphenyl)ethyl]amino}carbonyl)amino]-1,2-benzisothiazole-3-carboxamide,
N-[(3S)-1-Azabicyclo[2.2.2]oct-3-yl]-6-[({[2-(3-methoxyphenyl)ethyl]amino}carbonyl)amino]-1,2-benzisothiazole-3-carboxamide,
N-[(3S)-1-Azabicyclo[2.2.2]oct-3-yl]-6-{[(cyclopentylamino)carbonyl]amino}-1,2-benzisothiazole-3-carboxamide,
N-[(3S)-1-Azabicyclo[2.2.2]oct-3-yl]-6-{[(propylamino)carbonyl]amino}-1,2-benzisothiazole-3-carboxamide,
N-[(3R)-1-Azabicyclo[2.2.2]oct-3-yl]-5-({[(4-fluorobenzyl)amino]carbonyl}amino)-1H-indazole-3-carboxamide,
N-[(3R)-1-Azabicyclo[2.2.2]oct-3-yl]-5-({[(3-methoxybenzyl)amino]carbonyl}amino)-1H-indazole-3-carboxamide,
N-[(3R)-1-Azabicyclo[2.2.2]oct-3-yl]-5-{[(cyclopentylamino)carbonyl]amino}-1H-indazole-3-carboxamide,
N-[(3S)-1-Azabicyclo[2.2.2]oct-3-yl]-5-({[(3-methoxybenzyl)amino]carbonyl}amino)-1H-indazole-3-carboxamide,
N-[(3S)-1-Azabicyclo[2.2.2]oct-3-yl]-5-({[(4-fluorobenzyl)amino]carbonyl}amino)-1H-indazole-3-carboxamide,
N-[(3S)-1-Azabicyclo[2.2.2]oct-3-yl]-6-{[(propylamino)carbonyl]amino}-1,2-benzisothiazole-3-carboxamide hydroformate,
N-[(3R)-1-Azabicyclo[2.2.2]oct-3-yl]-5-{[(propylamino)carbonyl]amino}-1H-indazole-3-carboxamide hydroformate,
N-[(3S)-1-Azabicyclo[2.2.2]oct-3-yl]-5-{[(propylamino)carbonyl]amino}-1H-indazole-3-carboxamide hydroformate,
N-[(3S)-1-Azabicyclo[2.2.2]oct-3-yl]-5-({[(4-fluorobenzyl)amino]carbonyl}amino)-1H-indazole-3-carboxamide hydroformate,
N-[(3R)-1-Azabicyclo[2.2.2]oct-3-yl]-5-({[(4-fluorobenzyl)amino]carbonyl}amino)-1H-indazole-3-carboxamide hydroformate,
N-[(3R)-1-Azabicyclo[2.2.2]oct-3-yl]-5-{[(cyclopentylamino)carbonyl]amino}-1H-indazole-3-carboxamide hydroformate,
N-[(3S)-1-Azabicyclo[2.2.2]oct-3-yl]-6-(1,3-thiazol-2-ylamino)-1,2-benzisothiazole-3-carboxamide hydroformate,
N-[(3S)-1-Azabicyclo[2.2.2]oct-3-yl]-6-(1H-1,2,3-triazol-4-yl)-1H-indazole-3-carboxamide dihydroformate,
N-[(3R)-1-Azabicyclo[2.2.2]oct-3-yl]-6-[1-(2-piperidin-1-ylethyl)-1H-1,2,3-triazol-4-yl]-1H-indazole-3-carboxamide dihydroformate,
Ethyl [4-(3-{[(3R)-1-azabicyclo[2.2.2]oct-3-ylamino]carbonyl}-1H-indazol-6-yl)-1H-1,2,3-triazol-1-yl]acetate hydroformate,
Benzyl(3-{[(3S)-1-azabicyclo[2.2.2]oct-3-ylamino]carbonyl}-1H-indazol-5-yl)carbamate,
Vinyl(3-{[(3S)-1-azabicyclo[2.2.2]oct-3-ylamino]carbonyl}-1H-indazol-5-yl)carbamate, and
physiologically acceptable salts thereof.

According to a further compound and/or method aspect of the invention, the compound of formulas I-IV is selected from (wherein compounds in their salt forms can also be in their non-salt forms):
N-[(3S)-1-Azabicyclo[2.2.2]oct-3-yl]-4-methoxy-1H-indazole-3-carboxamide,
N-[(3R)-1-Azabicyclo[2.2.2]oct-3-yl]-1,2-benzisoxazole-3-carboxamide hydroformate,
N-[(3S)-1-Azabicyclo[2.2.2]oct-3-yl]-1,2-benzisoxazole-3-carboxamide hydroformate,
N-[(3S)-1-Azabicyclo[2.2.2]oct-3-yl]-6-(1,3-oxazol-2-yl)-1,2-benzisothiazole-3-carboxamide hydroformate,
N-[(3S)-1-Azabicyclo[2.2.2]oct-3-yl]-7-bromo-6-methoxy-1H-indazole-3-carboxamide,
N-[(3S)-1-Azabicyclo[2.2.2]oct-3-yl]-1,8-dihydropyrrolo[3,2-g]indazole-3-carboxamide,
N-[(3R)-1-Azabicyclo[2.2.2]oct-3-yl]-1-benzyl-6-(difluoromethoxy)-1H-indazole-3-carboxamide hydroformate,
N-[(3S)-1-Azabicyclo[2.2.2]oct-3-yl]-1-(3-thienyl)-1H-indazole-3-carboxamide hydroformate,
N-[(3S)-1-Azabicyclo[2.2.2]oct-3-yl]-5-(difluoromethoxy)-1H-indazole-3-carboxamide,
N-[(3R)-1-Azabicyclo[2.2.2]oct-3-yl]-5-(difluoromethoxy)-1H-indazole-3-carboxamide,
N-[(3R)-1-Azabicyclo[2.2.2]oct-3-yl]-5-(5-methyl-1,3-thiazol-2-yl)-1H-indazole-3-carboxamide hydroformate,
N-[(3S)-1-Azabicyclo[2.2.2]oct-3-yl]-7-methoxy-1H-indazole-3-carboxamide hydroformate,
N-[(3S)-1-Azabicyclo[2.2.2]oct-3-yl]-7-fluoro-6-methoxy-1H-indazole-3-carboxamide hydroformate,
N-[(3S)-1-Azabicyclo[2.2.2]oct-3-yl]-4-fluoro-5-methoxy-1H-indazole-3-carboxamide hydroformate,
N-[(3S)-1-Azabicyclo[2.2.2]oct-3-yl]-6-(difluoromethoxy)-1H-indazole-3-carboxamide,
N-[(3R)-1-Azabicyclo[2.2.2]oct-3-yl]-6-(difluoromethoxy)-1H-indazole-3-carboxamide,
N-[(3R)-1-Azabicyclo[2.2.2]oct-3-yl]-5-(4-methyl-1,3-thiazol-2-yl)-1H-indazole-3-carboxamide hydroformate,
N-[(3S)-1-Azabicyclo[2.2.2]oct-3-yl]-5-(5-methyl-1,3-thiazol-2-yl)-1H-indazole-3-carboxamide hydroformate,
N-[(3S)-1-Azabicyclo[2.2.2]oct-3-yl]-5-cyclopropyl-6-methoxy-1H-indazole-3-carboxamide hydroformate,
N-[(3S)-1-Azabicyclo[2.2.2]oct-3-yl]-6-methoxy-5-(3-thienyl)-1H-indazole-3-carboxamide hydroformate,
N-[(3S)-1-azabicyclo[2.2.2]oct-3-yl]-5-[3-(benzyloxy)pyrrolidin-1-yl]-1H-indazole-3-carboxamide hydroformate,
N-[(3S)-1-Azabicyclo[2.2.2]oct-3-yl]-5-(5-methyl-1,3-thiazol-2-yl)-1H-indazole-3-carboxamide hydrochloride,
N-[(3S)-1-Azabicyclo[2.2.2]oct-3-yl]-5-[3-(methyloxy)pyrrolidin-1-yl]-1H-indazole-3-carboxamide hydroformate,
N-[(3S)-1-Azabicyclo[2.2.2]oct-3-yl]-5-[3-(hydroxy)pyrrolidin-1-yl]-1H-indazole-3-carboxamide hydroformate,
N-[(3S)-1-Azabicyclo[2.2.2]oct-3-yl]-5-[(1-methylpyrrolidin-3-yl)oxy]-1H-indazole-3-carboxamide dihydroformate, N-[(3S)-1-Azabicyclo[2.2.2]oct-3-yl]-6-(5-methyl-1,3-thiazol-2-yl)-1H-indazole-3-carboxamide hydrochloride,
N-(1-Azabicyclo[2.2.2]oct-3-ylmethyl)-5-(trifluoromethoxy)-1H-indazole-3-carboxamide hydroformate,
N-(1-Azabicyclo[2.2.2]oct-3-ylmethyl)-6-methoxy-1H-indazole-3-carboxamide hydroformate,
N-[(3S)-1-Azabicyclo[2.2.2]oct-3-yl]-5-(cyclopropylmethoxy)-1H-indazole-3-carboxamide hydroformate,
N-[(3S)-1-Azabicyclo[2.2.2]oct-3-yl]-5-(cyclopentyloxy)-1H-indazole-3-carboxamide hydroformate,
N-[(3S)-1-Azabicyclo[2.2.2]oct-3-yl]-5-(2,2,2-trifluoroethoxy)-1H-indazole-3-carboxamide hydroformate,
N-[(3S)-1-Azabicyclo[2.2.2]oct-3-yl]-6-(cyclopropylmethoxy)-1H-indazole-3-carboxamide hydroformate,
N-[(3S)-1-Azabicyclo[2.2.2]oct-3-yl]-6-(2,2,2-trifluoroethoxy)-1H-indazole-3-carboxamide hydroformate,
N-[(3S)-1-Azabicyclo[2.2.2]oct-3-yl]-5-(benzyloxy)-1H-indazole-3-carboxamide hydroformate,
N-[(3S)-1-Azabicyclo[2.2.2]oct-3-yl]-5-(tetrahydro-2H-pyran-4-yloxy)-1H-indazole-3-carboxamide hydroformate,
N-[(3S)-1-Azabicyclo[2.2.2]oct-3-yl]-5-(2,3-dihydro-1H-inden-2-yloxy)-1H-indazole-3-carboxamide hydroformate,
N-[(3S)-1-Azabicyclo[2.2.2]oct-3-yl]-5-[2-(dimethylamino)ethoxy]-1H-indazole-3-carboxamide dihydroformate,
N-[(3S)-1-Azabicyclo[2.2.2]oct-3-yl]-5-(2-pyrrolidin-1-ylethoxy)-1H-indazole-3-carboxamide dihydroformate,
N-[(3S)-1-Azabicyclo[2.2.2]oct-3-yl]-5-bromo-1-(ethyl)-1H-indazole-3-carboxamide,
N-[(3S)-1-Azabicyclo[2.2.2]oct-3-yl]-6-bromo-1-(ethyl)-1H-indazole-3-carboxamide,
N-[(3S)-1-Azabicyclo[2.2.2]oct-3-yl]-5-bromo-1-(cyclopropylmethyl)-1H-indazole-3-carboxamide,
N-[(3S)-1-Azabicyclo[2.2.2]oct-3-yl]-5-bromo-1-(2,2,2-trifluoroethyl)-1H-indazole-3-carboxamide,
N-[(3S)-1-Azabicyclo[2.2.2]oct-3-yl]-5-[(dimethylamino)methyl]-1H-indazole-3-carboxamide dihydroformate,
N-[(3S)-1-Azabicyclo[2.2.2]oct-3-yl]-5-[(diethylamino)methyl]-1H-indazole-3-carboxamide dihydroformate,
N-[(3S)-1-Azabicyclo[2.2.2]oct-3-yl]-5-[(pyrrolidin-1-yl)methyl]-1H-indazole-3-carboxamide dihydroformate,
N-[(3S)-1-Azabicyclo[2.2.2]oct-3-yl]-5-[(1-benzylpyrrolidin-3-yl)oxy]-1H-indazole-3-carboxamide dihydroformate,
N-[(3S)-1-Azabicyclo[2.2.2]oct-3-yl]-N-ethyl-6-methoxy-1H-indazole-3-carboxamide,
N-[(3S)-1-Azabicyclo[2.2.2]oct-3-yl]-N-ethyl-5-trifluoromethoxy-1H-indazole-3-carboxamide,
N-[(3S)-1-Azabicyclo[2.2.2]oct-3-yl]-N-cyclopropylmethyl-6-methoxy-1H-indazole-3-carboxamide hydroformate,
N-[(3S)-1-Azabicyclo[2.2.2]oct-3-yl]-N-cyclopropylmethyl-1H-indazole-3-carboxamide hydroformate,
N-[(3S)-1-Azabicyclo[2.2.2]oct-3-yl]-N-cyclopropylmethyl-5-trifluoromethoxy-1H-indazole-3-carboxamide hydroformate,
N-[(3S)-1-Azabicyclo[2.2.2]oct-3-yl]-6-(4-methyl-1,3-thiazol-2-yl)-1H-indazole-3-carboxamide hydrochloride,
N-[(3S)-1-Azabicyclo[2.2.2]oct-3-yl]-1-ethyl-5-(1,3-thiazol-2-yl)-1H-indazole-3-carboxamide hydroformate,
N-[(3S)-1-Azabicyclo[2.2.2]oct-3-yl]-1-cyclopropylmethyl-5-(1,3-thiazol-2-yl)-1H-indazole-3-carboxamide hydroformate,
N-[(3S)-1-Azabicyclo[2.2.2]oct-3-yl]-1-(2,2,2-trifluoroethyl)-5-(1,3-thiazol-2-yl)-1H-indazole-3-carboxamide hydroformate,
N-[(3S)-1-Azabicyclo[2.2.2]oct-3-yl]-1-ethyl-6-(1,3-thiazol-2-yl)-1H-indazole-3-carboxamide hydroformate,
N-[(3R)-1-Azabicyclo[2.2.2]oct-3-yl]-5-(3-formylcyclohex-1-en-1-yl)-1H-indazole-3-carboxamide hydroformate,
N-[(3S)-1-Azabicyclo[2.2.2]oct-3-yl]-6-[3-(2-methoxyethoxy)propoxy]-1,2-benzisothiazole-3-carboxamide hydroformate,
N-[(3S)-1-Azabicyclo[2.2.2]oct-3-yl]-6-(4-cyclohexylpiperazin-1-yl)-1,2-benzisothiazole-3-carboxamide hydroformate,
N-[(3S)-1-Azabicyclo[2.2.2]oct-3-yl]-6-(4-ethylpiperazin-1-yl)-1,2-benzisothiazole-3-carboxamide hydroformate,
N-[(3S)-1-Azabicyclo[2.2.2]oct-3-yl]-6-[4-(3-furoyl)piperazin-1-yl]-1,2-benzisothiazole-3-carboxamide hydroformate,
N-[(3S)-1-Azabicyclo[2.2.2]oct-3-yl]-5-(3-ethoxypyrrolidin-1-yl)-1,2-benzisothiazole-3-carboxamide,
N-[(3S)-1-Azabicyclo[2.2.2]oct-3-yl]-6-(3-ethoxypyrrolidin-1-yl)-1,2-benzisothiazole-3-carboxamide,
N-[(3S)-1-Azabicyclo[2.2.2]oct-3-yl]-5-(3-methoxypyrrolidin-1-yl)-1,2-benzisothiazole-3-carboxamide,
6-Amino-N-[(3S)-1-azabicyclo[2.2.2]oct-3-yl]-1,2-benzisoxazole-3-carboxamide,
5-Amino-N-[(3S)-1-azabicyclo[2.2.2]oct-3-yl]-1-(2,2,2-trifluoroethyl)-1H-indazole-3-carboxamide,
5-Amino-N-[(3S)-1-azabicyclo[2.2.2]oct-3-yl]-1-(cyclopropylmethyl)-1H-indazole-3-carboxamide,
5-Amino-N-[(3S)-1-azabicyclo[2.2.2]oct-3-yl]-1-(ethyl)-1H-indazole-3-carboxamide,
6-Amino-N-[(3S)-1-azabicyclo[2.2.2]oct-3-yl]-1-(ethyl)-1H-indazole-3-carboxamide,
Methyl 4-[(3-{[(3S)-1-azabicyclo[2.2.2]oct-3-ylamino]carbonyl}-1H-indazol-5-yl)amino]butanoate dihydroformate,
Methyl 4-[(3-{[(3S)-1-azabicyclo[2.2.2]oct-3-ylamino]carbonyl}-1H-indazol-6-yl)amino]butanoate dihydroformate,
tert-Butyl {2-[(3-{[(3S)-1-azabicyclo[2.2.2]oct-3-ylamino]carbonyl}-1,2-benzisothiazol-6-yl)amino]ethyl}propylcarbamate hydroformate,
N-[(3R)-1-Azabicyclo[2.2.2]oct-3-yl]-5-[(1,3-thiazol-2-ylmethyl)amino]-1H-indazole-3-carboxamide hydroformate,
N-[(3R)-1-Azabicyclo[2.2.2]oct-3-yl]-5-(dimethylamino)-1H-indazole-3-carboxamide hydroformate,
N-[(3R)-1-Azabicyclo[2.2.2]oct-3-yl]-1-(2-methoxyethyl)-5-[(2-methoxyethyl)amino]-1H-indazole-3-carboxamide hydroformate,
N-[(3S)-1-Azabicyclo[2.2.2]oct-3-yl]-6-{[2-(diethylamino)-2-oxoethyl]amino}-1,2-benzisothiazole-3-carboxamide hydroformate,
N-[(3R)-1-Azabicyclo[2.2.2]oct-3-yl]-5-(butylamino)-1H-indazole-3-carboxamide hydroformate,
N-[(3S)-1-Azabicyclo[2.2.2]oct-3-yl]-6-[(cyclopropylmethyl)amino]-1,2-benzisothiazole-3-carboxamide hydroformate,
N-[(3S)-1-Azabicyclo[2.2.2]oct-3-yl]-6-(dimethylamino)-1,2-benzisothiazole-3-carboxamide hydroformate,
N-[(3R)-1-Azabicyclo[2.2.2]oct-3-yl]-6-(diethylamino)-1,2-benzisothiazole-3-carboxamide hydroformate,
N-[(3S)-1-Azabicyclo[2.2.2]oct-3-yl]-6-[(cyclopropylcarbonyl)amino]-1-(cyclopropylmethyl)-1H-indazole-3-carboxamide,
5-Amino-N-[(3S)-1-azabicyclo[2.2.2]oct-3-yl]-1-(trifluoroacetyl)-1H-indazole-3-carboxamide dihydroformate, N-[(3S)-1-Azabicyclo[2.2.2]oct-3-yl]-1-(cyclopropylcarbonyl)-5-[(cyclopropylcarbonyl)amino]-1H-indazole-3-carboxamide hydroformate,
N-[(3S)-1-Azabicyclo[2.2.2]oct-3-yl]-1-[(4-methoxyphenyl)acetyl]-5-{[(4-methoxyphenyl)acetyl]amino}-1H-indazole-3-carboxamide hydroformate,
N-[(3S)-1-Azabicyclo[2.2.2]oct-3-yl]-6-[(cyclopropylcarbonyl)amino]-1,2-benzisothiazole-3-carboxamide hydroformate,
6-(Acetylamino)-N-[(3S)-1-azabicyclo[2.2.2]oct-3-yl]-1,2-benzisothiazole-3-carboxamide hydroformate,
N-[(3S)-1-Azabicyclo[2.2.2]oct-3-yl]-6-{[(dimethylamino)sulfonyl]amino}-1,2-benzisothiazole-3-carboxamide hydroformate,
5-Amino-N-[(3S)-1-azabicyclo[2.2.2]oct-3-yl]-1-(benzylsulfonyl)-1H-indazole-3-carboxamide dihydroformate,
N-[(3S)-1-Azabicyclo[2.2.2]oct-3-yl]-1-(cyclopropylmethyl)-6-{[(propylamino)carbonyl]amino}-1H-indazole-3-carboxamide,
N(3)-[(3S)-1-Azabicyclo[2.2.2]oct-3-yl]-N(1)-(3-methoxybenzyl)-5-({[(3-methoxybenzyl)amino]carbonyl}amino)-1H-indazole-1,3-dicarboxamide,
N(3)-[(3S)-1-Azabicyclo[2.2.2]oct-3-yl]-N(1)-(4-fluorobenzyl)-5-({[(4-fluorobenzyl)amino]carbonyl}amino)-1H-indazole-1,3-dicarboxamide,
N(3)-[(3R)-1-Azabicyclo[2.2.2]oct-3-yl]-N(1)-cyclopentyl-5-{[(cyclopentylamino)carbonyl]amino}-1H-indazole-1,3-dicarboxamide hydroformate,
N(3)-[(3S)-1-Azabicyclo[2.2.2]oct-3-yl]-N(1)-propyl-5-{[(propylamino)carbonyl]amino}-1H-indazole-1,3-dicarboxamide,
N-[(3R)-1-Azabicyclo[2.2.2]oct-3-yl]-5-({[(cyclopropylmethyl)amino]carbonothioyl}amino)-1H-indazole-3-carboxamide hydroformate,
N-[(3S)-1-Azabicyclo[2.2.2]oct-3-yl]-6-({[(cyclopropylmethyl)amino]carbonothioyl}amino)-1,2-benzisothiazole-3-carboxamide hydroformate,
N-[(3S)-1-Azabicyclo[2.2.2]oct-3-yl]-6-{[(propylmethylamino)carbonothioyl]amino}-1,2-benzisothiazole-3-carboxamide hydroformate,
N-[(3S)-1-Azabicyclo[2.2.2]oct-3-yl]-6-{[(tert-butylamino)carbonothioyl]amino}-1,2-benzisothiazole-3-carboxamide hydroformate,
N-[(3R)-1-Azabicyclo[2.2.2]oct-3-yl]-5-{[(sec-butylamino)carbonyl]amino}-1H-indazole-3-carboxamide hydroformate,
N-[(3S)-1-Azabicyclo[2.2.2]oct-3-yl]-1-ethyl-6-{[(propylamino)carbonyl]amino}-1H-indazole-3-carboxamide hydroformate,
N-[(3S)-1-Azabicyclo[2.2.2]oct-3-yl]-1-(cyclopropylmethyl)-5-{[(propylamino)carbonyl]amino}-1H-indazole-3-carboxamide hydroformate,
N-[(3S)-1-Azabicyclo[2.2.2]oct-3-yl]-1-(2,2,2-trifluoroethyl)-5-{[(propylamino)carbonyl]amino}-1H-indazole-3-carboxamide hydroformate,
N-[(3S)-1-Azabicyclo[2.2.2]oct-3-yl]-1-(ethyl)-5-{[(propylamino)carbonyl]amino}-1H-indazole-3-carboxamide hydroformate,
Isopropyl{3-{[(3R)-1-azabicyclo[2.2.2]oct-3-ylamino]carbonyl}-1H-indazol-5-yl}carbamate hydroformate,
Isopropyl{3-{[(3R)-1-azabicyclo[2.2.2]oct-3-ylamino]carbonyl}-1-[(isopropylamino)carbonyl]-1H-indazol-5-yl}carbamate hydroformate,
N-[(3S)-1-Oxido-1-azabicyclo[2.2.2]oct-3-yl]-1H-indazole-3-carboxamide,
N-[(3S)-1-Azabicyclo[2.2.2]oct-3-yl]-5-hydroxy-1H-indazole-3-carboxamide hydrobromide,
N-[(3S)-1-Azabicyclo[2.2.2]oct-3-yl]-6-hydroxy-1H-indazole-3-carboxamide hydrobromide,
N-[(3S)-1-Azabicyclo[2.2.2]oct-3-yl]-5-{[(diethylamino)carbonyl]amino}-1H-indazole-3-carboxamide hydroformate,
N-[(3S)-1-Azabicyclo[2.2.2]oct-3-yl]-5-[(pyrrolidin-1-ylcarbonyl)amino]-1H-indazole-3-carboxamide hydroformate,
N-[(3S)-1-Azabicyclo[2.2.2]oct-3-yl]-6-[(pyrrolidin-1-ylcarbonyl)amino]-1H-indazole-3-carboxamide hydroformate,
N-[(3S)-1-Azabicyclo[2.2.2]oct-3-yl]-6-(2-oxopyrrolidin-1-yl)-1,2-benzisothiazole-3-carboxamide hydroformate,
N-[(3S)-1-Azabicyclo[2.2.2]oct-3-yl]-5-(2-oxopyrrolidin-1-yl)-1,2-benzisothiazole-3-carboxamide hydroformate,
N-[(3S)-1-Azabicyclo[2.2.2]oct-3-yl]-6-(2-oxo-4-phenylpyrrolidin-1-yl)-1,2-benzisothiazole-3-carboxamide hydroformate,
N-[(3S)-1-Azabicyclo[2.2.2]oct-3-yl]-6-(2-oxoimidazolidin-1-yl)-1,2-benzisothiazole-3-carboxamide hydroformate,
N-[(3S)-1-Azabicyclo[2.2.2]oct-3-yl]-5-(2-oxoimidazolidin-1-yl)-1H-indazole-3-carboxamide hydroformate,
N-[(3S)-1-Azabicyclo[2.2.2]oct-3-yl]-5-(2-oxo-3-propylimidazolidin-1-yl)-1H-indazole-3-carboxamide hydroformate,
N-[(3S)-1-Azabicyclo[2.2.2]oct-3-yl]-6-{[2-(propylamino)ethyl]amino}-1,2-benzisothiazole-3-carboxamide hydroformate,
N-[(3S)-1-Azabicyclo[2.2.2]oct-3-yl]-6-(3-methyl-2-oxoimidazolidin-1-yl)-1,2-benzisothiazole-3-carboxamide hydroformate,
N-[(3S)-1-Azabicyclo[2.2.2]oct-3-yl]-6-(3-isopropyl-2-oxoimidazolidin-1-yl)-1,2-benzisothiazole-3-carboxamide hydroformate,
N-[(3S)-1-Azabicyclo[2.2.2]oct-3-yl]-6-(3-propyl-2-oxoimidazolidin-1-yl)-1,2-benzisothiazole-3-carboxamide hydroformate,
N-[(3S)-1-Azabicyclo[2.2.2]oct-3-yl]-5-bromo-1,2-benzisoxazole-3-carboxamide,
N-[(3S)-1-Azabicyclo[2.2.2]oct-3-yl]-6-bromo-1,2-benzisoxazole-3-carboxamide,
N-[(3S)-1-Azabicyclo[2.2.2]oct-3-yl]-5-(3-methyl-2-oxoimidazolidin-1-yl)-1,2-benzisothiazole-3-carboxamide,
N-[(3S)-1-Azabicyclo[2.2.2]oct-3-yl]-5-(3-isopropyl-2-oxoimidazolidin-1-yl)-1,2-benzisothiazole-3-carboxamide,
N-[(3S)-1-Azabicyclo[2.2.2]oct-3-yl]-5-(3-propyl-2-oxoimidazolidin-1-yl)-1,2-benzisothiazole-3-carboxamide,
6-[Acetyl(methyl)amino]-N-[(3S)-1-azabicyclo[2.2.2]oct-3-yl]-1,2-benzisothiazole-3-carboxamide hydroformate,
N-[(3S)-1-Azabicyclo[2.2.2]oct-3-yl]-6-[methyl(propionyl)amino]-1,2-benzisothiazole-3-carboxamide hydroformate,
N-[(3S)-1-Azabicyclo[2.2.2]oct-3-yl]-6-methoxy-N-methyl-1H-indazole-3-carboxamide hydroformate,
N-[(3S)-1-Azabicyclo[2.2.2]oct-3-yl]-5-[3-(benzyloxy)pyrrolidin-1-yl]-1-ethyl-1H-indazole-3-carboxamide hydroformate,
N-[(3S)-1-Azabicyclo[2.2.2]oct-3-yl]-6-[(cyclopropylcarbonyl)amino]-1-ethyl-1H-indazole-3-carboxamide,
N-[(3S)-1-Azabicyclo[2.2.2]oct-3-yl]-5-[(cyclopropylcarbonyl)amino]-1-cyclopropylmethyl-1H-indazole-3-carboxamide,
N-[(3S)-1-Azabicyclo[2.2.2]oct-3-yl]-5-[(cyclopropylcarbonyl)amino]-1-(2,2,2-trifluoroethyl)-1H-indazole-3-carboxamide, N-[(3S)-1-Azabicyclo[2.2.2]oct-3-yl]-1-(2-methoxyethyl)-6-(1,3-thiazol-2-yl)-1H-indazole-3-carboxamide hydroformate, N-[(3S)-1-Azabicyclo[2.2.2]oct-3-yl]-1-(cyclopropylmethyl)-6-(1,3-thiazol-2-yl)-1H-indazole-3-carboxamide hydroformate, N-[(3S)-1-Azabicyclo[2.2.2]oct-3-yl]-1-(tetrahydrofuran-3-yl)-6-(1,3-thiazol-2-yl)-1H-indazole-3-carboxamide hydroformate, N-[(3S)-1-Azabicyclo[2.2.2]oct-3-yl]-5-[3-(benzyloxy)pyrrolidin-1-yl]-1-(cyclopropylmethyl)-1H-indazole-3-carboxamide hydroformate, N-[(3S)-1-Azabicyclo[2.2.2]oct-3-yl]-6-[3-(benzyloxy)pyrrolidin-1-yl]-1-ethyl-1H-indazole-3-carboxamide hydroformate, tert-Butyl 3-[3-{[(3S)-1-azabicyclo[2.2.2]oct-3-ylamino]carbonyl}-6-(1,3-thiazol-2-yl)-1H-indazol-1-yl]pyrrolidine-1-carboxylate hydroformate, N-[(3S)-1-Azabicyclo[2.2.2]oct-3-yl]-1-pyrrolidin-3-yl-6-(1,3-thiazol-2-yl)-1H-indazole-3-carboxamide, N-[(3S)-1-Azabicyclo[2.2.2]oct-3-yl]-6-(1,3-thiazol-2-yl)-1-(2-thienylmethyl)-1H-indazole-3-carboxamide hydroformate, N-[(3S)-1-Azabicyclo[2.2.2]oct-3-yl]-1-(2-phenoxyethyl)-6-(1,3-thiazol-2-yl)-1H-indazole-3-carboxamide hydroformate, and physiologically acceptable salts thereof.

Preferred aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials.

Acids that were used in the preparation of the bicyclobase amide were commercially available or were prepared by known procedures described in the literature or as described below. For example, indazole-3-carboxylic acid was commercially available. Positional isomers of indazole carboxylic acid were prepared from the requisite bromo-2-methylanilines by diazotization followed by metal-halogen exchange and trapping with carbon dioxide (Se e.g., DeLucca, G. V. Substituted 2H-1,3-Diazapin-2-one Useful as an HIV Protease Inhibitor, U.S. Pat. No. 6,313,110 B1, Nov. 6, 2001; and Sun, J. H.; Teleha, C. A.; Yan, J. S.; Rodgers, J. D.; Nugiel, D. A. *Efficient Synthesis of 5-(Bromomethyl)- and 5-(Aminomethyl)-1-THP-Indazole. J. Org. Chem.* 1997, 62, 5627-5629). A variety of the simple substituted indazole-3-acids, such as the bromoindazole acids, were prepared from the corresponding isatins by basic hydrolysis, diazotization, and reduction (Snyder, H. R.; et al. *J. Am. Chem. Soc.* 1952, 74, 2009).

Some substituted indazole-3-acids were prepared by modifying existing indazole acids or esters. For example, 5-nitroindazole-3-acid was prepared by nitration of indazole-3-acid (Kamm, O.; Segur, J. B. *Org. Syn. Coll. Vol* 1. 1941, 372). 6-Nitroindazole-3-acid was prepared from 3-iodo-6-nitroindazole using copper (I) cyanide followed by hydrolysis. Some non-aromatic heterocyclic derivatives were prepared from the bromides by metal-halogen exchange, trapping of indazole aryllithiums with ketones, followed by reduction or acid mediated elimination. Trapping of the indazole aryllithiums with amides provided ketones and aldehydes that served as useful precursors for, among other things, reductive aminations. Aromatic substituted indazole-3-acids were prepared from the bromides via palladium mediated cross-coupling with boronic acids or aryl zinc reagents (Reeder, M. R.; et. al. *Org. Proc. Res. Devel.* 2003, 7, 696). 4-Bromo-5-methoxyindazole- and 7-bromo-6-methoxyindazole-3-carboxylic acids were prepared from the corresponding methoxyindazole-3-carboxylates by bromination and saponification. 4-Fluoro-5-methoxyindazole- and 7-fluoro-6-methoxyindazole-3-carboxylic acids were prepared from the corresponding methoxyindazole-3-carboxylates by fluorination and saponification. 5-Bromo-4-nitroindazole- and 6-bromo-7-nitroindazole-3-carboxylic acids were prepared from the corresponding bromoindazole-3-carboxylates by nitration and saponification. Subjecting the nitro bromides to hydrogenolysis provided 4-aminoindazole- and 7-aminoindazole-3-carboxylic acids. The aminoindazole esters were transformed to additional useful acid analogs by reductive amination, alkylation, and acylation strategies. N-1-Alkylated indazole-3-carboxylic acids were prepared from the corresponding indazole esters by standard alkylation procedures. N-1-Arylated indazole-3-carboxylic acids were prepared from the corresponding indazole esters by copper mediated cross couplings with boronic acids. Phenol derivatives were prepared from the corresponding methoxy acids using boron tribromide.

Some substituted indazole-3-acids were prepared from simple benzene derivatives. For example, 5-difluoromethoxyindazole-3-acid was prepared from 3-bromo-4-nitrophenol by reaction with ethyl difluoroacetate, reaction with diethyl malonate, decarboxylative saponification, esterification, reduction of the nitro group, and diazotization. 6-Difluoromethoxyindazole-3-acid was prepared in a similar manner from 2-bromo-5-difluoromethoxynitrobenzene. The 2-bromo-5-difluoromethoxynitrobenzene used in that preparation was prepared from 4-nitrophenol by ether formation, nitro reduction with concomitant protection as the amide, nitration, amide hydrolysis, and a Sandmeyer reaction with copper (I) bromide. 6-Benzyloxyindazole-3-carboxylic acid and ester was prepared from 4-methoxynitrobenzene by nitro reduction with concomitant protection as the amide, nitration, amide hydrolysis, Sandmeyer reaction with copper (I) bromide, and demethylation. The phenol was alkylated with benzyl bromide and the arylbromide was subjected to reaction with diethyl malonate, decarboxylative saponification, esterification, reduction of the nitro group, and diazotization. The 5-benzyloxy analog was prepared in a similar manner from 4-benzyloxy-2-bromonitrobenzene (Parker, K. A.; Mindt, T. L. *Org. Lett.* 2002, 4, 4265.) The benzyl group was removed by hydrogenolysis and the resulting phenol was transformed to ether derivatives via either alkylation or Mitsunobu reaction conditions. 4-Methoxyindazole acid was prepared from 4-methoxyaniline by amide formation, nitration, amide hydrolysis, Sandmeyer reaction with copper (I) bromide, nitro reduction, isatin formation and rearrangement to the indazole, followed by hydrogenolytic removal of the bromine.

The benzisoxazole-, benzisoxazole-, and benzothiazolecarboxylic acids were prepared using similar strategies outlined for the indazole acids. For example, ethyl 6-bromobenzisoxazole-3-carboxylate was prepared from 2,5-dibromonitrobenzene by reaction with diethyl malonate, saponification and decarboxylation, and reaction with isoamylnitrite. Ethyl benzisoxazole-3-carboxylate was obtained by hydrogenolysis of the 6-bromo derivative. 4-Benzothiazolecarboxylic acid was prepared from 2-amino-4-chloro-benzothiazole by reaction with isoamyl nitrite followed by metal-halogen exchange and trapping with carbon dioxide. 5-Benzothiazolecarboxylic acid was prepared from 4-chloro-3-nitrobenzoic acid by reaction with $Na_2S$ and sodium hydroxide followed by reduction with zinc in formic acid. 3-Benzisothiazolecarboxylic acid was prepared from thiophenol by reaction with oxalyl chloride and aluminum chloride followed by treatment with hydroxylamine, hydrogen peroxide, and sodium hydroxide.

The bicycloamines, 3-aminoquinuclidine and the R- and S-enantiomers thereof, used in the preparation of the bicyclobase amides were commercially available. The N-alkylated quinuclidines were prepared by acylation of 3-aminoquinuclidine followed by reduction of the amide. 3-Aminomethylquinuclidine was prepared from 3-quinuclidinone by the action of p-tolylsulfonylmethyl isocyanide followed by hydrogenation of the nitrile.

The bicyclobase amides were prepared from the acids and the bicycloamines using standard peptide coupling agents, such as HBTU, HATU, or HOBt and EDCI, or by converting the acids to the corresponding acid chloride and then reaction with the bicycloamine (Macor, J. E.; Gurley, D.; Lanthorn, T.; Loch, J.; Mack, R. A.; Mullen, G.; Tran, O.; Wright, N.; and J. E. Macor et al., "The 5-HT3-Antagonwast Tropisetron (ICS 205-930) was a Potent and Selective α-7 Nicotinic Receptor Partial Agonist," *Bioorg. Med. Chem. Lett.* 2001, 9, 319-321). The couplings were generally performed at room temperatures for 18-24 hours. The resultant adducts were isolated and purified by standard techniques, such as chromatography or recrystallization, practiced by those skilled in the art.

One of ordinary skill in the art will recognize that compounds of Formulas I-IV can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I-IV can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formulas I-IV, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other α-7 agonists, PDE4 inhibitors, calcium channel blockers, muscarinic m1 and m2 modulators, adenosine receptor modulators, amphakines NMDA-R modulators, mGluR modulators, dopamine modulators, serotonin modulators, canabinoid modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to Aβ peptides and thereby inhibit the binding of the peptides to α7nACh receptor subtypes. See, e.g., WO 99/62505.

The present invention further includes methods of treatment that involve activation of α-7 nicotinic receptors. Thus, the present invention includes methods of selectively activating/stimulating α-7 nicotinic receptors in a patient (e.g., a mammal such as a human) wherein such activation/stimulation has a therapeutic effect, such as where such activation may relieve conditions involving neurological syndromes, such as the loss of memory, especially long-term memory. Such methods comprise administering to a patient (e.g., a mammal such as a human) in need thereof, an effective amount of a compound of Formulas I-IV, alone or as part of a formulation, as disclosed herein.

In accordance with a method aspect of the invention, there is provided a method of treating a patient (e.g., a mammal such as a human) suffering from a disease state (e.g., memory impairment) comprising administering to the patient a compound according to Formulas I-IV. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a patient (e.g., a mammal such as a human) comprising administering an effective amount of a compound according to Formulas I-IV.

In accordance with a method aspect of the invention there is provided a method for the treatment or prophylaxis of a disease or condition resulting from defective or malfunctioning nicotinic acetylcholine receptors, particularly α7nACh receptors, in a patient (e.g., a mammal such as a human) comprising administering an effective amount of a compound according to Formulas I-IV.

In accordance with a method aspect of the invention there is provided a method for the treatment or prophylaxis of a disease or condition resulting from suppressed nicotinic acetylcholine receptor transmission in a patient (e.g., a mammal such as a human) comprising administering an amount of a compound according to Formulas I-IV effective to activate α7nACh receptors.

In accordance with another method aspect of the invention there is provided a method for the treatment or prophylaxis of a psychotic disorder, a cognition impairment (e.g., memory impairment), or neurodegenerative disease in a patient (e.g., a mammal such as a human) comprising administering an effective amount of a compound according to Formulas I-IV.

In accordance with another method aspect of the invention there is provided a method for the treatment or prophylaxis of a disease or condition resulting from loss of cholinergic synapses in a patient (e.g., a mammal such as a human) comprising administering an effective amount of a compound according to Formulas I-IV.

In accordance with another method aspect of the invention there is provided a method for the treatment or prophylaxis of a neurodegenerative disorder by activation of α7nACh receptors in a patient (e.g., a mammal such as a human) comprising administering an effective amount of a compound according to Formulas I-IV.

In accordance with another method aspect of the invention there is provided a method for protecting neurons in a patient (e.g., a mammal such as a human) from neurotoxicity induced by activation of α7nACh receptors comprising administering an effective amount of a compound according to Formulas I-IV.

In accordance with another method aspect of the invention there is provided a method for the treatment or prophylaxis of a neurodegenerative disorder by inhibiting the binding of Aβ peptides to α7nACh receptors in a patient (e.g., a mammal such as a human) comprising administering an effective amount of a compound according to Formulas I-IV.

In accordance with another method aspect of the invention there is provided a method for protecting neurons in a patient (e.g., a mammal such as a human) from neurotoxicity induced by Aβ peptides comprising administering an effective amount of a compound according to Formulas I-IV.

In accordance with another method aspect of the invention there is provided a method for alleviating inhibition of cholinergic function induced by Aβ peptides in a patient (e.g., a mammal such as a human) comprising administering an effective amount of a compound according to Formulas I-IV.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., *Characterisation of the binding of [3H]methyllycaconitine: a new radioligand for labelling alpha 7-type neuronal nicotinic acetylcholine receptors*. Neuropharmacology, 1999. 38(5): p. 679-90. As agonists for α7nACh receptors, the compounds are useful in the prophylaxis and treatment of a variety of diseases and conditions associated with the central nervous system. Nicotinic acetylcholine receptors are ligand-gastrol ion-channel receptors that are composed of five subunit proteins which form a central ion-conducting pore. Presently, there are eleven known neuronal nAch receptor subunits (α2-α9 and β2-β4). There are also five further subunits expressed in the peripheral nervous system (α1, β1, γ, δ, ε).

The nACh receptor subtypes can be homopentameric or heteropentameric. The subtype which has received considerable attention is the homopentameric α7 receptor subtype formed from five α7 subunits. The α7nACh receptors exhibit a high affinity for nicotine (agonist) and for α-bungarotoxin (antagonist). Studies have shown the α7nACh receptor agonists can be useful in the treatment of psychotic diseases, neurodegenerative diseases, and cognitive impairments, among other things. While nicotine is a known agonist, there is a need for the development of other α7nACh receptor agonists, especially selective agonists, which are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kem et al., Toxicon, 9:23, 1971. Anabaseine is a potent activator of mammalian nicotinic receptors. See, e.g., Kem, Amer. Zoologist, 25, 99, 1985. Certain anabaseine analogs such as anabasine and DMAB (3-[4-(dimethylamino)benzylidene]-3,4,5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabaseine, also known as GTS-21 and DMXB (see, e.g., U.S. Pat. No. 5,741,802), is a selective partial α7nACh receptor agonist that has been studied extensively. For example, abnormal sensory inhibition is a sensory processing deficit in schizophrenics and GTS-21 has been found to increase sensory inhibition through interaction with α7nACh receptors. See, e.g., Stevens et al., Psychopharmacology, 136: 320-27 (1998).

Another compound which is known to be a selective α7nACh receptor agonist is Tropisetron, i.e., 1αH, 5αH-tropan-3α-yl indole-3-carboxylate. See J. E. Macor et al., *The 5-HT3-Antagonist Tropisetron (ICS 205-930) is a Potent and Selective A7 Nicotinic Receptor Partial Agonist*. Bioorg. Med. Chem. Lett. 2001, 319-321).

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27; and Shytle et al., Molecular Psychiatry, (2002), 7, pp. 525-535.

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formulas I-IV.

Neurodegenerative disorders included within the methods of the present invention include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α7nACh receptor agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formulas I-IV.

Thus, in accordance with a further embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I-IV.

Amyloid precursor protein (APP) and Aβ peptides derived therefrom, e.g., $A\beta_{1-40}$, $A\beta_{1-42}$, and other fragments, are known to be involved in the pathology of Alzhemier's disease. The $A\beta_{1-42}$ peptides are not only implicated in neurotoxicity but also are known to inhibit cholinergic transmitter function. Further, it has been determined that Aβ peptides bind to α7nACh receptors. Thus, agents which block the binding of the Aβ peptides to α-7 nAChRs are useful for treating neurodegenerative diseases. See, e.g., WO 99/62505. In addition, stimulation α7nACh receptors can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formulas I-IV to inhibit the binding of an amyloid beta peptide (preferably, $A\beta_{1-42}$) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α7nACh receptors can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formulas I-IV.

Agonists for the α7nACh receptor subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formulas I-IV.

As noted above, agonists for the α7nACh receptor subtypes can also be used in the treatment of nicotine addiction, inducing smoking cessation, treating pain, and treating jetlag, obesity, diabetes, and inflammation. Thus, in accordance with an embodiment of the invention there is provided a method of treating a patient suffering from nicotine addiction, pain, jetlag, obesity and/or diabetes, or a method of inducing smoking cessation in a patient comprising administering to the patient an effective amount of a compound according to Formulas I-IV.

The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds with affinity for the α7nACh receptor on macrophages may be useful for human inflammatory diseases including rheumatoid arthritis, diabetes and sepsis. See, e.g., Czura, C J et al., J. Intern. Med., 2005, 257(2), 156-66.

Thus, in accordance with an embodiment of the invention there is provided a method of treating a patient (e.g., a mammal, such as a human) suffering from an inflammatory disease, such as, but not limited to, rheumatoid arthritis, diabetes or sepsis, comprising administering to the patient an effective amount of a compound according to Formulas I-IV.

In addition, due to their affinity to α7nACh receptors, labeled derivatives of the compounds of Formulas I-IV (e.g., $C^{11}$ or $F^{18}$ labeled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) comprising administering to the patient an effective amount of a compound according to Formulas I-IV.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to patients, e.g., mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

Using the following procedures and further procedures described below, the following compounds in Examples 1-315 were prepared. Other synthesis examples are described in U.S. patent application Ser. No. 10/669,645, hereby incorporated by reference.

EXAMPLES

All spectra were recorded at 300 MHz on a Bruker Instruments NMR unless otherwise stated. Coupling constants (J) are in Hertz (Hz) and peaks are listed relative to TMS (δ 0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies. Analytical HPLC was performed on 4.6 mm×100 mm Xterra $RP_{18}$ 3.5μ columns using a gradient of 20/80 to 80/20 water (0.1% formic acid)/acetonitrile (0.1% formic acid) over 6 min. Preparative HPLC was performed on 30 mm×100 mm Xtera Prep $RP_{18}$ 5μ columns using an 8 min gradient of 95/5 to 20/80 water (0.1% formic acid)/acetonitrile (0.1% formic acid).

Acid Preparations.

The following procedures (1-27) detail the preparation of the indazole, benzothiazole, benzisothiazole, and benzisoxazole acids that were not commercially available.

Procedure 1

Procedure 1 provides a method of preparation of 1,3-benzothiazole carboxylic acids from chloro nitrobenzoic acids.

To a solution of 4-chloro-3-nitrobenzoic acid (99.2 mmol) in N,N-dimethylformamide (400 mL) was added potassium carbonate (254 mmol). After 30 min, ethyl iodide (119 mmol) was added and the reaction mixture was heated at 50° C. for 4 h. Water (3 L) was added and the mixture was extracted with diethyl ether (2×500 mL). The organic extracts were combined, washed with brine (1 L), dried over anhydrous sodium sulfate and concentrated. The residue was crystallized from hexanes, thus providing the ester in 86% yield. $^1H$ NMR (500 MHz, $CDCl_3$) δ 8.51 (d, 1H), 8.17 (dd, 1H), 7.65 (d, 1H), 4.43 (q, 2H), 1.42 (t, 3H).

Sulfur (49.91 mmol) was dissolved in a solution of sodium sulfide nonahydrate (49.96 mmol) in water (60 mL). This solution was combined with a solution of ethyl 4-chloro-3-nitrobenzoate (85.36 mmol) in ethanol (100 mL) and the resulting mixture was heated at reflux for 3 h. The hot reaction mixture was poured into water (600 mL) and maintained for 15 min. The product was isolated by filtration and recrystallized from ethanol, thus providing the disulfide in 77% yield. $^1$H NMR (500 MHz, CDCl$_3$) δ 8.96 (d, 1H), 8.19 (dd, 1H), 7.88 (d, 1H), 4.43 (q, 2H), 1.41 (t, 3H).

A mixture of diethyl 4,4'-dithiobis(3-nitrobenzoate) (24.8 mmol) and zinc granules (234 mmol) in formic acid (600 mL) was heated to reflux for 48 h. The mixture was allowed to cool to room temperature and concentrated to dryness. The residue was partitioned between ethyl acetate (500 mL) and saturated aqueous sodium bicarbonate (500 mL). The organic layer was separated, dried over anhydrous sodium sulfate and concentrated. The residue was chromatographed on neutral Alumina (1/1 to 0/1 hexanes/dichloromethane), thus providing the thiazole in 51% yield. $^1$H NMR (500 MHz, CDCl$_3$) δ 9.08 (s, 1H), 8.83 (d, 1H), 8.14 (dd, 1H), 8.02 (d, 1H), 4.45 (q, 2H), 1.44 (t, 3H); MS (EI) m/z 208 (M$^+$+1).

To a solution of ethyl 1,3-benzothiazole-5-carboxylate (25.6 mmol) in a mixture of methanol (150 mL), tetrahydrofuran (40 mL) and water (5 mL) was added a 50% aqueous solution of sodium hydroxide (10 mL). The mixture was maintained at rt for 18 h and was concentrated. The residue was partitioned between water (300 mL) and diethyl ether (200 mL) and the organic layer was removed. Concentrated hydrochloric acid was added to the aqueous layer to adjust the pH to 4 and the mixture was extracted with ethyl acetate (3×300 mL). The combined extracts were washed with brine (200 mL), dried over anhydrous sodium sulfate, and concentrated thus providing the acid in 94% yield.

The following acids were prepared using this method:
1,3-benzothiazole-5-carboxylic acid
1,3-benzothiazole-6-carboxylic acid Procedure 2

Procedure 2 provides a method for the preparation of 1,3-benzothiazole-7-carboxylic acid from ethyl 3-aminobenzoate.

A solution of ethyl 3-aminobenzoate (90 mmol) in chlorobenzene (100 mL) was cooled to −10° C. and treated with sulfuric acid (45 mmol), dropwise. After 15 min, solid potassium thiocyanate (95 mmol) was added in several portions over 30 min followed by 18-crown-6 (250 mg). The mixture was heated at 100° C. for 10 h, allowed to cool to rt, and was maintained for an additional 4 h. The precipitated solids were isolated by filtration and were washed successively with chlorobenzene (25 mL) and hexanes (3×100 mL). The solid was suspended in water (300 mL) and the suspension was maintained 30 min. The product was isolated by filtration and washed with water (2×100 mL). The product was dried in a vacuum oven (55° C.) for 16 h, thus providing the thiocarbamate in 69% yield. $^1$H NMR (500 MHz, Me$_2$SO-d$_6$) δ 1.32 (t, J=7.5, 3H), 4.32 (q, J=7, 2H), 7.44-7.47 (m, 2H), 7.68-7.76 (m, 3H), 8.05 (s, 1H), 9.86 (s, 1H); MS (APCI) m/z 225 (M$^+$+1).

A solution of thiocarbamate (12.2 mmol) in chloroform (10 mL) was added dropwise over a period of 40 min to a vigorously maintained mixture of ethyl 3-[(aminocarbonothioyl)amino]benzoate (5.78 mmol), glacial acetic acid (10 mL) and chloroform (10 mL). The mixture was maintained 30 min at rt and then was heated at 70° C. for 4 h. The mixture was allowed to cool to room temperature and maintained for an additional 13 h. The volatiles were removed under reduced pressure and the solid residue was suspended in a mixture of chloroform (10 mL) and acetone (10 mL). The product was isolated by filtration, washed successively with acetone (5 mL) and hexanes (10 mL), and dried in a vacuum oven, thus providing the product in 95% yield as a mixture of ethyl 2-amino-1,3-benzothiazole-7-carboxylate hydrobromide and ethyl 2-amino-1,3-benzothiazole-5-carboxylate hydrobromide in a ratio of 95/5, respectively. This product was partitioned between saturated aqueous solution of sodium bicarbonate (25 mL) and a mixture of ethyl acetate (70 mL) and tetrahydrofuran (30 mL). The organic layer was separated, dried over anhydrous sodium sulfate and concentrated. The residue was crystallized form ethyl acetate, thus providing pure ethyl 2-amino-1,3-benzothiazole-7-carboxylate. $^1$H NMR (500 MHz, Me$_2$SO-d$_6$) δ 1.35 (t, J=7.5, 3H), 4.36 (q, J=7, 2H), 7.35 (t, J=7.5, 1H), 7.57 (d, J=7, 1H), 7.61 (bs, 2H), 7.65 (d, J=8, 1H); MS (EI) m/z 223 (M$^+$+1).

iso-Amylnitrite (53 mmol) was added to a solution of ethyl 2-amino-1,3-benzothiazole-7-carboxylate (5.40 g) in tetrahydrofuran (70 mL) and the mixture was heated at reflux for 4 h. The volatiles were removed under reduced pressure and the residue was purified by chromatography (0/100 to 5/95 methanol/dichloromethane), thus providing the ester in 71% yield. $^1$H NMR (500 MHz, CDCl$_3$) δ 1.47 (t, J=7.5, 3H), 4.49 (q, J=7, 2H), 7.62 (t, J=8, 1H), 8.20 (d, J=6.5, 1H), 8.33 (d, J=8, 1H), 9.12 (s, 1H); MS (EI) m/z 208 (M$^+$+1). A 50% aqueous sodium hydroxide (10 mL) was added to a 0° C. solution of ethyl 1,3-benzothiazole-7-carboxylate (16.89 mmol) in a mixture of methanol (65 mL), tetrahydrofuran (20 mL) and water (5 mL). The mixture was maintained at room temperature for 4 h and the volatiles were removed under reduced pressure. The residue was dissolved in water (100 mL) and concentrated hydrochloric acid was added to adjust the pH of the solution to 5. The mixture was cooled to 0° C. and maintained for 30 min. The product was isolated by filtration, washed with water (10 mL), and dried in vacuum oven (70° C.) for 16 h, thus providing the acid in 91% yield. $^1$H NMR (500 MHz, Me$_2$SO-d$_6$) δ 7.71 (t, J=7.5, 1H), 8.15 (d, J=7, 1H), 8.38 (d, J=8, 1H), 9.51 (s, 1H), 13.74 (bs, 1H); MS (APCI) m/z 178 (M$^+$−1).

Literature reference: Kunz et. al. U.S. Pat. No. 5,770,758.

Procedure 3

Procedure 3 provides a preparation of substituted benzisothiazole-3-carboxylic acids from the corresponding thiophenols.

To a solution of 3-methoxythiophenol (26.7 mmol) in ether (20 mL) was added oxalyl chloride (43 mmol) dropwise. The mixture was heated at reflux for 1.5 h, cooled to rt, and concentrated in vacuo. The resulting yellow oil was dissolved in dichloromethane (50 mL), cooled to 0° C., and was treated with aluminum chloride (32.0 mmol) in portions. The mixture was heated at reflux for 30 min, cooled to rt, and poured onto ice water with stifling. The organic layer was separated and successively washed with saturated, aqueous sodium bicarbonate, water, and brine. The organic layer was dried over magnesium sulfate, filtered and concentrated in vacuo. The residue was purified by chromatography (4/1 ethyl acetate/hexane), thus providing 6-methoxy-1-benzothiophene-2,3-dione in 47% yield as an orange solid.

To a mixture of the dione (0.44 mmol) in 30% aqueous solution of ammonium hydroxide (2.0 mL) was added 35% aqueous solution hydrogen peroxide (0.2 mL) and the reaction mixture was maintained for 12 h. The precipitated pink solids were isolated by filtration, washed with water, and dried under high vacuum, thus providing the amide in 42% yield.

To a solution of the amide (5.46 mmol) in methanol (100 mL) was added 10 N sodium hydroxide (12 mL). The mixture was heated at reflux for 12 h, cooled to rt, and was acidified to pH<2 by the slow addition of conc. hydrochloric acid. The organic layer was extracted with dichloromethane (2×) and was dried over sodium sulfate. The crude product was purified by chromatography (300/50/1 dichloromethane/methanol/formic acid), thus providing the acid in 89% as a pink solid. LC/MS (EI) $t_R$ 6.17 min, m/z 210 (M$^+$+1).

The following acids were prepared by this method:
Benzisothiazole-3-carboxylic acid.
6-Bromobenzisothiazole-3-carboxylic acid.
5-Bromobenzisothiazole-3-carboxylic acid.
6-Methoxybenzisothiazole-3-carboxylic acid
7-Methoxybenzisothiazole-3-carboxylic acid.
6-Trifluoromethoxybenzisothiazole-3-acid.
6-Ethoxybenzisothiazole-3-acid.
6-Cyclopropylmethoxybenzisothiazole-3-acid.

Procedure 4

Procedure 4 provides a method for the preparation of isatins from anilines and the conversion of the isatins to the corresponding indazole-3-carboxylic acids.

A solution of the substituted aniline (565 mL) in 6N hydrochloric acid (106 mL) was added to a suspension of 2,2,2-trichloro-1-ethoxyethanol (678 mL) and sodium sulfate (3.15 mol) in water (1.4 L) and the reaction mixture was stirred vigorously for 1 h. A solution of hydroxylamine hydrochloride (2.08 mol) in water (650 mL) was added in one portion and the reaction mixture was heated at 80° C. for 1.5 h. The reaction mixture was cooled to 10° C. and the precipitated solids were collected by filtration, washed with water, and dried to provide the amide in 91% yield.

The amide was added to sulfuric acid (1.9 L) and the reaction mixture was heated at 60° C. for 6 h. The reaction mixture was allowed to cool to room temperature and was cautiously poured onto ice (7 kg). The precipitated solids were collected by filtration, washed with water, and dried to provide the isatin in 61% yield.

The conversion of the substituted isatins to the corresponding indazole-3-carboxylic acids is essentially the same method as described for indazole-3-carboxylic acid: Snyder, H. R., et. al. *J. Am. Chem. Soc.* 1952, 74, 2009. The substituted isatin (22.1 mmol) was diluted with 1 N sodium hydroxide (24 mL) and was heated at 50° C. for 30 min. The burgundy solution was allowed to cool to rt and was maintained for 1 h. The reaction mixture was cooled to 0° C. and was treated with a 0° C. solution of sodium nitrite (22.0 mmol) in water (5.5 mL). This solution was added through a pipet submerged below the surface of a vigorously stirred solution of sulfuric acid (2.3 mL) in water (45 mL) at 0° C. The addition took 15 min and the reaction was maintained for an additional 30 min. A cold (0° C.) solution of tin (II) chloride dihydrate (52.7 mmol) in concentrated hydrochloric acid (20 mL) was added to the reaction mixture over 10 min and the reaction mixture was maintained for 60 min. The precipitated solids were isolated by filtration, washed with water, and dried to give a quantitative mass balance. This material was of sufficient purity ($^1$H NMR and LC/MS) to use in the next step without further purification. Alternatively, the acid was recrystallized from acetic acid to provide pure material.

The following acids were prepared using this method:
5-Chloro-1H-indazole-3-acid.
7-Methoxy-1H-indazole-3-acid.
5-Fluoro-1H-indazole-3-acid.
6-Fluoro-1H-indazole-3-acid.
5-Bromo-1H-indazole-3-acid.
6-Bromo-1H-indazole-3-acid.
5-Trifluoromethoxy-1H-indazole-3-acid.
6-Trifluoromethyl-1H-indazole-3-acid.
5-Methoxy-1H-indazole-3-acid.
6-Methoxy-1H-indazole-3-acid.
5-Methyl-1H-indazole-3-carboxylic acid.

Procedure 5

Procedure 5 provides a method for the preparation of bromoindazoles from bromomethylanilines.

Acetic anhydride (2.27 equiv.) was added to a cooled (0° C.) solution of bromomethylaniline (1.00 equiv.) in chloroform (1.5 mL/mmol) while maintaining the temperature below 40° C. The reaction mixture was allowed to warm to room temperature and was maintained for 1 h. Potassium acetate (0.29 eq) and isoamyl nitrite (2.15 equiv.) was added and the reaction mixture was heated at reflux for 18 h. The volatiles were removed under reduced pressure. Water (0.65 L/mol) was added to the residue and the mixture was concentrated. Concentrated hydrochloric acid (1 L/mol) was added to the residue and the mixture was heated at 50° C. for 2 h. The mixture was allowed to cool to room temperature and the pH was adjusted to 10 by the slow addition of a 50% aqueous sodium hydroxide solution. The mixture was diluted with water (0.65 L/mol) and was extracted with ethyl acetate (2×1.2 L/mol). The combined extracts were washed with brine (1 L/mol) and dried over anhydrous sodium sulfate. The organic solution was filtered through a plug of silica gel (ethyl acetate wash), concentrated, and the residue was triturated with heptane (1 L/mol). The solids were collected by filtration, rinsed with heptane, and dried in a vacuum oven, thus providing the brominated indazole in 60-80% yield.

Literature reference: George V. DeLucca, U.S. Pat. No. 6,313, 110.

The following indazoles were prepared using this method:
5-Bromo-1H-indazole.
6-Bromo-1H-indazole.

Procedure 6

Procedure 6 provides a method for the preparation of indazole carboxylic acid from bromoindazole.

To a solution of bromoindazole (1.00 equiv.) in anhydrous tetrahydrofuran (7 L/mol) at room temperature was added sodium hydride (60% in mineral oil, 1.11 equiv.) in several portions. The resulting solution was maintained for 30 min at room temperature and was then cooled to −60° C. A 1.3 M solution of sec-butyllithium in cyclohexane (2.1 equiv.) was added to the reaction mixture while maintaining the internal temperature below −50° C. The mixture was maintained for an additional 2 h at −50° C. A steady stream of anhydrous carbon dioxide was bubbled through the reaction mixture for 1 h. The flow was continued while the reaction mixture was allowed to warm to room temperature. Brine (6 L/mol) was added and the pH of the mixture was adjusted to 5 with concentrated hydrochloric acid. The mixture was extracted with warm ethyl acetate (3×8 L/mol) and the combined extracts were washed with small volume of brine, dried over anhydrous sodium sulfate, and concentrated. The residue was purified by chromatography on silica gel or by crystallization, thus providing the acid in 30-60% yield.

The following indazoles were prepared using this method:
1H-Indazole-5-carboxylic acid.
1H-Indazole-6-carboxylic acid.

Procedure 7

Procedure 7 provides a preparation of 1H-indazole-7-carboxylic acid from 2-amino-3-methylbenzoic acid.

To a solution of 2-amino-3-methylbenzoic acid (66.9 mmol) in N,N-dimethylformamide (200 mL) was added cesium carbonate (102 mmol). The mixture was stirred for 30 min. A solution of methyl iodide (67.0 mmol) in N,N-dimethylformamide (50 mL) was added dropwise and the reaction mixture was maintained for 18 h at rt. The reaction mixture was partitioned between water (1 L) and ether (200 mL) and the water layer was extracted with an additional volume of ether (100 mL). The combined extracts were washed with brine (500 mL), dried over anhydrous potassium carbonate, and concentrated, thus providing methyl 2-amino-3-methylbenzoate in 92% yield. $^1$H NMR (400 MHz, CDCl$_3$) δ 7.77 (d, 1H), 7.19 (d, 1H), 6.59 (t, 1H), 5.82 (bs, 2H), 3.86 (s, 3H), 2.17 (s, 3H).

To a solution of the ester (106 mmol) in chloroform (300 mL) was added acetic anhydride (239 mmol) while maintaining the temperature below 40° C. The reaction mixture was maintained at room temperature for 1 h when potassium acetate (30.6 mmol) and isoamyl nitrite (228 mmol) was added. The reaction mixture was heated at reflux for 24 h and was allowed to cool to room temperature. The reaction mixture was washed with a saturated, aqueous solution of sodium bicarbonate, dried over sodium sulfate, and concentrated. Methanol (100 mL) and 6 N hydrochloric acid (100 mL) were added to the residue and the mixture was maintained for 18 h at rt. The volatiles were removed under reduced pressure and the residue was triturated with ethyl acetate (100 mL). The product was isolated by filtration, washed with ethyl acetate (20 mL), and dried, thus providing methyl 1H-indazole-7-carboxylate hydrochloride in 68% yield. $^1$H NMR (500 MHz, Me$_2$SO-d$_6$) δ 13.3 (bs, 1H), 8.26 (d, 1H), 8.12 (d, 1H), 8.25 (dd, 1H), 7.27 (t, 1H), 3.97 (s, 3H); MS (APCI) m/z 177 (M$^+$+1).

A solution of the indazole (33.0 mmol) in methanol (100 mL) at 0° C. was treated with an 29% aqueous solution of potassium hydroxide (20 mL). The reaction mixture was allowed to warm to rt and was maintained for 18 h. The pH of the solution was adjusted to 5.5 by the addition of concentrated hydrochloric acid and the volatiles were removed under reduced pressure. The residue was partitioned between brine (100 mL) and ethyl acetate (200 mL) and the aqueous layer was extracted with additional warm ethyl acetate (200 mL). The combined organic extracts were dried over anhydrous sodium sulfate and concentrated. The residue was triturated with ethyl acetate (30 mL) and the solids were isolated by filtration, thus providing the acid in 94% yield.

Procedure 8

Procedure 8 provides a method for the preparation of 5-nitroindazole-3-acid from ethyl indazole-3-carboxylate.

Ethyl indazole-3-carboxylate (73.7 mmol) was dissolved in 20 mL concentrated sulfuric acid and the reaction mixture was cooled to 0° C. A mixture of concentrated sulfuric acid (12 mL) and 70% nitric acid (12 mL) was added dropwise over the course of 1 h. The mixture was stirred for an additional 1 h at 0° C. and was poured onto of crushed ice (200 g). The solid was collected by vacuum filtration, washed with several portions of water and dried in vacuo. The dried solid was suspended in 250 mL acetonitrile and the mixture was heated at reflux for 2 h. The mixture was allowed to cool to room temperature and the solid was collected and dried in vacuo, thus providing ethyl 5-nitroindazole-3-carboxylate in 53% yield as a colorless solid and ethyl 7-nitroindazole-3-carboxylate (5%) as a colorless solid. The esters were saponified using sodium hydroxide to provide the acids.

Literature reference: *Org. Synthesis, Coll. Vol.* 1, page 372.

The following acids were prepared using this method:
5-Nitro-1H-indazole-3-carboxylic acid.
7-Nitro-1H-indazole-3-carboxylic acid.
Ethyl 5-nitro-1H-indazole-3-carboxylate.
Ethyl 7-nitro-1H-indazole-3-carboxylate.

Procedure 9

Procedure 9 provides a method for the preparation of 6-nitroindazole-3-acid from 3-iodo-6-nitroindazole.

A 5 mL microwave reaction vessel was charged with 3-iodo-6-nitroindazole (1 mmol), copper (I) cyanide (2 mmol) and N,N-dimethylformamide (3 mL). The vessel was sealed and subjected to microwave irradiation at 185° C. for 600 sec. The reaction mixture was partitioned between ethyl acetate (100 mL) and water (100 mL) and the mixture was filtered through Celite. The organic layer was collected, washed with brine, dried (magnesium sulfate), and concentrated to give 122 mg of a 10 to 1 mixture of 3-cyano-6-nitroindazole and 6-nitroindazole as a yellow solid. The 10 to 1 mixture of 3-cyano-6-nitroindazole and 6-nitroindazole was dissolved in 10 N sodium hydroxide and the bright orange solution was heated at 100° C. for 1 h. The mixture was allowed to cool to room temperature and carefully acidified to pH 1 with 3 N hydrochloric acid. The solid was isolated and triturated with EtOAc, thus providing 51 mg of 6-nitroindazole-3-carboxylic acid as a brown solid.

3-Iodo-6-nitroindazole was prepared from 6-nitroindazole using the method of Collot, V.; et. al. *Tetrahedron* 1999, 55, 6917.

Procedure 10

Procedure 10 provides a method for the trapping of indazole aryllithiums with ketones and the coupling with 3-aminoquinuclidine to form heterocyclic derivatives.

tert-Butyl 6-bromoindazole-3-carboxylate was prepared from the acid by reaction with a 2-fold excess of di-tert-butyldicarbonate followed by treatment with sodium hydroxide. To a suspension of sodium hydride (60% mineral oil dispersion) (4.8 mmol) in tetrahydrofuran (40 mL) at 0° C. was slowly added a solution of tert-butyl 6-bromoindazole-3-carboxylate (4.0 mmol) in tetrahydrofuran (4 mL). After stirring for 0.5 h at 0° C., the mixture was cooled to −78° C. and a 1.7 M solution of tert-butyllithium in pentane (5.1 mmol) was added. After 0.5 h at −78° C., a solution of tetrahydropyran-4-one (5 mmol) in tetrahydrofuran (1 mL) was added dropwise. The mixture was stirred at −78° C. for 1 h and warmed to 0° C. The reaction mixture was quenched with saturated aqueous ammonium chloride and the mixture was partitioned between ethyl acetate (100 mL) and water (100 mL). The organic layer was separated, washed with brine (50 mL), dried (magnesium sulfate), and concentrated. The residue was purified by chromatography (70/30 ethyl acetate/hexanes) to yield 6-(4-hydroxytetrahydropyran-4-yl)-1H-indazole-3-carboxylic acid tert-butyl ester (68%) as a colorless solid.

6-(4-Hydroxytetrahydropyran-4-yl)-1H-indazole-3-carboxylic acid tert-butyl ester (0.86 mmol) was dissolved in trifluoroacetic acid (3 mL) and the mixture was maintained at room temperature for 16 h. The solvent was removed in vacuo and the residue was triturated with ethyl acetate to provide 6-(3,6-dihydro-2H-pyran-4-yl)-1H-indazole-3-carboxylic acid (76%). The acids were coupled with quinuclidine amine according to procedure A.

6-(4-Hydroxytetrahydropyran-4-yl)-1H-indazole-3-carboxylic acid tert-butyl ester (1.0 mmol) was taken up in trifluoroacetic acid (5 mL), triethylsilane (2 mL), and dichloromethane (3 mL) and the mixture was refluxed for 16 h. The solvent was removed in vacuo and the residue was triturated with ethyl acetate to provide 6-(tetrahydropyran-4-yl)-1H-indazole-3-carboxylic acid (60%) as a tan solid.

The following acids were prepared using this method:
6-[2,2,2-Trifluoro-1-hydroxy-1-(trifluoromethyl)ethyl]-1H-indazole-3-carboxylic acid.
5-(4-Hydroxytetrahydro-2H-pyran-4-yl)-1H-indazole-3-carboxylic acid.
6-(4-Hydroxytetrahydro-2H-pyran-4-yl)-1H-indazole-3-carboxylic acid.
5-(3,6-Dihydro-2H-pyran-4-yl)-1H-indazole-3-carboxylic acid.

6-(3,6-Dihydro-2H-pyran-4-yl)-1H-indazole-3-carboxylic acid.
5-(Tetrahydro-2H-pyran-4-yl)-1H-indazole-3-carboxylic acid.
6-(Tetrahydro-2H-pyran-4-yl)-1H-indazole-3-carboxylic acid.
5-Formyl-1H-indazole-3-carboxylic acid.
6-Formyl-1H-indazole-3-carboxylic acid.

Procedure 11

Procedure 11 provides a method for the preparation of 4-bromo-5-methoxyindazole-3-carboxylic acid from ethyl 5-methoxyindazole-3-carboxylate and describes further modifications to produce 4-substituted 5-methoxyindazole-3-acids.

N-Bromosuccinimide (24.0 mmol) was added to a solution of ethyl 5-methoxyindazole-3-carboxylate (20.0 mmol) in acetonitrile (200 mL). The reaction mixture was maintained for 16 h and was partitioned between water (150 mL) and ethyl acetate (250 mL). The layers were separated and the organic layer was washed with brine (50 mL), dried (magnesium sulfate), and concentrated. The residue was purified by chromatography using a gradient of 90/10 to 70/30 hexanes/ ethyl acetate, thus providing the 4-brominated product in 57% yield and trace quantities of the 6-brominated product. The 4-brominated ester was further derivatized using Suzuki (procedure G; 60-70% yields) or Negishi (procedure H; 20-40% yields) reaction conditions described below. The ester (3.82 mmol) was diluted with ethanol (10.0 mL) and 5 M sodium hydroxide (10.0 mL) and the reaction mixture was maintained for 4 h at ambient temperature. The reaction mixture was diluted with water (50 mL) and acidified to pH 1 with 6 N hydrochloric acid. The solids were collected by filtration, thus providing the acids in 80-95% yield.

The following compounds were prepared by this method:
4-Bromo-5-methoxy-1H-indazole-3-carboxylic acid.
6-Bromo-5-methoxy-1H-indazole-3-carboxylic acid.
7-Bromo-6-methoxy-1H-indazole-3-carboxylic acid.
5-Bromo-6-methoxy-1H-indazole-3-carboxylic acid.
5-Methoxy-4-(thiophen-2-yl)-1H-indazole-3-carboxylic acid.
5-Methoxy-4-(thiophen-3-yl)-1H-indazole-3-carboxylic acid.
6-Methoxy-5-(thiophen-3-yl)-1H-indazole-3-carboxylic acid.
5-Cyclopropyl-6-methoxy-1H-indazole-3-carboxylic acid.

Procedure 12

Procedure 12 provides a method for the preparation of 5-bromo-4-nitroindazole-3-carboxylic acid from ethyl 5-bromoindazole-3-carboxylate.

Ethyl 5-bromo-1H-indazole-3-carboxylate (5.02 mmol) was dissolved in sulfuric acid (20.0 mL) and was cooled to 0° C. A mixture of 70% nitric acid (7/3, nitric acid/water, 1.0 mL) and sulfuric acid (2.0 mL) was added dropwise and the reaction was maintained for 1 hour at 0° C. The reaction mixture was poured onto 100 mL of ice water and the solids collected by filtration, thus providing the product in 86% yield. The ester (3.82 mmol) was diluted with ethanol (10.0 mL) and 5 M sodium hydroxide (10.0 mL) and the reaction mixture was maintained for 4 h at ambient temperature. The reaction mixture was diluted with water (50 mL) and acidified to pH 1 with 6 N hydrochloric acid. The solids were collected by filtration, thus providing the acid in 82% yield Procedure 13

Procedure 13 provides a method for the preparation of N-1-alkylated indazole-3-carboxylic acids from the corresponding indazole ester.

To a solution of ethyl 5-methoxyindazole-3-carboxylate (1.50 mmol) in acetonitrile (15 mL) was added potassium carbonate (5.99 mmol) and methyl iodide (3.00 mol). The reaction was heated at 60° C. for 4 hours, allowed to cool to ambient temperature, and was partitioned between water (50 mL) and ethyl acetate (50 mL). The layers were separated and the organic later was washed with brine (25 mL), dried (magnesium sulfate), and concentrated. The residue was purified by chromatography using a gradient of 95/5 to 80/20 hexanes/ ethyl acetate to provide the 2-substituted indazole (17%) and the 1-substituted indazole (44%). The 1-substituted indazole (61 mg, 0.26 mmol) was suspended in ethanol (5.0 mL) and was warmed to facilitate dissolution. An aliquot of a 5.0 M solution of sodium hydroxide in water (2.00 mL) was added and the reaction mixture was maintained at ambient temperature for 16 h. The reaction mixture was diluted with water (50 mL) and was acidified with 6.0 N hydrochloric acid. The aqueous layer was extracted with ethyl acetate (3×50 mL) and the combined organic layers were washed with brine (25 mL), dried (magnesium sulfate), and concentrated, thus providing the acid in 95% yield.

The following compounds were prepared by this method:
5-Methoxy-1-methyl-1H-indazole-3-carboxylic acid.
5-Methoxy-1-ethyl-1H-indazole-3-carboxylic acid.
5-Methoxy-1-cyclopentyl-1H-indazole-3-carboxylic acid.
5-Methoxy-1-(2,2,2-trifluoroethyl)-1H-indazole-3-carboxylic acid.
5-Bromo-1-methyl-1H-indazole-3-carboxylic acid.
5-Bromo-1-ethyl-1H-indazole-3-carboxylic acid.
5-Bromo-1-cyclopropylmethyl-1H-indazole-3-carboxylic acid.
5-Bromo-1-(2,2,2-trifluoroethyl)-1H-indazole-3-carboxylic acid.
6-Bromo-1-methyl-1H-indazole-3-carboxylic acid.
6-Bromo-1-ethyl-1H-indazole-3-carboxylic acid.
6-Bromo-1-cyclopropylmethyl-1H-indazole-3-carboxylic acid.
6-Bromo-1-(2,2,2-trifluoroethyl)-1H-indazole-3-carboxylic acid.
1-Benzyl-6-difluoromethoxy-1H-indazole-3-carboxylic acid.
1-Benzyl-5-difluoromethoxy-1H-indazole-3-carboxylic acid.

Procedure 14

Procedure 14 provides a method for the demethylation of methoxyindazole acids and the coupling with 3-aminoquinuclidine to form hydroxy-substituted derivatives.

The methoxy indazole acid (10.4 mmol) was diluted with dichloromethane (100 mL) and the solution was cooled to −78° C. A 1.0 M solution of boron tribromide in dichloromethane (52 mmol, 5 eq.) was added dropwise over 30 min. The reaction mixture was allowed to warm to room temperature and was maintained for 24 h. The reaction was slowly quenched with MeOH (100 mL) and concentrated to dryness. The residue was purified by chromatography using a gradient of hexane/ethyl acetate (100/0 to 80/20) followed by elution with a mixture of ethyl acetate/methanol/triethylamine (70/ 30/1), thus providing the phenol (60-80%) as a brown solid. This procedure was also applied to N-[(3R)-1-azabicyclo [2.2.2]oct-3-yl]-6-hydroxy-1H-indazole-3-carboxamide, N-[(3R)-1-azabicyclo[2.2.2]oct-3-yl]-5-hydroxy-1H-indazole-3-carboxamide, and the benzisothiazole analogs with success.

The following compounds were prepared using this method:
5-Hydroxy-1H-indazole-3-carboxylic acid.
6-Hydroxy-1H-indazole-3-carboxylic acid.

5-Hydroxy-1,2-benzisothiazole-3-carboxylic acid.
6-Hydroxy-1,2-benzisothiazole-3-carboxylic acid
Procedure 15:

Procedure 15 provides a method for the preparation of 7-fluoro-6-methoxy-1H-indazole-3-carboxylic acid and 4-fluoro-5-methoxy-1H-indazole-3-carboxylic acid from the corresponding methoxyindazole acids.

1-Chloromethyl-4-fluoro-1,4-diazoniabicyclo[2.2.2]octane bis(tetrafluoroborate) (1.00 g, 2.82 mmol) was added to a solution of ethyl 6-methoxy-1H-indazole-3-carboxylate (500 mg, 2.27 mmol) in acetonitrile (15.0 mL) and the reaction mixture was maintained at rt for 18 h. The reaction was partitioned between water (50 mL) and ethyl acetate (50 mL) and the separated organic layer was washed with brine (25 mL), dried (magnesium sulfate), and concentrated. The residue was purified by chromatography (95/5 to 80/20 hexanes/ethyl acetate) to yield 541 mg (23%) of the fluorinated ester. A solution of the ester (124 mg, 0.520 mmol) in ethanol (5.00 mL) was diluted with 5.0 M of sodium hydroxide (2.00 mL) and the mixture was maintained at rt for 18 h. The reaction was acidified with 6 N hydrochloric acid and partitioned between water (50 mL) and ethyl acetate (50 mL). The layers were separated and the organic washed with brine (25 mL), dried (magnesium sulfate), and concentrated in vacuo to yield 109 mg (84%) of the acid.

The acid was coupled with the bicyclobase according to procedure A.

The following acid was prepared using this method:
7-Fluoro-6-methoxy-1H-indazole-3-carboxylic acid.
4-Fluoro-5-methoxy-1H-indazole-3-carboxylic acid.
Procedure 16:

Procedure 16 details the preparation of ethyl benzisoxazole-3-carboxylate from 2,5-dibromonitrobenzene.

Diethyl malonate (12.6 g, 79 mmol) was added to a suspension of sodium hydride (3.16 g, 132 mmol) in dimethylsulfoxide (60 ml) over 30 min. The temperature of the reaction rose to 60° C. and the mixture clarified. 1,4-Dibromo-2-nitrobenzene (10 g, 36.0 mmol) was added and the solution was maintained for 2 h at 100° C. The reaction mixture was allowed to cool to rt and was poured into ice (300 g-400 g). The precipitated solids were isolated by filtration and dried to provide 11.0 g of the product (89%).

The ester (11.0 g, 32.0 mmol) was diluted with a 2 N solution of sodium hydroxide (32 mL, 63 mmol) and the reaction mixture was maintained at room temperature for 16 h. The aqueous layer was extracted with dichloromethane (20 mL) and was acidified. The precipitated solids were isolated by filtration and dried to provide 7.00 g of the acid (89%).

Sulfuric acid (1 mL) was added to a solution of the acid (7.00 g, 27.0 mmol) in ethanol (60 ml). The reaction mixture was warmed to reflux, maintained for 2 h, and was concentrated under reduce pressure. The residue was partitioned between ethyl acetate (250 mL) and saturated sodium carbonate (50 mL) and the organic layer was washed with saturated sodium carbonate (50 mL) and brine (50 mL). The organic layer was dried (sodium sulfate) and concentrated to provide 8.00 g (98%) of the ester as a liquid.

Isoamylnitrite (225 mL) was added to a solution of the ester (420 g, 1.46 mol) in ethanol (3 L) in a 10 L three-necked round bottom flask and the mixture was warmed to 60° C. A solution of sodium ethoxide, prepared from sodium metal (33.5 g, 1.46 mmol) in ethanol (1 L) was added dropwise and the reaction mixture was maintained for 2 h. The reaction mixture was allowed to cool to rt and was neutralized with 2 N hydrochloric acid. The reaction mixture was extracted with ethyl acetate (4×2 L) and the combined organic layers were washed with water (2×1 L) and brine (2×1 L) and dried (sodium sulfate). The residue was purified by chromatography (1/1 to 0/1 hexane/ethyl acetate) to provide 110 g of the product (28%).

10% Palladium on carbon (1.5 g) and triethylamine (7.5 g, 82.4 mmol) were added to a solution of ethyl 6-bromobenzisoxazole-3-carboxylate (20 g, 0.081 mol) in ethanol (300 ml) at 0° C. under an atmosphere of nitrogen. The nitrogen atmosphere was removed by evacuation and replaced with hydrogen gas, and the reaction mixture was maintained for 1 hour. The hydrogen atmosphere was removed by evacuation and replaced with nitrogen gas, and the palladium removed by filtration through Celite. The filter cake was washed with ethanol (3×50 mL) and the filtrates were concentrated. The residue was dissolved in dichloromethane (200 mL) and the solution was washed with water (4×50 mL), dried (sodium sulfate) and evaporated to provide 13.0 g of the product as a yellow solid (96%). The ester was saponified using sodium hydroxide to provide the acid which was coupled with the bicyclobase according to procedure A.

Literature reference: Angell, R. M.; Baldwin, I. R.; Bamborough, P.; Deboeck, N. M.; Longstaff, T.; Swanson, S. WO04010995A1

The following acid and esters were prepared using this method:
Ethyl 6-bromo-1,2-benzisoxazole-3-carboxylate.
Ethyl 1,2-benzisoxazole-3-carboxylate.
1,2-Benzisoxazole-3-carboxylic acid.
Procedure 17:

Procedure 17 provides a method for the preparation of 5-difluoromethoxyindazole-3-acid from 3-bromo-4-nitrophenol.

3-Bromo-4-nitrophenol (10.0 mmol) was added to a suspension of sodium hydroxide (29.0 mmol) in N,N-dimethylformamide (15 mL) and the suspension was maintained for 15 min at rt. The reaction mixture was cooled to 0° C. and was treated with ethyl chlorodifluoroacetate (20.0 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 75% yield as a yellow oil.

Diethyl malonate (328 mmol) was added dropwise to a suspension of sodium hydride (328 mmol) in dimethylsulfoxide (40 mL) at 0° C. The reaction mixture was warmed to 60° C. and maintained for 0.5 h. A solution of the difluoromethyl ether (149 mmol) in dimethylsulfoxide (80 mL) was added dropwise and the reaction mixture was heated at 100° C. for 5 h. The cooled solution was poured onto ice water, and the aqueous layer was extracted with dichloromethane (3×100 mL). The combined organic layers were dried (magnesium sulfate) and concentrated to give the crude diester in 112% yield as an oil. The diester (167 mmol), sodium hydroxide (500 mmol), and water (335 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 5° C. and the solids were collected by filtration and dried to provide the acid in 61% yield.

Acetyl chloride (203 mmol) was added dropwise to ethanol (300 mL) at 0° C. After 0.5 h, the acid (101 mmol) was added and the reaction mixture was heated at reflux for 15 h. The reaction mixture was concentrated and the residue was partitioned between dichloromethane (200 mL) and saturated sodium bicarbonate (100 mL). The aqueous layer was further extracted with dichloromethane (2×200 mL) and the combined organic layers were dried (magnesium sulfate) and concentrated to provide the ester in 60% yield as a brown oil.

The ester (60.4 mmol) was dissolved in ethanol (103 mL), diluted with water (71 mL), and was treated with ammonium chloride (243 mmol) and iron powder (301 mmol). The reaction mixture was heated at reflux for 10 minutes and the suspension was filtrated through Celite and the filter cake was washed with ethanol three times. The filtrate was concentrated, the residue was suspended in 2 N hydrochloric acid and was stirred vigorously for 0.5 h. The aqueous layer was washed with ethyl acetate (3×50 mL) and the pH adjusted to 9-10 with 5 M sodium hydroxide. The aqueous layer was extracted with chloroform (3×100 mL) and the combined organic layers were dried (magnesium sulfate). Acetic anhydride (392 mmol), isoamyl nitrite (291 mmol), and potassium acetate (51.0 mmol) were added to the organic layer and the suspension was heated at reflux for 16 h. The solution was evaporated and the residue was partitioned between saturated sodium bicarbonate (50 mL) and dichloromethane (100 mL). The aqueous layer was further extracted with dichloromethane (2×100 mL) and the combined organic layers were dried (magnesium sulfate) and concentrated to provide the N-acetylindazole ester in 79% yield as a brown oil.

The ester (63.8 mmol), sodium hydroxide (193 mmol), and water (65 mL) were combined and the reaction was maintained for 24 h at 60° C. After cooling to rt, the aqueous layer was washed with dichloromethane (3×50 mL). The aqueous layer was adjusted to pH 1 with concentrated hydrochloric acid. The precipitated solids were collected by filtration, washed with water and dichloromethane, and dried to provide the acid in 27% yield.

The following acids were prepared according to this method:
5-(Difluoromethoxy)-1H-indazole-3-carboxylic acid.
Procedure 18:

Procedure 18 provides a method for the preparation of 6-difluoromethoxyindazole-3-acid from 4-nitrophenol.

4-Nitrophenol (162 mmol) was added to a suspension of sodium hydroxide (485 mmol) in N,N-dimethylformamide (150 mL) and the suspension was maintained for 15 min at rt. The reaction mixture was cooled to 0° C. and was treated with ethyl chlorodifluoroacetate (329 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 59% yield as a yellow oil.

The nitro ether (149 mmol) was dissolved in ethanol (37.5 mL), diluted with water (25 mL), and was treated with ammonium chloride (84.7 mmol) and iron powder (105 mmol). The reaction mixture was heated at reflux for 30 minutes and the suspension was filtered through Celite. The filter cake was washed with ethanol three times and the combined filtrates were concentrated. The residue was dissolved in water and the pH adjusted to 9-10 with 5 M sodium hydroxide. The aqueous layer was extracted with ethyl acetate (3×100 mL) and the combined organic layers were dried (magnesium sulfate) and concentrated to a yellow oil. The oil was dissolved in acetic anhydride (23.5 mmol) and the reaction mixture was maintained at rt for 16 h. The reaction mixture was diluted with water (50 mL) and was neutralized with solid sodium bicarbonate. The precipitated solids were isolated by filtration, washed with water, and dried to provide the acetamide in 62% yield as a light yellow solid.

Acetic anhydride (19.6 mmol) was added to a solution of the acetamide (13.2 mmol) in chloroform (20 mL) and the reaction mixture was warmed to reflux. Fuming nitric acid (16.0 mmol) was added dropwise and the reaction mixture was maintained at reflux for 30 min. The cooled solution was diluted with water (20 mL) and the aqueous layer was extracted with dichloromethane (3×10 mL). The combined organic layers were dried (magnesium sulfate) and concentrated to provide the nitro-amide in 83% yield.

The amide (11.0 mmol), sodium hydroxide (43.8 mmol), and water (10 mL) were combined and the reaction mixture was maintained for 1.5 hour at 60° C. the reaction was allowed to cool to rt and the precipitated solids were isolated by filtration, and washed with water, and dried to provide the aniline in 98% yield as a light yellow solid.

The aniline (15.7 mmol) was mixed with 40% hydrobromic acid (14.3 g) and water (10 mL) and the reaction mixture was warmed to 80-90° C. in order to completely dissolve the aniline. The reaction mixture was cooled to 0° C. and a solution of sodium nitrite (23.2 mmol) in water (5.3 mL) was added during a 15 min period. The solution was maintained for 40 minutes at 0-5° C. and filtered. Copper (I) bromide (18.8 mmol) was dissolved in 40% hydrobromic acid (21 mL) and was cooled to 0° C. The solution of the diazo salt was added slowly to the copper solution and the mixture was maintained for 30 min at 0-10° C. The reaction mixture was heated at 60° C. for 30 min and then at 100° C. for 10 min to ensure completion. The reaction mixture was allowed to cool to rt and was extracted with dichloromethane (3×40 mL). The combined organic layers were washed with 1 M sodium hydroxide, water, 1 N hydrochloric acid, and water. The organic layer was dried (magnesium sulfate) and concentrated to provide the nitro bromide in 76% yield as a light yellow solid.

Diethyl malonate (25.7 mmol) was added dropwise to a suspension of sodium hydride (25.8 mmol) in dimethylsulfoxide (5 mL) at 0° C. The reaction mixture was warmed to 60° C. and maintained for 30 min. A solution of the nitro bromide (11.7 mmol) in dimethylsulfoxide (7 mL) was added dropwise and the reaction mixture was heated at 100° C. for 5 h. The cooled solution was poured onto ice water and the aqueous layer was extracted with dichloromethane (3×100 mL). The combined organic layers were dried (magnesium sulfate) and concentrated to give the crude diester as an oil. The diester (11.7 mmol), sodium hydroxide (35 mmol), and water (20 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 0° C. and the solids were collected by filtration and dried to provide the acid in 64% yield.

Acetyl chloride (15.3 mmol) was added dropwise to ethanol (50 mL) at 0° C. After 30 min, the acid (7.69 mmol) was added and the reaction mixture was heated at reflux for 15 h. The reaction mixture was concentrated and the residue was partitioned between dichloromethane (20 mL) and saturated sodium bicarbonate (10 mL). The aqueous layer was further extracted with dichloromethane (2×20 mL) and the combined organic layers were dried (magnesium sulfate) and concentrated to provide the ester in 94% yield as a brown oil.

Acetic anhydride (6.0 mL) was added to a suspension of the ester (3.64 mmol), and acetic acid (7.0 mL) at 0° C. Zinc dust (14.6 mmol) was added in portions over 15 min and the reaction mixture was maintained for 30 min at 0° C. and then for 1.5 h at rt. Additional zinc powder (6.15 mmol) was added and the reaction maintained for 3 h. The suspension was filtered through Celite and the filtrate was concentrated. The residue was partitioned between saturated sodium bicarbonate (10 mL) and ethyl acetate (20 mL). The aqueous layer was further extracted with ethyl acetate (3×20 mL) and the combined organic layers were dried (magnesium sulfate) and concentrated to provide the acetamide in 92% yield as a brown oil.

Acetic anhydride (13.7 mmol), isoamyl nitrite (13.7 mmol), and potassium acetate (2.04 mmol) were added to a solution of the acetamide (3.92 mmol) in chloroform (20 mL) and the suspension was heated at reflux for 16 h. The solution was evaporated and the residue was partitioned between saturated sodium bicarbonate (10 mL) and dichloromethane (20 mL). The aqueous layer was further extracted with dichloromethane (2×20 mL) and the combined organic layers were dried (magnesium sulfate) and concentrated to provide the crude N-acetylindazole ester as a brown oil.

The ester (3.36 mmol), sodium hydroxide (10 mmol) and water (5 mL) were combined and the reaction was maintained for 24 h at 60° C. After cooling to rt, the aqueous layer was washed with dichloromethane (3×30 mL). The aqueous layer was adjusted to pH 1 with concentrated hydrochloric acid and the precipitated solids were collected by filtration, washed with water and dichloromethane, and dried to provide the acid in 26% yield.

The following acids were prepared according to this method:
6-(Difluoromethoxy)-1H-indazole-3-carboxylic acid.
Procedure 19:

Procedure 19 provides a method for the coupling between brominated benzisothiazole-3-carboxylic esters and brominated indazole-3-carboxylic esters and Grignard reagents to form alkyl- and heterocycle-substituted acids.

A 0.5 M solution of Grignard reagent (25.0 mmol, 3.7 eq) in tetrahydrofuran was diluted with tetrahydrofuran (60 mL) and treated with a 0.5 M solution of zinc chloride (25.0 mmol, 3.7 eq) in tetrahydrofuran at rt. After 10 min, the brominated ester (0.30 mmol) and bis(triphenylphosphine)palladium (II) chloride (0.95 mmol, 0.1 eq) were added to the suspension. The reaction mixture was maintained for 1 h at ambient temperature then at 65° C. for 1 h. The reaction was quenched with saturated ammonium chloride and was extracted with dichloromethane (3×). The extracts were dried over sodium sulfate and concentrated to dryness. The residue was purified by chromatography using a gradient of 100/0 to 90/10 dichloromethane/methanol to provide the alkyl- or aryl-substituted amide. The amide was dissolved in a mixture of methanol/tetrahydrofuran/water (90/10/20 mL) and was treated with sodium hydroxide (5.8 g). The mixture was heated at reflux for 12 h, cooled to rt, filtered, and was acidified to pH<2 by the slow addition of conc. hydrochloric acid. The aqueous layer was extracted with ethyl acetate (2×) and was dried over sodium sulfate. Concentration of the extracts gave the acid in 38% yield. The acid was coupled to the bicyclobases according to procedure A.

This procedure was used, with slight modifications, to derivatize brominated indazole-3-piperidine carboxamides with various Grignard reagents. The Grignard reagent of thiazole is commercially available. Alternatively, the aryllithium and the corresponding arylzinc reagent can be generated according to the procedure outlined by Reeder, M. R.; et. al. *Org. Proc. Res. Devel.* 2003, 7, 696. The zinc reagents of oxazole, 4-methylthiazole, and 5-methylthiazole were prepared according to this procedure.

The following acids were prepared using this method:
6-(1,3-Thiazol-2-yl)-1H-indazole-3-carboxylic acid.
5-(1,3-Thiazol-2-yl)-1H-indazole-3-carboxylic acid.
5-(4-Methyl-1,3-thiazol-2-yl)-1H-indazole-3-carboxylic acid.
5-(5-Methyl-1,3-thiazol-2-yl)-1H-indazole-3-carboxylic acid.
6-(4-Methyl-1,3-thiazol-2-yl)-1H-indazole-3-carboxylic acid.
6-(5-Methyl-1,3-thiazol-2-yl)-1H-indazole-3-carboxylic acid.
5-(1,3-Oxazol-2-yl)-1H-indazole-3-carboxylic acid.
6-(1,3-Oxazol-2-yl)-1H-indazole-3-carboxylic acid.
Procedure 20:

Procedure 20 provides a method for the preparation of alkoxy indazole acids from the corresponding benzyloxy indazole esters using alkylation conditions.

A solution of ethyl 5-(benzyloxy)-1H-indazole-3-carboxylate (2.70 mmol) in tetrahydrofuran (10 mL) was added dropwise to a 0° C. suspension of sodium hydride (60% mineral oil dispersion, 8.1 mmol) in tetrahydrofuran (54.0 mL). The reaction was maintained at 0° C. for 1 h. [β-(Trimethylsilyl)ethoxy]methyl chloride (3.2 mmol) was added and the reaction mixture was maintained for 1 h. The reaction was partitioned between water (50 mL) and ethyl acetate (50 mL) and the organic layer was washed with brine (25 mL), dried (magnesium sulfate), and concentrated. The residue was purified by chromatography (95/5 to 85/15 hexanes/ethyl acetate to provide the protected indazole in 89% yield.

Ethyl 5-(benzyloxy)-1-[2-(trimethylsilyl)ethoxy]methyl-1H-indazole-3-carboxylate (9.38 mmol) was added to a suspension of 10% palladium on carbon (249 mg) in ethanol (66.7 mL). The reaction was shaken under an atmosphere of hydrogen (50 psi) for 4.0 h. The reaction was filtered through Celite and concentrated to give the phenol in 87% yield as a white solid.

Cyclopropylmethyl bromide (1.19 mmol) and potassium carbonate (2.38 mmol) was added to a solution of 5-hydroxy-1-(2-trimethylsilanylethoxymethyl)-1H-indazole-3-carboxylic acid ethyl ester (5.94 mmol) in acetonitrile (10.0 mL) The suspension was heated at 60° C. for 4.0 h. The reaction was partitioned between water (50 mL) and ethyl acetate (50 mL) and the organic layer was washed with brine (25 mL), dried (magnesium sulfate), and concentrated. The residue was purified by chromatography (100/0 to 85/15 hexanes/ethyl acetate) to yield the purified ethyl ester. The ester was dissolved in ethanol (10 mL) and 5 N sodium hydroxide (3 mL) was added. The mixture was allowed to stand overnight and was diluted with water (20 mL) and acidified to pH 1 with 3 N hydrochloric acid. The solid was collected by vacuum filtration to give the acid in 72% yield as a white solid.

The following acids were prepared using this method:
5-(Cyclopropylmethoxy)-1-[2-(trimethylsilyl)ethoxy]methyl-1H-indazole-3-carboxylic acid.
6-(Cyclopropylmethoxy)-1-[2-(trimethylsilyl)ethoxy]methyl-1H-indazole-3-carboxylic acid.
5-(Cyclopentyloxy)-1-[2-(trimethylsilyl)ethoxy]methyl-1H-indazole-3-carboxylic acid.
6-(Cyclopentyloxy)-1-[2-(trimethylsilyl)ethoxy]methyl-1H-indazole-3-carboxylic acid.
5-(2,2,2-Trifluoroethoxy)-1-[2-(trimethylsilyl)ethoxy]methyl-1H-indazole-3-carboxylic acid.
6-(2,2,2-Trifluoroethoxy)-1-[2-(trimethylsilyl)ethoxy]methyl-1H-indazole-3-carboxylic acid.
Procedure 21:

Procedure 21 provides a method for the preparation of alkoxy indazole acids from the corresponding benzyloxy indazole esters using Mitsunobu conditions.

Diisopropyl azodicarboxylate (0.618 mmol) was added dropwise to a solution of ethyl 5-hydroxy-1-(2-trimethylsilanylethoxymethyl)-1H-indazole-3-carboxylate (0.594 mmol), 1-methyl-3-pyrrolidinol (0.594 mmol), and triphenylphosphine (0.594 mmol) in tetrahydrofuran (3.6 mL). The reaction was maintained for 16 h and was concentrated. The residue was purified by chromatography (100/0 to 90/10 ethyl acetate/[70/30/2 ethyl acetate/methanol/dimethylethylamine] to provide the ether product in 49% yield. The ester was saponified to provide the acid which was coupled to the bicyclobase using Procedure C.

The following acids were prepared using this method:
5-[(1-Methylpyrrolidin-3-yl)oxy]-1-{[2-(trimethylsilyl) ethoxy]methyl}-1H-indazole-3-carboxylic acid.
5-[(1-Benzylpyrrolidin-3-yl)oxy]-1-{[2-(trimethylsilyl) ethoxy]methyl}-1H-indazole-3-carboxylic acid.
5-[2-(Dimethylamino)ethoxy]-1-[2-(trimethylsilyl)ethoxy] methyl-1H-indazole-3-carboxylic acid.
5-(2-Pyrrolidin-1-ylethoxy)-1-[2-(trimethylsilyl)ethoxy] methyl-1H-indazole-3-carboxylic acid.
5-(2,3-Dihydro-1H-inden-2-yloxy)-1-[2-(trimethylsilyl) ethoxy]methyl-1H-indazole-3-carboxylic acid.
5-(Tetrahydro-2H-pyran-4-yloxy)-1-[2-(trimethylsilyl) ethoxy]methyl-1H-indazole-3-carboxylic acid.

Procedure 22:

Procedure 22 provides a method for the preparation of 1-(3-thienyl)-1H-indazole-3-carboxylic acid from the corresponding indazole ester.

Ethyl 1H-indazole-3-carboxylate (5.50 mmol), 3-thienylboronic acid (7.50 mmol), copper (II) acetate (5.01 mmol), triethylamine (24.7 mmol), and pyridine (40.4 mmol) were dissolved in 1,4-dioxane (39.8 mL). The reaction was maintained at rt for 16 h and was diluted with water (50 mL) and ethyl acetate (50 mL). The reaction mixture was filtered through Celite and the organic layer was washed with brine (25 mL), dried (magnesium sulfate), and concentrated. The residue was purified by chromatography (90/10 to 70/30 hexanes/ethyl acetate) to yield the N-arylindazole ester in 35% yield. The ester was saponified using standard conditions and the resultant acid was used in Procedure A.

Procedure 23:

Procedure 23 provides a method for the preparation of 1,8-dihydropyrrolo[3,2-g]indazole-3-carboxylic acid from ethyl 6-bromo-7-nitro-1H-indazole-3-carboxylate.

A 0.50 M solution of zinc chloride in tetrahydrofuran (11 ml) was added to a 0.50 M solution of (1,3-dioxolan-2-ylmethyl)magnesium bromide in tetrahydrofuran (11 mL) and the reaction mixture was maintained for 20 min. An aliquot (5.5 mL) of the zinc reagent solution was added to each of 4 microwave tubes containing ethyl 6-bromo-7-nitro-1H-indazole-3-carboxylate (143 mmol) and bis(tri-t-butylphosphine) palladium(0) (26 mg, 0.051 mmol). The reaction was heated in a microwave reactor at 160° C. for 10 min. The reaction was partitioned between water (50 mL) and ethyl acetate (50 mL), filtered through Celite and the organic layer was washed with brine (25 mL), dried (magnesium sulfate), and concentrated. The residue was purified by chromatography (80/20 to 60/40 hexanes/ethyl acetate) to yield the dioxolane product in 46% yield.

Ethyl 6-(1,3-dioxolan-2-ylmethyl)-7-nitro-1H-indazole-3-carboxylate (0.657 mmol) was added to a suspension of 10% palladium on carbon (100 mg) in ethanol (30 mL). The reaction mixture was shaken under an atmosphere of hydrogen gas for 4 h. The reaction mixture was filtered through Celite and concentrated to give the amine in 94% yield as an oil.

Ethyl 7-amino-6-(1,3-dioxolan-2-ylmethyl)-1H-indazole-3-carboxylate (0.371 mmol) was dissolved in tetrahydrofuran (30 mL) and treated with 6 M hydrogen chloride (5 mL). The reaction mixture was maintained for 16 h and was partitioned between water (30 mL) and ethyl acetate (30 mL). The organic layer was washed with brine (25 mL), dried (magnesium sulfate), and concentrated. The residue was purified by chromatography (90/10 to 70/30 hexanes/ethyl acetate) to yield the pyrrolidine in 72% yield.

Ethyl 1,8-dihydropyrrolo[3,2-g]indazole-3-carboxylate (0.266 mmol) was dissolved in ethanol (2 mL) and 5.0 M of sodium hydroxide (1.00 mL) and the reaction was maintained for 16 h. The reaction mixture was neutralized with 3 N hydrochloric acid and was partitioned between water (30 mL) and ethyl acetate (30 mL). The layers were separated and the organic layer was washed with brine (25 mL), dried (magnesium sulfate), and concentrated in vacuo to provide the acid in 41% yield. The acid was used without further purification.

Procedure 24:

Procedure 24 provides a method for the preparation of alkoxypyrrolidine substituted indazole-3-carboxylic acids from the corresponding nitro-1H-indazole-3-carboxylates.

[β-(Trimethylsilyl)ethoxy]methyl chloride (10.2 mmol) was added dropwise to a suspension of ethyl 5-nitro-1H-indazole-3-carboxylate (8.50 mmol) and N,N-diisopropylethylamine (25.5 mmol) in dichloromethane (20.0 mL). The heterogeneous reaction mixture was maintained at rt for 16 h whereupon the reaction mixture gradually became homogeneous. The reaction mixture was filtered through silica gel (ca. 40 g) and concentrated. The residue was diluted with ethanol (50.0 mL) and 10% palladium on carbon (200 mg) was added under a flow of nitrogen gas. The reaction was shaken under an atmosphere of hydrogen for 4 h and the reaction mixture was filtered through Celite and concentrated. The residue was purified by chromatography (70/30 to 50/50 hexanes/ethyl acetate) to yield the aniline in 60% yield as a 2/1 mixture of 1- and 2-SEM regioisomers.

Ethyl 5-amino-1-[2-(trimethylsilyl)ethoxy]methyl-1H-indazole-3-carboxylate (3.61 mmol) was combined with 1,4-dibromo-2-butanol (3.80 mmol) and potassium carbonate (3.47 mmol) in triethyl phosphate (10.0 mL) and the reaction was heated at 120° C. for 2 h. The reaction mixture was loaded onto a SCX column (3×10 g) and flushed with 5 volumes of methanol. The partially purified product was then eluted using 2.0 M ammonia in methanol and the product fractions were combined and concentrated. The residue was purified by chromatography (90/10 to 70/30 hexanes/ethyl acetate) to provide the pyrrolidine in 55% yield.

A solution of ethyl 5-(3-hydroxypyrrolidin-1-yl)-1-[2-(trimethylsilyl)ethoxy]methyl-1H-indazole-3-carboxylate (0.493 mmol) in tetrahydrofuran (20.0 mL) was cooled to −78° C. A 0.5 M solution of potassium bis(trimethylsilyl) amide in toluene (1.18 mL) was added dropwise and the reaction mixture was maintained for 30 min. 2,2,2-Trifluoroethyl nonafluorobutanesulfonate (0.493 mmol) was added and the reaction mixture was allowed to warm to room temperature and was maintained for 4 h. The reaction mixture was partitioned between water (50 mL) and ethyl acetate (50 mL) and the organic layer was washed with brine (25 mL), dried (magnesium sulfate), and concentrated. The residue was purified by chromatography (90/10 to 80/20 hexanes/ethyl acetate) to yield the alkoxypyrrolidine in 42% yield.

The ester (0.172 mmol) was dissolved in ethanol (5.0 mL) by warming slightly. A 5.0 M of sodium hydroxide (2.00 mL) was added and the reaction mixture was maintained overnight. The reaction mixture was diluted with water (50 mL), neutralized to pH 6-7 with 3.0 N hydrochloric acid, and was extracted with ethyl acetate (2×25 mL). The organic layer was washed with brine (25 mL), dried (magnesium sulfate), and concentrated to provide the acid in 89% yield. The acid was used with no further purification.

The following acids were prepared by this method:
5-[3-(Hydroxy)pyrrolidin-1-yl]-1-[2-(trimethylsilyl)ethoxy] methyl-1H-indazole-3-carboxylic acid.
5-[3-(Methoxy)pyrrolidin-1-yl]-1-[2-(trimethylsilyl)ethoxy] methyl-1H-indazole-3-carboxylic acid.
5-[3-(Benzyloxy)pyrrolidin-1-yl]-1-[2-(trimethylsilyl) ethoxy]methyl-1H-indazole-3-carboxylic acid.
5-[3-(2,2,2-Trifluoroethyl)pyrrolidin-1-yl]-1-[2-(trimethylsilyl)ethoxy]methyl-1H-indazole-3-carboxylic acid.

Procedure 25:

Procedure 25 provides a method for the preparation of aminomethyl substituted indazole-3-carboxylic acids from the corresponding bromides.

A solution of di-tert-butyldicarbonate (188 mmol) in tetrahydrofuran (50 mL) was cautiously added to a mixture of 5-bromo-1H-indazole-3-carboxylic acid (62.2 mmol) and 4-dimethylaminopyridine (19.0 mmol) in tert-butyl alcohol (150 mL) and tetrahydrofuran (150 mL) at 60° C. The mixture was maintained at 60° C. until gas evolution ceased (approx. 4 h). The reaction mixture was allowed to cool to rt, diluted with ethyl acetate, washed with water, sodium bicarbonate, and brine, dried (sodium sulfate) and concentrated. The residue was dissolved in 1/1 hexanes/ethyl acetate (~300 mL) and filtered through of silica gel (approx. 40 g). The silica was washed with additional 1/1 hexanes/ethyl acetate (500 mL) and the combined eluant was concentrated. The residue was dissolved in methanol (100 mL) and tetrahydrofuran (100 mL) and was treated with 2.0 M sodium hydroxide (100 mL). The reaction mixture was maintained for 2 h at rt and was partitioned between water (200 mL) and ethyl acetate (200 mL). The organic layer was washed with brine (50 mL), dried (magnesium sulfate), and concentrated. The residue was triturated with hexanes to provide the ester in 80% yield.

Into a 1-Neck round-bottom flask was added sodium hydride (60% mineral oil dispersion) (6.00 mmol) and tetrahydrofuran (90 mL) The reaction was cooled to −78° C. and a solution of tert-butyl 5-bromo-1H-indazole-3-carboxylate (4.00 mmol) in tetrahydrofuran (10.0 mL) was added. The reaction was heated at 25° C. and was maintained for 30 min. The reaction was cooled to −78° C. and tert-butyllithium in pentane (1.7 M, 3.6 mL) was added dropwise. The reaction was maintained at −78° C. for 15 minutes and N,N-dimethylformamide (20 mmol) was added. The reaction was maintained at −78° C. for 30 minutes, then quenched with methanol (0.5 mL) and allowed to warm to room temperature. The reaction was partitioned between water (100 mL) and ethyl acetate (100 mL) and the organic layer was washed with brine (25 mL), dried (magnesium sulfate), and concentrated. The residue was purified by chromatography (80/20 to 60/40 hexanes/ethyl acetate) to yield the benzaldehyde in 52% yield.

Sodium triacetoxyborohydride (4.74 mmol) was added to a suspension of tert-butyl 5-formyl-1H-indazole-3-carboxylate (2.03 mmol) and dimethylamine hydrochloride (4.74 mmol) in 1,2-dichloroethane (50.0 mL). The reaction mixture was maintained for 3 days at rt. The reaction mixture was washed with water (50 mL) and brine (25 mL), dried (magnesium sulfate), and concentrated. The residue was loaded onto a SCX column (10 g) and washed with 5 volumes of methanol. The purified product was then eluted using 2.0 M ammonia in methanol to provide the amine in 86% yield tert-Butyl 5-[(dimethylamino)methyl]-1H-indazole-3-carboxylate (1.74 mmol) was dissolved in trifluoroacetic acid (3.00 mL) and the reaction mixture was maintained for 16 h.

The reaction mixture was concentrated and was loaded onto a SCX column (10 g) and flushed with 5 volumes of methanol. The purified product was then eluted using 2.0 M ammonia in methanol to provide the acid in 90% yield.

The following compounds were prepared using this method:
5-[(Dimethylamino)methyl]-1H-indazole-3-carboxylic acid.
5-[(Diethylamino)methyl]-1H-indazole-3-carboxylic acid.
5-[(Pyrrolidin-1-yl)methyl]-1H-indazole-3-carboxylic acid.
tert-Butyl 5-bromo-1H-indazole-3-carboxylate.

Procedure 26:

Procedure 26 provides a method for the preparation of 4-methoxyindazole acid from 4-methoxyaniline.

A solution of 4-methoxyaniline (1.63 mol) in acetic acid (244 mL) was treated with acetic anhydride (244 mL) and zinc powder (30.8 mmol) and the reaction mixture was heated at reflux for 30 min. The suspension was allowed to cool to rt and was filtered and concentrated. The residue was diluted with water (200 mL) and the pH of the solution was adjusted to 8 with 10% sodium hydroxide. The precipitated solids were collected by filtration, washed with water (1 L), and dried to give the acetamide in 94% yield as a purple solid.

Concentrated nitric acid (210 mL) was added dropwise to a solution of the acetamide (1.52 mol) in dichloromethane (1.5 L) at rt. The reaction mixture was heated at reflux for 1 h and was allowed to cool to rt. The reaction mixture was washed with water (1.0 L), saturated sodium carbonate (1.0 L), and water (1.0 L). The organic layer was dried over anhydrous sodium sulfate and concentrated to provide the nitroacetamide in 83% yield as an orange solid.

A solution of the nitroacetamide (1.27 mol) in water (1.27 L) was treated with sodium hydroxide (5.07 mol) and the reaction mixture was heated at 60° C. for 2 h. The precipitated solids were collected by filtration, washed with water, and dried to provide the nitroaniline in 85% yield as an orange solid.

A solution of sodium nitrite (1.48 mol) in water (250 mL) was added to a cold (0-5° C.) solution of the nitroaniline (1.08 mol) in hydrobromic acid (4.87 mol) (prepared by heating the reaction mixture at 90° C. for 2 h). The reaction mixture was maintained for 40 min and was filtered. The filtrate was added dropwise to a cold (0-5° C.) solution of copper (I) bromide (1.81 mol) in hydrobromic acid (640 mL) and the reaction mixture was maintained for 30 min. The reaction mixture was warmed to 60° C. and was maintained for 30 min. The reaction mixture was warmed to reflux and was maintained for 1 h. The reaction mixture was diluted with water (2 L) and was extracted with dichloromethane (3×1 L). The combined organic layers were washed with 10% sodium hydroxide (1.0 L), water (2.0 L), 10% hydrochloric acid (1.6 L) and water (2.0 L), dried (magnesium sulfate) and concentrated. The residue was recrystallized from ethanol to provide the bromide in 50% yield as a yellow solid.

Iron powder (1.08 mol) and ammonium chloride (862 mmol) were added to a solution of the bromide (216 mmol) in ethanol (200 mL) and water (140 mL) and the reaction mixture was heated at reflux for 1 h. The suspension was filtered and concentrated and the residue was extracted with ethyl acetate (3×200 mL). The combined organic layers were dried (sodium sulfate) and concentrated to give the bromoaniline in 96% yield as a yellow liquid.

A solution of the bromoaniline (208 mmol) in 50% hydrochloric acid (40 mL) was added to a solution of trichloroacetaldehyde hydrate (312 mmol) and sodium sulfate (967 mmol) in water (450 mL) and the reaction mixture was maintained for 1 h. A solution of hydroxylamine hydrochloride (793 mmol) in water (240 mL) was added and the reaction mixture was heated at 60° C. for 2 h. The aqueous layer was decanted and the residual red oil, which solidifies upon standing, was purified by chromatography (6/6/1 petroleum ether/dichloromethane/ethyl acetate) to provide the α-oxime amide in 29% yield as a light yellow solid.

The α-oxime amide (58.6 mmol) was added in one portion to warm (40° C.) 90% sulfuric acid (16 mL) and the reaction mixture was heated at 60° C. for 30 min. The reaction mixture was allowed to cool to rt and was poured into ice water. The precipitated orange solids were collected by filtration and dried. The crude product was purified by chromatography (15/1 petroleum ether/ethyl acetate) to provide the isatin in 57% yield as a yellow solid.

The isatin (20.7 mmol) was mixed with 1 M sodium hydroxide (23 mL) and the reaction mixture was heated to 30-40° C. for 30 min. The reaction mixture was cooled to 0° C. and treated with a solution of sodium nitrite (20.7 mmol) in water (5.1 mL) and was maintained for 20 min. That solution was added dropwise to a cold (0-5° C.) solution of concentrated sulfuric acid (2.24 mL) in water (43.3 mL) and the reaction mixture was maintained for 0.5 h. A solution of tin (II) chloride (50.5 mmol) in concentrated hydrochloric acid (19.6 mL) was added dropwise and the reaction mixture was maintained at 0-5° C. for 1 h. The precipitated solids were isolated by filtration and dried to provide the indazole acid as a yellow solid (100% by mass).

Acetylchloride (18 mL) was added to methanol (180 mL) at 0° C. and the reaction mixture maintained for 1 h. The indazole acid (21.8 mmol) was added and the reaction mixture was heated at reflux for 3 h. The solution was concentrated to dryness and the residue was suspended in water and the pH adjusted to 7 with saturated sodium hydrogen carbonate. The mixture was extracted with ethyl acetate (3×100 mL), and the combined organic layers were dried (magnesium sulfate) and concentrated. The crude product was purified by chromatography (2/1 petroleum ether/ethyl acetate) to provide the indazole ester in 5% yield (two steps) as a yellow solid.

The indazole ester (1.02 mmol) was combined with 10% palladium on carbon (30 mg) and methanol (20 mL) under an atmosphere of hydrogen gas for 30 min at rt. The catalyst was removed by filtration and the eluent was concentrated to afford the de-brominated indazole ester in 24% yield as an orange solid.

1 M Sodium hydroxide (1.5 mL) was added to a solution of the de-brominated indazole ester (0.243 mmol) in methanol (3.0 mL) and the reaction mixture was heated at 60° C. for 3 h. The solution was concentrated, the pH adjusted to 1-2, and the solids collected by filtration to provide the indazole acid in 100% yield as a yellow solid.

Procedure 27:

Procedure 27 provides a method for the preparation of benzyloxy-substituted indazole-3-carboxylic acids and esters from the corresponding bromides.

Acetic anhydride (34 mL) and zinc dust (4.59 mmol) were added to a solution of 4-methoxynitrobenzene (230 mmol) in glacial acetic acid (34 mL) and the reaction mixture was heated at reflux for 0.5 h. The reaction mixture was poured into water (340 mL) and the pH of the solution was adjusted to 8 with 10% sodium hydroxide. The precipitated solids were isolated by filtration, washed with water (100 mL), and dried to provide the acetamide in 88% yield.

65% Nitric acid (22 mL) was added dropwise over 0.5 h to a solution of the acetamide (200 mmol) in dichloromethane (200 mL). The reaction mixture was maintained for 1 h at rt and was heated at reflux for 1 h. The reaction mixture was washed with water (200 mL), saturated sodium carbonate solution (100 mL), and water (200 mL). The combined organic layers were dried (magnesium sulfate) and concentrated to provide the nitro acetamide in 90% as a yellow solid.

The nitroacetamide (180 mmol) was added to 4 M sodium hydroxide (180 mL) and the reaction mixture was maintained for 2 h at 60° C. The precipitated solids were isolated by filtration, washed with water, and dried to provide the nitroaniline in 70% yield as a red solid.

A solution of sodium nitrite (11.8 g) in water (28 mL) was added dropwise over 0.5 h to a solution of the nitroaniline (125 mmol) in 40%. hydrobromic acid (110 g) at 10° C. The reaction mixture was maintained for 40 min at 0-10° C. and was filtered. The filtrate was added dropwise over 1 h to a 0° C., purple solution of copper (I) bromide (209 mmol) in hydrobromic acid (74 mL). The reaction mixture was allowed to warm to and maintained at rt for 30 min, was maintained at 60° C. for 0.5 h, and was heated at reflux for 1 h. The reaction mixture was partitioned between water (2.0 L) and dichloromethane (600 mL) and the aqueous layer was further extracted with dichloromethane (300 mL). The combined organic layers were washed with 10% sodium hydroxide (200 mL), water (600 mL), 10% hydrochloric acid (300 mL), and water (600 mL), dried (magnesium sulfate) and concentrated to provide the nitrobromide in 83% yield as a yellow oil.

A solution of boron tribromide (250 mmol) in dichloromethane (200 mL) was added drop wise over 1 h to a solution of the nitrobromide (100 mmol) in dichloromethane (250 mL) at −78° C. The reaction mixture was allowed to warm to rt and was maintained for 30 h. The reaction mixture was cooled to 0° C., quenched with water (300 mL) and the aqueous layer was extracted with ethyl acetate (2×300 mL). The combined organic layers were washed with saturated sodium bicarbonate (2×300 mL), dried (magnesium sulfate), and concentrated to provide the nitrophenol in 87% yield as a brown crystalline solid.

Benzyl bromide (131 mmol) and potassium carbonate (130 mmol) were added to a solution of the nitrophenol (87.0 mmol) in 2/1 acetonitrile/acetone (840 mL). The reaction mixture was heated at reflux for 17 h and was concentrated to dryness. The residue was suspended in ethyl acetate (756 mL), filtered, and the organic layer was washed with water (567 mL), 1 M hydrochloric acid (2×567 mL), and brine (567 mL). The organic layer was dried (magnesium sulfate) and concentrated to the benzyl ether in 78% yield.

Diethyl malonate (890 mmol) was added drop wise over 1 h to a suspension of sodium hydride (520 mmol) in dimethylsulfoxide (100 mL) at 0° C. The benzyl ether (44.0 mmol) was added and the reaction mixture was heated at 100° C. for 5 h. The reaction mixture was poured into ice water and was extracted with ethyl acetate (3×70 mL). The combined organic layers were dried (magnesium sulfate) and concentrated to provide the diethylmalonate addition product. The diethylmalonate addition product was diluted with a 4 M solution of sodium hydroxide (100 mL) and the reaction mixture was heated at 60° C. for 6 h. The solution was extracted with dichloromethane (3×50 mL) and the aqueous layer was adjusted to pH 1 with concentrated hydrochloric acid. The reaction mixture was heated at 60° C. for 1 h, allowed to cool to rt, and was extracted with ethyl acetate (3×50 mL). The combined organic layers were dried (magnesium sulfate) and concentrated to provide the phenylacetic acid in 78% yield as a solid.

The phenylacetic acid (350 mmol) was added to a freshly prepared solution of ethanolic hydrochloric acid [acetyl chloride (5 mL) was added to ethanol (100 mL)] and the reaction mixture was heated at reflux for 20 h. The reaction mixture was concentrated to dryness and the residue was partitioned between saturated sodium bicarbonate (200 mL) and ethyl acetate (150 mL). The aqueous layer was extracted with ethyl acetate (2×50 mL) and the combined organic layers were dried (magnesium sulfate), filtered and concentrated to provide the ester in 77% yield.

The nitro ester (27.0 mmol) was dissolved in acetic acid (60 mL) and acetic anhydride (44 mL) and was cooled to 0° C. Zinc dust (153 mmol) was added and the reaction mixture was allowed to warm to rt and was maintained for 2 h. Additional quantities of zinc dust (2×45.9 mmol) were added during a 3 h course of time. After 1 h, the reaction mixture was filtered and the filter cake was washed with ethanol (100 mL). The combined filtrates were concentrated and the residue was partitioned between saturated sodium bicarbonate and ethyl acetate (50 mL). The solution was extracted with ethyl acetate (2×50 mL) and the combined organic layers were dried (magnesium sulfate), filtered and concentrated to provide the acetamide in 82% yield.

Isoamyl nitrite (47.2 g) was added dropwise over 30 min to a solution of the acetamide (21.0 mmol) in chloroform (80 mL) and acetic anhydride (45 mL). Solid potassium acetate (7.13 mmol) was added in several portions and the reaction mixture was heated at reflux for 1.5 h. The reaction mixture was washed with water (2×80 mL) and brine (80 mL), dried (magnesium sulfate), and concentrated to provide the acetylated indazole ester in 68% yield.

The acetylated indazole ester (15.0 mmol) was suspended in 2 M sodium hydroxide (35 mL) and the reaction mixture was heated at 60° C. for 24 h. The pH of the solution was adjusted to 1-2 with concentrated hydrochloric acid and the solids were collected by filtration and dried to provide 6-benzyloxy-1H-indazole-3-carboxylic acid in 28% yield as a yellow solid.

6-Benzyloxy-1H-indazole-3-carboxylic acid (1.85 mmol) was added to a freshly prepared solution of ethanolic hydrochloric acid [prepared from ethanol (20 mL) and acetyl chloride (5 mL)] and the reaction mixture was heated at reflux for 25 h and was concentrated. The residue was partitioned between saturated sodium bicarbonate (20 mL) and ethyl acetate (20 mL) and the layers were separated. The aqueous layer was extracted with ethyl acetate (2×20 mL) and the combined organic layers were dried (magnesium sulfate) and concentrated. The residue was purified by chromatography (300/1 dichloromethane/methanol) to provide the product in 36.4% yield. Alternatively, the ester can be obtained from the acetylated indazole ester by maintaining the acetylated material in 2 M ammonia in methanol for 30 min.

The following acids were prepared using this method:
6-Benzyloxy-1H-indazole-3-carboxylic acid.
5-Benzyloxy-1H-indazole-3-carboxylic acid (from 4-benzyloxy-2-bromonitrobenzene: Parker, K. A.; Mindt, T. L. *Org. Lett.* 2002, 4, 4265.).
Ethyl 6-benzyloxy-1H-indazole-3-carboxylate.
Ethyl 5-benzyloxy-1H-indazole-3-carboxylate.
Base Preparations.

The following procedures (28-29) detail the preparation of the bicyclobases that were not commercially available.
Procedure 28:

Procedure 28 provides a method for the preparation of N-alkylated 3-aminoquinuclidines from 3-aminoquinuclidine.

Cyclopropanecarbonyl chloride (12 mmol) was added dropwise to a solution of (R)-3-aminoquinuclidine (10 mmol) and N,N-diisopropylethylamine (30 mmol) in dichloromethane (100 mL). The resulting solution was maintained at rt for 4 h and was evaporated to dryness. The crude amide was dissolved in tetrahydrofuran (150 mL) and was treated with lithium aluminum hydride (66 mmol) in small portions. The reaction mixture was quenched with sodium sulfate decahydrate and the resulting slurry was diluted with tetrahydrofuran and filtered through Celite. The filtrate was concentrated and the residue was then diluted with freshly prepared methanolic hydrogen chloride (generated by the dropwise addition of 3 mL of acetyl chloride into 30 mL of methanol) and maintained at rt for 15 min. The residue obtained by the removal of the volatiles was recrystallized (2-propanol/methanol) to provide the secondary amine in 41% yield as a colorless solid.

The following bases were prepared using this method:
(3R)—N-(Cyclopropylmethyl)quinuclidin-3-amine dihydrochloride.
(3S)—N-(Cyclopropylmethyl)quinuclidin-3-amine dihydrochloride.
(3R)—N-(Methyl)quinuclidin-3-amine dihydrochloride.
(3S)—N-(Methyl)quinuclidin-3-amine dihydrochloride.
(3R)—N-(Ethyl)quinuclidin-3-amine dihydrochloride.
(3S)—N-(Ethyl)quinuclidin-3-amine dihydrochloride.
Procedure 29:

Procedure 29 provides a method for the preparation of 1-(1-azabicyclo[2.2.2]oct-3-yl)methanamine dihydrochloride from quinuclidinone.

A solution of p-tolylsulfonylmethyl isocyanide (50 mmol) in ethanol (4 mL) was added to a suspension of quinuclidone (40 mmol) in ethylene glycol dimethyl ether (155 mL) at −5° C. Solid potassium tert-butoxide (130 mmol) was added in portions over 20 min. The Reaction mixture was maintained for 30 min at −5° C. and was then allowed to warm to the rt and maintained for an additional 3 h. The reaction mixture was filtered and was diluted with saturated hydrochloric acid in isopropanol. The reaction mixture was filtered and diluted with ether. The resulting precipitate was collected by filtration to provide the nitrile in 88% yield as a yellow solid.

The solution of the nitrile (35 mmol) in methanol (720 mL) was cooled to 5° C. and was treated with concentrated hydrochloric acid (12 mL) and 10% palladium on carbon (9.6 g). The reaction mixture was maintained under an atmosphere of hydrogen gas for 4.5 h at the rt. The catalyst was removed by filtration and the filtrate was concentrated to afford a yellow solid. The solid was dissolved in methanol and was diluted with ethyl ether. The resulting precipitate was collected by filtration to provide the nitrile in 32% yield as a yellow solid.
Representative Procedures.

The following procedures (A-AG) detail the preparation of the bicyclobase analogs.
Procedure A.

Procedure A provides a method for the coupling between 3-aminoquinuclidine and carboxylic acids to form carboxamide derivatives.

To a solution of the carboxylic acid (16.1 mmol) in N,N-dimethylformamide (65 mL) was added HBTU (16.1 mmol), catalytic amount of dimethylaminopyridine, N,N-diisopropylethylamine (96.6 mmol) and 4 Å activated molecular sieves (2.6 g). The reaction mixture was maintained at room temperature for 2 h under nitrogen and then 3-aminoquinuclidine dihydrochloride (16.1 mmol) was added. After 18 h, the solvent was removed under reduced pressure. The oily residue was partitioned between saturated, aqueous sodium bicarbonate (25 mL) and dichloromethane (100 mL). The aqueous layer was further extracted with 9/1 dichloromethane/methanol (5×100 mL) and the combined organic layers were concentrated. The residue was purified by chromatography [90/10/1 dichloromethane/methanol/ammonium hydroxide or 1/1 to 0/1 ethyl acetate/(70/30/1 ethyl acetate/methanol/ammonium hydroxide)] or by preparative HPLC, thus providing the product in 30%-70% yield.

The following compounds were prepared using this method:

Example 1

N-[(3S)-1-Azabicyclo[2.2.2]oct-3-yl]-5-chloro-1H-indazole-3-carboxamide hydroformate

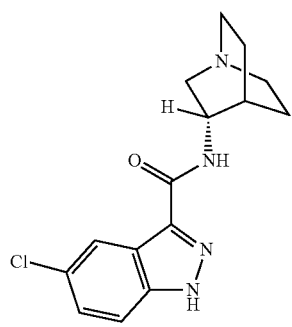

Prepared using Procedure A in 29% yield. $^1$H NMR (CD$_3$OD) δ 8.52 (s, 1H), 8.18 (s, 1H), 7.59 (d, J=8.9, 1H), 7.41 (dd, J=8.9, 1.9, 1H), 4.51 (m, 1H), 3.80 (m, 1H), 3.44 (m, 5H), 2.36 (m, 1H), 2.24 (m, 1H), 2.09 (m, 2H), 1.86 (m, 1H); LC/MS (EI) $t_R$ 2.75, m/z 305 (M$^+$+1).

Example 2

N-[(3S)-1-Azabicyclo[2.2.2]oct-3-yl]-5-fluoro-1H-indazole-3-carboxamide hydroformate

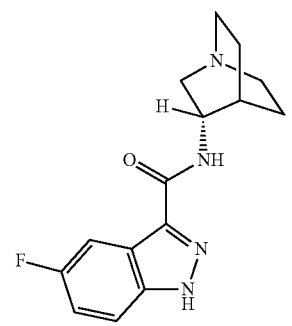

Prepared using Procedure A in 15% yield. LC/MS (EI) $t_R$ 2.86, m/z 289 (M$^+$+1).

Example 3

N-[(3R)-1-Azabicyclo[2.2.2]oct-3-yl]-5-chloro-1H-indazole-3-carboxamide hydroformate

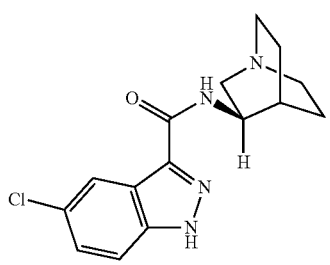

Prepared using Procedure A in 30% yield. LC/MS (EI) $t_R$ 2.76, m/z 305 (M$^+$+1).

Example 4

N-[(3R)-1-Azabicyclo[2.2.2]oct-3-yl]-5-fluoro-1H-indazole-3-carboxamide hydroformate

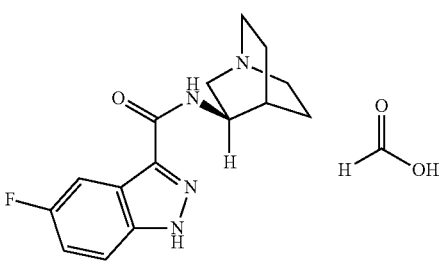 [SMILES: O=C(N[C@H]1CN2CCC1CC2)c1n[nH]c2ccc(F)cc12 ; O=CO]

Prepared using Procedure A in 27% yield. LC/MS (EI) $t_R$ 2.53, m/z 289 (M$^+$+1).

Example 5

N-[(3R)-1-Azabicyclo[2.2.2]oct-3-yl]-5-(trifluoromethoxy)-1H-indazole-3-carboxamide hydroformate

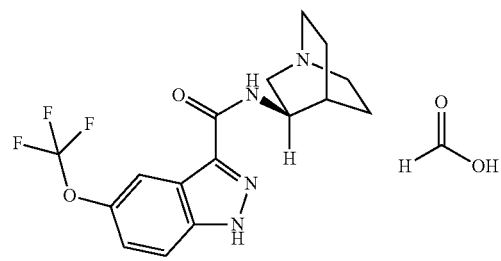 [SMILES: O=C(N[C@H]1CN2CCC1CC2)c1n[nH]c2ccc(OC(F)(F)F)cc12 ; O=CO]

Prepared using Procedure A in 32% yield. LC/MS (EI) $t_R$ 5.15, m/z 355 (M$^+$+1).

Example 6

N-[(3R)-1-Azabicyclo[2.2.2]oct-3-yl]-5-methoxy-1H-indazole-3-carboxamide hydroformate

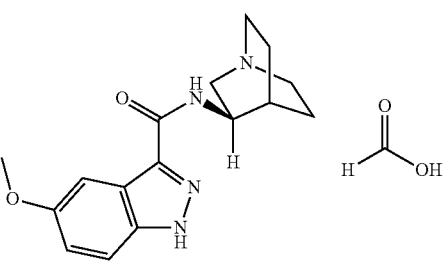 [SMILES: COc1ccc2[nH]nc(C(=O)N[C@H]3CN4CCC3CC4)c2c1 ; O=CO]

Prepared using Procedure A in 38% yield. LC/MS (EI) $t_R$ 2.53, m/z 301 (M$^+$+1).

Example 7

N-[(3S)-1-Azabicyclo[2.2.2]oct-3-yl]-5-(trifluoromethoxy)-1H-indazole-3-carboxamide hydroformate

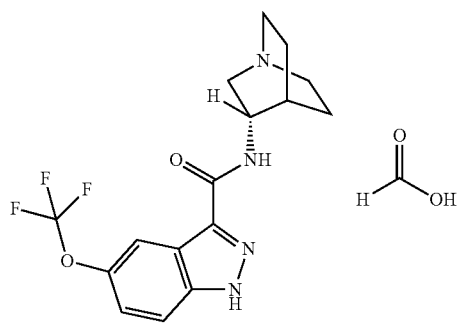 [SMILES: O=C(N[C@@H]1CN2CCC1CC2)c1n[nH]c2ccc(OC(F)(F)F)cc12 ; O=CO]

Prepared using Procedure A in 27% yield. LC/MS (EI) $t_R$ 5.13, m/z 355 (M$^+$+1).

Example 8

N-[(3S)-1-Azabicyclo[2.2.2]oct-3-yl]-5-methoxy-1H-indazole-3-carboxamide hydroformate

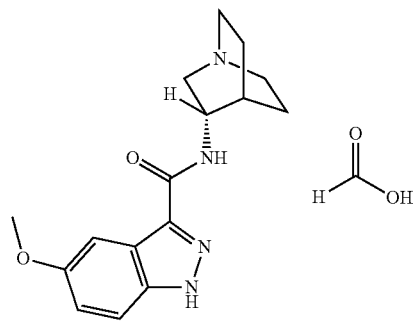 [SMILES: COc1ccc2[nH]nc(C(=O)N[C@@H]3CN4CCC3CC4)c2c1 ; O=CO]

Prepared using Procedure A in 34% yield. LC/MS (EI) $t_R$ 2.53, m/z 301 (M$^+$+1).

Example 9

N-[(3R)-1-Azabicyclo[2.2.2]oct-3-yl]-6-(trifluoromethyl)-1H-indazole-3-carboxamide

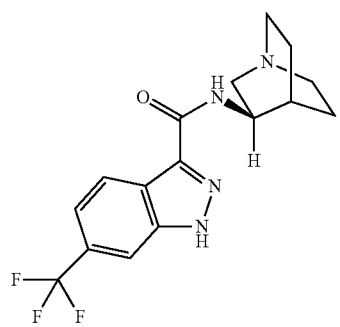 [SMILES: O=C(N[C@H]1CN2CCC1CC2)c1n[nH]c2cc(C(F)(F)F)ccc12]

Prepared using Procedure A in 43% yield. LC/MS (EI) $t_R$ 5.06, m/z 339 (M$^+$+1).

Example 10

N-[(3S)-1-Azabicyclo[2.2.2]oct-3-yl]-6-(trifluoromethyl)-1H-indazole-3-carboxamide

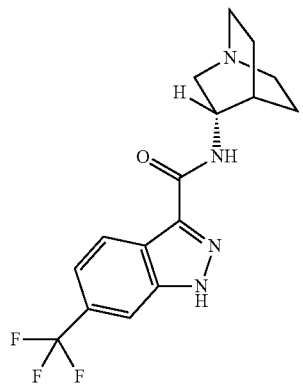 [SMILES: O=C(N[C@@H]1CN2CCC1CC2)c1n[nH]c2cc(C(F)(F)F)ccc12]

Prepared using Procedure A in 45% yield. LC/MS (EI) $t_R$ 5.06, m/z 339 (M$^+$+1).

Example 11

N-[(3S)-1-Azabicyclo[2.2.2]oct-3-yl]-6-methoxy-1H-indazole-3-carboxamide

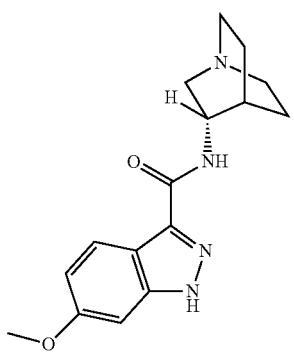 [SMILES: COc1ccc2c(C(=O)N[C@@H]3CN4CCC3CC4)n[nH]c2c1]

Prepared using Procedure A in 63% yield. LC/MS (EI) $t_R$ 2.53, m/z 301 (M$^+$+1).

Example 12

N-[(3R)-1-Azabicyclo[2.2.2]oct-3-yl]-6-methoxy-1H-indazole-3-carboxamide

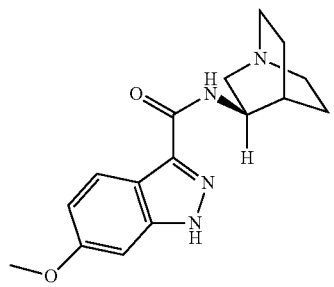 [SMILES: COc1ccc2c(C(=O)N[C@H]3CN4CCC3CC4)n[nH]c2c1]

Prepared using Procedure A in 57% yield. LC/MS (EI) $t_R$ 2.53, m/z 301 (M$^+$+1).

Example 13

N-[(3R)-1-Azabicyclo[2.2.2]oct-3-yl]-6-fluoro-1H-indazole-3-carboxamide

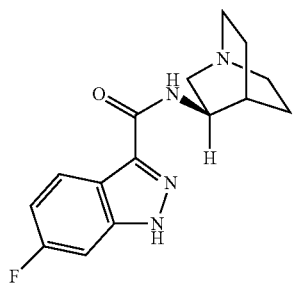 [SMILES: O=C(N[C@H]1CN2CCC1CC2)c1n[nH]c2cc(F)ccc12]

Prepared using Procedure A in 62% yield. LC/MS (EI) $t_R$ 2.53, m/z 289 (M$^+$+1).

Example 14

N-[(3S)-1-Azabicyclo[2.2.2]oct-3-yl]-6-fluoro-1H-indazole-3-carboxamide

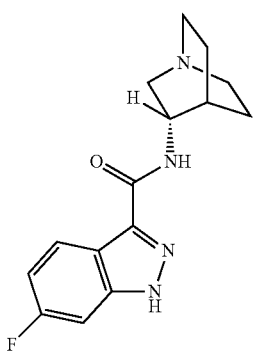 [SMILES: O=C(N[C@@H]1CN2CCC1CC2)c1n[nH]c2cc(F)ccc12]

Prepared using Procedure A in 62% yield. LC/MS (EI) $t_R$ 2.53, m/z 289 (M$^+$+1).

Example 15

N-[(3S)-1-Azabicyclo[2.2.2]oct-3-yl]-4-methoxy-1H-indazole-3-carboxamide

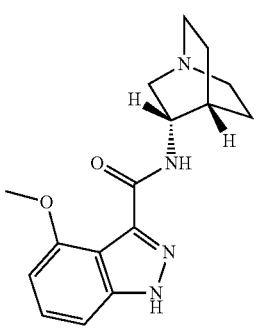

Prepared using Procedure A in 14% yield. LC/MS (EI) $t_R$ 2.50, m/z 301 (M$^+$+1).

Example 16

N-[(3R)-1-Azabicyclo[2.2.2]oct-3-yl]-1,2-benzisoxazole-3-carboxamide hydroformate

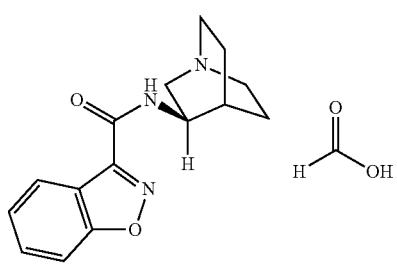 [SMILES: O=C(N[C@H]1CN2CCC1CC2)c1noc2ccccc12 ; O=CO]

Prepared using Procedure A in 20% yield. LC/MS (EI) $t_R$ 3.09, m/z 272 (M$^+$+1).

Example 17

N-[(3S)-1-Azabicyclo[2.2.2]oct-3-yl]-1,2-benzisoxazole-3-carboxamide hydroformate

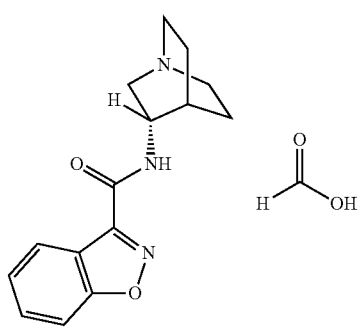 [SMILES: O=C(N[C@@H]1CN2CCC1CC2)c1noc2ccccc12 ; O=CO]

Prepared using Procedure A in 20% yield. LC/MS (EI) $t_R$ 3.12, m/z 272 (M$^+$+1).

Example 18

N-[(3S)-1-Azabicyclo[2.2.2]oct-3-yl]-6-(1,3-oxazol-2-yl)-1,2-benzisothiazole-3-carboxamide hydroformate

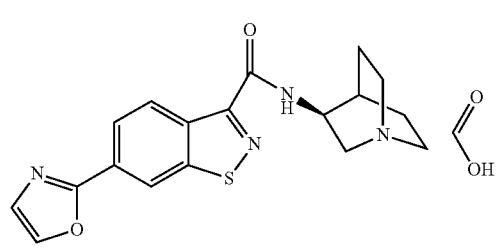

Prepared using Procedure A in 30% yield. LC/MS (EI) $t_R$ 3.40, m/z 355 (M$^+$+1).

Example 19

N-[(3S)-1-Azabicyclo[2.2.2]oct-3-yl]-6-[2,2,2-trifluoro-1-hydroxy-1-(trifluoromethyl)ethyl]-1H-indazole-3-carboxamide

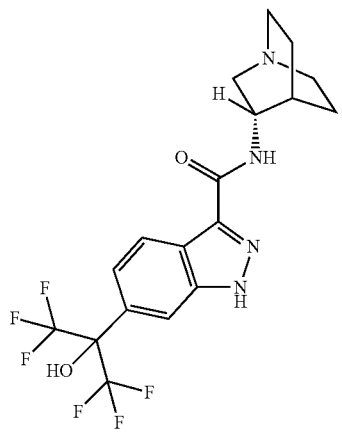 [SMILES: O=C(N[C@@H]1CN2CCC1CC2)c1n[nH]c2cc(C(O)(C(F)(F)F)C(F)(F)F)ccc12]

Prepared using Procedure A in 9% yield. LC/MS (EI) $t_R$ 4.94, m/z 437 (M$^+$+1).

Example 20

N-[(3R)-1-Azabicyclo[2.2.2]oct-3-yl]-6-(3,6-dihydro-2H-pyran-4-yl)-1H-indazole-3-carboxamide hydroformate

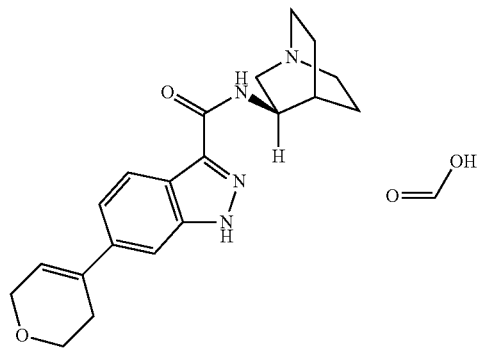 [SMILES: O=C(N[C@H]1CN2CCC1CC2)c1n[nH]c2cc(C3=CCOCC3)ccc12 ; O=CO]

Prepared using Procedure A in 24% yield. LC/MS (EI) $t_R$ 3.62, m/z 353 (M$^+$+1).

Example 21

N-[(3S)-1-Azabicyclo[2.2.2]oct-3-yl]-6-(3,6-dihydro-2H-pyran-4-yl)-1H-indazole-3-carboxamide hydroformate

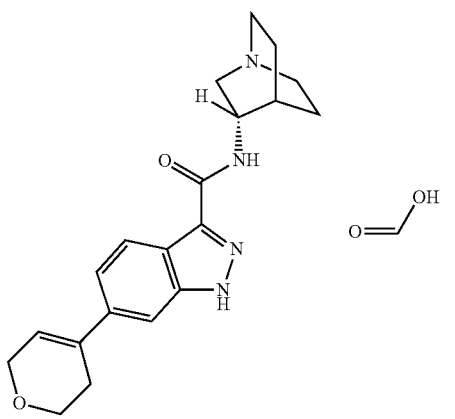 [SMILES: O=C(N[C@@H]1CN2CCC1CC2)c1n[nH]c2cc(C3=CCOCC3)ccc12 ; O=CO]

Prepared using Procedure A in 23% yield. LC/MS (EI) $t_R$ 3.50, m/z 353 (M$^+$+1).

Example 22

N-[(3S)-1-Azabicyclo[2.2.2]oct-3-yl]-5-methoxy-1-methyl-1H-indazole-3-carboxamide

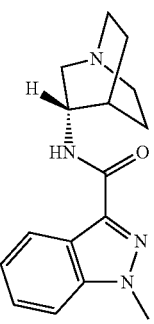

Prepared using Procedure A in 40% yield. LC/MS (EI) $t_R$ 3.03, m/z 315 (M$^+$+1).

Example 23

N-[(3S)-1-Azabicyclo[2.2.2]oct-3-yl]-5-methoxy-1-ethyl-1H-indazole-3-carboxamide

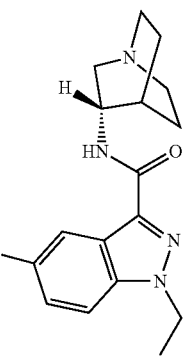

Prepared using Procedure A in 63% yield. LC/MS (EI) $t_R$ 3.26, m/z 329 (M$^+$+1).

Example 24

N-[(3S)-1-Azabicyclo[2.2.2]oct-3-yl]-5-methoxy-1-cyclopentyl-1H-indazole-3-carboxamide

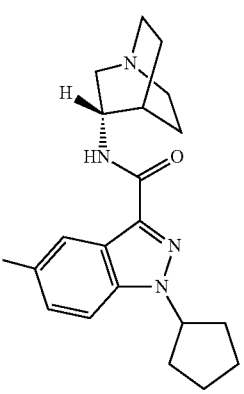

Prepared using Procedure A in 87% yield. LC/MS (EI) $t_R$ 5.45, m/z 369 (M$^+$+1).

Example 25

N-[(3S)-1-Azabicyclo[2.2.2]oct-3-yl]-7-bromo-6-methoxy-1H-indazole-3-carboxamide

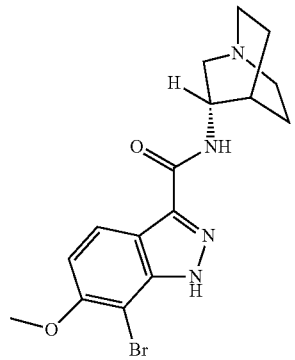 [SMILES: COc1ccc2c(C(=O)N[C@@H]3CN4CCC3CC4)n[nH]c2c1Br]

Prepared using Procedure A in 12% yield. LC/MS (EI) $t_R$ 4.36, m/z 379/381 (M$^+$+1).

Example 26

N-[(3S)-1-Azabicyclo[2.2.2]oct-3-yl]-1,8-dihydropyrrolo[3,2-g]indazole-3-carboxamide

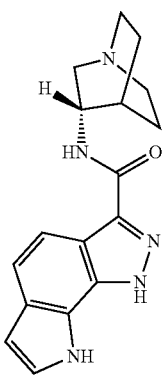 [SMILES: O=C(N[C@@H]1CN2CCC1CC2)c1n[nH]c2c1ccc1cc[nH]c12]

Prepared using Procedure A in 35% yield. LC/MS (EI) $t_R$ 2.20, m/z 310 (M$^+$+1).

Example 27

N-[(3R)-1-Azabicyclo[2.2.2]oct-3-yl]-1-benzyl-6-(difluoromethoxy)-1H-indazole-3-carboxamide hydroformate

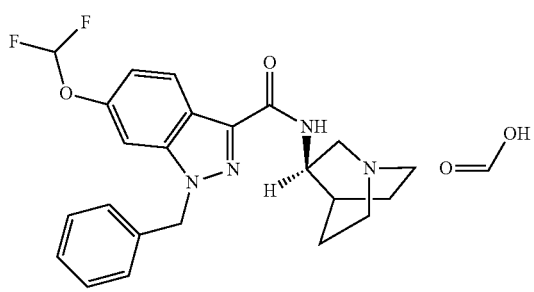

Prepared using Procedure A in 18% yield. LC/MS (EI) $t_R$ 5.27, m/z 427 (M$^+$+1).

Example 28

N-[(3S)-1-Azabicyclo[2.2.2]oct-3-yl]-1-(3-thienyl)-1H-indazole-3-carboxamide hydroformate

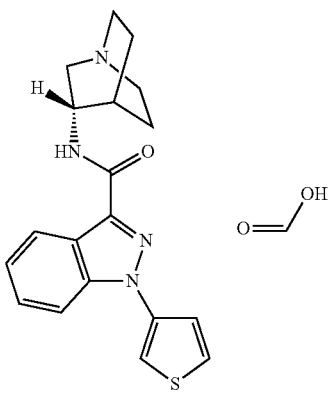 [SMILES: O=C(N[C@@H]1CN2CCC1CC2)c1nn(-c2ccsc2)c2ccccc12 ; O=CO]

Prepared using Procedure A in 16% yield. LC/MS (EI) $t_R$ 5.10, m/z 353 (M$^+$+1).

Example 29

N-[(3S)-1-Azabicyclo[2.2.2]oct-3-yl]-5-(difluoromethoxy)-1H-indazole-3-carboxamide

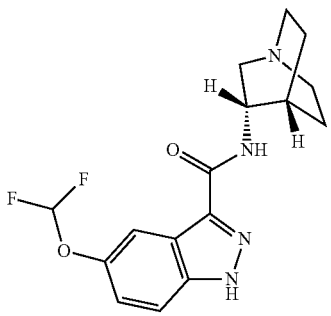

Prepared using Procedure A in 30% yield. LC/MS (EI) $t_R$ 4.41, m/z 337 (M$^+$+1).

Example 30

N-[(3R)-1-Azabicyclo[2.2.2]oct-3-yl]-5-(difluoromethoxy)-1H-indazole-3-carboxamide

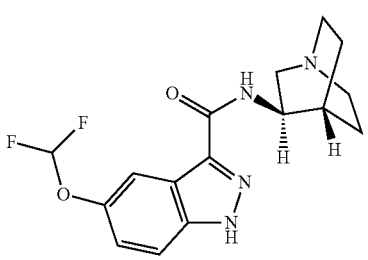

Prepared using Procedure A in 16% yield. LC/MS (EI) $t_R$ 4.27, m/z 337 (M$^+$+1).

Example 31

N-[(3R)-1-Azabicyclo[2.2.2]oct-3-yl]-5-(5-methyl-1,3-thiazol-2-yl)-1H-indazole-3-carboxamide hydroformate

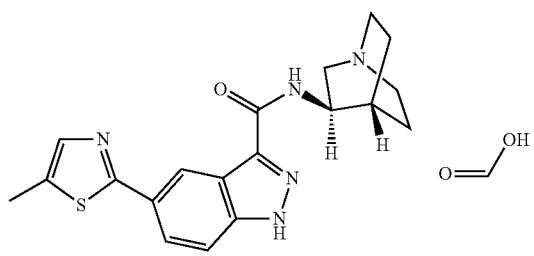

Prepared using Procedure A in 5.3% yield. LC/MS (EI) $t_R$ 2.93, m/z 368 (M$^+$+1).

Example 32

N-[(3S)-1-Azabicyclo[2.2.2]oct-3-yl]-7-methoxy-1H-indazole-3-carboxamide hydroformate

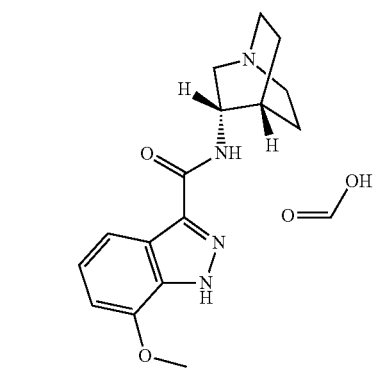

Prepared using Procedure A in 12% yield. LC/MS (EI) $t_R$ 2.43, m/z 301 (M$^+$+1).

Example 33

N-[(3S)-1-Azabicyclo[2.2.2]oct-3-yl]-7-fluoro-6-methoxy-1H-indazole-3-carboxamide hydroformate

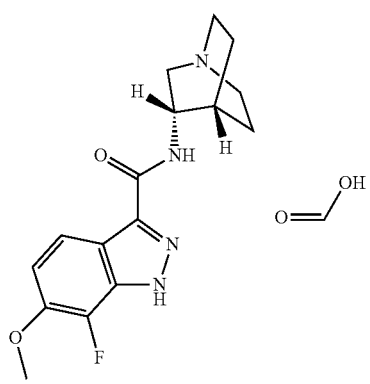

Prepared using Procedure A in 20% yield. LC/MS (EI) $t_R$ 268.00, m/z 319 (M$^+$+1).

Example 34

N-[(3S)-1-Azabicyclo[2.2.2]oct-3-yl]-4-fluoro-5-methoxy-1H-indazole-3-carboxamide hydroformate

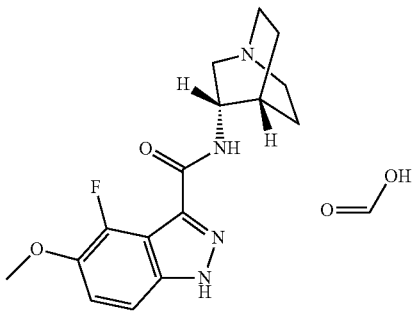

Prepared using Procedure A in 29% yield. LC/MS (EI) $t_R$ 2.40, m/z 319 (M$^+$+1).

Example 35

N-[(3S)-1-Azabicyclo[2.2.2]oct-3-yl]-6-(difluoromethoxy)-1H-indazole-3-carboxamide

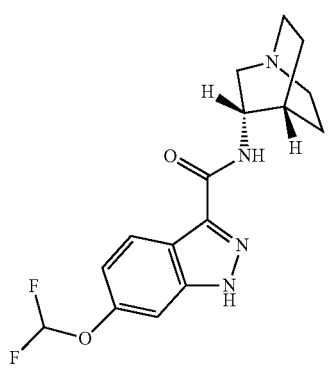

Prepared using Procedure A in 34% yield. LC/MS (EI) $t_R$ 3.71, m/z 337 (M$^+$+1).

Example 36

N-[(3R)-1-Azabicyclo[2.2.2]oct-3-yl]-6-(difluoromethoxy)-1H-indazole-3-carboxamide

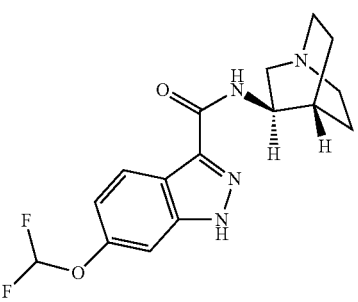

Prepared using Procedure A in 22% yield. LC/MS (EI) $t_R$ 3.72, m/z 337 (M$^+$+1).

Example 37

N-[(3R)-1-Azabicyclo[2.2.2]oct-3-yl]-5-(4-methyl-1,3-thiazol-2-yl)-1H-indazole-3-carboxamide hydroformate

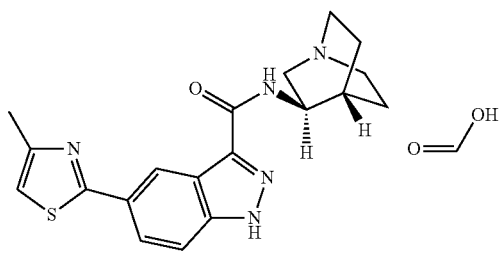

Prepared using Procedure A in 24% yield. LC/MS (EI) $t_R$ 4.34, m/z 368 (M$^+$+1).

Example 38

N-[(3S)-1-Azabicyclo[2.2.2]oct-3-yl]-5-(5-methyl-1,3-thiazol-2-yl)-1H-indazole-3-carboxamide hydroformate

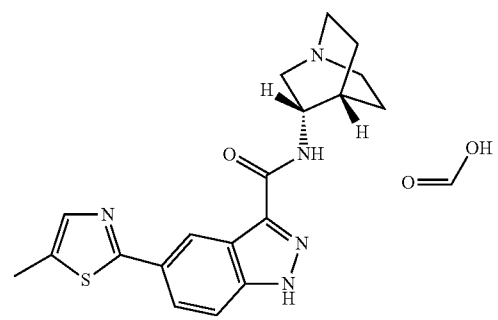

Prepared using Procedure A in 21% yield. LC/MS (EI) $t_R$ 4.50, m/z 368 (M$^+$+1).

Example 39

N-[(3S)-1-Azabicyclo[2.2.2]oct-3-yl]-5-cyclopropyl-6-methoxy-1H-indazole-3-carboxamide hydroformate

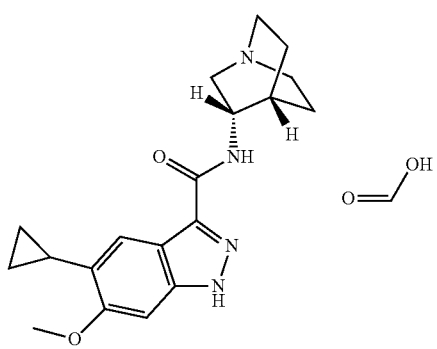

Prepared using Procedure A in 10% yield. LC/MS (EI) $t_R$ 4.66, m/z 341 (M$^+$+1).

Example 40

N-[(3S)-1-Azabicyclo[2.2.2]oct-3-yl]-6-methoxy-5-(3-thienyl)-1H-indazole-3-carboxamide hydroformate

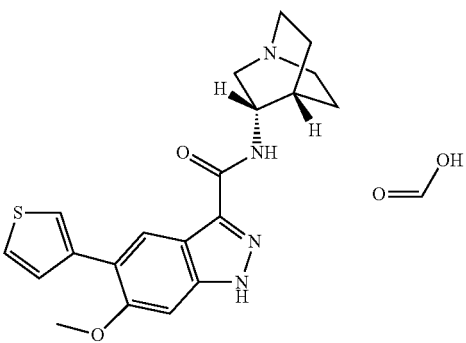

Prepared using Procedure A in 13% yield. LC/MS (EI) $t_R$ 5.10, m/z 383 (M$^+$+1).

Example 41

N-[(3S)-1-azabicyclo[2.2.2]oct-3-yl]-5-[3-(benzyloxy)pyrrolidin-1-yl]-1H-indazole-3-carboxamide hydroformate

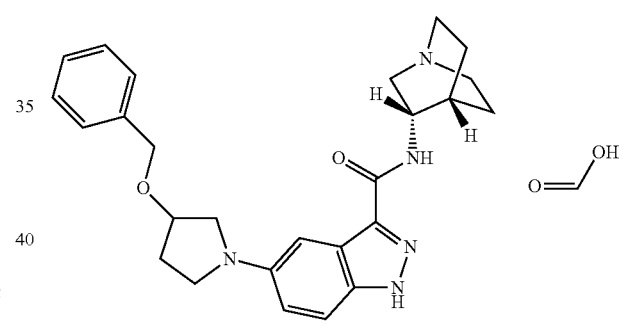

Prepared using Procedure A in 4% yield. LC/MS (EI) $t_R$ 5.26, m/z 446 (M$^+$+1).

Example 42

N-[(3S)-1-Azabicyclo[2.2.2]oct-3-yl]-5-[3-(methyloxy)pyrrolidin-1-yl]-1H-indazole-3-carboxamide hydroformate

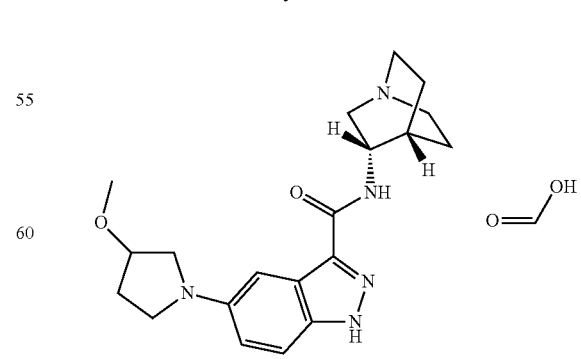

Prepared using Procedure A in 46% yield. LC/MS (EI) $t_R$ 2.39, m/z 370 (M$^+$+1).

Example 43

N-[(3S)-1-Azabicyclo[2.2.2]oct-3-yl]-5-[3-(hydroxy)pyrrolidin-1-yl]-1H-indazole-3-carboxamide hydroformate

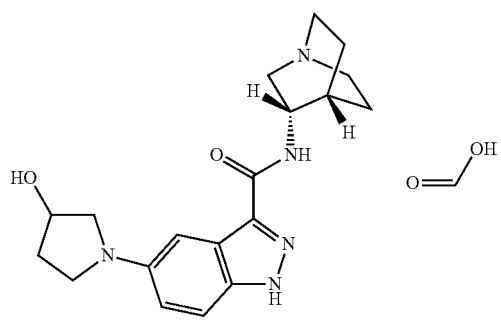

Prepared using Procedure A in 13% yield. LC/MS (EI) $t_R$ 2.39, m/z 356 (M$^+$+1).

Example 44

N-[(3S)-1-Azabicyclo[2.2.2]oct-3-yl]-5-[(1-methylpyrrolidin-3-yl)oxy]-1H-indazole-3-carboxamide dihydroformate

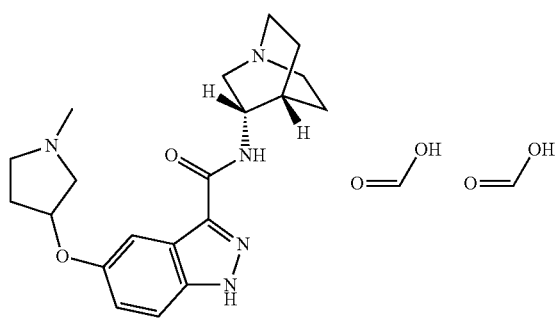

Prepared using Procedure A in 40% yield. LC/MS (EI) $t_R$ 1.89, m/z 370 (M$^+$+1).

Example 45

N-(1-Azabicyclo[2.2.2]oct-3-ylmethyl)-5-(trifluoromethoxy)-1H-indazole-3-carboxamide hydroformate

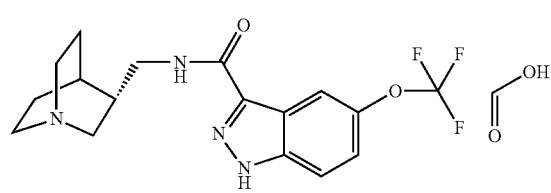

Prepared using Procedure A in 25% yield. LC/MS (EI) $t_R$ 5.15, m/z 369 (M$^+$+1).

Example 46

N-(1-Azabicyclo[2.2.2]oct-3-ylmethyl)-6-methoxy-1H-indazole-3-carboxamide hydroformate

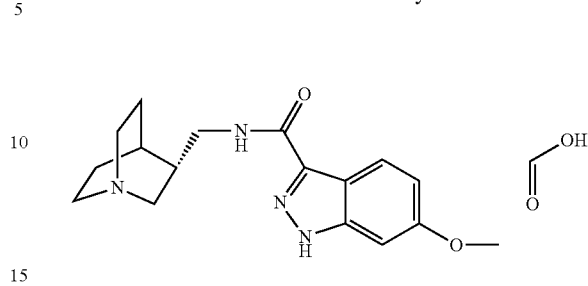

Prepared using Procedure A in 25% yield. LC/MS (EI) $t_R$ 2.80, m/z 315 (M$^+$+1).

Example 47

N-[(3S)-1-Azabicyclo[2.2.2]oct-3-yl]-5-(cyclopropylmethoxy)-1H-indazole-3-carboxamide hydroformate

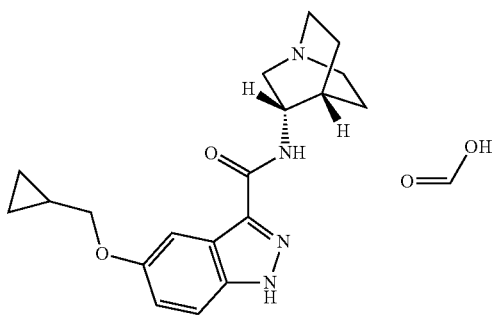

Prepared using Procedure A in 37% yield. LC/MS (EI) $t_R$ 4.66, m/z 341 (M$^+$+1).

Example 48

N-[(3S)-1-Azabicyclo[2.2.2]oct-3-yl]-5-(cyclopentyloxy)-1H-indazole-3-carboxamide hydroformate

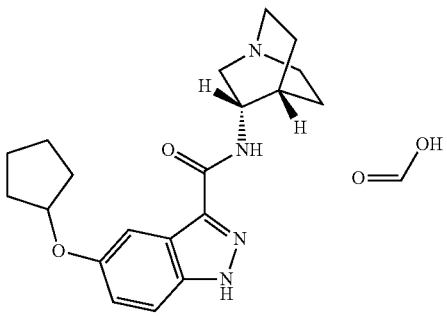

Prepared using Procedure A in 30% yield. LC/MS (EI) $t_R$ 4.90, m/z 355 (M$^+$+1).

Example 49

N-[(3S)-1-Azabicyclo[2.2.2]oct-3-yl]-5-(2,2,2-trifluoroethoxy)-1H-indazole-3-carboxamide hydroformate

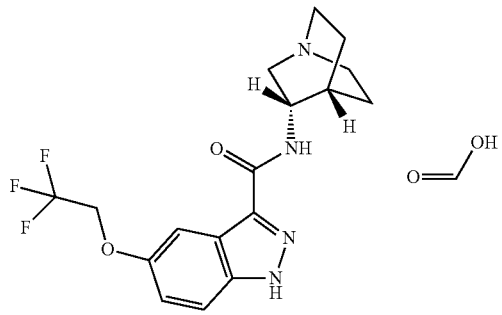

Prepared using Procedure A mod in 40% yield. LC/MS (EI) $t_R$ 4.70, m/z 369 (M$^+$+1).

Example 50

N-[(3S)-1-Azabicyclo[2.2.2]oct-3-yl]-6-(cyclopropylmethoxy)-1H-indazole-3-carboxamide hydroformate

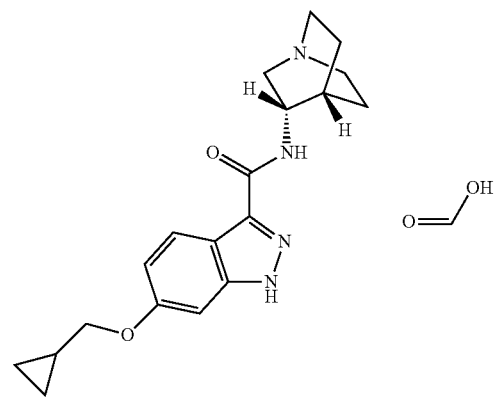

Prepared using Procedure A in 36% yield. LC/MS (EI) $t_R$ 4.59, m/z 341 (M$^+$+1).

Example 51

N-[(3S)-1-Azabicyclo[2.2.2]oct-3-yl]-6-(2,2,2-trifluoroethoxy)-1H-indazole-3-carboxamide hydroformate

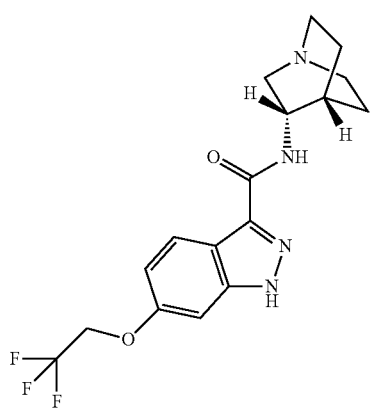

Prepared using Procedure A in 78% yield. LC/MS (EI) $t_R$ 4.75, m/z 369 (M$^+$+1).

Example 52

N-[(3S)-1-Azabicyclo[2.2.2]oct-3-yl]-5-(benzyloxy)-1H-indazole-3-carboxamide hydroformate

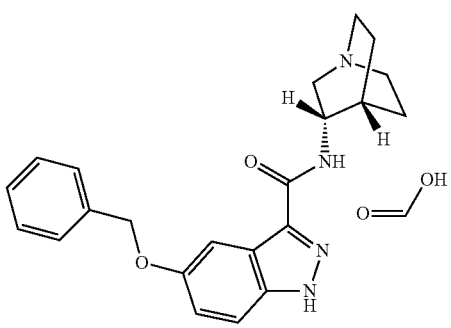

Prepared using Procedure A in 33% yield. LC/MS (EI) $t_R$ 5.09, m/z 377 (M$^+$+1).

Example 53

N-[(3S)-1-Azabicyclo[2.2.2]oct-3-yl]-5-(tetrahydro-2H-pyran-4-yloxy)-1H-indazole-3-carboxamide hydroformate

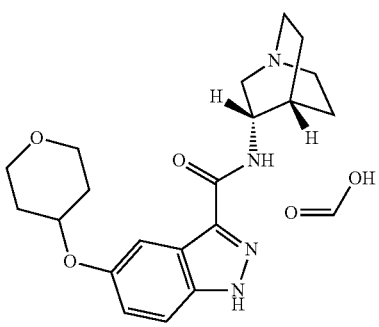

Prepared using Procedure A in 67% yield. LC/MS (EI) $t_R$ 2.79, m/z 371 (M$^+$+1).

Example 54

N-[(3S)-1-Azabicyclo[2.2.2]oct-3-yl]-5-(2,3-dihydro-1H-inden-2-yloxy)-1H-indazole-3-carboxamide hydroformate

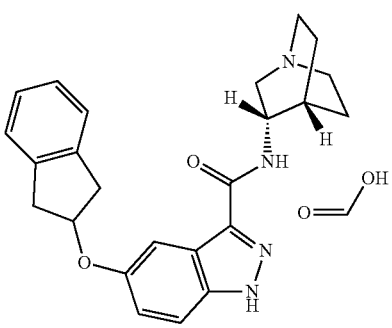

Prepared using Procedure A in 37% yield. LC/MS (EI) $t_R$ 4.26, m/z 403 (M$^+$+1).

Example 55

N-[(3S)-1-Azabicyclo[2.2.2]oct-3-yl]-5-[2-(dimethylamino)ethoxy]-1H-indazole-3-carboxamide dihydroformate

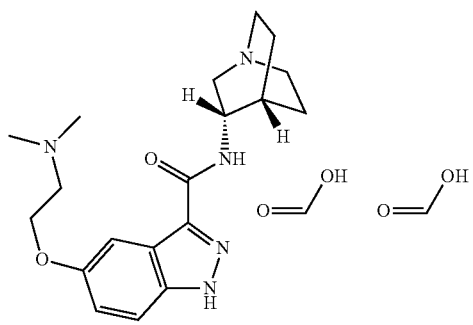

Prepared using Procedure A mod in 24% yield. LC/MS (EI) $t_R$ 1.90, m/z 358 (M$^+$+1).

Example 56

N-[(3S)-1-Azabicyclo[2.2.2]oct-3-yl]-5-(2-pyrrolidin-1-ylethoxy)-1H-indazole-3-carboxamide dihydroformate

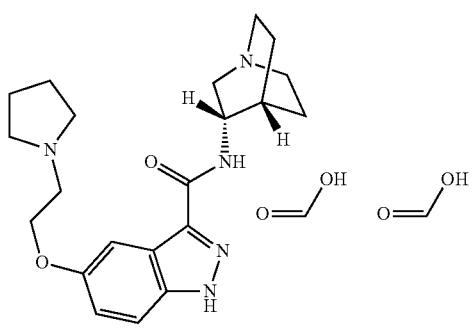

Prepared using Procedure A in 49% yield. LC/MS (EI) $t_R$ 1.88, m/z 384 (M$^+$+1).

Example 57

N-[(3S)-1-Azabicyclo[2.2.2]oct-3-yl]-6-methoxy-N-methyl-1H-indazole-3-carboxamide hydroformate

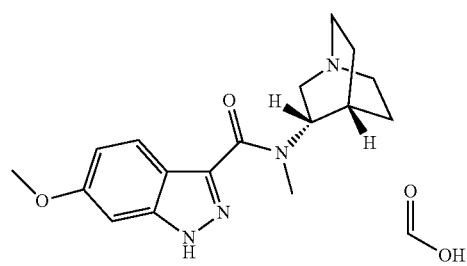

Prepared using Procedure A in 12% yield. LC/MS (EI) $t_R$ 2.52, m/z 315 (M$^+$+1).

Procedure B.

Procedure B provides a method for the coupling between 3-aminoquinuclidine and benzisothiazole carboxylic acids to form carboxamide derivatives.

To a solution of 6-methoxybenzisothiazole-3-carboxylic acid (61 mg, 0.30 mmol) in a 5/1 mixture of tetrahydrofuran/N,N-dimethylformamide (12 mL) was added diisopropylethylamine (0.2 mL, 1.1 mmol) and (115 mg, 0.6 mmol) 3-(R)-aminoquinuclidine dihydrochloride. The mixture was cooled to 0° C., and HATU (115 mg, 0.3 mmol) was added in one portion. The reaction mixture was allowed to warm to rt and was maintained overnight. The mixture was partitioned between saturated aqueous potassium carbonate solution and a 95/5 mixture of dichloromethane/methanol. The aqueous layer was extracted with 95/5 dichloromethane/methanol (2×), and the combined organic layers were washed with brine and dried over sodium sulfate. The crude product was purified by chromatography (90/10/1 dichloromethane/methanol/ammonium hydroxide) or by preparative HPLC, thus providing the amide in 75% yield as a colorless solid.

The following compounds were prepared using this method:

Example 58

N-[(3R)-1-Azabicyclo[2.2.2]oct-3-yl]-6-(trifluoromethoxy)-1,2-benzisothiazole-3-carboxamide hydroformate

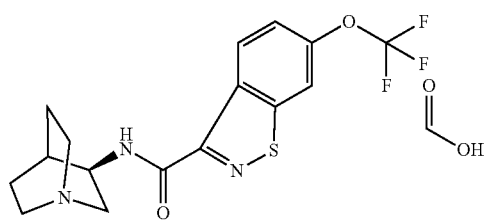

Prepared using Procedure B in 17% yield. $^1$H NMR (CD$_3$OD) δ 8.85 (d, J=9.0, 1H), 8.49 (s, 1H), 8.13 (s, 1H), 7.48 (d, J=9.0, 1H), 4.55 (m, 1H), 3.88-3.80 (m, 1H), 3.53-3.30 (m, 5H), 2.40 (m, 1H), 2.32-2.27 (m, 1H), 2.16-2.10 (m, 2H), 1.99-1.91 (m, 1H); LC/MS (EI) $t_R$ 4.58, m/z 372 (M$^+$+1).

Example 59

N-[(3R)-1-Azabicyclo[2.2.2]oct-3-yl]-6-ethoxy-1,2-benzisothiazole-3-carboxamide hydroformate

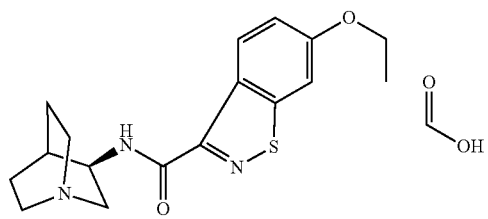

Prepared using Procedure B in 37% yield. LC/MS (EI) $t_R$ 4.42, m/z 332 (M$^+$+1).

Example 60

N-[(3S)-1-Azabicyclo[2.2.2]oct-3-yl]-6-ethoxy-1,2-benzisothiazole-3-carboxamide hydroformate

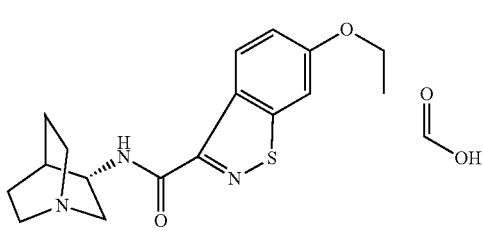

Prepared using Procedure B in 12% yield. LC/MS (EI) $t_R$ 4.31, m/z 332 (M$^+$+1).

Example 61

N-[(3S)-1-Azabicyclo[2.2.2]oct-3-yl]-6-(trifluoromethoxy)-1,2-benzisothiazole-3-carboxamide hydroformate

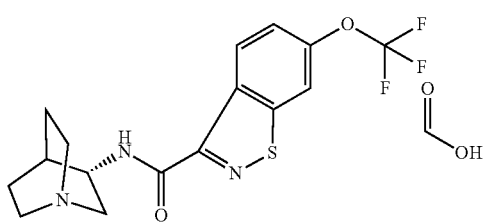

Prepared using Procedure B in 41% yield. LC/MS (EI) $t_R$ 4.62, m/z 372 (M$^+$+1).

Example 62

N-[(3R)-1-Azabicyclo[2.2.2]oct-3-yl]-6-(cyclopropylmethoxy)-1,2-benzisothiazole-3-carboxamide

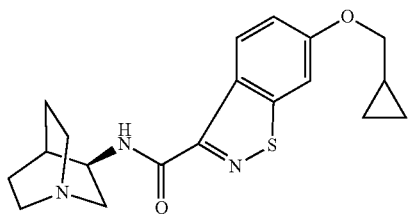 [SMILES: O=C(N[C@H]1CN2CCC1CC2)c1nsc2cc(OCC3CC3)ccc12]

Prepared using Procedure B in 36% yield. LC/MS (EI) $t_R$ 4.34, m/z 358 (M$^+$+1).

Example 63

N-[(3S)-1-Azabicyclo[2.2.2]oct-3-yl]-6-(cyclopropylmethoxy)-1,2-benzisothiazole-3-carboxamide

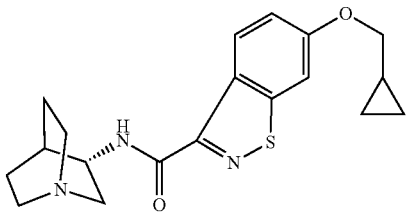 [SMILES: O=C(N[C@@H]1CN2CCC1CC2)c1nsc2cc(OCC3CC3)ccc12]

Prepared using Procedure B in 53% yield. LC/MS (EI) $t_R$ 4.33, m/z 358 (M$^+$+1).

Procedure C.

Procedure C provides a method for the coupling between 3-aminoquinuclidine and carboxylic acids to form carboxamide derivatives.

To a solution of the carboxylic acid (4.77 mmol) in N,N-dimethylformamide (14 mL) was added N,N-diisopropylethylamine (19 mmol) and 3-aminoquinuclidine dihydrochloride (4.29 mmol). The reaction mixture was maintained at room temperature for 30 min under nitrogen and then HATU (4.76 mol) was added. After 18 h, the reaction mixture was filtered through Celite (methanol rinse) and was divided equally amongst 3 SCX columns. The columns were washed with methanol (100 mL each) and the basic components were eluted with 2 M ammonia in methanol (100 mL each) and concentrated. The residue was purified by chromatography [1/1 to 0/1 ethyl acetate/(70/30/1 ethyl acetate/methanol/ammonium hydroxide)] or by preparative HPLC, thus providing the product in 15%-50% yield.

The following compounds were prepared using this method:

Example 64

N-[(3S)-1-Azabicyclo[2.2.2]oct-3-yl]-5-(tetrahydro-2H-pyran-4-yl)-1H-indazole-3-carboxamide

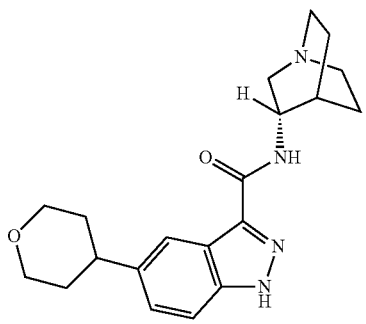 [SMILES: O=C(N[C@@H]1CN2CCC1CC2)c1n[nH]c2ccc(C3CCOCC3)cc12]

Prepared using Procedure C in 22% yield. $^1$H NMR (CD$_3$OD) δ 8.07 (s, 1H), 7.53 (d, J=8.4, 1H), 7.38 (d, J=8.4, 1H), 4.25 (m, 1H), 4.08 (m, 2H), 3.60 (m, 2H), 3.36 (m, 1H), 3.15 (m, 1H), 3.0-2.8 (m, 5H), 2.11 (m, 1H), 2.05 (m, 1H), 2.0-1.7 (m, 6H), 1.62 (m, 1H); LC/MS (EI) $t_R$ 3.44, m/z 355 (M$^+$+1).

Example 65

N-[(3S)-1-Azabicyclo[2.2.2]oct-3-yl]-5-(hydroxy)-1H-indazole-3-carboxamide

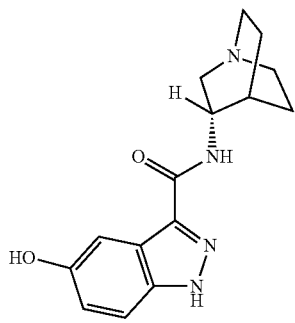 [SMILES: O=C(N[C@@H]1CN2CCC1CC2)c1n[nH]c2ccc(O)cc12]

Prepared using Procedure C or Procedure AA. $^1$H NMR (400 MHz, Me$_2$SO-d$_6$) δ 13.30 (s, 1H), 9.32 (s, 1H), 8.07 (d, J=7.6, 1H), 7.43 (m, 1H), 6.94 (m, 1H), 4.01 (m, 1H), 3.12 (m, 1H), 2.93 (m, 1H), 2.72 (m, 4H), 1.89 (m, 1H), 1.80 (m, 1H), 1.61 (m, 2H), 1.33 (m, 1H); LC/MS (EI) m/z 288 (M$^+$+1).

Example 66

N-[(3S)-1-Azabicyclo[2.2.2]oct-3-yl]-6-hydroxy-1H-indazole-3-carboxamide hydroformate

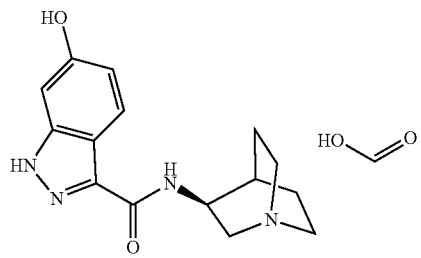 [SMILES: O=C(N[C@@H]1CN2CCC1CC2)c1n[nH]c2cc(O)ccc12 ; O=CO]

Prepared using Procedure C or Procedure AA in 11% yield. LC/MS (EI) t$_R$ 2.35, m/z 288 (M$^+$+1).

Example 67

N-[(3R)-1-azabicyclo[2.2.2]oct-3-yl]-6-hydroxy-1H-indazole-3-carboxamide hydroformate

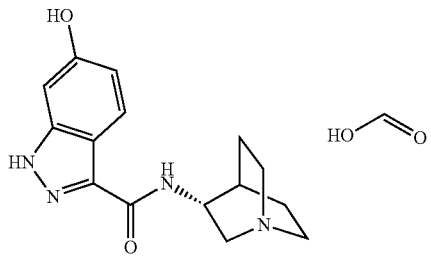 [SMILES: O=C(N[C@H]1CN2CCC1CC2)c1n[nH]c2cc(O)ccc12 ; O=CO]

Prepared using Procedure C or Procedure AA in 11% yield. LC/MS (EI) t$_R$ 2.37, m/z 287 (M$^+$+1).

Example 68

N-[(3S)-1-Azabicyclo[2.2.2]oct-3-yl]-6-(trifluoromethoxy)-1H-indazole-3-carboxamide hydroformate

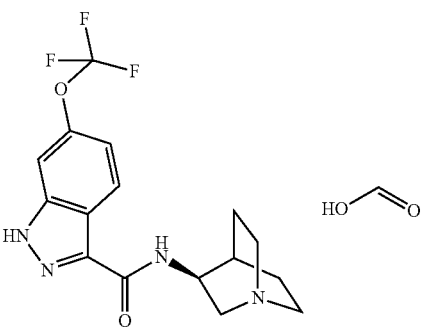 [SMILES: O=C(N[C@@H]1CN2CCC1CC2)c1n[nH]c2cc(OC(F)(F)F)ccc12 ; O=CO]

Prepared using Procedure C in 17% yield. LC/MS (EI) t$_R$ 4.85, m/z 355 (M$^+$+1).

Example 69

N-[(3R)-1-Azabicyclo[2.2.2]oct-3-yl]-6-(trifluoromethoxy)-1H-indazole-3-carboxamide hydroformate

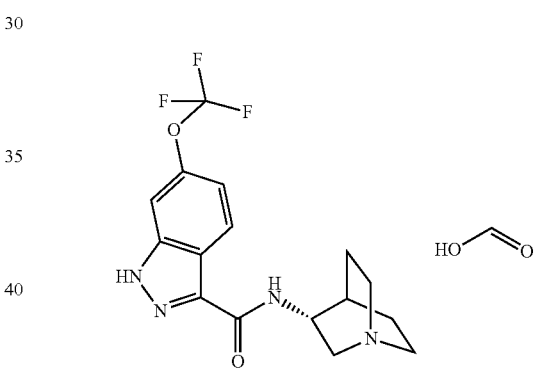

Prepared using Procedure C in 14% yield. LC/MS (EI) t$_R$ 4.84, m/z 355 (M$^+$+1).

Example 70

N-[(3S)-1-Azabicyclo[2.2.2]oct-3-yl]-7-(trifluoromethoxy)-1H-indazole-3-carboxamide hydroformate

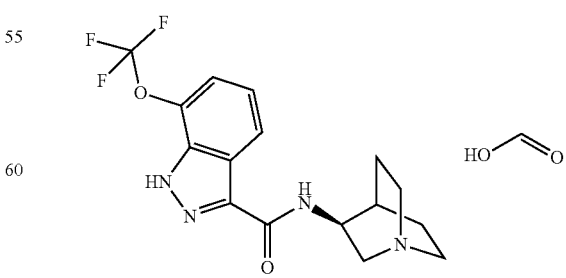

Prepared using Procedure C in 41% yield. LC/MS (EI) t$_R$ 4.71, m/z 355 (M$^+$+1).

Example 71

N-[(3R)-1-Azabicyclo[2.2.2]oct-3-yl]-7-(trifluoromethoxy)-1H-indazole-3-carboxamide hydroformate

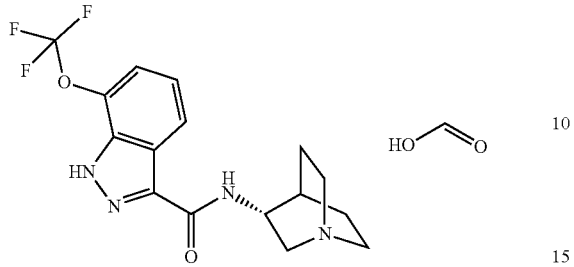

Prepared using Procedure C in 41% yield. LC/MS (EI) $t_R$ 4.73, m/z 355 (M$^+$+1).

Example 72

N-[(3S)-1-Azabicyclo[2.2.2]oct-3-yl]-5-(nitro)-1H-indazole-3-carboxamide

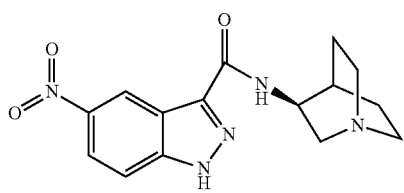 [SMILES: O=C(N[C@@H]1CN2CCC1CC2)c1n[nH]c2ccc([N+](=O)[O-])cc12]

Prepared using Procedure C in 73% yield. LC/MS (EI) $t_R$ 3.43, m/z 316 (M$^+$+1).

Example 73

N-[(3S)-1-Azabicyclo[2.2.2]oct-3-yl]-6-(hydroxy)-1,2-benzisothiazole-3-carboxamide

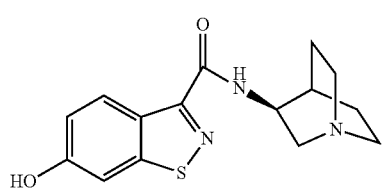 [SMILES: O=C(N[C@@H]1CN2CCC1CC2)c1nsc2cc(O)ccc12]

Prepared using Procedure C or Procedure AA in 70% yield. LC/MS (EI) $t_R$ 2.75, m/z 304 (M$^+$+1).

Example 74

N-[(3S)-1-Azabicyclo[2.2.2]oct-3-yl]-6-nitro-1H-indazole-3-carboxamide

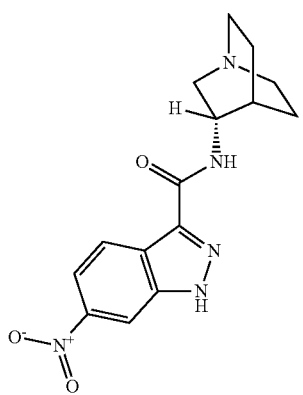 [SMILES: O=C(N[C@@H]1CN2CCC1CC2)c1n[nH]c2cc([N+](=O)[O-])ccc12]

Prepared using Procedure C in 18% yield. LC/MS (EI) $t_R$ 2.42, m/z 316 (M$^+$+1).

Example 75

N-[(3S)-1-Azabicyclo[2.2.2]oct-3-yl]-5-nitro-1H-indazole-3-carboxamide

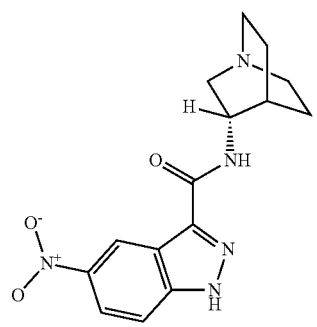 [SMILES: O=C(N[C@@H]1CN2CCC1CC2)c1n[nH]c2ccc([NH+]([O-])O)cc12]

Prepared using Procedure C in 31% yield. LC/MS (EI) $t_R$ 3.18, m/z 316 (M$^+$+1).

Example 76

N-[(3R)-1-Azabicyclo[2.2.2]oct-3-yl]-5-(tetrahydro-2H-pyran-4-yl)-1H-indazole-3-carboxamide

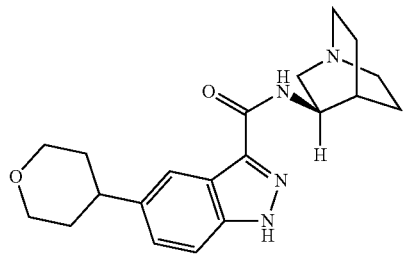 [SMILES: O=C(N[C@H]1CN2CCC1CC2)c1n[nH]c2ccc(C3CCOCC3)cc12]

Prepared using Procedure C in 23% yield. LC/MS (EI) $t_R$ 3.33, m/z 355 (M$^+$+1).

Example 77

N-[(3R)-1-Azabicyclo[2.2.2]oct-3-yl]-5-(nitro)-1H-indazole-3-carboxamide

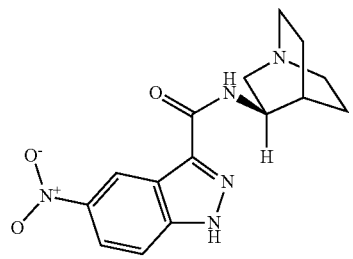 [SMILES: O=C(N[C@H]1CN2CCC1CC2)c1n[nH]c2ccc([NH+]([O-])O)cc12]

Prepared using Procedure C in 28% yield. LC/MS (EI) $t_R$ 2.43, m/z 316 (M$^+$+1).

Example 78

N-[(3R)-1-Azabicyclo[2.2.2]oct-3-yl]-6-(4-hydroxytetrahydro-2H-pyran-4-yl)-1H-indazole-3-carboxamide

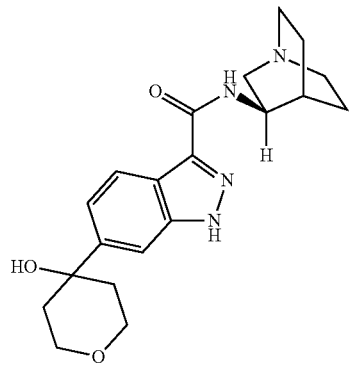 [SMILES: O=C(N[C@H]1CN2CCC1CC2)c1n[nH]c2cc(C3(O)CCOCC3)ccc12]

Prepared using Procedure C in 20% yield. LC/MS (EI) $t_R$ 2.39, m/z 371 (M$^+$+1).

Example 79

N-[(3S)-1-Azabicyclo[2.2.2]oct-3-yl]-6-(4-hydroxytetrahydro-2H-pyran-4-yl)-1H-indazole-3-carboxamide

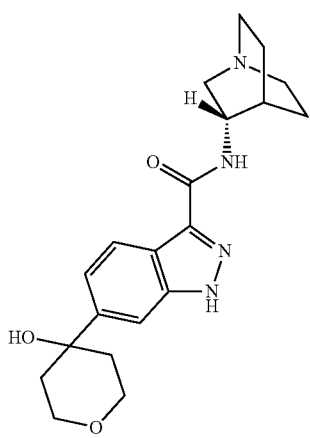 [SMILES: O=C(N[C@@H]1CN2CCC1CC2)c1n[nH]c2cc(C3(O)CCOCC3)ccc12]

Prepared using Procedure C in 30% yield. LC/MS (EI) $t_R$ 2.39, m/z 371 (M$^+$+1).

Example 80

N-[(3S)-1-Azabicyclo[2.2.2]oct-3-yl]-7-(nitro)-1H-indazole-3-carboxamide

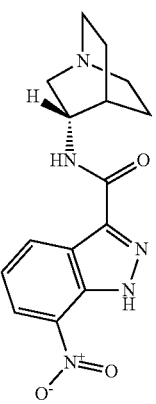 [SMILES: O=C(N[C@@H]1CN2CCC1CC2)c1n[nH]c2c([N+](=O)[O-])cccc12]

Prepared using Procedure C in 17% yield. LC/MS (EI) $t_R$ 2.99, m/z 316 (M$^+$+1).

Example 81

N-[(3S)-1-Azabicyclo[2.2.2]oct-3-yl]-5-(3,6-dihydro-2H-pyran-4-yl)-1H-indazole-3-carboxamide hydroformate

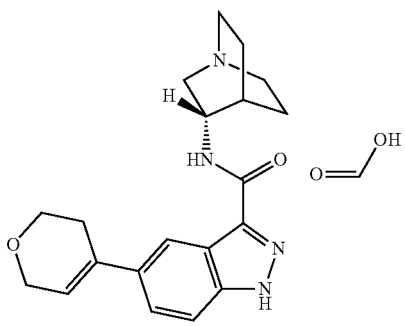

Prepared using Procedure C in 15% yield. LC/MS (EI) $t_R$ 3.20, m/z 353 (M$^+$+1).

Example 82

N-[(3R)-1-Azabicyclo[2.2.2]oct-3-yl]-5-(3,6-dihydro-2H-pyran-4-yl)-1H-indazole-3-carboxamide

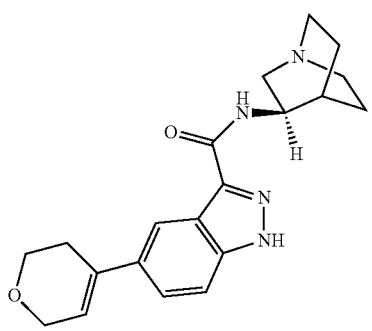 [SMILES: O=C(N[C@H]1CN2CCC1CC2)c1n[nH]c2ccc(C3=CCOCC3)cc12]

Prepared using Procedure C in 21% yield. LC/MS (EI) $t_R$ 3.90, m/z 353 (M$^+$+1).

Example 83

N-[(3R)-1-Azabicyclo[2.2.2]oct-3-yl]-4-bromo-5-methoxy-1H-indazole-3-carboxamide hydroformate

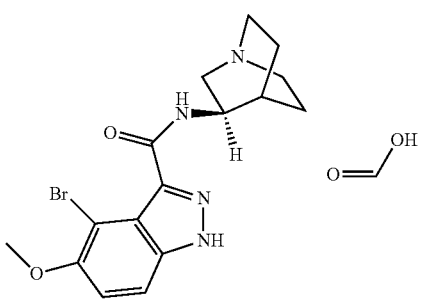 [SMILES: COc1ccc2[nH]nc(C(=O)N[C@H]3CN4CCC3CC4)c2c1Br ; O=CO]

Prepared using Procedure C in 26% yield. LC/MS (EI) $t_R$ 2.54, m/z 381/383 (M$^+$+1).

Example 84

N-[(3S)-1-Azabicyclo[2.2.2]oct-3-yl]-4-bromo-5-methoxy-1H-indazole-3-carboxamide hydroformate

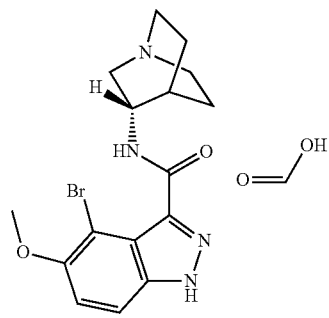

Prepared using Procedure C in 12% yield. LC/MS (EI) $t_R$ 2.54, m/z 381/383 (M$^+$+1).

Example 85

N-[(3S)-1-Azabicyclo[2.2.2]oct-3-yl]-5-bromo-4-nitro-1H-indazole-3-carboxamide

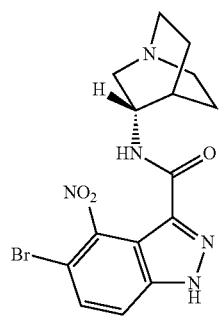 [SMILES: O=C(N[C@@H]1CN2CCC1CC2)c1n[nH]c2ccc(Br)c([N+](=O)[O-])c12]

Prepared using Procedure C in 25% yield. LC/MS (EI) $t_R$ 4.73, m/z 394/396 (M$^+$+1).

Example 86

N-[(3S)-1-Azabicyclo[2.2.2]oct-3-yl]-5-(formyl)-1H-indazole-3-carboxamide hydroformate

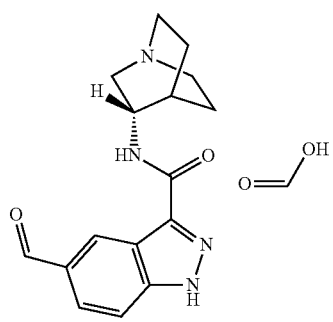

Prepared using Procedure C in 51% yield. LC/MS (EI) $t_R$ 2.35, m/z 299 (M$^+$+1).

Example 87

N-[(3S)-1-Azabicyclo[2.2.2]oct-3-yl]-6-(tetrahydro-2H-pyran-4-yl)-1H-indazole-3-carboxamide

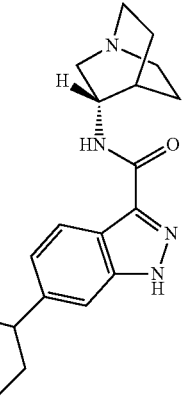

Prepared using Procedure C in 59% yield. LC/MS (EI) $t_R$ 2.37, m/z 355 (M$^+$+1).

Example 88

N-[(3R)-1-Azabicyclo[2.2.2]oct-3-yl]-6-(tetrahydro-2H-pyran-4-yl)-1H-indazole-3-carboxamide

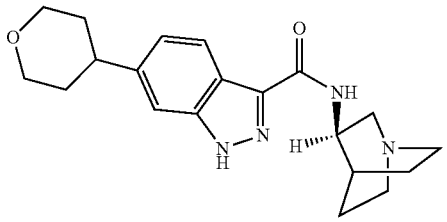 [SMILES: O=C(N[C@H]1CN2CCC1CC2)c1n[nH]c2cc(C3CCOCC3)ccc12]

Prepared using Procedure C in 52% yield. LC/MS (EI) $t_R$ 3.22, m/z 355 (M$^+$+1).

Example 89

N-[(3S)-1-Azabicyclo[2.2.2]oct-3-yl]-5-methoxy-1-(2,2,2-trifluoroethyl)-1H-indazole-3-carboxamide

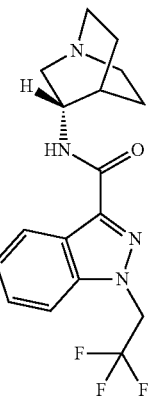

Prepared using Procedure C in 81% yield. LC/MS (EI) $t_R$ 5.02, m/z 383 (M$^+$+1).

Example 90

N-[(3S)-1-Azabicyclo[2.2.2]oct-3-yl]-5-bromo-1-(ethyl)-1H-indazole-3-carboxamide

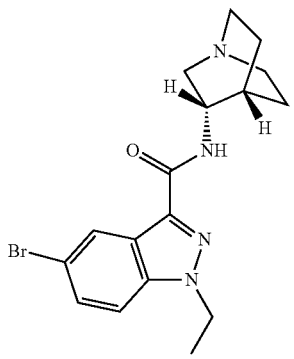

Prepared using Procedure C in 64% yield. LC/MS (EI) $t_R$ 3.94, m/z 377/379 (M$^+$+1).

Example 91

N-[(3S)-1-Azabicyclo[2.2.2]oct-3-yl]-6-bromo-1-(ethyl)-1H-indazole-3-carboxamide

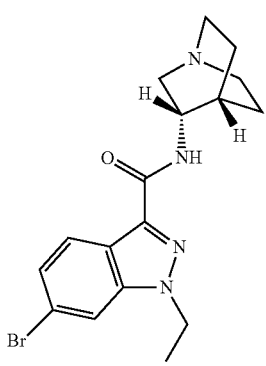

Prepared using Procedure C in 72% yield. LC/MS (EI) $t_R$ 3.90, m/z 377/379 (M$^+$+1).

Example 92

N-[(3S)-1-Azabicyclo[2.2.2]oct-3-yl]-5-bromo-1-(cyclopropylmethyl)-1H-indazole-3-carboxamide

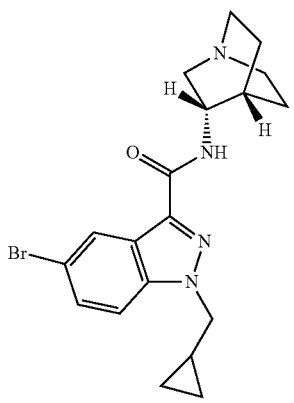

Prepared using Procedure C in 70% yield. LC/MS (EI) $t_R$ 4.20, m/z 403/405 (M$^+$+1).

Example 93

N-[(3S)-1-Azabicyclo[2.2.2]oct-3-yl]-5-bromo-1-(2,2,2-trifluoroethyl)-1H-indazole-3-carboxamide

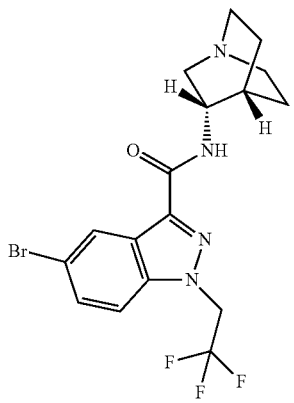

Prepared using Procedure C in 61% yield. LC/MS (EI) $t_R$ 4.10, m/z 431/433 (M$^+$+1).

Example 94

N-[(3S)-1-Azabicyclo[2.2.2]oct-3-yl]-5-[(dimethylamino)methyl]-1H-indazole-3-carboxamide dihydroformate

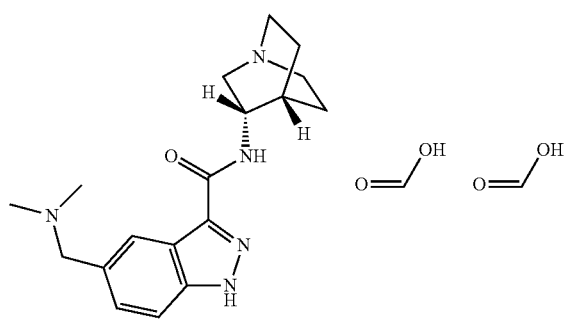

Prepared using Procedure C in 35% yield. LC/MS (EI) $t_R$ 1.30, m/z 328 (M$^+$+1).

Example 95

N-[(3S)-1-Azabicyclo[2.2.2]oct-3-yl]-5-[(diethylamino)methyl]-1H-indazole-3-carboxamide dihydroformate

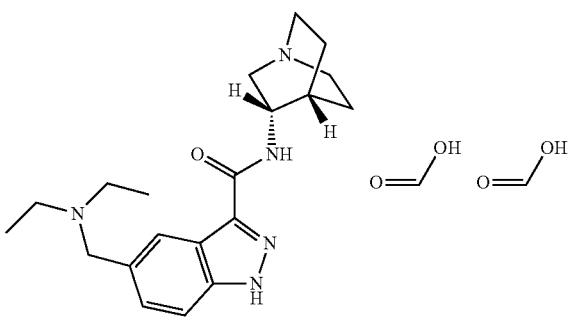

Prepared using Procedure C in 29% yield. LC/MS (EI) $t_R$ 1.32, m/z 356 (M$^+$+1).

Example 96

N-[(3S)-1-Azabicyclo[2.2.2]oct-3-yl]-5-[(pyrrolidin-1-yl)methyl]-1H-indazole-3-carboxamide dihydroformate

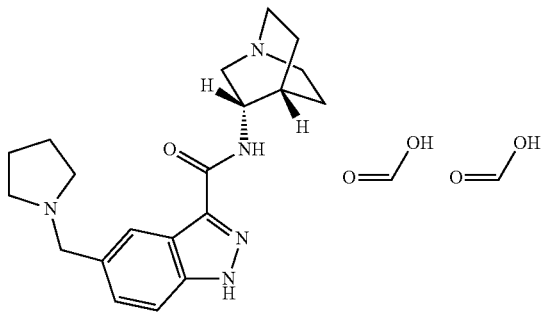

Prepared using Procedure C in 39% yield. LC/MS (EI) $t_R$ 1.34, m/z 354 (M$^+$+1).

Example 97

N-[(3S)-1-Azabicyclo[2.2.2]oct-3-yl]-5-[(1-benzylpyrrolidin-3-yl)oxy]-1H-indazole-3-carboxamide dihydroformate

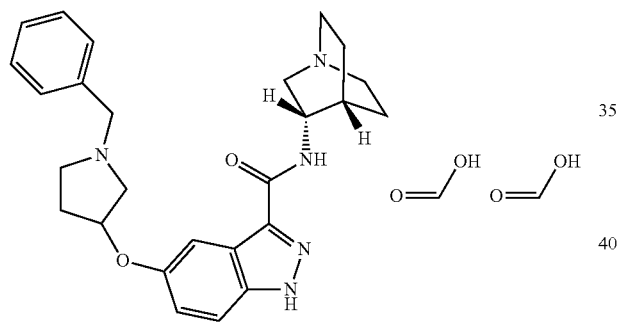

Prepared using Procedure C in 33% yield. LC/MS (EI) $t_R$ 2.35, m/z 446 (M$^+$+1).

Example 98

N-[(3S)-1-Azabicyclo[2.2.2]oct-3-yl]-N-ethyl-6-methoxy-1H-indazole-3-carboxamide

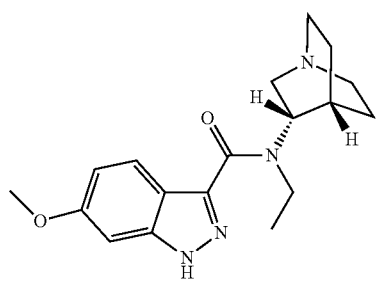

Prepared using Procedure C in 7% yield. LC/MS (EI) $t_R$ 2.78, m/z 329 (M$^+$+1).

Example 99

N-[(3S)-1-Azabicyclo[2.2.2]oct-3-yl]-N-ethyl-5-trifluoromethoxy-1H-indazole-3-carboxamide

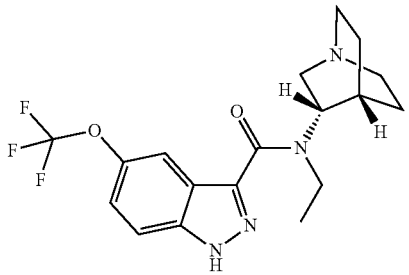

Prepared using Procedure C in 1% yield. LC/MS (EI) $t_R$ 3.83, m/z 383 (M$^+$+1).

Example 100

N-[(3S)-1-Azabicyclo[2.2.2]oct-3-yl]-N-cyclopropylmethyl-6-methoxy-1H-indazole-3-carboxamide hydroformate

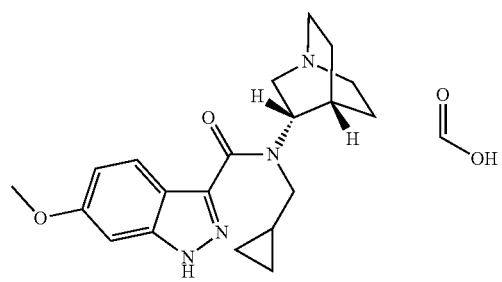

Prepared using Procedure C in 7% yield. LC/MS (EI) $t_R$ 3.56, m/z 355 (M$^+$+1).

Example 101

N-[(3S)-1-Azabicyclo[2.2.2]oct-3-yl]-N-cyclopropylmethyl-1H-indazole-3-carboxamide hydroformate

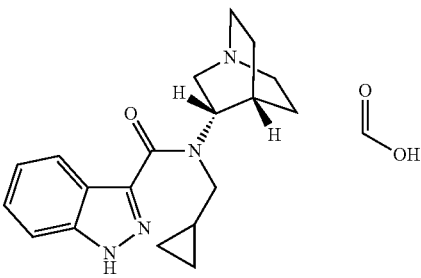

Prepared using Procedure C in 8% yield. LC/MS (EI) $t_R$ 3.42, m/z 325 (M$^+$+1).

Example 102

N-[(3S)-1-Azabicyclo[2.2.2]oct-3-yl]-N-cyclopropylmethyl-5-trifluoromethoxy-1H-indazole-3-carboxamide hydroformate

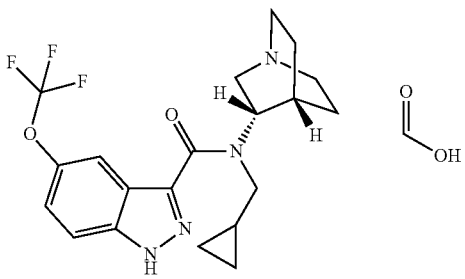

Prepared using Procedure C in 5% yield. LC/MS (EI) $t_R$ 3.99, m/z 409 (M$^+$+1).

Example 103

N-[(3S)-1-Azabicyclo[2.2.2]oct-3-yl]-6-(hydroxy)-1H-indazole-3-carboxamide

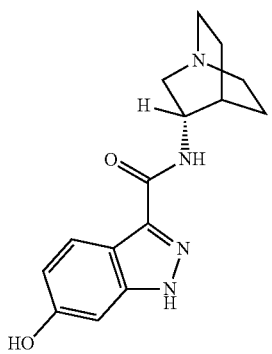

Prepared using Procedure C in 40% yield. LC/MS (EI) $t_R$ 9.80 [95/5 to 5/95 water (0.1% formic acid)/acetonitrile (0.1% formic acid)], m/z 287 (M$^+$+1).

Example 104

N-[(3S)-1-Azabicyclo[2.2.2]oct-3-yl]-5-(hydroxymethyl)-1H-indazole-3-carboxamide

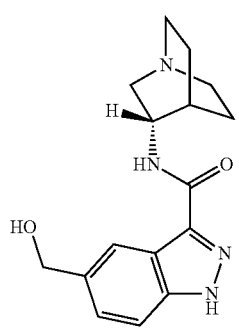 [SMILES: O=C(N[C@@H]1CN2CCC1CC2)c1n[nH]c2ccc(CO)cc12]

Prepared from Example 86 by sodium borohydride reduction in 12% yield. LC/MS (EI) $t_R$ 1.99, m/z 301 (M$^+$+1).

Example 105

N-[(3S)-1-Azabicyclo[2.2.2]oct-3-yl]-5-(cyclopentylamino)-1H-indazole-3-carboxamide

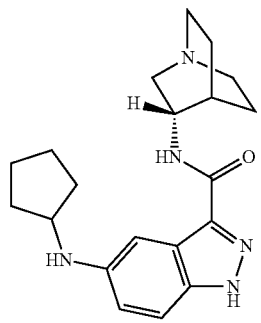 [SMILES: O=C(N[C@@H]1CN2CCC1CC2)c1n[nH]c2ccc(NC3CCCC3)cc12]

Prepared using Procedure C. The acid was prepared from ethyl 5-nitro-1H-indazole-3-carboxylate via reduction, reductive amination, and saponification in 46% yield. LC/MS (EI) $t_R$ 1.92, m/z 354 (M$^+$+1).

Procedure D.

Procedure D provides a method for the coupling between 3-aminoquinuclidine and carboxylic acids to form carboxamide derivatives.

The coupling reaction and purification was performed according to procedures A and C (indazoles, benzthiazoles) or according to procedure B (benzisothiazoles). The free base was dissolved in methanol (3.5 mL/mmol starting acid) and treated with 1N hydrochloric acid in ether (3.5 mL/mmol starting acid). The resulting suspension was diluted with ether (7 mL/mmol starting acid) and was maintained at room temperature for 2 h. The solids were collected by filtration, rinsed with ether, and dried, thus providing the hydrochloride salt in 40-60% yield.

The following compounds were prepared using this method:

Example 106

N-[(3R)-1-Azabicyclo[2.2.2]oct-3-yl]-5-ethynyl-1H-indazole-3-carboxamide hydrochloride

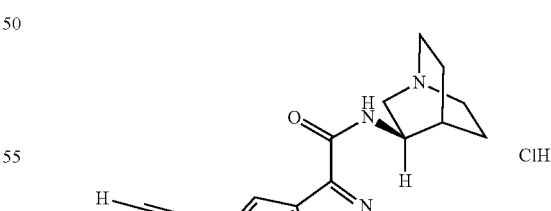

Prepared using Procedure D in 42% yield. $^1$H NMR (500 MHz, Me$_2$SO-d$_6$) δ 14.02 (s, 1H), 10.42 (s, 1H), 8.89 (d, J=7.0, 1H), 8.27 (s, 1H), 7.67 (d, J=8.5, 1H), 7.49 (dd, J=8.0, 1.0, 1H), 4.44 (m, 1H), 3.62 (m, 1H), 3.34 (m, 2H), 3.21 (m, 4H), 2.21 (m, 1H), 2.09 (m, 1H), 1.93 (m, 2H), 1.73 (m, 1H); LC/MS (EI) $t_R$ 2.61, m/z 295 (M$^+$+1).

Example 107

N-[(3S)-1-Azabicyclo[2.2.2]oct-3-yl]-5-(5-methyl-1,3-thiazol-2-yl)-1H-indazole-3-carboxamide hydrochloride

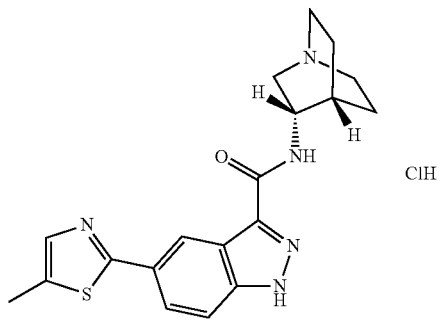

Prepared using Procedure D in 56% yield. LC/MS (EI) $t_R$ 5.53, m/z 368 (M$^+$+1).

Example 108

N-[(3S)-1-Azabicyclo[2.2.2]oct-3-yl]-6-(3,6-dihydro-2H-pyran-4-yl)-1H-indazole-3-carboxamide hydrochloride

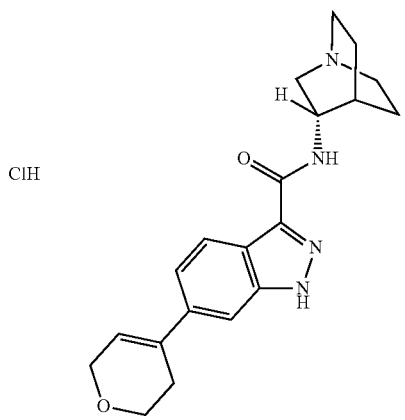 [SMILES: Cl ; O=C(N[C@@H]1CN2CCC1CC2)c1n[nH]c2cc(C3=CCOCC3)ccc12]

Prepared using Procedure D in 29% yield. LC/MS (EI) $t_R$ 3.20, m/z 353 (M$^+$+1).

Example 109

N-[(3S)-1-Azabicyclo[2.2.2]oct-3-yl]-6-(5-methyl-1,3-thiazol-2-yl)-1H-indazole-3-carboxamide hydrochloride

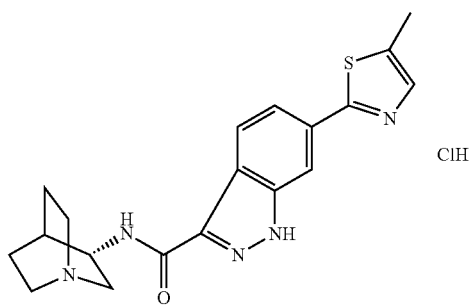 [SMILES: Cc1cnc(-c2ccc3c(C(=O)N[C@@H]4CN5CCC4CC5)n[nH]c3c2)s1 ; Cl]

Prepared using Procedure D. LC/MS (EI) $t_R$ 13.28 [Analytical HPLC was performed on 4.6 mm×250 mm YMC ODS-AQ S-5 120 m columns using a gradient of 05/95 to 95/05 acetonitrile (0.05% trifluoroacetic acid)/water (0.05% trifluoroacetic acid) over 35 min], m/z 368 (M$^+$+1).

Example 110

N-[(3S)-1-Azabicyclo[2.2.2]oct-3-yl]-6-(4-methyl-1,3-thiazol-2-yl)-1H-indazole-3-carboxamide hydrochloride

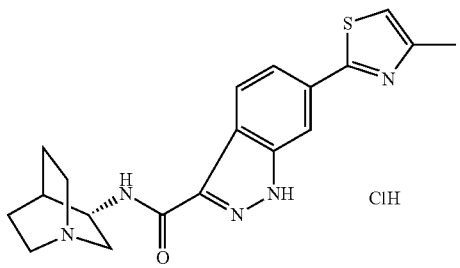 [SMILES: Cc1csc(-c2ccc3c(C(=O)N[C@@H]4CN5CCC4CC5)n[nH]c3c2)n1 ; Cl]

Prepared using Procedure D in 57% yield. LC/MS (EI) $t_R$ 14.00, m/z 367 (ES-Neg) (M$^+$).

Example 111

N-[(3S)-1-Azabicyclo[2.2.2]oct-3-yl]-5-(trifluoromethoxy)-1H-indazole-3-carboxamide hydrochloride

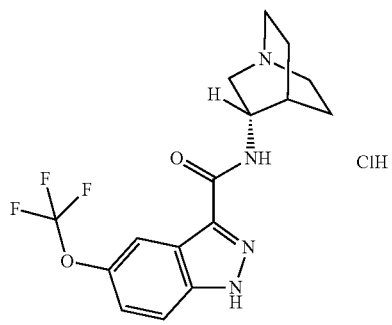 [SMILES: O=C(N[C@@H]1CN2CCC1CC2)c1n[nH]c2ccc(OC(F)(F)F)cc12 ; Cl]

Prepared using Procedure D in 60% yield. LC/MS (EI) $t_R$ 5.13, m/z 355 (M$^+$+1).

Example 112

N-[(3S)-1-Azabicyclo[2.2.2]oct-3-yl]-6-(1,3-thiazol-2-yl)-1H-indazole-3-carboxamide hydrochloride

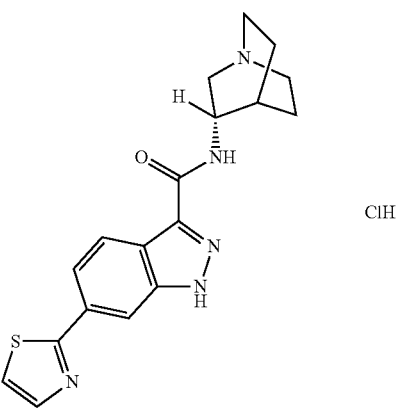 [SMILES: O=C(N[C@@H]1CN2CCC1CC2)c1n[nH]c2cc(-c3nccs3)ccc12 ; Cl]

Prepared using Procedure D in 68% yield. LC/MS (EI) $t_R$ 2.58, m/z 354 (M$^+$+1).

Example 113

N-[(3R)-1-Azabicyclo[2.2.2]oct-3-yl]-6-(1,3-thiazol-2-yl)-1H-indazole-3-carboxamide hydrochloride

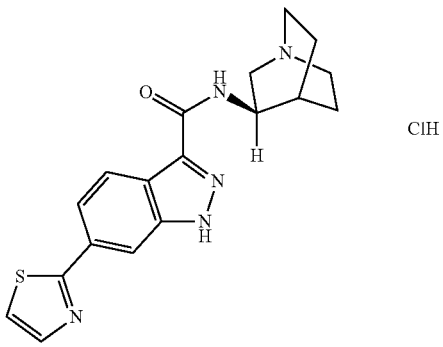 [SMILES: O=C(N[C@H]1CN2CCC1CC2)c1n[nH]c2cc(-c3nccs3)ccc12 ; Cl]

Prepared using Procedure D in 38% yield. LC/MS (EI) $t_R$ 2.58, m/z 354 (M$^+$+1).

Example 114

N-[(3R)-1-Azabicyclo[2.2.2]oct-3-yl]-6-methoxy-1H-indazole-3-carboxamide hydrochloride

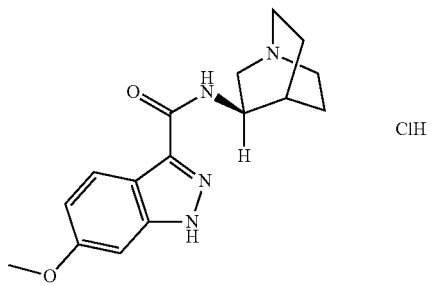 [SMILES: COc1ccc2c(C(=O)N[C@H]3CN4CCC3CC4)n[nH]c2c1 ; Cl]

Prepared using Procedure D in 68% yield. LC/MS (EI) $t_R$ 2.53, m/z 301 (M$^+$+1).

Procedure E

Procedure E provides a method for the formation of carboxamide derivatives from methyl 3-quinuclidinecarboxylic acid ester.

To a solution of the amine in toluene was added 1.0 M solution of trimethylaluminum in toluene (1.1 eq) at 0° C. After 30 min, an additional 1.1 eq of trimethylaluminum was added followed by a solution of methyl 3-quinuclidinecarboxylic acid ester hydrochloride salt (1.1 eq) in dioxane (5 mL). The reaction mixture was heated at 70° C. for 10 h, allowed to cool to rt, and was poured onto a cold (0° C.), aqueous solution of sodium bicarbonate. The aqueous layer was extracted with 5% methanol in methylene chloride (2×30 mL) and the combined organic layers were washed with brine and concentrated. The residue was purified by preparative HPLC.

Procedure F

Procedure F provides a method for the reduction of the carboxamide to form secondary amine derivatives.

To a solution of the amide (50 mg) in tetrahydrofuran (4 mL) was added lithium aluminum hydride (4.0 eq). The reaction mixture was heated at reflux for 4 h, was cooled to 0° C., and was cautiously quenched with ethanol. The resultant slurry was poured onto ice water and extracted with 5% methanol in dichloromethane (3×) and the combined organic layers were concentrated. The residue was purified by preparative HPLC.

Procedure G.

Procedure G provides a method for the coupling between brominated and iodinated aminoquinuclidinecarboxamides and boronic acids to form aryl-substituted derivatives.

In a 5 mL microwave reaction vessel was added the bromide (0.286 mmol), the boronic acid (0.588 mmol), tris(dibenzylideneacetone)dipalladium (0) (0.0289 mmol), tri-tert-butylphosphine tetrafluoroborate (0.0579 mmol), and potassium carbonate (0.810 mmol). The vessel was evacuated, back-filled with argon gas, and the contents diluted with N,N-dimethylformamide (5.0 mL). The vessel was sealed and subjected to microwave irradiation at 200° C. for 600 s. The contents of the reaction were filtered through Celite (methanol wash) and loaded on a 5 g SCX column. The column was washed with methanol (50 mL) and the product was eluted with 2 M ammonia in methanol and concentrated. The residue was purified by preparative HPLC, thus providing the product in 15-40% yield.

The following compounds were prepared using this method:

Example 115

N-[(3S)-1-Azabicyclo[2.2.2]oct-3-yl]-5-methoxy-4-(3-thienyl)-1H-indazole-3-carboxamide hydroformate

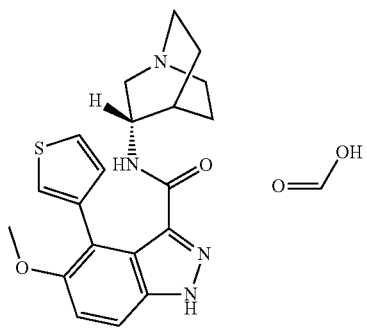 [SMILES: COc1ccc2[nH]nc(C(=O)N[C@@H]3CN4CCC3CC4)c2c1-c1ccsc1 ; O=CO]

Prepared using Procedure G or C in 37% yield. $^1$H NMR (CD$_3$OD) δ 8.39 (s, 1H), 7.57 (d, J=9.1, 1H), 7.46 (m, 1H), 7.39 (d, J=9.1, 1H), 7.36 (m, 1H), 7.23 (m, 1H), 4.03 (m, 1H), 3.79 (s, 3H), 3.59 (m, 1H), 3.3-3.2 (m, 5H), 2.81 (m, 1H), 2.10 (m, 1H), 1.97 (m, 2H), 1.79 (m, 1H). LC/MS (EI) $t_R$ 2.60, m/z 383 (M$^+$+1).

Example 116

N-[(3S)-1-Azabicyclo[2.2.2]oct-3-yl]-5-methoxy-4-(2-thienyl)-1H-indazole-3-carboxamide hydroformate

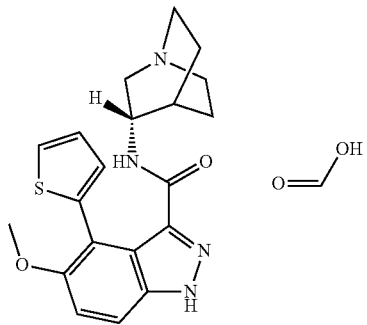 [SMILES: COc1ccc2[nH]nc(C(=O)N[C@@H]3CN4CCC3CC4)c2c1-c1cccs1 ; O=CO]

Prepared using Procedure G or C in 12% yield. LC/MS (EI) $t_R$ 2.62, m/z 383 (M$^+$+1).

Example 117

N-[(3R)-1-Azabicyclo[2.2.2]oct-3-yl]-5-methoxy-4-(2-thienyl)-1H-indazole-3-carboxamide hydroformate

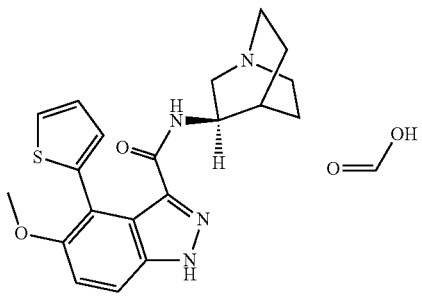 [SMILES: COc1ccc2[nH]nc(C(=O)N[C@H]3CN4CCC3CC4)c2c1-c1cccs1 ; O=CO]

Prepared using Procedure G or C in 16% yield. LC/MS (EI) $t_R$ 2.37, m/z 383 (M$^+$+1).

Procedure H.

Procedure H provides a method for the coupling between brominated 3-aminoquinuclidinecarboxamides and Grignard reagents to form alkyl-substituted derivatives.

A 5 mL microwave reaction vessel was charged with bis(triphenylphosphine)palladium (II) chloride (0.030 mmol, 0.1 eq) and the bromide (0.30 mmol). The vessel was evacuated and back-filled with argon gas. In a separate reaction vessel, solution of the Grignard (1.2 mmol, 4 eq) was added to a 0.5 M solution of zinc chloride (1.2 mmol, 4 eq) in tetrahydrofuran at rt. The suspension was maintained for 30 min and the entire contents were transferred to the reaction vessel via cannula. The vessel was sealed and subjected to microwave irradiation at 100° C. for 600 sec with a pre-stir time of 60 s. The reaction was quenched with acetic acid (0.5 mL), diluted with methanol, and was transferred to a SCX column. The column was washed with methanol (50 mL) and the product was eluted with 2 M ammonia in methanol (50 mL) and concentrated. The residue was purified by chromatography [90/10/1 dichloromethane/methanol/ammonium hydroxide or 1/1 to 0/1 ethyl acetate/(70/30/1 ethyl acetate/methanol/ammonium hydroxide)] or by preparative HPLC, thus providing the product in 20-50% yield.

The Grignard reagent of thiazole is commercially available. Alternatively, the aryllithium and the corresponding arylzinc reagent can be generated according to the procedure outlined by Reeder, M. R.; et. al. *Org. Proc. Res. Devel.* 2003, 7, 696. The zinc reagents of oxazole, 1-methylimidazole, and related reagents were prepared according to this procedure.

The following compounds were prepared using this method:

Example 118

N-[(3S)-1-Azabicyclo[2.2.2]oct-3-yl]-5-cyclopentyl-1H-indazole-3-carboxamide

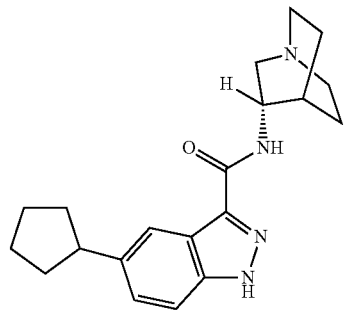 [SMILES: O=C(N[C@@H]1CN2CCC1CC2)c1n[nH]c2ccc(C3CCCC3)cc12]

Prepared using Procedure H in 21% yield. $^1$H NMR (CD$_3$OD) δ 8.07 (s, 1H), 7.50 (d, J=8.7, 1H), 7.36 (d, J=8.7, 1H), 4.21 (m, 1H), 3.36 (m, 1H), 3.15 (m, 1H), 3.02 (m, 1H), 3.0-2.8 (m, 4H), 2.2-2.0 (m, 3H), 2.0-1.5 (m, 10H). LC/MS (EI) $t_R$ 5.11, m/z 339 (M$^+$+1).

Example 119

N-[(3S)-1-Azabicyclo[2.2.2]oct-3-yl]-6-(1,3-thiazol-2-yl)-1H-indazole-3-carboxamide hydroformate

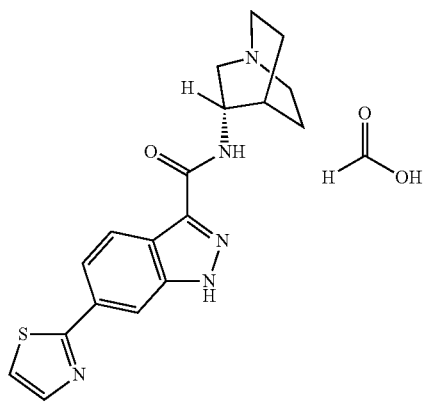

Prepared using Procedure H in 37% yield. LC/MS (EI) $t_R$ 4.28, m/z 354 (M$^+$+1).

Example 120

N-[(3R)-1-Azabicyclo[2.2.2]oct-3-yl]-5-(1,3-thiazol-2-yl)-1H-indazole-3-carboxamide hydroformate

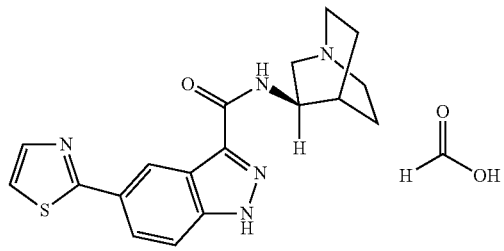

Prepared using Procedure H in 18% yield. LC/MS (EI) $t_R$ 2.54, m/z 354 (M$^+$+1).

Example 121

N-[(3R)-1-Azabicyclo[2.2.2]oct-3-yl]-6-(1,3-thiazol-2-yl)-1H-indazole-3-carboxamide hydroformate

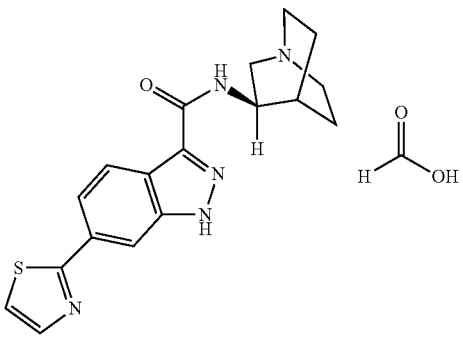

Prepared using Procedure H in 18% yield. LC/MS (EI) $t_R$ 2.58, m/z 354 (M$^+$+1).

Example 122

N-[(3S)-1-Azabicyclo[2.2.2]oct-3-yl]-5-(1,3-thiazol-2-yl)-1H-indazole-3-carboxamide hydroformate

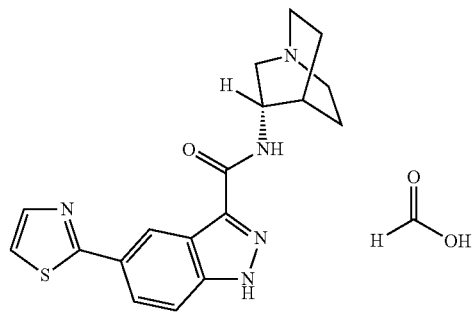 [SMILES: O=C(N[C@@H]1CN2CCC1CC2)c1n[nH]c2ccc(-c3nccs3)cc12 ; O=CO]

Prepared using Procedure H in 12% yield. LC/MS (EI) $t_R$ 3.96, m/z 354 (M$^+$+1).

Example 123

N-[(3S)-1-Azabicyclo[2.2.2]oct-3-yl]-6-(prop-1-yn-1-yl)-1H-indazole-3-carboxamide hydroformate

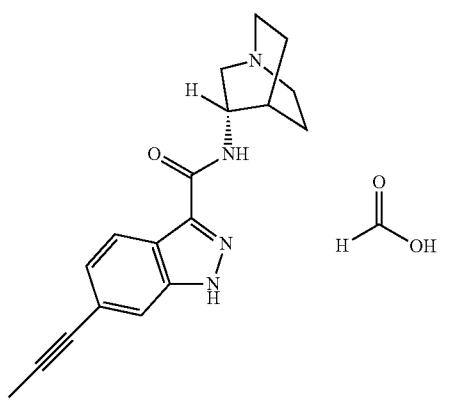 [SMILES: CC#Cc1ccc2c(C(=O)N[C@@H]3CN4CCC3CC4)n[nH]c2c1 ; O=CO]

Prepared using Procedure H in 24% yield. LC/MS (EI) $t_R$ 4.97, m/z 309 (M$^+$+1).

Example 124

N-[(3S)-1-Azabicyclo[2.2.2]oct-3-yl]-5-(1,3-oxazol-2-yl)-1H-indazole-3-carboxamide

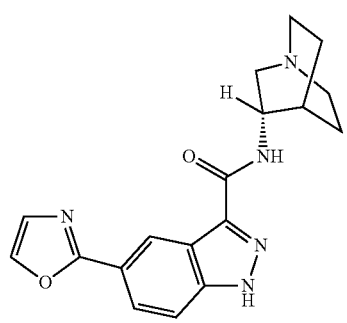 [SMILES: O=C(N[C@@H]1CN2CCC1CC2)c1n[nH]c2ccc(-c3ncco3)cc12]

Prepared using Procedure H in 71% yield. LC/MS (EI) $t_R$ 2.58, m/z 338 (M$^+$+1).

Example 125

N-[(3S)-1-Azabicyclo[2.2.2]oct-3-yl]-6-(1,3-oxazol-2-yl)-1H-indazole-3-carboxamide

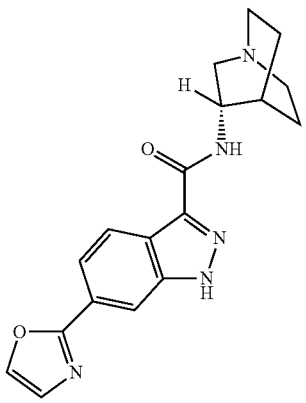 [SMILES: O=C(N[C@@H]1CN2CCC1CC2)c1n[nH]c2cc(-c3ncco3)ccc12]

Prepared using Procedure H in 85% yield. LC/MS (EI) $t_R$ 2.61, m/z 338 (M$^+$+1).

Example 126

N-[(3R)-1-Azabicyclo[2.2.2]oct-3-yl]-5-(1,3-oxazol-2-yl)-1H-indazole-3-carboxamide

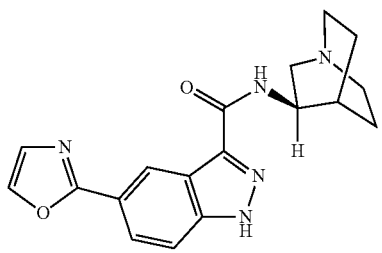 [SMILES: O=C(N[C@H]1CN2CCC1CC2)c1n[nH]c2ccc(-c3ncco3)cc12]

Prepared using Procedure H in 55% yield. LC/MS (EI) $t_R$ 3.12, m/z 338 (M$^+$+1).

Example 127

N-[(3R)-1-Azabicyclo[2.2.2]oct-3-yl]-6-(1,3-oxazol-2-yl)-1H-indazole-3-carboxamide

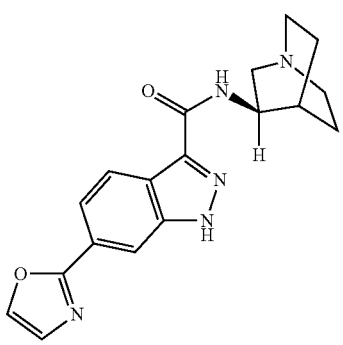 [SMILES: O=C(N[C@H]1CN2CCC1CC2)c1n[nH]c2cc(-c3ncco3)ccc12]

Prepared using Procedure H in 72% yield. LC/MS (EI) $t_R$ 2.64, m/z 338 (M$^+$+1).

Example 128

N-[(3R)-1-Azabicyclo[2.2.2]oct-3-yl]-6-(1-methyl-1H-imidazol-2-yl)-1H-indazole-3-carboxamide hydroformate

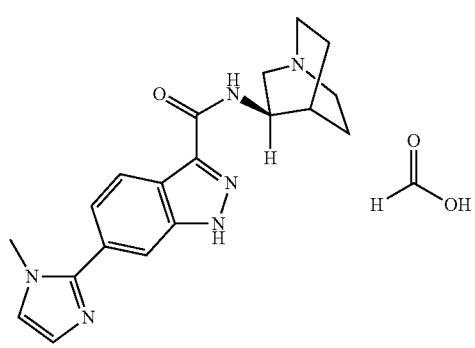 [SMILES: Cn1ccnc1-c1ccc2c(C(=O)N[C@H]3CN4CCC3CC4)n[nH]c2c1 ; O=CO]

Prepared using Procedure H in 11% yield. LC/MS (EI) $t_R$ 1.21, m/z 351 (M$^+$+1).

Example 129

N-[(3S)-1-Azabicyclo[2.2.2]oct-3-yl]-6-(1-methyl-1H-imidazol-2-yl)-1H-indazole-3-carboxamide hydroformate

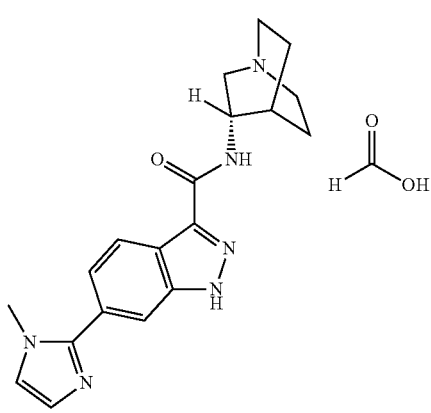

Prepared using Procedure H in 18% yield. LC/MS (EI) $t_R$ 1.23, m/z 351 (M$^+$+1).

Example 130

N-[(3R)-1-Azabicyclo[2.2.2]oct-3-yl]-5-cyclopentyl-1H-indazole-3-carboxamide

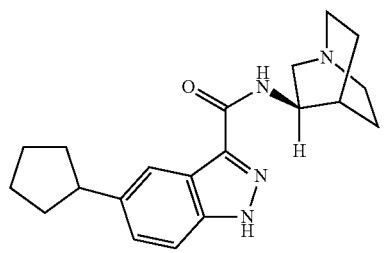 [SMILES: O=C(N[C@H]1CN2CCC1CC2)c1n[nH]c2ccc(C3CCCC3)cc12]

Prepared using Procedure H in 25% yield. LC/MS (EI) $t_R$ 5.27, m/z 339 (M$^+$+1).

Example 131

N-[(3R)-1-Azabicyclo[2.2.2]oct-3-yl]-6-cyclopentyl-1H-indazole-3-carboxamide

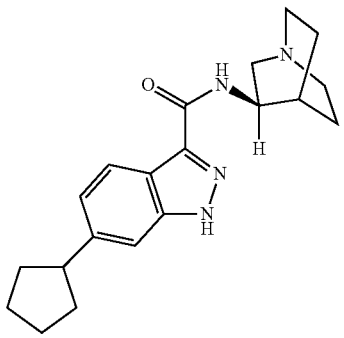 [SMILES: O=C(N[C@H]1CN2CCC1CC2)c1n[nH]c2cc(C3CCCC3)ccc12]

Prepared using Procedure H in 30% yield. LC/MS (EI) $t_R$ 5.11, m/z 339 (M$^+$+1).

Example 132

N-[(3S)-1-Azabicyclo[2.2.2]oct-3-yl]-6-cyclopentyl-1H-indazole-3-carboxamide

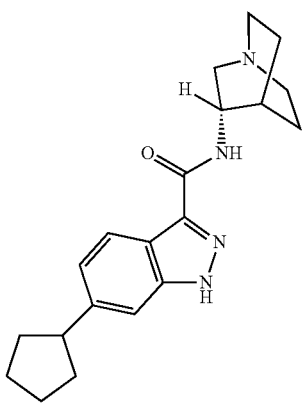 [SMILES: O=C(N[C@@H]1CN2CCC1CC2)c1n[nH]c2cc(C3CCCC3)ccc12]

Prepared using Procedure H in 38% yield. LC/MS (EI) $t_R$ 5.10, m/z 339 (M$^+$+1).

Example 133

N-[(3S)-1-Azabicyclo[2.2.2]oct-3-yl]-6-cyclohexyl-1H-indazole-3-carboxamide hydroformate

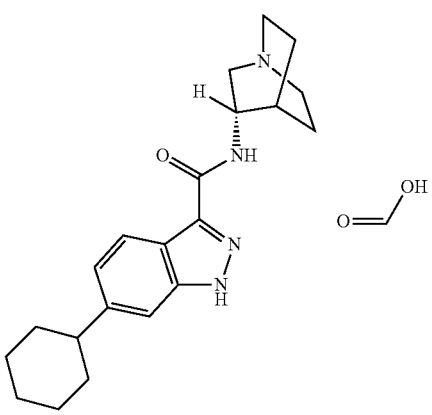 [SMILES: O=C(N[C@@H]1CN2CCC1CC2)c1n[nH]c2cc(C3CCCCC3)ccc12 ; O=CO]

Prepared using Procedure H in 11% yield. LC/MS (EI) $t_R$ 5.37, m/z 353 (M$^+$+1).

Example 134

N-[(3R)-1-Azabicyclo[2.2.2]oct-3-yl]-6-cyclohexyl-1H-indazole-3-carboxamide hydroformate

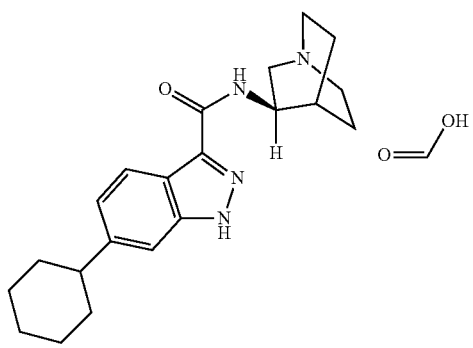

Prepared using Procedure H in 12% yield. LC/MS (EI) $t_R$ 5.33, m/z 353 (M$^+$+1).

Example 135

N-[(3S)-1-Azabicyclo[2.2.2]oct-3-yl]-6-cyclohexyl-1H-indazole-3-carboxamide

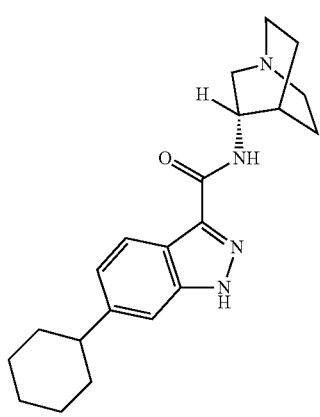 [SMILES: O=C(N[C@@H]1CN2CCC1CC2)c1n[nH]c2cc(C3CCCCC3)ccc12]

Prepared using Procedure H in 32% yield. LC/MS (EI) $t_R$ 5.37, m/z 353 (M$^+$+1).

Example 136

N-[(3R)-1-Azabicyclo[2.2.2]oct-3-yl]-6-cyclohexyl-1H-indazole-3-carboxamide

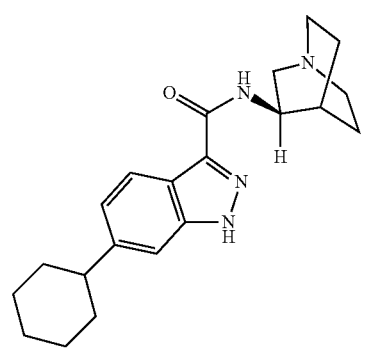 [SMILES: O=C(N[C@H]1CN2CCC1CC2)c1n[nH]c2cc(C3CCCCC3)ccc12]

Prepared using Procedure H in 10% yield. LC/MS (EI) $t_R$ 5.39, m/z 353 (M$^+$+1).

Example 137

N-[(3S)-1-Azabicyclo[2.2.2]oct-3-yl]-6-(propyl)-1H-indazole-3-carboxamide hydroformate

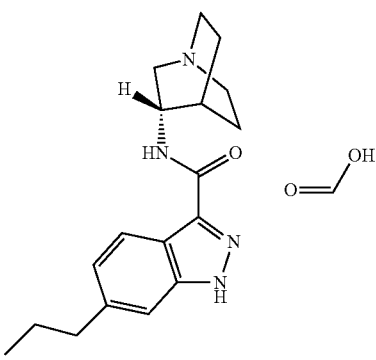 [SMILES: CCCc1ccc2c(C(=O)N[C@@H]3CN4CCC3CC4)n[nH]c2c1 ; O=CO]

Prepared using Procedure H in 6% yield. LC/MS (EI) $t_R$ 4.84, m/z 315 (M$^+$+1).

Example 138

N-[(3S)-1-Azabicyclo[2.2.2]oct-3-yl]-5-(ethyl)-1H-indazole-3-carboxamide hydroformate

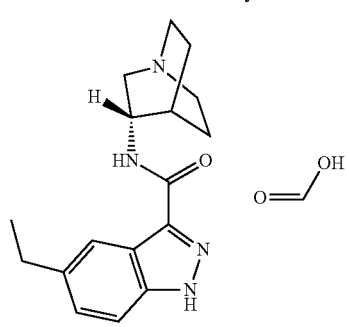

Prepared using Procedure H in 19% yield. LC/MS (EI) $t_R$ 4.48, m/z 299 (M$^+$+1).

Example 139

N-[(3S)-1-Azabicyclo[2.2.2]oct-3-yl]-6-(4-methyl-1,3-thiazol-2-yl)-1H-indazole-3-carboxamide

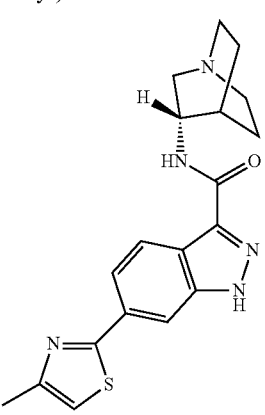

Prepared using Procedure H in 43% yield. LC/MS (EI) $t_R$ 4.98, m/z 368 (M$^+$+1).

Example 140

N-[(3S)-1-Azabicyclo[2.2.2]oct-3-yl]-6-(5-methyl-1,3-thiazol-2-yl)-1H-indazole-3-carboxamide

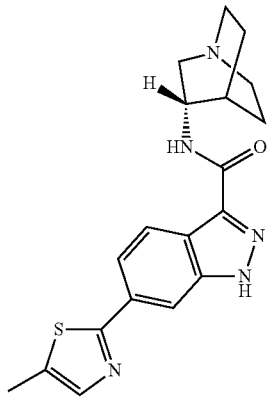 [SMILES: Cc1cnc(-c2ccc3c(C(=O)N[C@@H]4CN5CCC4CC5)n[nH]c3c2)s1]

Prepared using Procedure H in 30% yield. LC/MS (EI) $t_R$ 4.96, m/z 368 (M$^+$+1).

Example 141

N-[(3R)-1-Azabicyclo[2.2.2]oct-3-yl]-6-(5-methyl-1,3-thiazol-2-yl)-1H-indazole-3-carboxamide

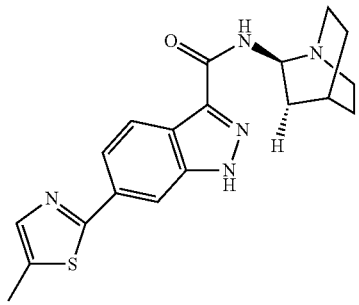

Prepared using Procedure H in 30% yield. LC/MS (EI) $t_R$ 5.01, m/z 368 (M$^+$+1).

Example 142

N-[(3R)-1-Azabicyclo[2.2.2]oct-3-yl]-6-(4-methyl-1,3-thiazol-2-yl)-1H-indazole-3-carboxamide

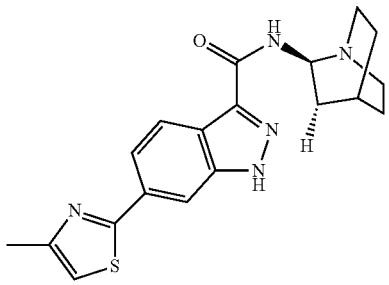

Prepared using Procedure H in 56% yield. LC/MS (EI) $t_R$ 4.59, m/z 368 (M$^+$+1).

Example 143

N-[(3S)-1-Azabicyclo[2.2.2]oct-3-yl]-5-(butyl)-1H-indazole-3-carboxamide hydroformate

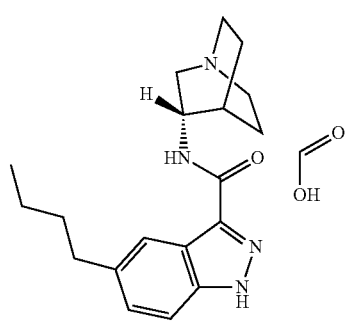

Prepared using Procedure H in 15% yield. LC/MS (EI) $t_R$ 5.41, m/z 327 (M$^+$+1).

Example 144

N-[(3S)-1-Azabicyclo[2.2.2]oct-3-yl]-4-cyclopropyl-5-methoxy-1H-indazole-3-carboxamide hydroformate

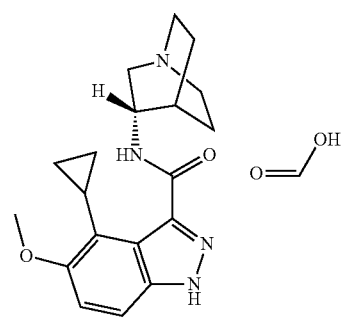

Prepared using Procedure H in 20% yield. LC/MS (EI) $t_R$ 2.73, m/z 341 (M$^+$+1).

Example 145

N-[(3S)-1-Azabicyclo[2.2.2]oct-3-yl]-4-ethyl-5-methoxy-1H-indazole-3-carboxamide hydroformate

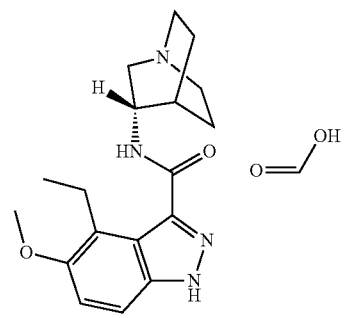

Prepared using Procedure H in 10% yield. LC/MS (EI) $t_R$ 2.42, m/z 329 (M$^+$+1).

Example 146

N-[(3S)-1-Azabicyclo[2.2.2]oct-3-yl]-6-(4-methyl-1,3-thiazol-2-yl)-1H-indazole-3-carboxamide hydroformate

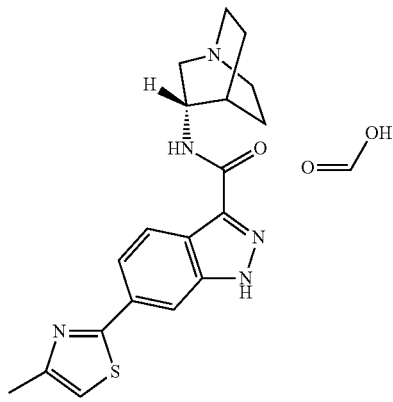

Prepared using Procedure H in 24% yield. LC/MS (EI) $t_R$ 4.98, m/z 368 (M$^+$+1).

Example 147

N-[(3S)-1-Azabicyclo[2.2.2]oct-3-yl]-1-ethyl-5-(1,3-thiazol-2-yl)-1H-indazole-3-carboxamide hydroformate

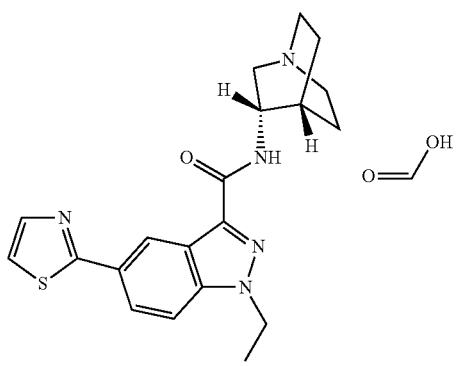

Prepared using Procedure H in 61% yield. LC/MS (EI) $t_R$ 3.63, m/z 382 (M$^+$+1).

Example 148

N-[(3S)-1-Azabicyclo[2.2.2]oct-3-yl]-1-cyclopropylmethyl-5-(1,3-thiazol-2-yl)-1H-indazole-3-carboxamide hydroformate

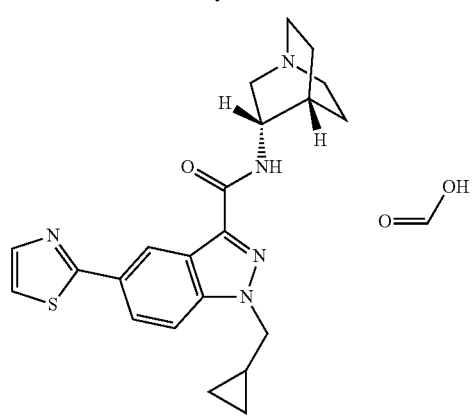

Prepared using Procedure H in 10% yield. LC/MS (EI) $t_R$ 3.97, m/z 408 (M$^+$+1).

Example 149

N-[(3S)-1-Azabicyclo[2.2.2]oct-3-yl]-1-(2,2,2-trifluoroethyl)-5-(1,3-thiazol-2-yl)-1H-indazole-3-carboxamide hydroformate

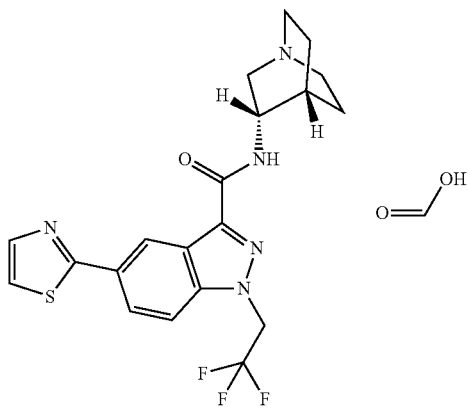

Prepared using Procedure H in 18% yield. LC/MS (EI) $t_R$ 3.87, m/z 436 (M$^+$+1).

Example 150

N-[(3S)-1-Azabicyclo[2.2.2]oct-3-yl]-1-ethyl-6-(1,3-thiazol-2-yl)-1H-indazole-3-carboxamide hydroformate

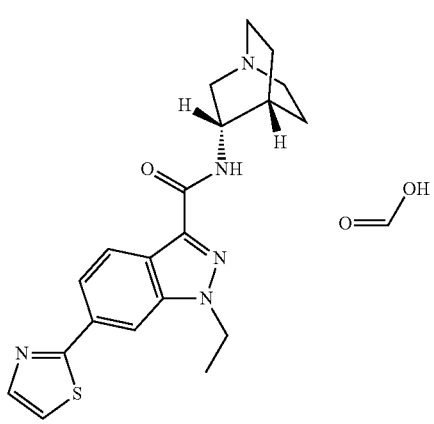

Prepared using Procedure H in 32% yield. LC/MS (EI) $t_R$ 3.67, m/z 382 (M$^+$+1).

Example 151

N-[(3S)-1-Azabicyclo[2.2.2]oct-3-yl]-6-(1,3-thiazol-2-yl)-1,2-benzisothiazole-3-carboxamide hydroformate

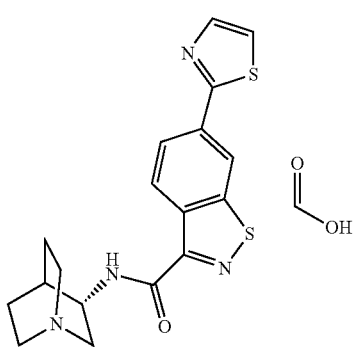

Prepared using Procedure H in 16% yield. LC/MS (EI) $t_R$ 5.20, m/z 371 (M$^+$+1).

Example 152

N-[(3R)-1-Azabicyclo[2.2.2]oct-3-yl]-6-(1,3-thiazol-2-yl)-1,2-benzisothiazole-3-carboxamide hydroformate

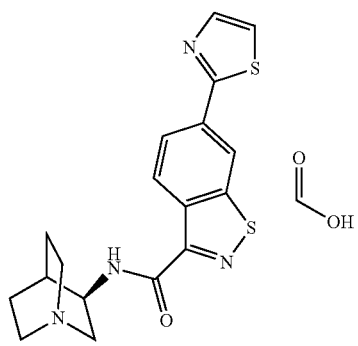

Prepared using Procedure H in 36% yield. LC/MS (EI) $t_R$ 5.16, m/z 371 (M$^+$+1).

Example 153

N-[(3S)-1-Azabicyclo[2.2.2]oct-3-yl]-5-(methyl)-1H-indazole-3-carboxamide hydroformate

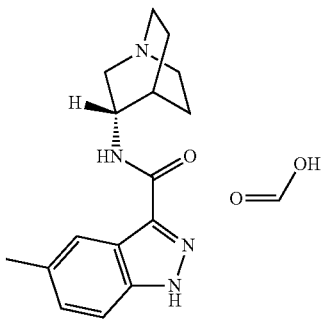 [SMILES: Cc1ccc2[nH]nc(C(=O)N[C@@H]3CN4CCC3CC4)c2c1 ; O=CO]

Prepared using Procedure H or C in 13% yield. LC/MS (EI) $t_R$ 3.18, m/z 285 (M$^+$+1).

Procedure I.

Procedure I provides a method for the coupling between brominated 3-aminoquinuclidinecarboxamides and acetylenes to form alkynyl-substituted derivatives.

A 5 mL microwave reaction vessel was charged with bis(triphenylphosphine)palladium (II) chloride (0.0597 mmol, 0.1 eq), copper (I) iodide (0.0719 mmol, 0.12 eq.), triphenylphosphine (0.124 mmol, 0.2 eq.), and the bromide (0.578 mmol). The vessel was evacuated and back-filled with argon gas. The alkyne (0.71 mmol, 1.2 eq), diethylamine (3.5 mL), and N,N-dimethylformamide (1.5 mL) were added and the vessel was sealed and subjected to microwave irradiation at 120° C. for 1500 sec. The reaction was reduced under vacuum to ~1.5 mL and was transferred to a SCX column. The column was washed with methanol (50 mL) and the product was eluted with 2 M ammonia in methanol (50 mL) and concentrated. The residue was purified by chromatography [1/1 to 0/1 ethyl acetate/(70/30/1 ethyl acetate/methanol/ammonium hydroxide)] to provide the silylacetylene in 90-95% yield. The silane was dissolved in tetrahydrofuran (2.5 mL) and was treated with tetrabutylammonium fluoride (0.6 mL of a 1 M solution in tetrahydrofuran). The reaction mixture was maintained for 11 h and was transferred to a SCX column. The column was washed with methanol (50 mL) and the product was eluted with 2 M ammonia in methanol (50 mL) and concentrated. The residue was purified by preparative HPLC, thus providing the product in 40-60% yield.

The following compounds were prepared using this method:

Example 154

N-[(3R)-1-Azabicyclo[2.2.2]oct-3-yl]-5-ethynyl-1H-indazole-3-carboxamide hydroformate

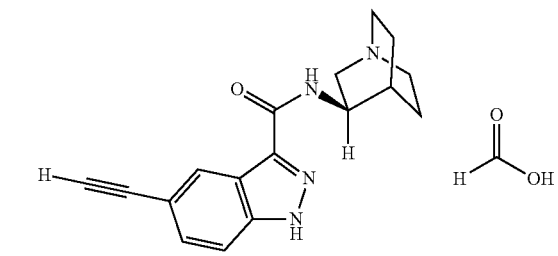 [SMILES: C#Cc1ccc2[nH]nc(C(=O)N[C@H]3CN4CCC3CC4)c2c1 ; O=CO]

Prepared using Procedure I in 36% yield. $^1$H NMR (CD$_3$OD) δ 8.41 (s, 1H), 8.33 (s, 1H), 7.58 (d, J=8.7, 1H), 7.49 (dd, J=8.7, 1.4, 1H), 4.53 (m, 1H), 3.82 (m, 1H), 3.47 (s, 1H), 3.31 (m, 5H), 2.38 (m, 1H), 2.27 (m, 1H), 2.10 (m, 2H), 1.93 (m, 1H); LC/MS (EI) $t_R$ 2.61, m/z 295 (M$^+$+1).

Example 155

N-[(3R)-1-Azabicyclo[2.2.2]oct-3-yl]-6-ethynyl-1H-indazole-3-carboxamide hydroformate

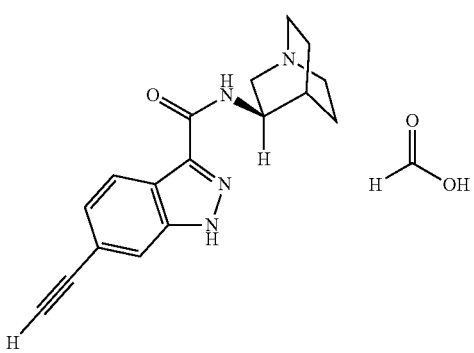 [SMILES: C#Cc1ccc2c(C(=O)N[C@H]3CN4CCC3CC4)n[nH]c2c1 ; O=CO]

Prepared using Procedure I in 40% yield. LC/MS (EI) $t_R$ 2.73, m/z 295 (M$^+$+1).

Example 156

N-[(3S)-1-Azabicyclo[2.2.2]oct-3-yl]-6-ethynyl-1H-indazole-3-carboxamide hydroformate

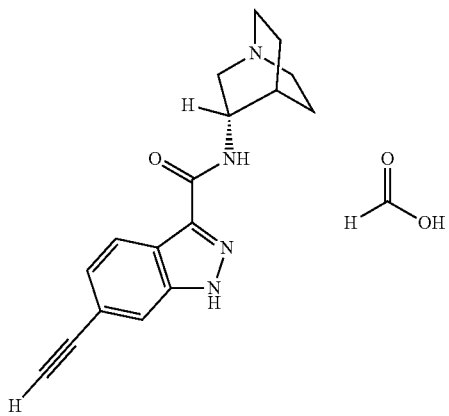 [SMILES: C#Cc1ccc2c(C(=O)N[C@@H]3CN4CCC3CC4)n[nH]c2c1 ; O=CO]

Prepared using Procedure I in 29% yield. LC/MS (EI) $t_R$ 2.73, m/z 295 (M$^+$+1).

Example 157

N-[(3S)-1-Azabicyclo[2.2.2]oct-3-yl]-5-ethynyl-1H-indazole-3-carboxamide hydroformate

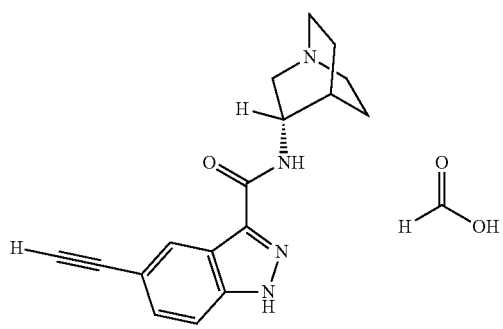 [SMILES: C#Cc1ccc2[nH]nc(C(=O)N[C@@H]3CN4CCC3CC4)c2c1 ; O=CO]

Prepared using Procedure I in 30% yield. LC/MS (EI) $t_R$ 2.63, m/z 295 (M$^+$+1).

Example 158

N-[(3R)-1-Azabicyclo[2.2.2]oct-3-yl]-6-(pent-1-yn-1-yl)-1H-indazole-3-carboxamide hydroformate

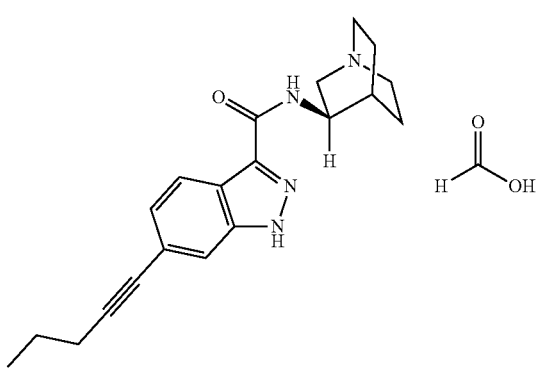 [SMILES: CCCC#Cc1ccc2c(C(=O)N[C@H]3CN4CCC3CC4)n[nH]c2c1 ; O=CO]

Prepared using Procedure I in 37% yield. LC/MS (EI) $t_R$ 5.28, m/z 337 (M$^+$+1).

Example 159

N-[(3R)-1-Azabicyclo[2.2.2]oct-3-yl]-6-(phenylethynyl)-1H-indazole-3-carboxamide hydroformate

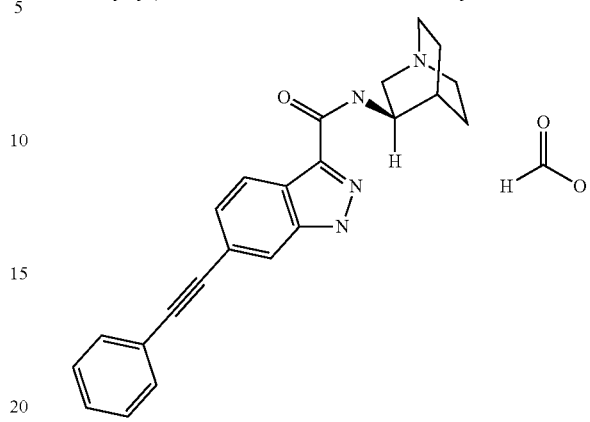

Prepared using Procedure I in 36% yield. LC/MS (EI) $t_R$ 5.46, m/z 371 (M$^+$+1).

Example 160

N-[(3S)-1-Azabicyclo[2.2.2]oct-3-yl]-6-ethynyl-1,2-benzisothiazole-3-carboxamide hydroformate

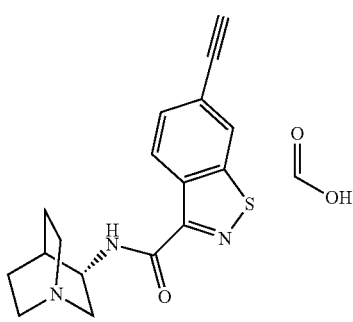

Prepared using Procedure I in 9% yield. LC/MS (EI) $t_R$ 4.24, m/z 312 (M$^+$+1).

Example 161

N-[(3R)-1-Azabicyclo[2.2.2]oct-3-yl]-6-ethynyl-1,2-benzisothiazole-3-carboxamide hydroformate

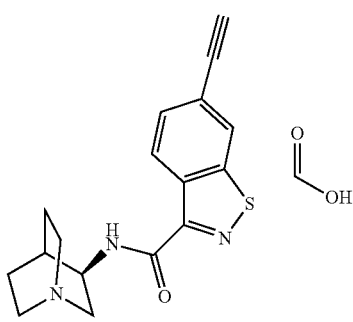

Prepared using Procedure I in 5% yield. LC/MS (EI) $t_R$ 5.22, m/z 312 (M$^+$+1).

Procedure J.

Procedure J provides a method for the coupling between brominated 3-aminoquinuclidinecarboxamides and cyclic alkenes to form cycloalkenyl-substituted derivatives.

A 5 mL microwave reaction vessel was charged with palladium (II) acetate (0.012 mmol, 0.04 eq), tri-o-tolylphosphine (0.030 mmol, 0.1 eq.), and the bromide (0.358 mmol). The vessel was evacuated and back-filled with argon gas. The alkene (0.30 mmol), diisopropylethylamine (63 μL), and N,N-dimethylformamide (2.8 mL) were added and the vessel was sealed and subjected to microwave irradiation at 220° C. for 300 sec. The reaction was transferred to a SCX column and the column was washed with methanol (50 mL). The product was eluted with 2 M ammonia in methanol (50 mL) and concentrated. The residue was purified by chromatography [1/1 to 0/1 ethyl acetate/(70/30/1 ethyl acetate/methanol/ammonium hydroxide)] and was further purified by preparative HPLC, thus providing the product in 7-40% yield.

The following compounds were prepared using this method:

Example 162

N-[(3R)-1-Azabicyclo[2.2.2]oct-3-yl]-5-(cyclohex-1-en-1-yl)-1H-indazole-3-carboxamide hydroformate

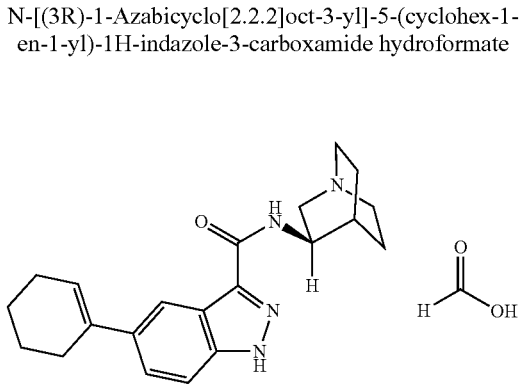

Prepared using Procedure J in 7% yield. $^1$H NMR (CD$_3$OD) δ 8.48 (s, 1H), 8.05 (s, 1H), 7.53 (d, J=8.7, 1H), 7.37 (dd, J=8.7, 1.6, 1H), 5.77 (m, 1H), 4.52 (m, 1H), 3.81 (m, 1H), 3.35 (m, 5H), 2.38 (m, 1H), 2.27 (m, 1H), 2.10 (m, 2H), 1.93 (m, 1H); LC/MS (EI) $t_R$ 5.14, m/z 351 (M$^+$+1).

Example 163

N-[(3R)-1-Azabicyclo[2.2.2]oct-3-yl]-5-(3-formyl-cyclohex-1-en-1-yl)-1H-indazole-3-carboxamide hydroformate

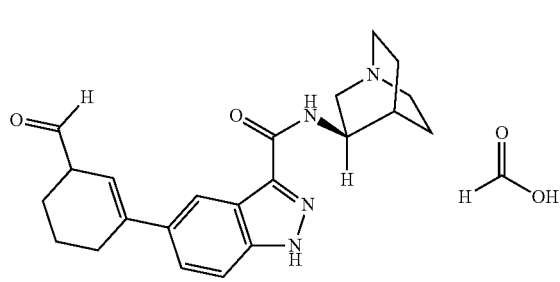 [SMILES: O=CC1C=C(c2ccc3[nH]nc(C(=O)N[C@H]4CN5CCC4CC5)c3c2)CCC1 ; O=CO]

Prepared using Procedure J in 1% yield. LC/MS (EI) $t_R$ 4.91, m/z 379 (M$^+$+1).

Example 164

N-[(3S)-1-Azabicyclo[2.2.2]oct-3-yl]-6-(tetrahydrofuran-3-yl)-1H-indazole-3-carboxamide hydroformate

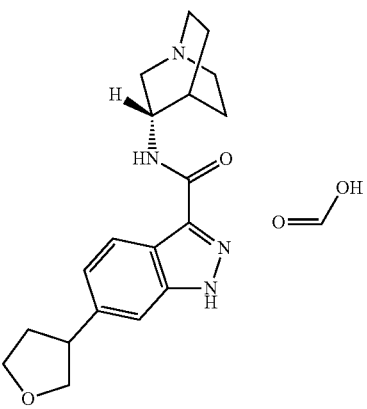

Prepared using Procedure J followed by hydrogenation in 2% yield. LC/MS (EI) $t_R$ 3.59, m/z 341 (M$^+$+1).

Procedure K.

Procedure K provides a method for the coupling between brominated 3-aminoquinuclidinecarboxamides and nickel (II) cyanide to form cyano-substituted derivatives.

A 5 mL microwave reaction vessel was charged with nickel (II) cyanide (3.11 mmol, 5.4 eq) and the bromide (0.578 mmol). The vessel was evacuated, back-filled with argon gas, and diluted with N-methylpyrrolidinone (5.0 mL). The vessel was sealed and subjected to microwave irradiation at 200° C. for 2400 sec. The reaction was transferred to a SCX column and the column was washed with methanol (50 mL). The product was eluted with 2 M ammonia in methanol (50 mL) and concentrated. The residue was purified by preparative HPLC, thus providing the product in 10-40% yield.

Literature Reference: Arvella, R. K.; Leadbeater, N. E. *J. Org. Chem.* 2003, 68, 9122.

The following compounds were prepared using this method:

Example 165

N-[(3R)-1-Azabicyclo[2.2.2]oct-3-yl]-6-cyano-1,2-benzisothiazole-3-carboxamide hydroformate

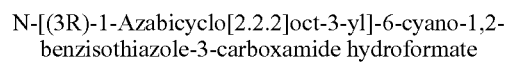

Prepared using Procedure K in 41% yield. $^1$H NMR (CD$_3$OD) δ 8.94 (d, J=8.5, 1H), 8.63 (s, 1H), 7.83 (d, J=8.5, 1H), 4.55 (m, 1H), 3.89-3.81 (m, 1H), 3.53-3.31 (m, 5H), 2.42 (m, 1H), 2.26-2.16 (m, 1H), 2.14-2.03 (m, 2H), 1.99-1.91 (m, 1H); LC/MS (EI) $t_R$ 3.68, m/z 313 (M$^+$+1).

Example 166

N-[(3R)-1-Azabicyclo[2.2.2]oct-3-yl]-6-cyano-1H-indazole-3-carboxamide hydroformate

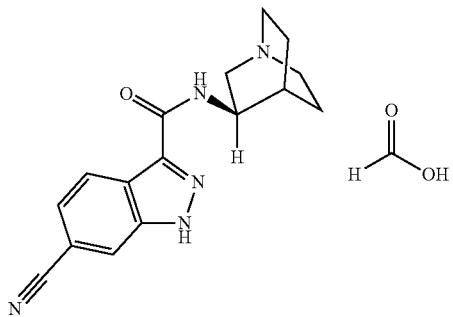 [SMILES: N#Cc1ccc2c(C(=O)N[C@H]3CN4CCC3CC4)n[nH]c2c1 ; O=CO]

Prepared using Procedure K in 39% yield. LC/MS (EI) $t_R$ 2.59, m/z 296 (M$^+$+1).

Example 167

N-[(3R)-1-Azabicyclo[2.2.2]oct-3-yl]-5-cyano-1H-indazole-3-carboxamide hydroformate

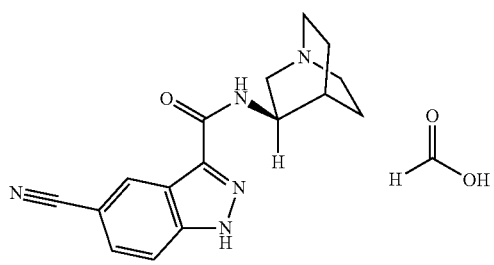 [SMILES: N#Cc1ccc2[nH]nc(C(=O)N[C@H]3CN4CCC3CC4)c2c1 ; O=CO]

Prepared using Procedure K in 52% yield. LC/MS (EI) $t_R$ 2.55, m/z 296 (M$^+$+1).

Example 168

N-[(3S)-1-Azabicyclo[2.2.2]oct-3-yl]-5-cyano-1H-indazole-3-carboxamide hydroformate

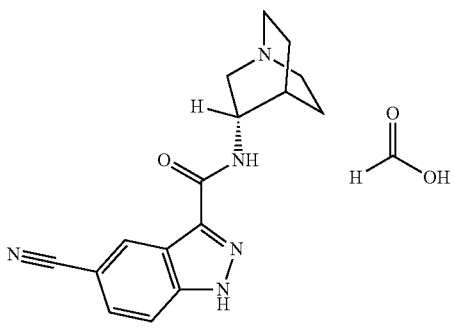 [SMILES: N#Cc1ccc2[nH]nc(C(=O)N[C@@H]3CN4CCC3CC4)c2c1 ; O=CO]

Prepared using Procedure K in 18% yield. LC/MS (EI) $t_R$ 2.47, m/z 296 (M$^+$+1).

Example 169

N-[(3S)-1-Azabicyclo[2.2.2]oct-3-yl]-6-cyano-1H-indazole-3-carboxamide hydroformate

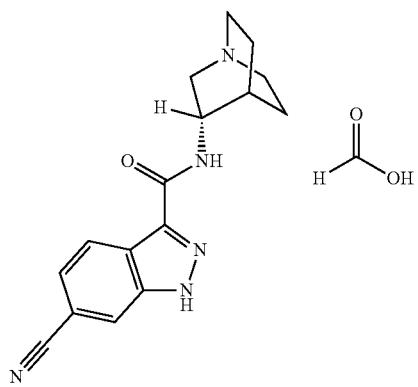 [SMILES: N#Cc1ccc2c(C(=O)N[C@@H]3CN4CCC3CC4)n[nH]c2c1 ; O=CO]

Prepared using Procedure K in 42% yield. LC/MS (EI) $t_R$ 2.47, m/z 296 (M$^+$+1).

Example 170

N-[(3S)-1-Azabicyclo[2.2.2]oct-3-yl]-6-cyano-1,2-benzisothiazole-3-carboxamide hydroformate Prepared using Procedure K in 48% yield. LC/MS (EI) $t_R$ 2.99, m/z 313 (M$^+$+1).

Example 171

N-[(3R)-1-Azabicyclo[2.2.2]oct-3-yl]-6-cyano-1,2-benzisothiazole-3-carboxamide hydrotrifluoroacetate Prepared using Procedure K in 41% yield. LC/MS (EI) $t_R$ 3.68, m/z 313 (M$^+$+1).

Example 172

N-[(3S)-1-Azabicyclo[2.2.2]oct-3-yl]-6-cyano-1,2-benzisothiazole-3-carboxamide hydrotrifluoroacetate

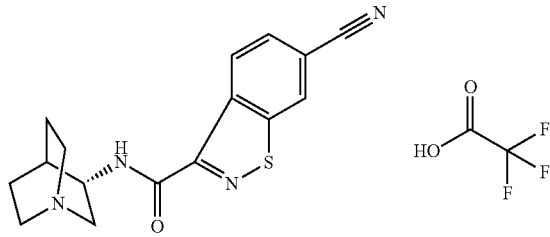 [SMILES: N#Cc1ccc2c(C(=O)N[C@@H]3CN4CCC3CC4)nsc2c1 ; O=C(O)C(F)(F)F]

Prepared using Procedure K in 48% yield. LC/MS (EI) $t_R$ 2.99, m/z 313 (M$^+$+1).

Procedure L.

Procedure L provides a method for the coupling between brominated 3-aminoquinuclidinecarboxamides and phenols to form biaryl ether derivatives.

A 2.5 mL microwave reaction vessel was charged with copper (II) triflate (0.144 mmol, 0.5 eq.), cesium carbonate (0.565 mmol, 2 eq.), benzoic acid (0.402 mmol, 1.4 eq.), and the bromide (0.284 mmol). The vessel was evacuated and back-filled with argon gas. A 0.5 M solution of the phenol in N,N-dimethylformamide (1.2 mL, 0.60 mmol, 2.1 eq), and N,N-dimethylformamide (1.3 mL) were added and the vessel was sealed and subjected to microwave irradiation at 200° C. for 2400 sec. The reaction mixture was transferred to a SCX column and the column was washed with methanol (50 mL). The product was eluted with 2 M ammonia in methanol (50 mL) and concentrated. The residue was purified by chromatography [1/1 to 0/1 ethyl acetate/(70/30/1 ethyl acetate/methanol/ammonium hydroxide)] and was further purified by preparative HPLC, thus providing the product in 10-40% yield.

The following compounds were prepared using this method:

Example 173

N-[(3R)-1-Azabicyclo[2.2.2]oct-3-yl]-5-phenoxy-1H-indazole-3-carboxamide hydroformate

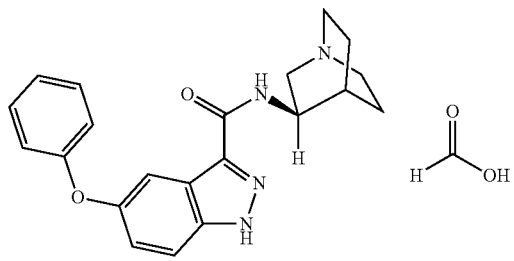 [SMILES: O=C(N[C@H]1CN2CCC1CC2)c1n[nH]c2ccc(Oc3ccccc3)cc12 ; O=CO]

Prepared using Procedure L in 2% yield. $^1$H NMR (CD$_3$OD) δ 8.53 (s, 1H), 7.71 (d, J=1.8, 1H), 7.63 (d, J=9.0, 1H), 7.37 (dd, J=8.4, 7.5, 2H), 7.23 (dd, J=9.0. 2.3, 1H), 7.12 (t, J=7.4, 2H), 7.01 (d, J=8.8, 1H), 4.52 (m, 1H), 3.81 (m, 1H), 3.35 (m, 5H), 2.38 (m, 1H), 2.27 (m, 1H), 2.10 (m, 2H), 1.93 (m, 1H); LC/MS (EI) $t_R$ 5.02, m/z 363 (M$^+$+1).

Procedure M.

Procedure M provides a method for the coupling between aniline or phenol bearing aminoquinuclidinecarboxamides and alkylating agents to form secondary aniline- or ether-substituted derivatives.

To a solution of N-[(3S)-1-azabicyclo[2.2.2]oct-3-yl]-6-hydroxy-1,2-benzisothiazole-3-carboxamide (0.400 mol) in N,N-dimethylformamide (6 mL) was added potassium carbonate (2.00 mol) and cyclopropylmethyl bromide (0.47 mmol). The reaction was maintained for 16 h and the solvent was removed in vacuo. The residue was extracted with 10/1 dichloromethane/methanol (3×) and the combined extracts were concentrated. The residue was purified by preparative HPLC using an 8 min gradient of 95/5 to 20/80 water (0.1% formic acid)/acetonitrile (0.1% formic acid), thus providing the product in 32% yield.

The following compounds were prepared by this method:

Example 174

N-[(3S)-1-Azabicyclo[2.2.2]oct-3-yl]-6-[3-(2-methoxyethoxy)propoxy]-1,2-benzisothiazole-3-carboxamide hydroformate

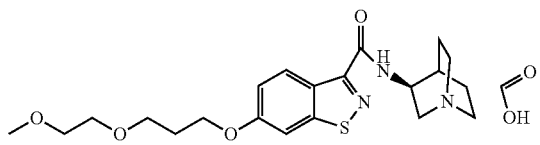

Prepared using Procedure M in 30% yield. $^1$H NMR (CD$_3$OD) δ 8.55 (d, J=9.0, 1H), 8.38 (broad, 1H), 7.37 (s, 1H), 7.05 (d, J=9.0, 1H), 4.55 (m, 1H), 3.95 (t, J=9.0, 1H), 3.70-3.45 (m, 11H), 3.31 (s, 3H), 2.40 (m, 1H), 2.30 (m, 1H), 2.15 (m, 2H), 2.05 (m, 2H), 1.30 (t, J=6.0, 2H). LC/MS (EI) $t_R$ 2.88, m/z 420 (M$^+$+1).

Example 175

N-[(3S)-1-Azabicyclo[2.2.2]oct-3-yl]-6-(cyclopropylmethoxy)-1,2-benzisothiazole-3-carboxamide hydroformate

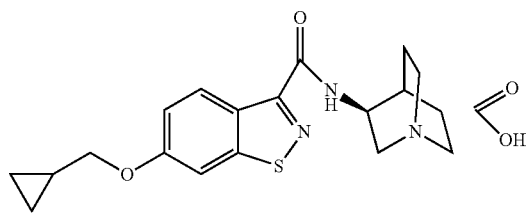

Prepared using Procedure M in 32% yield. LC/MS (EI) $t_R$ 3.48, m/z 358 (M$^+$+1).

Procedure N.

Procedure N provides a method for the hydrolysis of nitrile-substituted 3-aminoquinuclidinecarboxamides to form carboxyl-substituted derivatives.

A 2.5 mL microwave reaction vessel was charged with the nitrile (0.195 mmol), water (2.0 mL), and 2 N sodium hydroxide (0.5 mL). The vessel was sealed and subjected to microwave irradiation at 200° C. for 1800 sec. The reaction was acidified with acetic acid (~1.5 mL) and was transferred to a SCX column. The column was washed with methanol (50 mL) and the product was eluted with 2 M ammonia in methanol (50 mL) and concentrated. The residue was purified by preparative HPLC, thus providing the product in 5-30% yield.

The following compounds were prepared using this method:

Example 176

3-{[(3R)-1-Azabicyclo[2.2.2]oct-3-ylamino]carbonyl}-1H-indazole-6-carboxylic acid hydroformate

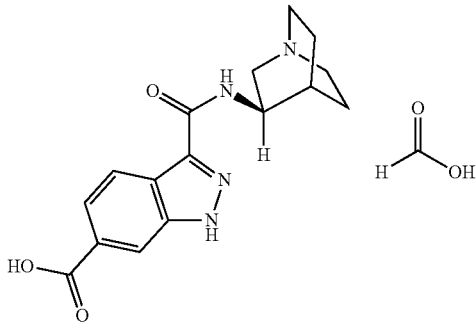 [SMILES: O=C(O)c1ccc2c(C(=O)N[C@H]3CN4CCC3CC4)n[nH]c2c1 ; O=CO]

Prepared using Procedure N in 3% yield. $^1$H NMR (CD$_3$OD) δ 8.39 (s, 1H), 8.25 (s, 1H), 8.21 (d, J=8.6, 1H), 7.89 (dd, J=8.6, 1.2, 1H), 4.53 (m, 1H), 3.84 (m, 1H), 3.37 (m, 5H), 2.39 (m, 1H), 2.28 (m, 1H), 2.11 (m, 2H), 1.94 (m, 1H); LC/MS (EI) t$_R$ 2.37, m/z 315 (M$^+$+1).

Procedure O.

Procedure O provides a method for the coupling between brominated 3-aminoquinuclidinecarboxamides and amines to form amino-substituted derivatives.

In a 5 mL microwave reaction vessel was added the bromide (133 mg, 0.37 mmol), tris(dibenzylideneacetone)dipalladium (0) (34 mg, 0.04 mmol), cesium bicarbonate (213 mg, 1.1 mmol), and (2'-dicyclohexylphosphanylbiphenyl-2-yl) dimethylamine (30 mg, 0.07 mmol). The vial was then evacuated and back-filled with argon gas. The mixture of solids was then diluted with the amine (0.7 mL), dioxane (1 mL), and triethylamine (0.5 mL) and the reaction vessel was sealed. The reaction mixture was subjected to microwave irradiation at 120° C. for 1800 s. The reaction mixture was filtered through a plug of Celite and concentrated in vacuo. The crude product was purified by chromatography (90/10/1 dichloromethane/methanol/ammonium hydroxide), thus providing the product in 34% yield as a colorless solid.

The following compounds were prepared using this method:

Example 177

N-[(3S)-1-Azabicyclo[2.2.2]oct-3-yl]-5-(2,5-dimethyl-1H-pyrrol-1-yl)-1H-indazole-3-carboxamide

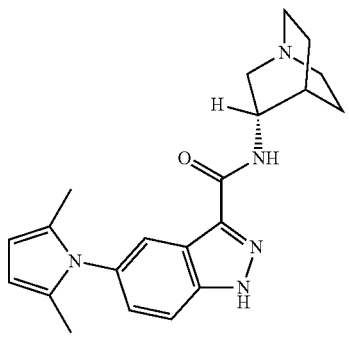 [SMILES: Cc1ccc(C)n1-c1ccc2[nH]nc(C(=O)N[C@@H]3CN4CCC3CC4)c2c1]

Prepared using Procedure O in 13% yield. $^1$H NMR (CD$_3$OD) δ d 8.09 (dd, J=1.9, 0.7, 1H), 7.55 (dd, J=8.8, 0.7, 1H), 7.41 (dd, J=8.8, 1.9, 1H), 5.82 (s, 2H), 4.22 (m, 1H), 3.35 (m, 1H), 3.03 (m, 1H), 3.0-2.8 (m, 4H), 2.06 (m, 1H), 2.00 (m, 1H), 1.99 (s, 6H), 1.79 (m, 2H), 1.55 (m, 1H); LC/MS (EI) t$_R$ 5.00, m/z 364 (M$^+$+1).

Example 178

N-[(3S)-1-Azabicyclo[2.2.2]oct-3-yl]-5-(1H-pyrrol-1-yl)-1H-indazole-3-carboxamide

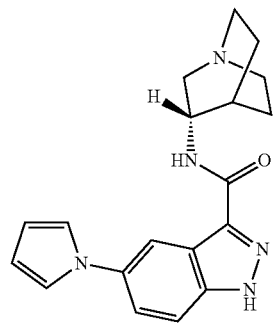 [SMILES: O=C(N[C@@H]1CN2CCC1CC2)c1n[nH]c2ccc(-n3cccc3)cc12]

Prepared using Procedure O in 7% yield. LC/MS (EI) t$_R$ 4.94, m/z 336 (M$^+$+1).

Example 179

N-[(3R)-1-Azabicyclo[2.2.2]oct-3-yl]-5-(1H-pyrrol-1-yl)-1H-indazole-3-carboxamide

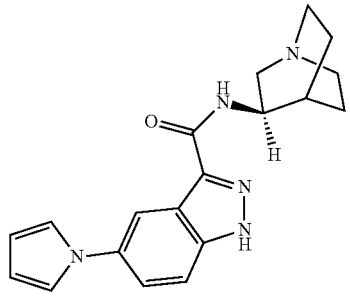 [SMILES: O=C(N[C@H]1CN2CCC1CC2)c1n[nH]c2ccc(-n3cccc3)cc12]

Prepared using Procedure O in 26% yield. LC/MS (EI) t$_R$ 4.79, m/z 336 (M$^+$+1).

Procedure P.

Procedure P provides a method for the coupling between brominated 3-aminoquinuclidinecarboxamides and cyclic, secondary amines to form amino-substituted derivatives.

A 2.5 mL microwave reaction vessel was charged with tris(dibenzylideneacetone)dipalladium (0) (0.060 mmol, 0.1 eq), [2'-(dimethylamino)biphenyl-2-yl]dicyclohexylphosphine (0.060 mmol, 0.1 eq), and the bromide (0.550 mmol). The vessel was evacuated and back-filled with argon gas. The amine (0.66 mmol, 1.2 eq) and a 1 M solution of lithium hexamethyldisilazide in tetrahydrofuran (1.7 mmol, 3 eq) were added and the vessel was sealed and heated at 65° C. for 15 h. The reaction was transferred to a SCX column and the column was washed with methanol (50 mL). The product was eluted with 2 M ammonia in methanol (50 mL) and concentrated. The residue was purified by preparative HPLC, thus providing the product in 30-50% yield.

Literature reference: Harris, M. C.; Huang, X.; Buchwald, S. L. *Org. Lett.* 2002, 4, 2885.

The following compounds were prepared using this method:

Example 180

N-[(3S)-1-Azabicyclo[2.2.2]oct-3-yl]-5-pyrrolidin-1-yl-1H-indazole-3-carboxamide

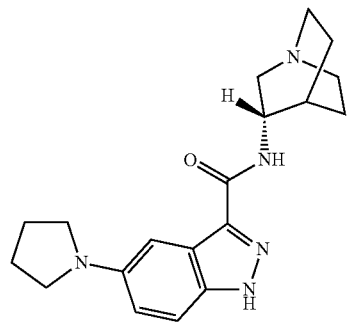 [SMILES: O=C(N[C@@H]1CN2CCC1CC2)c1n[nH]c2ccc(N3CCCC3)cc12]

Prepared using Procedure P in 24% yield. $^1$H NMR (CD$_3$OD) δ 7.43 (d, J=9.1, 1H), 7.20 (s, 1H), 6.98 (d, J=9.1, 1H), 4.20 (m, 1H), 3.5-3.2 (m, 5H), 3.15 (m, 1H), 3.0-2.8 (m, 4H), 2.2-2.0 (m, 6H), 1.79 (m, 2H), 1.55 (m, 1H); LC/MS (EI) t$_R$ 2.53, m/z 340 (M$^+$+1).

Example 181

N-[(3S)-1-Azabicyclo[2.2.2]oct-3-yl]-6-(4-cyclohexylpiperazin-1-yl)-1,2-benzisothiazole-3-carboxamide hydroformate

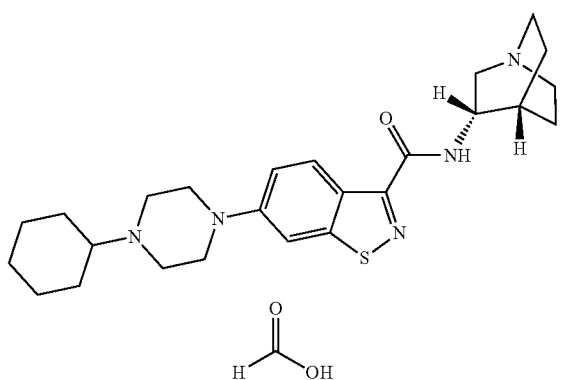

Prepared using Procedure P in 52% yield. LC/MS (EI) t$_R$ 2.40, m/z 454 (M$^+$+1).

Example 182

N-[(3S)-1-Azabicyclo[2.2.2]oct-3-yl]-6-(4-ethylpiperazin-1-yl)-1,2-benzisothiazole-3-carboxamide hydroformate

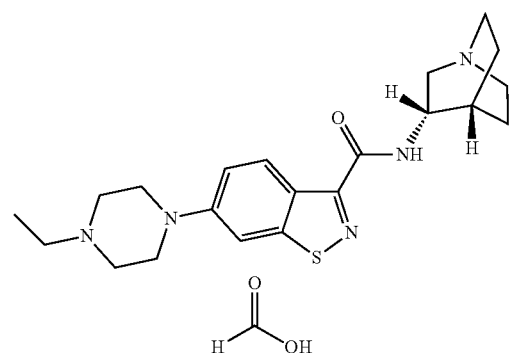

Prepared using Procedure P in 51% yield. LC/MS (EI) t$_R$ 1.57, m/z 400 (M$^+$+1).

Example 183

N-[(3S)-1-Azabicyclo[2.2.2]oct-3-yl]-6-[4-(3-furoyl)piperazin-1-yl]-1,2-benzisothiazole-3-carboxamide hydroformate

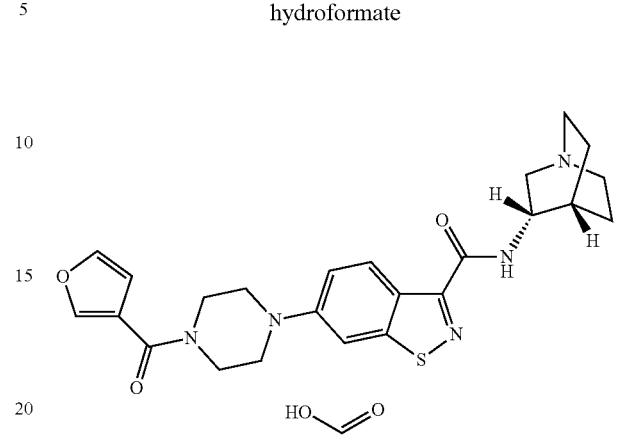

Prepared using Procedure P in 50% yield. LC/MS (EI) t$_R$ 4.61, m/z 466 (M$^+$+1).

Example 184

N-[(3S)-1-Azabicyclo[2.2.2]oct-3-yl]-5-(3-ethoxypyrrolidin-1-yl)-1,2-benzisothiazole-3-carboxamide

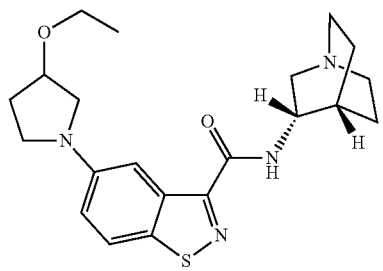

Prepared using Procedure P in 58% yield. LC/MS (EI) t$_R$ 3.87, m/z 401 (M$^+$+1).

Example 185

N-[(3S)-1-Azabicyclo[2.2.2]oct-3-yl]-6-(3-ethoxypyrrolidin-1-yl)-1,2-benzisothiazole-3-carboxamide

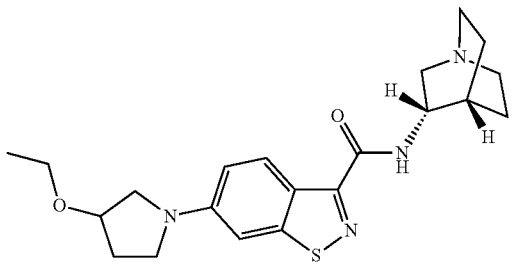

Prepared using Procedure P in 41% yield. LC/MS (EI) t$_R$ 3.67, m/z 401 (M$^+$+1).

Example 186

N-[(3S)-1-Azabicyclo[2.2.2]oct-3-yl]-5-(3-methoxy-pyrrolidin-1-yl)-1,2-benzisothiazole-3-carboxamide

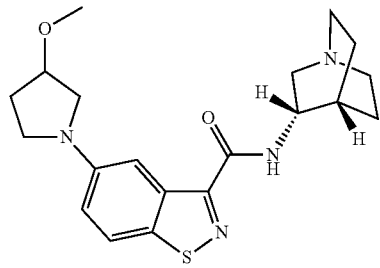

Prepared using Procedure P in 19% yield. LC/MS (EI) $t_R$ 3.63, m/z 387 (M$^+$+1).

Example 187

N-[(3S)-1-Azabicyclo[2.2.2]oct-3-yl]-6-pyrrolidin-1-yl-1H-indazole-3-carboxamide

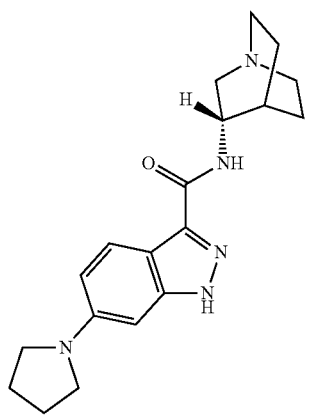 [SMILES: O=C(N[C@@H]1CN2CCC1CC2)c1n[nH]c2cc(N3CCCC3)ccc12]

Prepared using Procedure P in 24% yield. LC/MS (EI) $t_R$ 4.63, m/z 340 (M$^+$+1).

Example 188

N-[(3S)-1-Azabicyclo[2.2.2]oct-3-yl]-6-piperidin-1-yl-1H-indazole-3-carboxamide hydrotrifluoroacetate

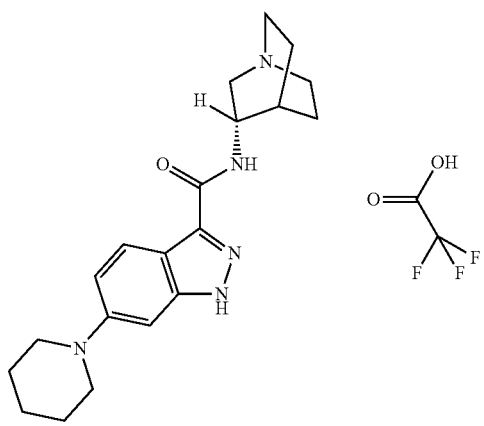 [SMILES: O=C(N[C@@H]1CN2CCC1CC2)c1n[nH]c2cc(N3CCCCC3)ccc12 ; O=C(O)C(F)(F)F]

Prepared using Procedure P in 51% yield. LC/MS (EI) $t_R$ 1.88, m/z 354 (M$^+$+1).

Example 189

N-[(3R)-1-Azabicyclo[2.2.2]oct-3-yl]-5-piperidin-1-yl-1H-indazole-3-carboxamide hydroformate

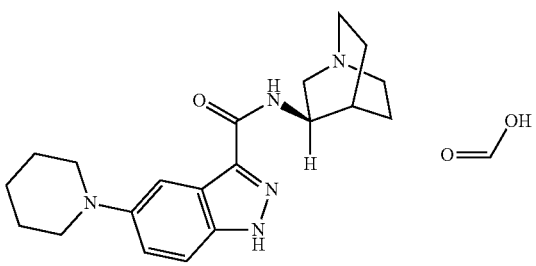 [SMILES: O=C(N[C@H]1CN2CCC1CC2)c1n[nH]c2ccc(N3CCCCC3)cc12 ; O=CO]

Prepared using Procedure P in 26% yield. LC/MS (EI) $t_R$ 1.60, m/z 354 (M$^+$+1).

Example 190

N-[(3R)-1-Azabicyclo[2.2.2]oct-3-yl]-6-morpholin-4-yl-1H-indazole-3-carboxamide

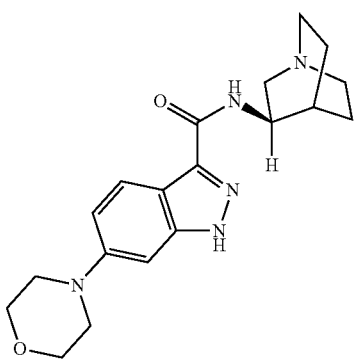 [SMILES: O=C(N[C@H]1CN2CCC1CC2)c1n[nH]c2cc(N3CCOCC3)ccc12]

Prepared using Procedure P in 25% yield. LC/MS (EI) $t_R$ 2.60, m/z 356 (M$^+$+1).

Example 191

N-[(3S)-1-Azabicyclo[2.2.2]oct-3-yl]-6-(morpholin-4-yl)-1H-indazole-3-carboxamide

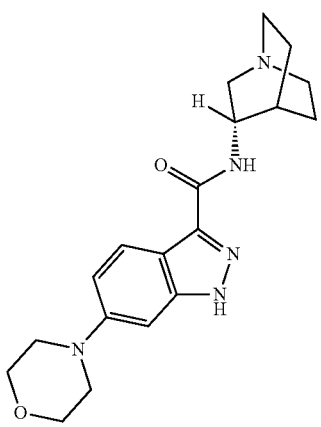 [SMILES: O=C(N[C@@H]1CN2CCC1CC2)c1n[nH]c2cc(N3CCOCC3)ccc12]

Prepared using Procedure P in 16% yield. LC/MS (EI) $t_R$ 2.42, m/z 356 (M$^+$+1).

Example 192

N-[(3S)-1-Azabicyclo[2.2.2]oct-3-yl]-5-[3-(benzyloxy)pyrrolidin-1-yl]-1-ethyl-1H-indazole-3-carboxamide hydroformate

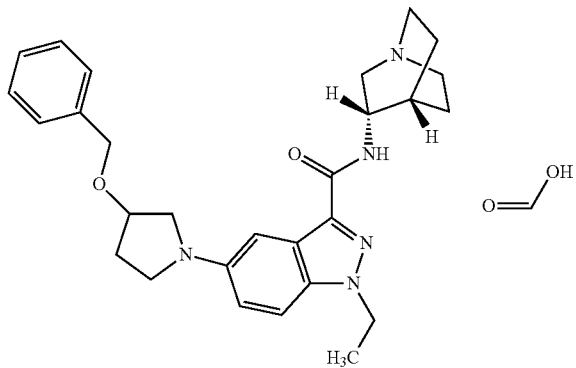

Prepared using Procedure P in 24% yield. LC/MS (EI) $t_R$ 4.53, m/z 474 (M$^+$+1).

Example 193

N-[(3S)-1-Azabicyclo[2.2.2]oct-3-yl]-6-[3-(benzyloxy)pyrrolidin-1-yl]-1-ethyl-1H-indazole-3-carboxamide hydroformate

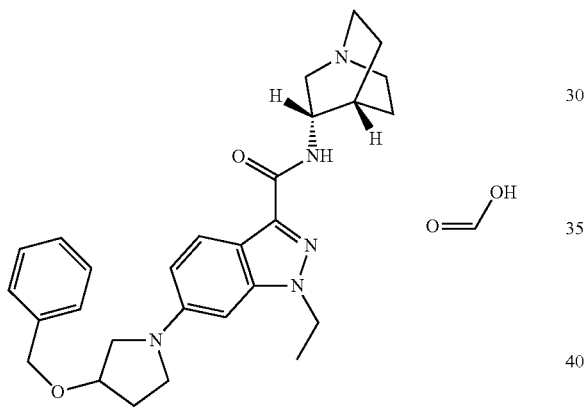

Prepared using Procedure P in 48% yield. LC/MS (EI) $t_R$ 4.55 min, m/z 474 (M$^+$+1).

Example 194

N-[(3S)-1-Azabicyclo[2.2.2]oct-3-yl]-5-[3-(benzyloxy)pyrrolidin-1-yl]-1-(cyclopropylmethyl)-1H-indazole-3-carboxamide hydroformate

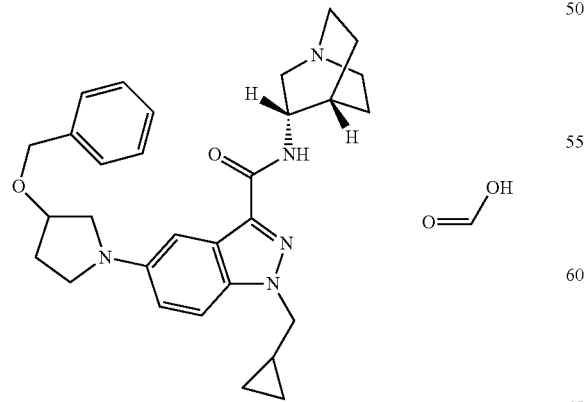

Prepared using Procedure P in 51% yield. LC/MS (EI) $t_R$ 4.67 min, m/z 500 (M$^+$+1).

Procedure Q

Procedure Q provides a method for the coupling between brominated aminoquinuclidinecarboxamides and benzophenone imine to form aniline derivatives.

The mixture of N-[(3S)-1-azabicyclo[2.2.2]oct-3-yl]-6-bromo-1,2-benzisothiazole-3-carboxamide (6.30 mmol), palladium acetate (1.00 mmol), and 9,9-dimethyl-4,5-bis(diphenylphosphino)xanthene (Xantphos) (0.700 mmol) was evacuated and back-fill with Ar gas. The solids were diluted with tetrahydrofuran (150 mL) and treated with cesium carbonate (7.00 mmol) and benzophenone imine (6.80 mmol). The reaction mixture was heated at reflux for 16 h. The reaction mixture was concentrated and redissolved in a mixture of tetrahydrofuran (90 mL) and 3 N hydrochloric acid (30 mL). The reaction mixture was maintained for 2 h and was concentrated. The residue was purified by chromatography using a mixture of 70/30/1 ethyl acetate/methanol/ammonium hydroxide, thus providing the aniline in 79% yield. The aniline was used directly in subsequent reactions.

The following compounds were prepared by this method:

Example 195

6-Amino-N-[(3S)-1-azabicyclo[2.2.2]oct-3-yl]-1,2-benzisoxazole-3-carboxamide

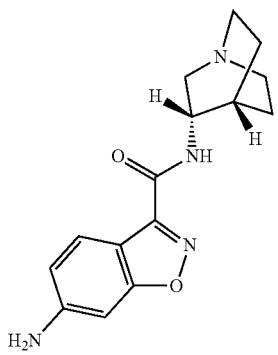

Prepared using Procedure Q in 72% yield. LC/MS (EI) $t_R$ 2.44, m/z 287 (M$^+$+1).

Example 196

6-Amino-N-[(3S)-1-azabicyclo[2.2.2]oct-3-yl]-1,2-benzisothiazole-3-carboxamide

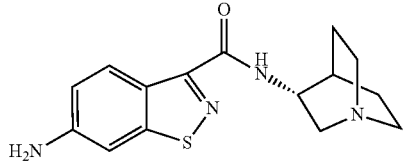 [SMILES: Nc1ccc2c(C(=O)N[C@H]3CN4CCC3CC4)nsc2c1]

Prepared using Procedure Q in 69% yield. LC/MS (EI) $t_R$ 2.86, m/z 303 (M$^+$+1).

Example 197

6-Amino-N-[(3R)-1-azabicyclo[2.2.2]oct-3-yl]-1,2-benzisothiazole-3-carboxamide

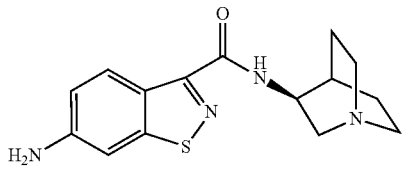 [SMILES: Nc1ccc2c(C(=O)N[C@@H]3CN4CCC3CC4)nsc2c1]

Prepared using Procedure Q in 73% yield. LC/MS (EI) $t_R$ 2.84, m/z 303 (M$^+$+1).

Example 198

5-Amino-N-[(3S)-1-azabicyclo[2.2.2]oct-3-yl]-1-(2,2,2-trifluoroethyl)-1H-indazole-3-carboxamide

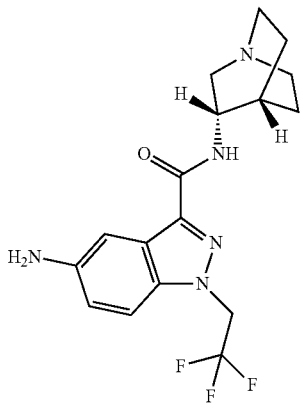

Prepared using Procedure Q in 64% yield. LC/MS (EI) $t_R$ 1.43, m/z 368 (M$^+$+1).

Example 199

5-Amino-N-[(3S)-1-azabicyclo[2.2.2]oct-3-yl]-1-(cyclopropylmethyl)-1H-indazole-3-carboxamide

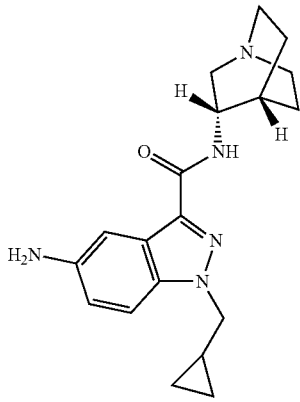

Prepared using Procedure Q in 67% yield. LC/MS (EI) $t_R$ 1.43, m/z 340 (M$^+$+1).

Example 200

5-Amino-N-[(3S)-1-azabicyclo[2.2.2]oct-3-yl]-1-(ethyl)-1H-indazole-3-carboxamide

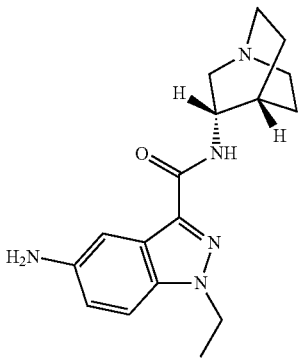

Prepared using Procedure Q in 68% yield. LC/MS (EI) $t_R$ 1.34, m/z 314 (M$^+$+1).

Example 201

6-Amino-N-[(3S)-1-azabicyclo[2.2.2]oct-3-yl]-1-(ethyl)-1H-indazole-3-carboxamide

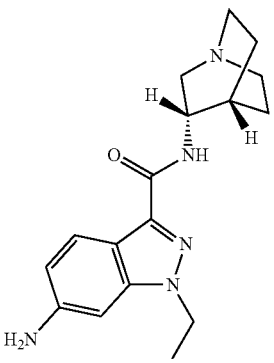

Prepared using Procedure Q in 61% yield. LC/MS (EI) $t_R$ 1.36, m/z 314 (M$^+$+1).

Procedure R

Procedure R provides a method for the reduction of nitro aminoquinuclidinecarboxamides to form aniline derivatives.

A mixture of the nitro compound (1.06 mmol) and 10% palladium on carbon (100 mg) in a Parr shaker bottle was diluted with methanol (100 mL). The reaction vessel was pressurized to 30 psi with hydrogen gas and was maintained for 3 h. The reaction was evacuated, back-filled with nitrogen gas, and the catalyst removed by filtration through Celite. The organic layer was concentrated to provide the amine product (91%). The aniline was used directly in subsequent reactions.

The following compounds were prepared by this method:

Example 202

6-Amino-N-[(3S)-1-azabicyclo[2.2.2]oct-3-yl]-1H-indazole-3-carboxamide

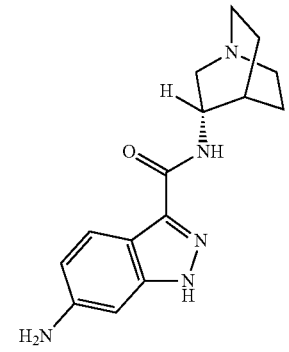 [SMILES: Nc1ccc2c(C(=O)N[C@@H]3CN4CCC3CC4)n[nH]c2c1]

Prepared using Procedure R in 4% yield. LC/MS (EI) $t_R$ 1.85, m/z 386 (M$^+$+1).

Example 203

5-Amino-N-[(3R)-1-azabicyclo[2.2.2]oct-3-yl]-1H-indazole-3-carboxamide

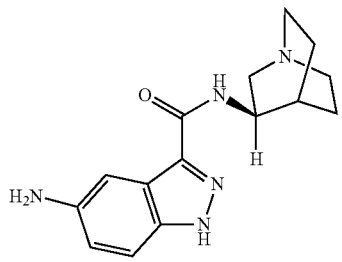 [SMILES: Nc1ccc2[nH]nc(C(=O)N[C@H]3CN4CCC3CC4)c2c1]

Prepared using Procedure R in 91% yield. LC/MS (EI) $t_R$ 1.36, m/z 286 (M$^+$+1).

Example 204

5-Amino-N-[(3S)-1-azabicyclo[2.2.2]oct-3-yl]-1H-indazole-3-carboxamide

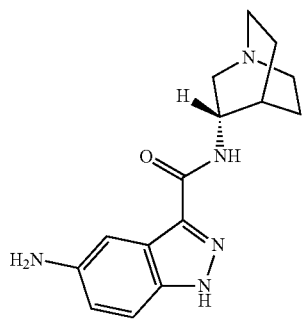 [SMILES: Nc1ccc2[nH]nc(C(=O)N[C@@H]3CN4CCC3CC4)c2c1]

Prepared using Procedure R in 95% yield. LC/MS (EI) $t_R$ 1.30, m/z 286 (M$^+$+1).

Example 205

4-Amino-N-[(3S)-1-azabicyclo[2.2.2]oct-3-yl]-1H-indazole-3-carboxamide

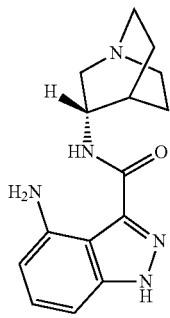 [SMILES: Nc1cccc2[nH]nc(C(=O)N[C@@H]3CN4CCC3CC4)c12]

Prepared from Example 87 using Procedure R in 97% yield. LC/MS (EI) $t_R$ 2.53, m/z 286 (M$^+$+1).

Example 206

7-Amino-N-[(3S)-1-azabicyclo[2.2.2]oct-3-yl]-1H-indazole-3-carboxamide

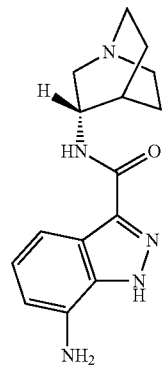 [SMILES: Nc1cccc2c(C(=O)N[C@@H]3CN4CCC3CC4)n[nH]c12]

Prepared from the corresponding 6-bromo-7-nitro analog using Procedure R in 11% yield. LC/MS (EI) $t_R$ 1.79, m/z 286 (M$^+$+1).

Procedure S.

Procedure S provides a method for the coupling between 3-aminoquinuclidine and carboxaldehydes to form secondary amine derivatives.

The suspension of 1H-indazole-4-carboxaldehyde (100 mg), 3-aminoquinuclidine dihydrochloride salt (1.0 eq), and 4 Å molecular sieves in dioxane (4 mL) was heated at reflux for 4 h. The reaction mixture was allowed to cool to rt and was treated with sodium triacetoxyborohydride (3 eq). The reaction mixture was maintained at rt for 2 h and was poured into water, extracted with 5% methanol in dichloromethane (2×30 mL), and the combined extracts were concentrated. The residue was purified by preparative HPLC.

The following compounds were prepared using this method:

Example 207

N-[(3R)-1-Azabicyclo[2.2.2]oct-3-yl]-5-[(2-methoxyethyl)amino]-1H-indazole-3-carboxamide dihydroformate

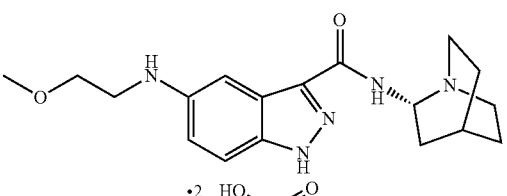

Prepared using Procedure S in 48% yield. $^1$H NMR (CD$_3$OD) δ 7.42 (d, J=9.0, 1H), 7.37 (s, 1H), 7.0 (d, J=9.0, 1H), 4.55 (m, 1H), 4.05 (m, 1H), 3.85 (m, 2H), 3.61-3.50 (m, 8H), 3.35 (s, 3H), 2.49-3.0 (m, 2H), 2.20 (m, 2H), 2.05 (m, 1H). LC/MS (EI) $t_R$ 1.65, m/z 344 (M$^+$+1).

Example 208

N-[(3S)-1-Azabicyclo[2.2.2]oct-3-yl]-5-[(cyclopropylmethyl)amino]-1H-indazole-3-carboxamide dihydroformate

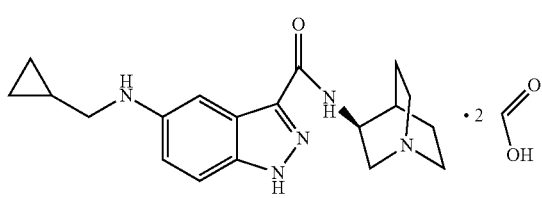 [SMILES: O=C(N[C@@H]1CN2CCC1CC2)c1n[nH]c2ccc(NCC3CC3)cc12 ; O=CO]

Prepared using Procedure S in 42% yield. LC/MS (EI) $t_R$ 1.77, m/z 340 (M$^+$+1).

Example 209

Methyl 4-[(3-{[(3S)-1-azabicyclo[2.2.2]oct-3-ylamino]carbonyl}-1H-indazol-5-yl)amino]butanoate dihydroformate

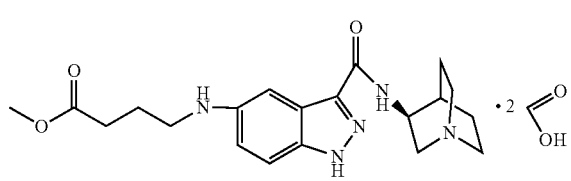 [SMILES: COC(=O)CCCNc1ccc2[nH]nc(C(=O)N[C@@H]3CN4CCC3CC4)c2c1 ; O=CO]

Prepared using Procedure S in 62% yield. LC/MS (EI) $t_R$ 1.36, m/z 386 (M$^+$+1).

Example 210

Methyl 4-[(3-{[(3S)-1-azabicyclo[2.2.2]oct-3-ylamino]carbonyl}-1H-indazol-6-yl)amino]butanoate dihydroformate

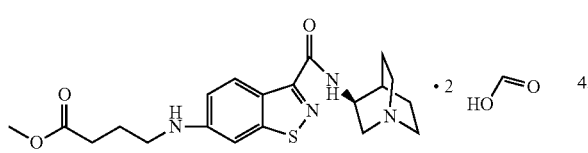

Prepared using Procedure S in 55% yield. LC/MS (EI) $t_R$ 2.62, m/z 403 (M$^+$+1).

Example 211 tert-Butyl {2-[(3-{[(3S)-1-azabicyclo[2.2.2]oct-3-ylamino]carbonyl}-1,2-benzisothiazol-6-yl)amino]ethyl}propylcarbamate dihydroformate

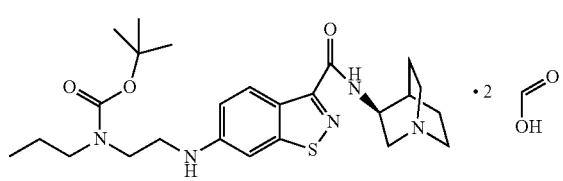 [SMILES: CCCN(CCNc1ccc2c(C(=O)N[C@@H]3CN4CCC3CC4)nsc2c1)C(=O)OC(C)(C)C ; O=CO]

Prepared using Procedure S in 63% yield. LC/MS (EI) $t_R$ 5.59, m/z 488 (M$^+$+1).

Example 212

N-[(3R)-1-Azabicyclo[2.2.2]oct-3-yl]-5-[(1,3-thiazol-2-ylmethyl)amino]-1H-indazole-3-carboxamide dihydroformate

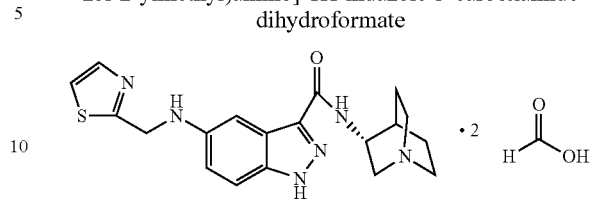

Prepared using Procedure S in 30% yield. LC/MS (EI) $t_R$ 2.84, m/z 383 (M$^+$+1).

Example 213

N-[(3S)-1-Azabicyclo[2.2.2]oct-3-yl]-5-(dimethylamino)-1H-indazole-3-carboxamide dihydroformate

Prepared using Procedure S in 52% yield. LC/MS (EI) $t_R$ 1.68, m/z 314 (M$^+$+1).

Example 214

N-[(3R)-1-Azabicyclo[2.2.2]oct-3-yl]-1-(2-methoxyethyl)-5-[(2-methoxyethyl)amino]-1H-indazole-3-carboxamide dihydroformate

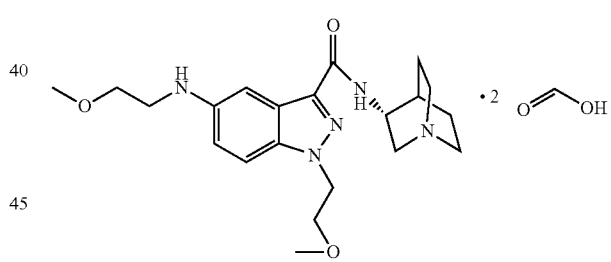

Prepared using Procedure S in 9% yield. LC/MS (EI) $t_R$ 2.84, m/z 402 (M$^+$+1).

Example 215

N-[(3S)-1-Azabicyclo[2.2.2]oct-3-yl]-6-{[2-(diethylamino)-2-oxoethyl]amino}-1,2-benzisothiazole-3-carboxamide dihydroformate

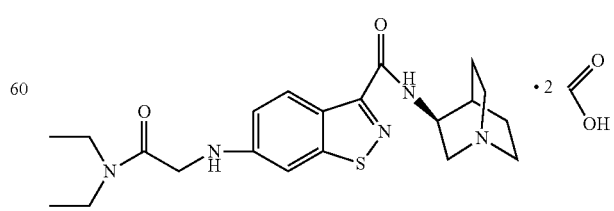

Prepared using Procedure S in 67% yield. LC/MS (EI) $t_R$ 3.67, m/z 416 (M$^+$+1).

Example 216

N-[(3R)-1-Azabicyclo[2.2.2]oct-3-yl]-5-(butylamino)-1H-indazole-3-carboxamide dihydroformate

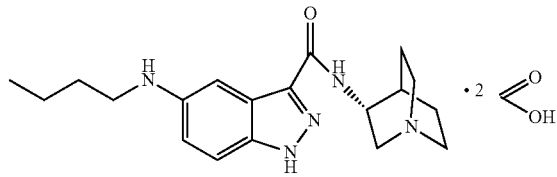 [SMILES: CCCCNc1ccc2[nH]nc(C(=O)N[C@H]3CN4CCC3CC4)c2c1 ; O=CO]

Prepared using Procedure S in 47% yield. LC/MS (EI) $t_R$ 2.38, m/z 342 (M$^+$+1).

Example 217

N-[(3S)-1-Azabicyclo[2.2.2]oct-3-yl]-6-[(cyclopropylmethyl)amino]-1,2-benzisothiazole-3-carboxamide dihydroformate

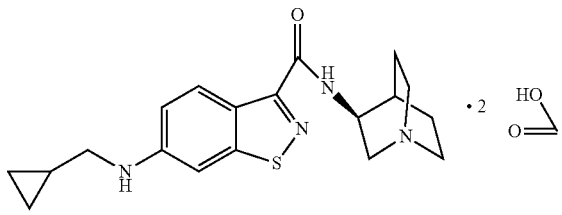 [SMILES: O=C(N[C@@H]1CN2CCC1CC2)c1nsc2cc(NCC3CC3)ccc12 ; O=CO]

Prepared using Procedure S in 45% yield. LC/MS (EI) $t_R$ 4.50, m/z 357 (M$^+$+1).

Example 218

N-[(3S)-1-Azabicyclo[2.2.2]oct-3-yl]-6-(dimethylamino)-1,2-benzisothiazole-3-carboxamide dihydroformate

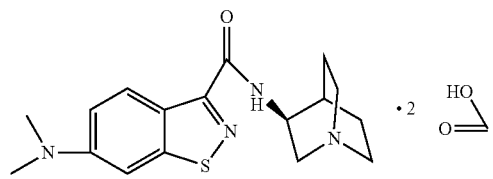 [SMILES: CN(C)c1ccc2c(C(=O)N[C@@H]3CN4CCC3CC4)nsc2c1 ; O=CO]

Prepared using Procedure S in 51% yield. LC/MS (EI) $t_R$ 2.53, m/z 331 (M$^+$+1).

Example 219

N-[(3R)-1-Azabicyclo[2.2.2]oct-3-yl]-6-(diethylamino)-1,2-benzisothiazole-3-carboxamide dihydroformate

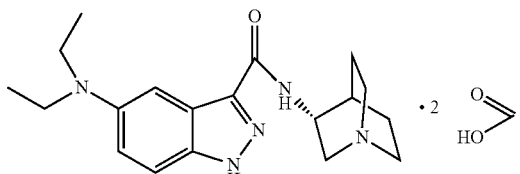

Prepared using Procedure S in 60% yield. LC/MS (EI) $t_R$ 1.36, m/z 342 (M$^+$+1).

Procedure T.

Procedure T provides a method for the coupling between amino aminoquinuclidinecarboxamides and acylating agents to form carboxamide derivatives.

To a solution of 5-amino-N-[(3S)-1-azabicyclo[2,2,2]oct-3-yl]-1H-indazole-3-carboxamide (0.42 mmol) in pyridine (2 mL) and N,N-dimethylformamide (2 mL) was added the trifluoroacetic anhydride (0.55 mmol). The mixture was maintained at ambient temperature for 16 h and was concentrated in vacuo. The residue was purified by preparative HPLC, thus providing the product in 30% yield and the bis-acylated product in 5% yield.

The following compounds were prepared by this method:

Example 220

N-[(3S)-1-Azabicyclo[2.2.2]oct-3-yl]-5-{[(4-methoxyphenyl)acetyl]amino}-1H-indazole-3-carboxamide hydroformate

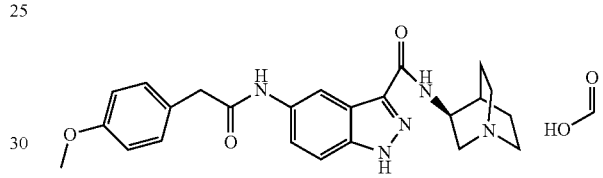

Prepared using Procedure T in 31% yield. $^1$H NMR (CD$_3$OD) δ 8.52 (s, 1H), 8.42 (s. 1H), 7.64-7.43 (m, 6H), 5.32 (s, 2H), 4.72 (m, 1H), 3.94 (m, 1H), 3.70-3.40 (m, 4H), 2.51 (m, 1H), 2.50 (m, 1H), 2.20 (m, 2H), 2.06 (m, 1H). LC/MS (EI) $t_R$ 4.94, m/z 434 (M$^+$+1).

Example 221

N-[(3S)-1-Azabicyclo[2.2.2]oct-3-yl]-6-[(cyclopropylcarbonyl)amino]-1-(cyclopropylmethyl)-1H-indazole-3-carboxamide

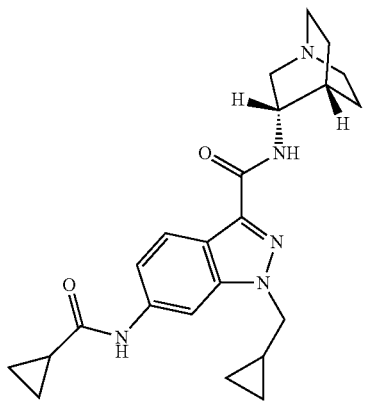

Prepared using Procedure T in 45% yield. LC/MS (EI) $t_R$ 4.77, m/z 408 (M$^+$+1).

Example 222

N-[(3S)-1-Azabicyclo[2.2.2]oct-3-yl]-5-[(trifluoroacetyl)amino]-1H-indazole-3-carboxamide hydroformate

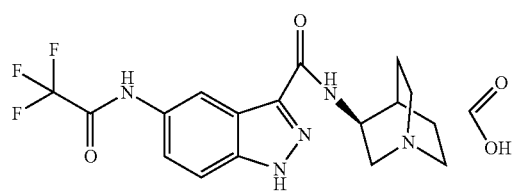

Prepared using Procedure T in 30% yield. LC/MS (EI) $t_R$ 3.28, m/z 382 (M$^+$+1).

Example 223

N-[(3S)-1-Azabicyclo[2.2.2]oct-3-yl]-5-[(cyclopropylcarbonyl)amino]-1H-indazole-3-carboxamide hydroformate

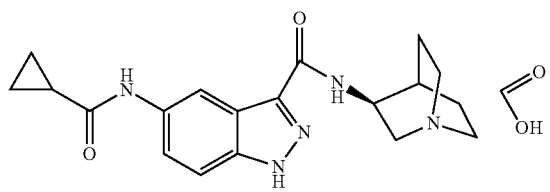

Prepared using Procedure T in 30% yield. LC/MS (EI) $t_R$ 2.61, m/z 354 (M$^+$+1).

Example 224

5-Amino-N-[(3S)-1-azabicyclo[2.2.2]oct-3-yl]-1-(trifluoroacetyl)-1H-indazole-3-carboxamide dihydroformate

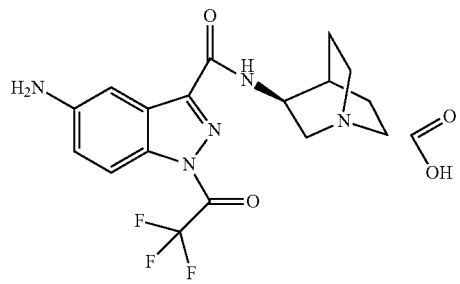

Prepared using Procedure T in 30% yield. LC/MS (EI) $t_R$ 2.92, m/z 382 (M$^+$+1).

Example 225

N-[(3S)-1-Azabicyclo[2.2.2]oct-3-yl]-1-(cyclopropylcarbonyl)-5-[(cyclopropylcarbonyl)amino]-1H-indazole-3-carboxamide hydroformate

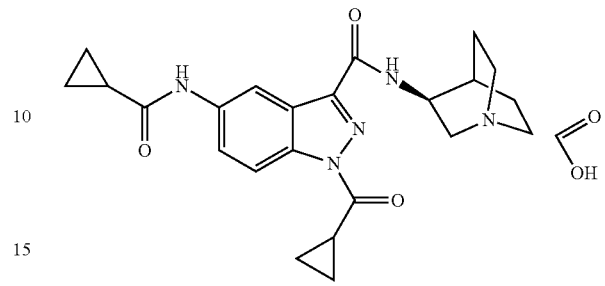

Prepared using Procedure T in 30% yield. LC/MS (EI) $t_R$ 5.09, m/z 422 (M$^+$+1).

Example 226

N-[(3S)-1-Azabicyclo[2.2.2]oct-3-yl]-1-[(4-methoxyphenyl)acetyl]-5-{[(4-methoxyphenyl)acetyl]amino}-1H-indazole-3-carboxamide hydroformate

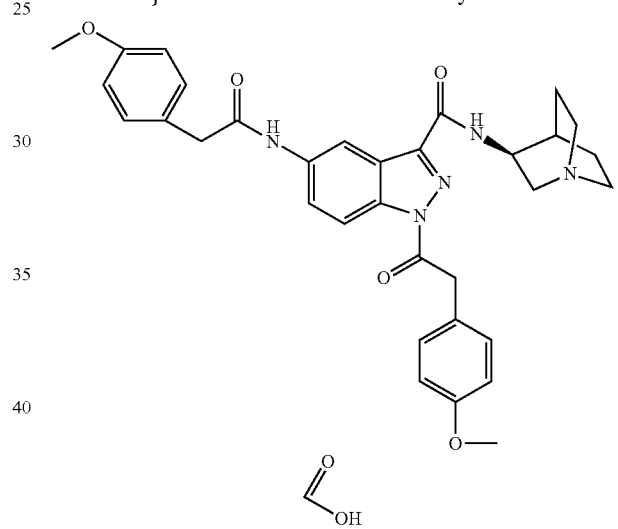

Prepared using Procedure T in 31% yield. LC/MS (EI) $t_R$ 5.44, m/z 583 (M$^+$+1).

Example 227

N-[(3S)-1-Azabicyclo[2.2.2]oct-3-yl]-6-[(cyclopropylcarbonyl)amino]-1,2-benzisothiazole-3-carboxamide hydroformate

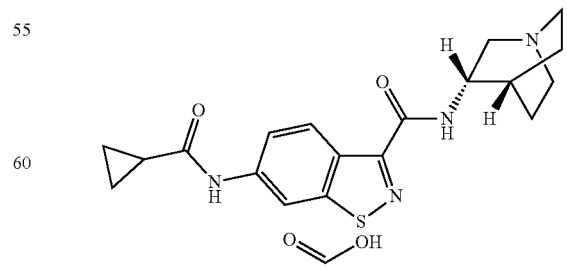

Prepared using Procedure T in 60% yield. LC/MS (EI) $t_R$ 3.66, m/z 371 (M$^+$+1).

Example 228

6-(Acetylamino)-N-[(3S)-1-azabicyclo[2.2.2]oct-3-yl]-1,2-benzisothiazole-3-carboxamide hydroformate

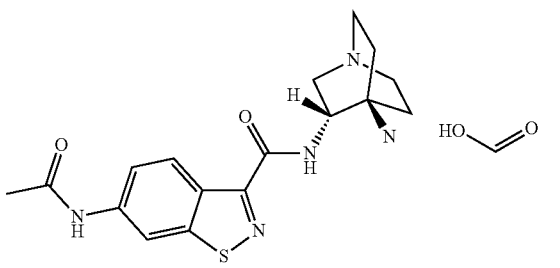

Prepared using Procedure T in 60% yield. LC/MS (EI) $t_R$ 2.42, m/z 345 (M$^+$+1).

Example 229

N-[(3S)-1-Azabicyclo[2.2.2]oct-3-yl]-6-[(cyclopropylcarbonyl)amino]-1-ethyl-1H-indazole-3-carboxamide

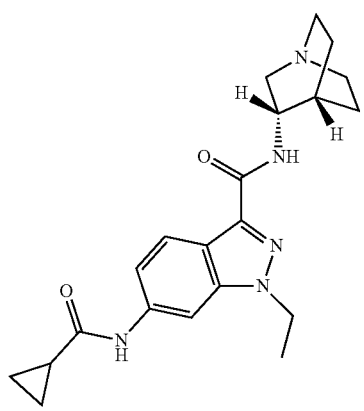

Prepared using Procedure T in 33% yield. LC/MS (EI) $t_R$ 3.44, m/z 382 (M$^+$+1).

Example 230

N-[(3S)-1-Azabicyclo[2.2.2]oct-3-yl]-5-[(cyclopropylcarbonyl)amino]-1-cyclopropylmethyl-1H-indazole-3-carboxamide

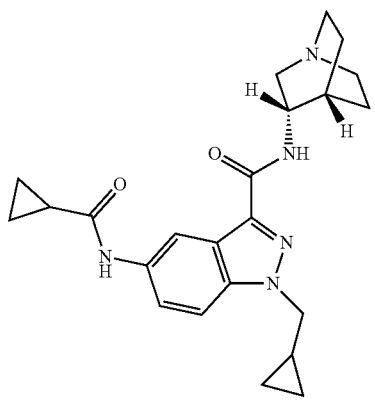

Prepared using Procedure T in 44% yield. LC/MS (EI) $t_R$ 3.68, m/z 408 (M$^+$+1).

Example 231

N-[(3S)-1-Azabicyclo[2.2.2]oct-3-yl]-5-[(cyclopropylcarbonyl)amino]-1-(2,2,2-trifluoroethyl)-1H-indazole-3-carboxamide

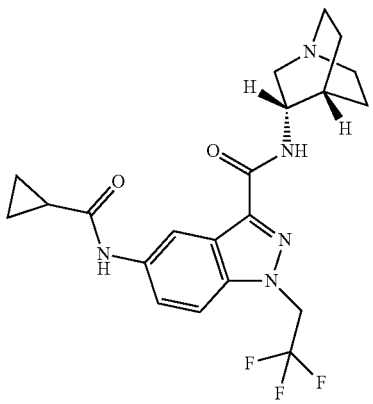

Prepared using Procedure T in 47% yield. LC/MS (EI) $t_R$ 3.66, m/z 436 (M$^+$+1).

Procedure U.

Procedure U provides a method for the coupling between amino aminoquinuclidinecarboxamides and sulfonylating agents to form sulfonamide derivatives.

Ethanesulfonyl chloride (0.25 mmoL) was added to a solution of the amine (0.20 mmol) in a mixture of pyridine (2 mL) and N,N-dimethylformamide (1 mL). The mixture was maintained at ambient temperature for 16 h and was concentrated in vacuo. The residue was purified by preparative HPLC, thus providing the product in 60% yield and the bis-sulfonylated product in 20% yield.

The following compounds were prepared by this method:

Example 232

N-[(3R)-1-Azabicyclo[2.2.2]oct-3-yl]-5-[(ethylsulfonyl)amino]-1H-indazole-3-carboxamide hydroformate

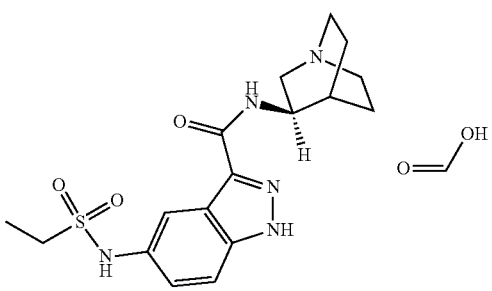 [SMILES: CCS(=O)(=O)Nc1ccc2[nH]nc(C(=O)N[C@H]3CN4CCC3CC4)c2c1 ; O=CO]

Prepared using Procedure U in 32% yield. $^1$H NMR (CD$_3$OD) δ 8.09 (s, 1H), 7.55 (d, J=8.9, 1H), 7.41 (d, J=8.9, 1H), 4.20 (m, 1H), 3.35 (m, 1H), 3.08 (q, J=7.4, 2H), 3.02 (m, 1H), 3.0-2.8 (m, 4H), 2.06 (m, 1H), 2.00 (m, 1H), 1.79 (m, 2H), 1.55 (m, 1H), 1.32 (t, J=7.4, 3H); LC/MS (EI) $t_R$ 2.37, m/z 378 (M$^+$+1).

Example 233

N-[(3R)-1-Azabicyclo[2.2.2]oct-3-yl]-6-[(ethylsulfonyl)amino]-1,2-benzisothiazole-3-carboxamide

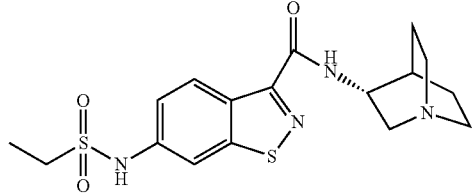 [SMILES: CCS(=O)(=O)Nc1ccc2c(C(=O)N[C@H]3CN4CCC3CC4)nsc2c1]

Prepared using Procedure U in 74% yield. LC/MS (EI) $t_R$ 2.85, m/z 395 (M$^+$+1).

Example 234

N-[(3S)-1-Azabicyclo[2.2.2]oct-3-yl]-6-[(ethylsulfonyl)amino]-1,2-benzisothiazole-3-carboxamide

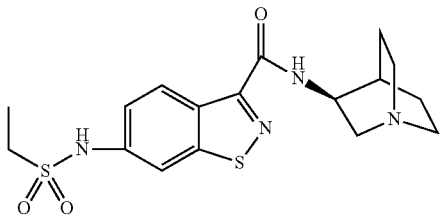 [SMILES: CCS(=O)(=O)Nc1ccc2c(C(=O)N[C@@H]3CN4CCC3CC4)nsc2c1]

Prepared using Procedure U in 73% yield. LC/MS (EI) $t_R$ 2.82, m/z 395 (M$^+$+1).

Example 235

N-[(3R)-1-Azabicyclo[2.2.2]oct-3-yl]-6-[(methylsulfonyl)amino]-1,2-benzisothiazole-3-carboxamide

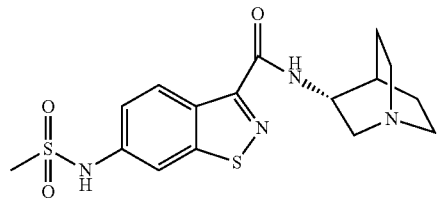 [SMILES: CS(=O)(=O)Nc1ccc2c(C(=O)N[C@H]3CN4CCC3CC4)nsc2c1]

Prepared using Procedure U in 71% yield. LC/MS (EI) $t_R$ 2.84, m/z 381 (M$^+$+1).

Example 236

N-[(3S)-1-Azabicyclo[2.2.2]oct-3-yl]-6-[(methylsulfonyl)amino]-1,2-benzisothiazole-3-carboxamide

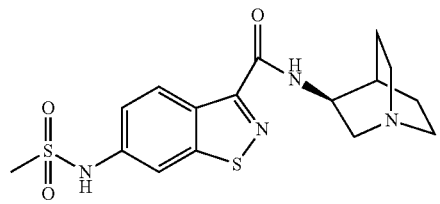 [SMILES: CS(=O)(=O)Nc1ccc2c(C(=O)N[C@@H]3CN4CCC3CC4)nsc2c1]

Prepared using Procedure U in 69% yield. LC/MS (EI) $t_R$ 2.82, m/z 381 (M$^+$+1).

Example 237

N-[(3S)-1-Azabicyclo[2.2.2]oct-3-yl]-5-[(benzylsulfonyl)amino]-1H-indazole-3-carboxamide hydroformate

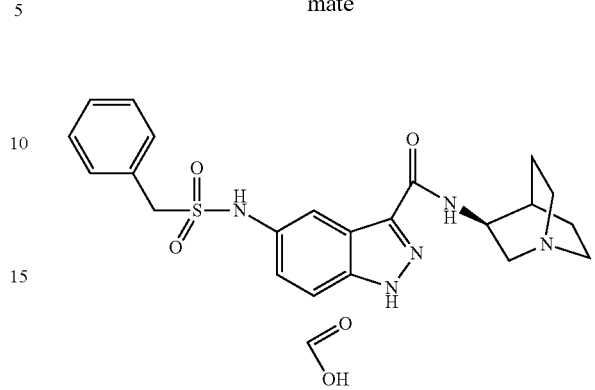

Prepared using Procedure U in 35% yield. LC/MS (EI) $t_R$ 4.64, m/z 440 (M$^+$+1).

Example 238

N-[(3S)-1-Azabicyclo[2.2.2]oct-3-yl]-6-{[(dimethylamino)sulfonyl]amino}-1,2-benzisothiazole-3-carboxamide hydroformate

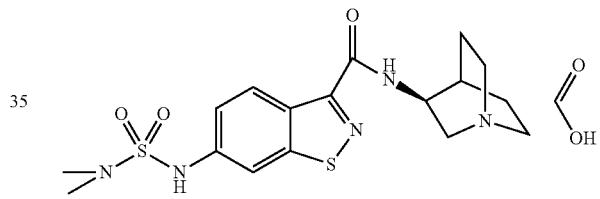

Prepared using Procedure U in 48% yield. LC/MS (EI) $t_R$ 3.53, m/z 410 (M$^+$+1).

Example 239

5-Amino-N-[(3S)-1-azabicyclo[2.2.2]oct-3-yl]-1-(benzylsulfonyl)-1H-indazole-3-carboxamide dihydroformate

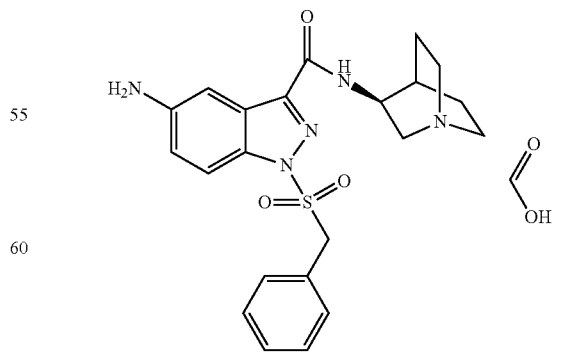

Prepared using Procedure U in 35% yield. LC/MS (EI) $t_R$ 4.29, m/z 440 (M$^+$+1).

Example 240

N-[(3S)-1-Azabicyclo[2.2.2]oct-3-yl]-5-[(methylsulfonyl)amino]-1H-indazole-3-carboxamide hydroformate

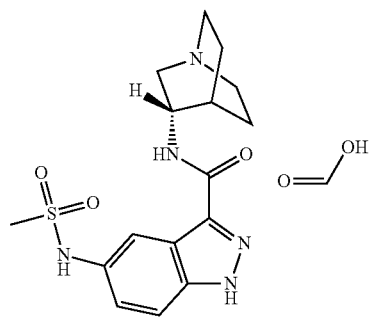

Prepared using Procedure U in 19% yield. LC/MS (EI) $t_R$ 1.61, m/z 364 (M$^+$+1).

Example 241

N-[(3S)-1-Azabicyclo[2.2.2]oct-3-yl]-5-[(ethylsulfonyl)amino]-1H-indazole-3-carboxamide hydroformate

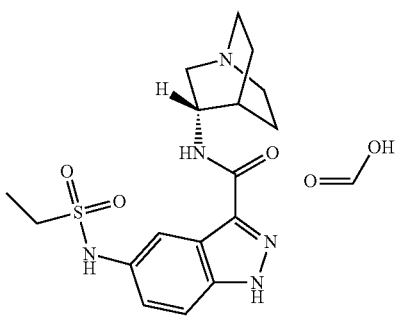

Prepared using Procedure U in 10% yield. LC/MS (EI) $t_R$ 2.43, m/z 378 (M$^+$+1).

Example 242

N-[(3S)-1-Azabicyclo[2.2.2]oct-3-yl]-4-[(methylsulfonyl)amino]-1H-indazole-3-carboxamide

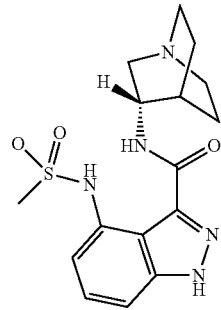

Prepared using Procedure U in 9% yield. LC/MS (EI) $t_R$ 3.96, m/z 364 (M$^+$+1).

Procedure V.

Procedure V provides a method for the coupling between amino aminoquinuclidinecarboxamides and isocyanates to form urea derivatives.

To the amine (0.40 mmol) in a mixture of pyridine (2 mL) and N,N-dimethylformamide (1 mL) was added 5-chloro-2-methylphenyl isocyanate (0.53 mmol). The reaction mixture was maintained at ambient temperature for 16 h and was concentrated in vacuo. The residue was purified by chromatography (70/30/1 ethyl acetate/methanol/ammonium hydroxide), thus providing the product in 78% yield.

The following compounds were prepared by this method:

Example 243

N-[(3S)-1-Azabicyclo[2.2.2]oct-3-yl]-6-[({[2-(2,6-dichlorophenyl)ethyl]amino}carbonyl)amino]-1,2-benzisothiazole-3-carboxamide

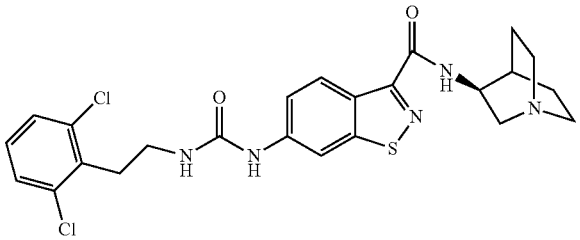 [SMILES: O=C(NCCc1c(Cl)cccc1Cl)Nc1ccc2c(C(=O)N[C@@H]3CN4CCC3CC4)nsc2c1]

Prepared using Procedure V in 70% yield. $^1$H NMR (CD$_3$OD) δ 8.68 (d, J=9.0, 1H), 8.46 (s, 1H), 7.47-7.30 (m, 3H), 7.33 (d, J=9.0, 1H), 3.97 (m, 1H), 3.96 (t, J=12.0, 1H), 3.64 (t, J=6.0, 2H), 3.50-3.30 (m, 6H), 2.52 (m, 1H), 2.40 (m, 1H), 2.20 (m, 2H), 2.10 (m, 1H). LC/MS (EI) $t_R$ 5.55, m/z 518 (M$^+$+1).

Example 244

N-[(3S)-1-Azabicyclo[2.2.2]oct-3-yl]-1-(cyclopropylmethyl)-6-{[(propylamino)carbonyl]amino}-1H-indazole-3-carboxamide

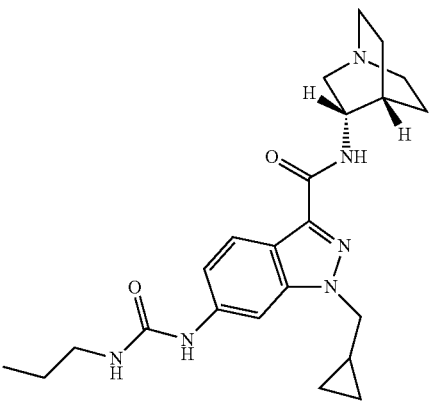

Prepared using Procedure V in 32% yield. LC/MS (EI) $t_R$ 4.88, m/z 425 (M$^+$+1).

Example 245

N-[(3S)-1-Azabicyclo[2.2.2]oct-3-yl]-6-({[(3-cyanophenyl)amino]carbonyl}-amino)-1,2-benzisothiazole-3-carboxamide

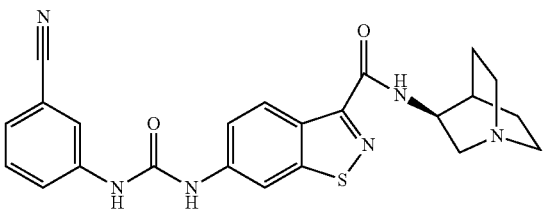 [SMILES: N#Cc1cccc(NC(=O)Nc2ccc3c(C(=O)N[C@@H]4CN5CCC4CC5)nsc3c2)c1]

Prepared using Procedure V in 40% yield. LC/MS (EI) $t_R$ 5.74, m/z 447 (M$^+$+1).

Example 246

N-[(3R)-1-Azabicyclo[2.2.2]oct-3-yl]-6-[({[2-(4-fluorophenyl)ethyl]amino}carbonyl)amino]-1,2-benzisothiazole-3-carboxamide

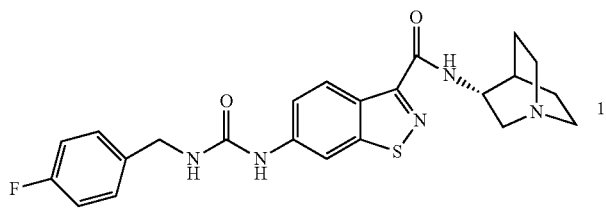

Prepared using Procedure V in 50% yield. LC/MS (EI) $t_R$ 5.42, m/z 454 (M$^+$+1).

Example 247

N-[(3R)-1-Azabicyclo[2.2.2]oct-3-yl]-6-({[(3,4-dimethylphenyl)amino]carbonyl}amino)-1,2-benzisothiazole-3-carboxamide

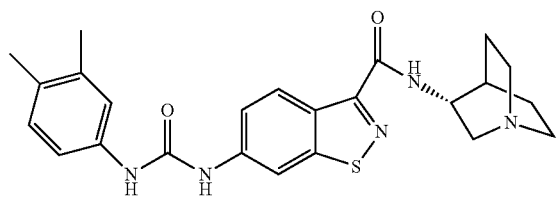 [SMILES: Cc1ccc(NC(=O)Nc2ccc3c(C(=O)N[C@H]4CN5CCC4CC5)nsc3c2)cc1C]

Prepared using Procedure V in 76% yield. LC/MS (EI) $t_R$ 5.79, m/z 450 (M$^+$+1).

Example 248

N-[(3R)-1-Azabicyclo[2.2.2]oct-3-yl]-6-({[(2,5-dimethylphenyl)amino]carbonyl}amino)-1,2-benzisothiazole-3-carboxamide

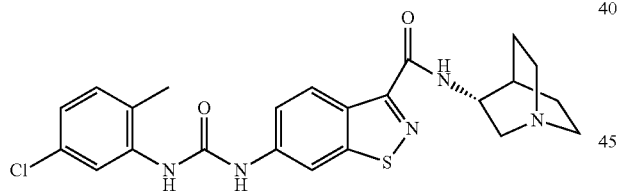

Prepared using Procedure V in 78% yield. LC/MS (EI) $t_R$ 5.92, m/z 470 (M$^+$+1).

Example 249

N-[(3R)-1-Azabicyclo[2.2.2]oct-3-yl]-6-({[(4-methylbenzyl)amino]carbonyl}amino)-1,2-benzisothiazole-3-carboxamide

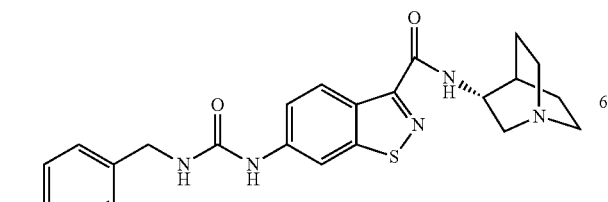

Prepared using Procedure V in 40% yield. LC/MS (EI) $t_R$ 5.78, m/z 450 (M$^+$+1).

Example 250

N-[(3S)-1-Azabicyclo[2.2.2]oct-3-yl]-6-[({[2-(4-methylphenyl)ethyl]amino}carbonyl)amino]-1,2-benzisothiazole-3-carboxamide

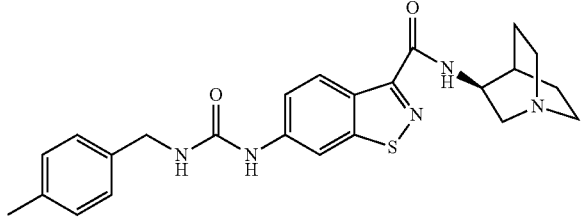 [SMILES: Cc1ccc(CNC(=O)Nc2ccc3c(C(=O)N[C@@H]4CN5CCC4CC5)nsc3c2)cc1]

Prepared using Procedure V in 71% yield. LC/MS (EI) $t_R$ 5.54, m/z 450 (M$^+$+1).

Example 251

N-[(3S)-1-Azabicyclo[2.2.2]oct-3-yl]-6-[({[2-(3-methoxyphenyl)ethyl]amino}carbonyl)amino]-1,2-benzisothiazole-3-carboxamide

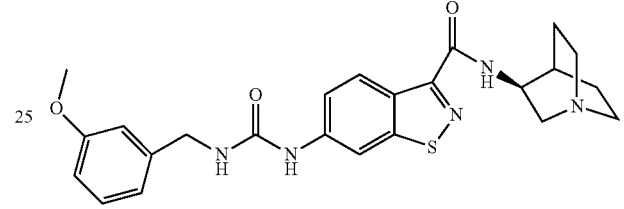

Prepared using Procedure V in 74% yield. LC/MS (EI) $t_R$ 5.37, m/z 466 (M$^+$+1).

Example 252

N-[(3S)-1-Azabicyclo[2.2.2]oct-3-yl]-6-{[(cyclopentylamino)carbonyl]amino}-1,2-benzisothiazole-3-carboxamide

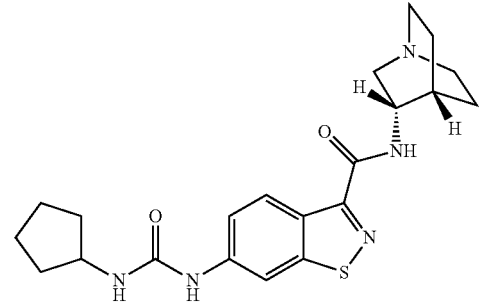

Prepared using Procedure V in 63% yield. LC/MS (EI) $t_R$ 5.34, m/z 414 (M$^+$+1).

Example 253

N-[(3S)-1-Azabicyclo[2.2.2]oct-3-yl]-6-{[(propylamino)carbonyl]amino}-1,2-benzisothiazole-3-carboxamide

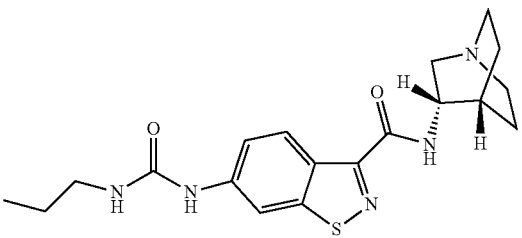

Prepared using Procedure V in 70% yield. LC/MS (EI) $t_R$ 4.40, m/z 388 (M$^+$+1).

Example 254

N-[(3R)-1-Azabicyclo[2.2.2]oct-3-yl]-5-({[(4-fluorobenzyl)amino]carbonyl}amino)-1H-indazole-3-carboxamide

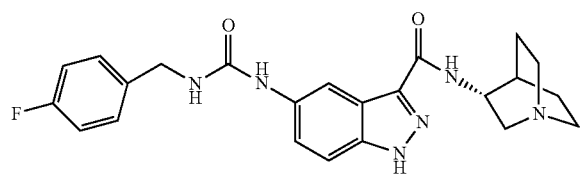 [SMILES: O=C(NCc1ccc(F)cc1)Nc1ccc2[nH]nc(C(=O)N[C@H]3CN4CCC3CC4)c2c1]

Prepared using Procedure V in 65% yield. LC/MS (EI) $t_R$ 5.03, m/z 397 (M$^+$+1).

Example 255

N-[(3R)-1-Azabicyclo[2.2.2]oct-3-yl]-5-({[(3-methoxybenzyl)amino]carbonyl}amino)-1H-indazole-3-carboxamide

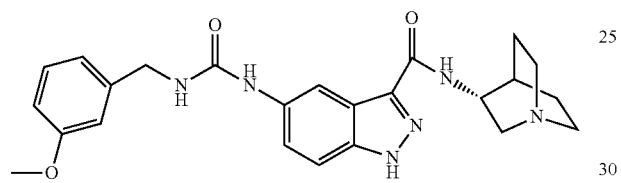

Prepared using Procedure V in 68% yield. LC/MS (EI) $t_R$ 5.02, m/z 449 (M$^+$+1).

Example 256

N-[(3R)-1-Azabicyclo[2.2.2]oct-3-yl]-5-{[(cyclopentylamino)carbonyl]amino}-1H-indazole-3-carboxamide

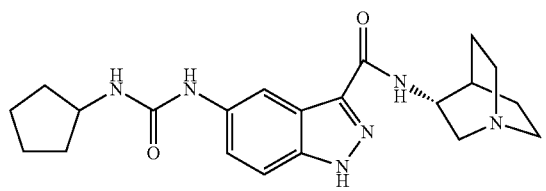 [SMILES: O=C(Nc1ccc2[nH]nc(C(=O)N[C@H]3CN4CCC3CC4)c2c1)NC1CCCC1]

Prepared using Procedure V in 54% yield. LC/MS (EI) $t_R$ 4.24, m/z 397 (M$^+$+1).

Example 257

N-[(3S)-1-Azabicyclo[2.2.2]oct-3-yl]-5-({[(3-methoxybenzyl)amino]carbonyl}amino)-1H-indazole-3-carboxamide

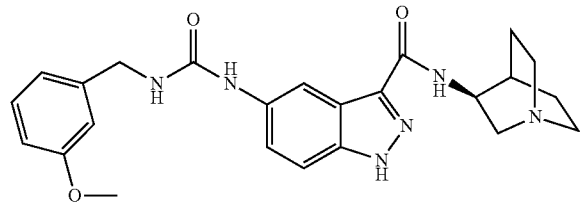 [SMILES: COc1cccc(CNC(=O)Nc2ccc3[nH]nc(C(=O)N[C@@H]4CN5CCC4CC5)c3c2)c1]

Prepared using Procedure V in 64% yield. LC/MS (EI) $t_R$ 4.75, m/z 434 (M$^+$+1).

Example 258

N-[(3S)-1-Azabicyclo[2.2.2]oct-3-yl]-5-({[(4-fluorobenzyl)amino]carbonyl}amino)-1H-indazole-3-carboxamide

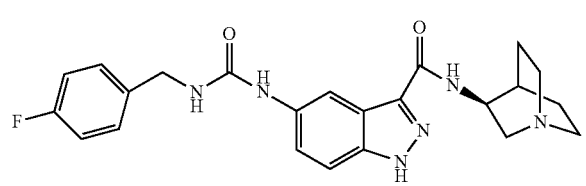 [SMILES: O=C(NCc1ccc(F)cc1)Nc1ccc2[nH]nc(C(=O)N[C@@H]3CN4CCC3CC4)c2c1]

Prepared using Procedure V in 57% yield. LC/MS (EI) $t_R$ 5.03, m/z 397 (M$^+$+1).

Example 259

N-[(3S)-1-Azabicyclo[2.2.2]oct-3-yl]-6-{[(propylamino)carbonyl]amino}-1,2-benzisothiazole-3-carboxamide hydroformate

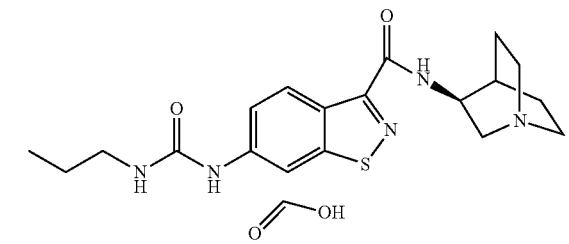

Prepared using Procedure V in 70% yield. LC/MS (EI) $t_R$ 4.78, m/z 388 (M$^+$+1).

Example 260

N-[(3R)-1-Azabicyclo[2.2.2]oct-3-yl]-5-{[(propylamino)carbonyl]amino}-1H-indazole-3-carboxamide hydroformate

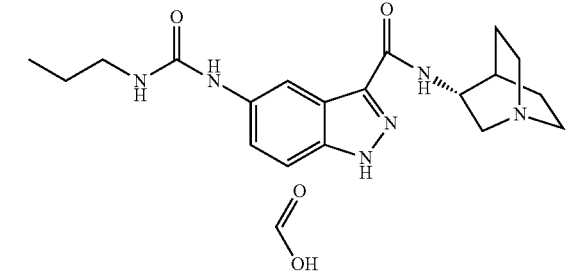

Prepared using Procedure V in 35% yield. LC/MS (EI) $t_R$ 2.87, m/z 371 (M$^+$+1).

Example 261

N-[(3S)-1-Azabicyclo[2.2.2]oct-3-yl]-5-{[(propylamino)carbonyl]amino}-1H-indazole-3-carboxamide hydroformate

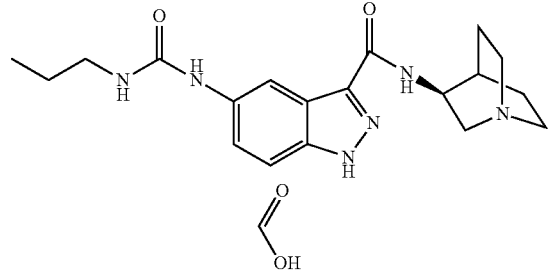

Prepared using Procedure V in 30% yield. LC/MS (EI) $t_R$ 2.91, m/z 371 (M$^+$+1).

Example 262

N-[(3S)-1-Azabicyclo[2.2.2]oct-3-yl]-5-({[(4-fluorobenzyl)amino]carbonyl}amino)-1H-indazole-3-carboxamide hydroformate

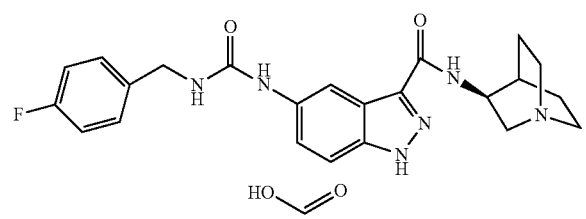

Prepared using Procedure V in 41% yield. LC/MS (EI) $t_R$ 5.03, m/z 397 (M$^+$+1).

Example 263

N-[(3R)-1-Azabicyclo[2.2.2]oct-3-yl]-5-({[(4-fluorobenzyl)amino]carbonyl}amino)-1H-indazole-3-carboxamide hydroformate

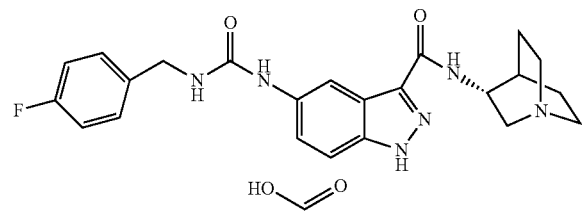

Prepared using Procedure V in 36% yield. LC/MS (EI) $t_R$ 5.02, m/z 437 (M$^+$+1).

Example 264

N-[(3R)-1-Azabicyclo[2.2.2]oct-3-yl]-5-{[(cyclopentylamino)carbonyl]amino}-1H-indazole-3-carboxamide hydroformate

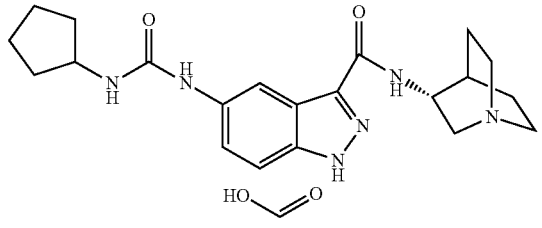

Prepared using Procedure V in 34% yield. LC/MS (EI) $t_R$ 4.24, m/z 397 (M$^+$+1).

Example 265

N(3)-[(3S)-1-Azabicyclo[2.2.2]oct-3-yl]-N(1)-(3-methoxybenzyl)-5-({[(3-methoxybenzyl)amino]carbonyl}amino)-1H-indazole-1,3-dicarboxamide

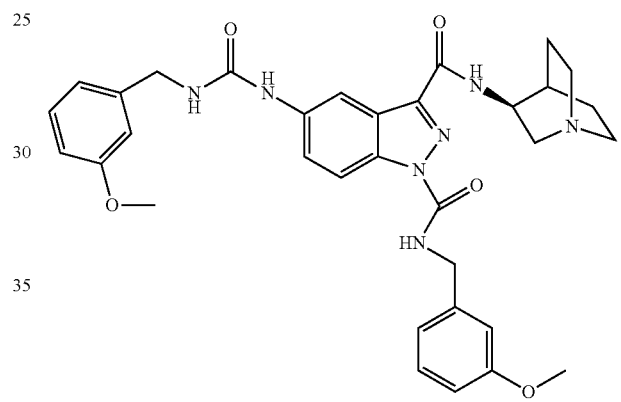

Prepared using Procedure V in 14% yield. LC/MS (EI) $t_R$ 5.74, m/z 612 (M$^+$+1).

Example 266

N(3)-[(3S)-1-Azabicyclo[2.2.2]oct-3-yl]-N(1)-(4-fluorobenzyl)-5-({[(4-fluorobenzyl)amino]carbonyl}amino)-1H-indazole-1,3-dicarboxamide

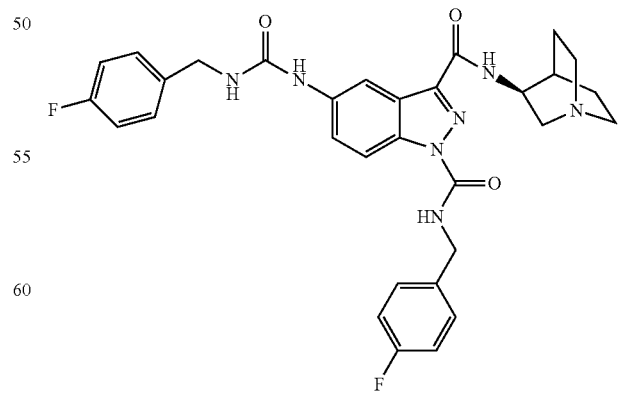

Prepared using Procedure V in 13% yield. LC/MS (EI) $t_R$ 5.81, m/z 588 (M$^+$+1).

Example 267

N(3)-[(3R)-1-Azabicyclo[2.2.2]oct-3-yl]-N(1)-cyclopentyl-5-{[(cyclopentylamino)carbonyl]amino}-1H-indazole-1,3-dicarboxamide hydroformate

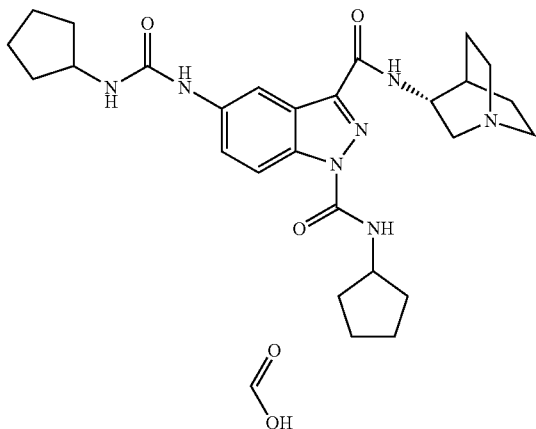

Prepared using Procedure V in 13% yield. LC/MS (EI) $t_R$ 5.51, m/z 508 (M$^+$+1).

Example 268

N(3)[(3S)-1-Azabicyclo[2.2.2]oct-3-yl]-N(1)-propyl-5-{[(propylamino)carbonyl]amino}-1H-indazole-1,3-dicarboxamide

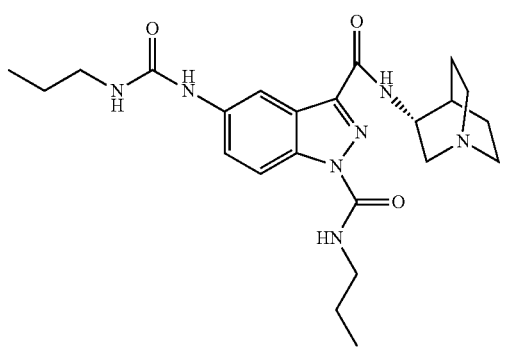

Prepared using Procedure V in 9.4% yield. LC/MS (EI) $t_R$ 5.24, m/z 456 (M$^+$+1).

Example 269

N-[(3R)-1-Azabicyclo[2.2.2]oct-3-yl]-5-({[(cyclopropylmethyl)amino]carbonothioyl}amino)-1H-indazole-3-carboxamide hydroformate

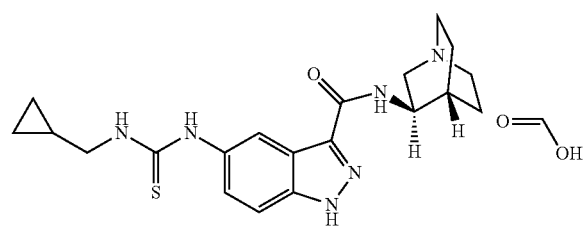

Prepared using Procedure V in 47% yield. LC/MS (EI) $t_R$ 2.75, m/z 399 (M$^+$+1).

Example 270

N-[(3S)-1-Azabicyclo[2.2.2]oct-3-yl]-6-({[(cyclopropylmethyl)amino]carbonothioyl}amino)-1,2-benzisothiazole-3-carboxamide hydroformate

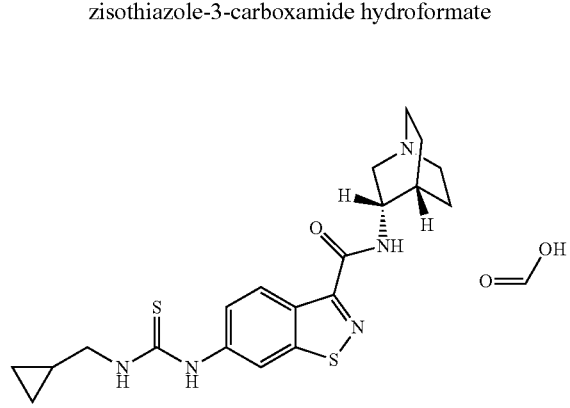

Prepared using Procedure V in 26% yield. LC/MS (EI) $t_R$ 3.98, m/z 416 (M$^+$+1).

Example 271

N-[(3S)-1-Azabicyclo[2.2.2]oct-3-yl]-6-{[(propylmethylamino)carbonothioyl]amino}-1,2-benzisothiazole-3-carboxamide hydroformate

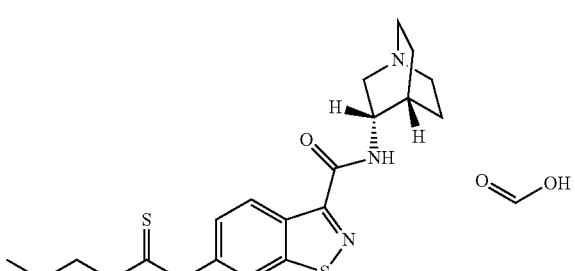

Prepared using Procedure V in 60% yield. LC/MS (EI) $t_R$ 3.01, m/z 404 (M$^+$+1).

Example 272

N-[(3S)-1-Azabicyclo[2.2.2]oct-3-yl]-6-{[(tert-butylamino)carbonothioyl]amino}-1,2-benzisothiazole-3-carboxamide hydroformate

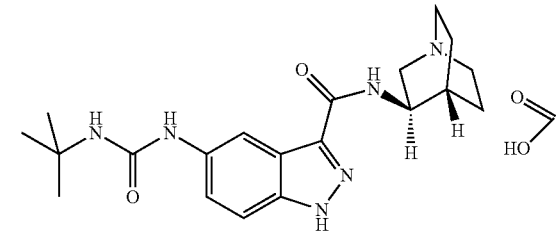

Prepared using Procedure V in 47% yield. LC/MS (EI) $t_R$ 3.65, m/z 385 (M$^+$+1).

Example 273

N-[(3R)-1-Azabicyclo[2.2.2]oct-3-yl]-5-{[(sec-butylamino)carbonyl]amino}-1H-indazole-3-carboxamide hydroformate

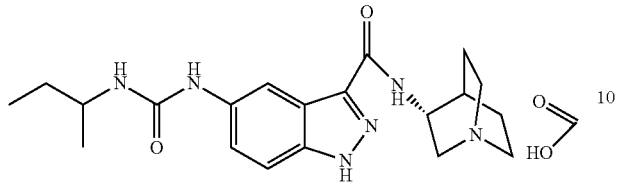

Prepared using Procedure V in 43% yield. LC/MS (EI) $t_R$ 2.46, m/z 385 (M$^+$+1).

Example 274

N-[(3S)-1-Azabicyclo[2.2.2]oct-3-yl]-1-ethyl-6-{[(propylamino)carbonyl]amino}-1H-indazole-3-carboxamide hydroformate

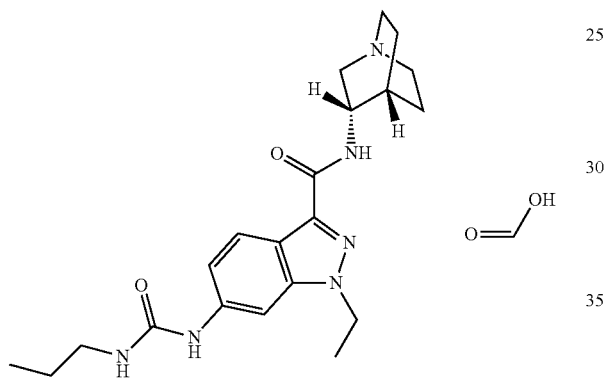

Prepared using Procedure V in 11% yield. LC/MS (EI) $t_R$ 3.50, m/z 399 (M$^+$+1).

Example 275

N-[(3S)-1-Azabicyclo[2.2.2]oct-3-yl]-1-(cyclopropylmethyl)-5-{[(propylamino)carbonyl]amino}-1H-indazole-3-carboxamide hydroformate

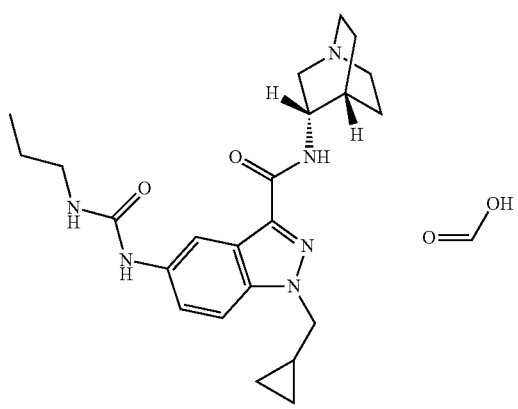

Prepared using Procedure V in 56% yield. LC/MS (EI) $t_R$ 3.74, m/z 425 (M$^+$+1).

Example 276

N-[(3S)-1-Azabicyclo[2.2.2]oct-3-yl]-1-(2,2,2-trifluoroethyl)-5-{[(propylamino)carbonyl]amino}-1H-indazole-3-carboxamide hydroformate

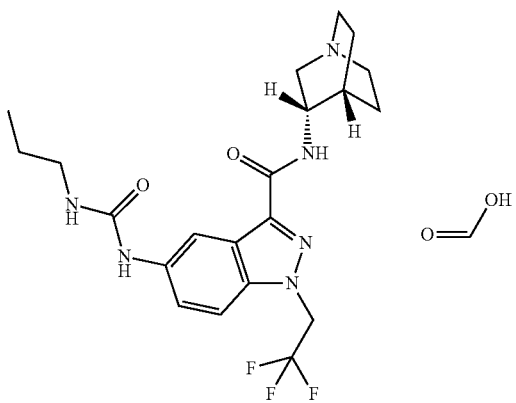

Prepared using Procedure V in 40% yield. LC/MS (EI) $t_R$ 3.72, m/z 453 (M$^+$+1).

Example 277

N-[(3S)-1-Azabicyclo[2.2.2]oct-3-yl]-1-(ethyl)-5-{[(propylamino)carbonyl]amino}-1H-indazole-3-carboxamide hydroformate

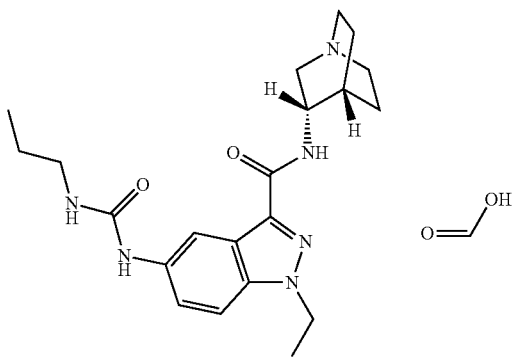

Prepared using Procedure V in 37% yield. LC/MS (EI) $t_R$ 3.44, m/z 399 (M$^+$+1).

Procedure W

Procedure W provides a method for the coupling between amino aminoquinuclidinecarboxamides and halogenated heterocycles to form N-heteroarylaniline derivatives.

To a solution of 6-amino-N-[(3S)-1-azabicyclo[2.2.2]octy-3-yl]-1,2-benisothiazole-3-carboxamide (0.175 mmol) in a mixture of toluene (0.5 mL) and 2-propanol (0.5 mL) was added 2-bromothiazole (0.18 mmol) an potassium carbonate (0.21 mmol). The reaction mixture was subjected to microwave irradiation at 180° C. for 600 s, and was concentrated. The residue was resuspended in 95/5 dichloromethane/methanol and was filtered and concentrated. The residue was purified by preparative HPLC, thus providing the product in 10% yield.

The following compounds were prepared using this method:

Example 278

N-[(3S)-1-Azabicyclo[2.2.2]oct-3-yl]-6-(1,3-thiazol-2-ylamino)-1,2-benzisothiazole-3-carboxamide hydroformate

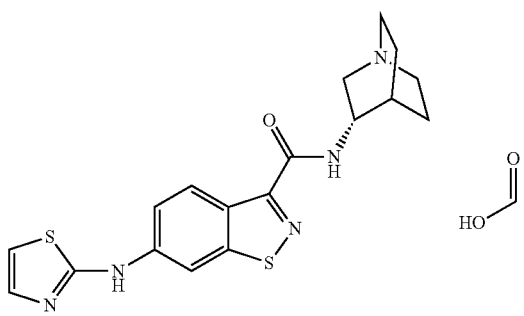 [SMILES: O=C(N[C@@H]1CN2CCC1CC2)c1nsc2cc(Nc3nccs3)ccc12 ; O=CO]

Prepared using Procedure W in 10% yield. LC/MS (EI) $t_R$ 4.78, m/z 386 (M$^+$+1).

Procedure X

Procedure X provides a method for the coupling between acetylenic aminoquinuclidinecarboxamides and azides to form triazole derivatives.

N-[(3S)-1-Azabicyclo[2.2.2]oct-3-yl]-6-ethynyl-1H-indazole-3-carboxamide (0.300 mol) and azidotrimethylsilane (0.30 mmol) were suspended in water (0.6 mL) and tert-butyl alcohol (0.6 mL). Sodium ascorbate (0.20 mol) was added to the reaction mixture followed by a solution of copper(II) sulfate pentahydrate (0.030 mmol) in water (30 μL). The reaction was stirred vigorously for 12 hours, and was concentrated. The residue was redissolved in methanol and was filtered and concentrated. The residue was purified by preparative HPLC, thus providing the product in 6% yield.

The following compounds were prepared by this method:

Example 279

N-[(3S)-1-Azabicyclo[2.2.2]oct-3-yl]-6-(1H-1,2,3-triazol-4-yl)-1H-indazole-3-carboxamide dihydroformate

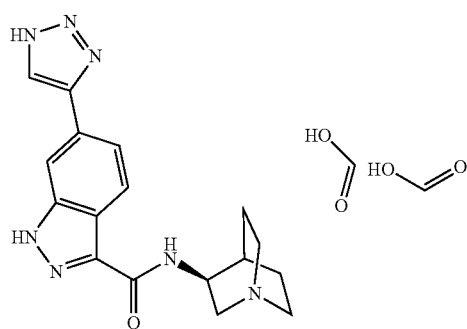

Prepared using Procedure X in 6% yield. $^1$H NMR (CD$_3$OD) δ 8.69 (s, 1H), 8.27 (s, 1H), 7.97 (d, 1H, J=8.8), 7.72 (d, J=8.8), 4.58-4.43 (m, 1, 3.91-3.84 (m, 1, 3.49-3.38 (m, 4, 2.43-1.97 (m, 6. LC/MS (EI) $t_R$ 2.77, m/z 338 (M$^+$+1).

Example 280

N-[(3R)-1-Azabicyclo[2.2.2]oct-3-yl]-6-[1-(2-piperidin-1-ylethyl)-1H-1,2,3-triazol-4-yl]-1H-indazole-3-carboxamide dihydroformate

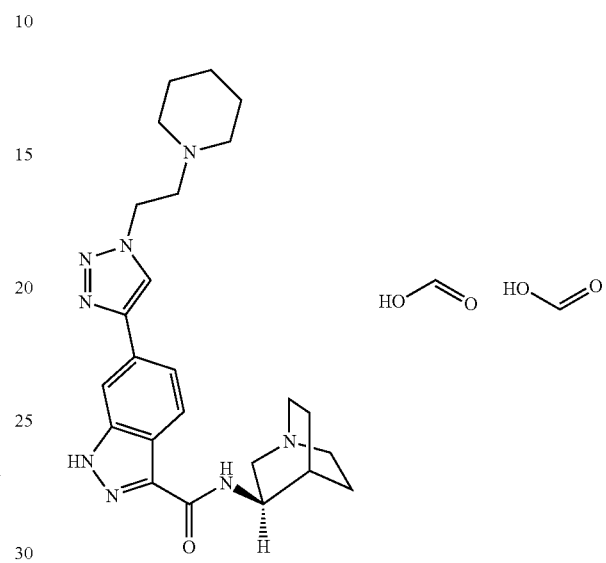

Prepared using Procedure X in 55% yield. LC/MS (EI) $t_R$ 2.04, m/z 449 (M$^+$+1).

Example 281

Ethyl [4-(3-{[(3R)-1-azabicyclo[2.2.2]oct-3-ylamino]carbonyl}-1H-indazol-6-yl)-1H-1,2,3-triazol-1-yl]acetate dihydroformate

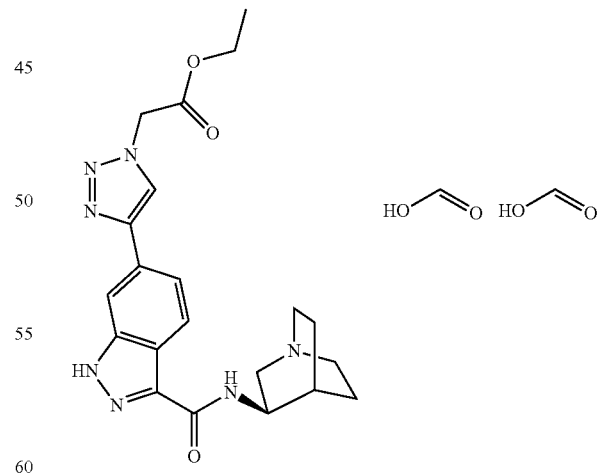

Prepared using Procedure X in 20% yield. LC/MS (EI) $t_R$ 3.15, m/z 424 (M$^+$+1).

Procedure Y.

Procedure Y provides a method for the coupling between amino aminoquinuclidinecarboxamides and chloroformates to form carbamate derivatives.

Benzyl chloroformate (0.58 mmoL) was added to a solution of the amine (0.52 mmol) in N,N-dimethylformamide (1 mL) and pyridine (2 mL) and the reaction mixture was maintained for 16 h. The reaction mixture was concentrated and the residue was purified by preparative HPLC, thus providing the product in 54% yield and the bis-carbamate in 12% yield.

The following compounds were prepared by this method:

Example 282

Benzyl(3-{[(3S)-1-azabicyclo[2.2.2]oct-3-ylamino]carbonyl}-1H-indazol-5-yl)carbamate

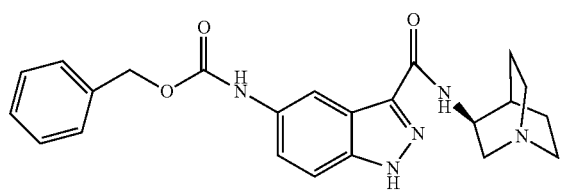 [SMILES: O=C(Nc1ccc2[nH]nc(C(=O)N[C@@H]3CN4CCC3CC4)c2c1)OCc1ccccc1]

Prepared using Procedure Y in 54% yield. $^1$H NMR (CD$_3$OD) δ 8.59 (s, 1H), 8.51 (s, 1H), 7.65 (s, 1H), 7.41 (d, J=9.0, 1H), 7.19 (d, J=9.0, 1H), 7.05 (d, J=9.0, 1H), 7.05 (d, J=9.0, 1H), 6.94 (d, J=9.0, 1H), 4.62 (m, 1H), 3.95 (m, 1H), 3.87 (s, 3H), 3.50-3.30 (m, 4H), 2.48 (m, 1H), 2.37 (m, 1H), 2.20 (m, 2H), 2.02 (m, 1H). LC/MS (EI) t$_R$ 5.33, m/z 420 (M$^+$+1).

Example 283

Vinyl(3-{[(3S)-1-azabicyclo[2.2.2]oct-3-ylamino]carbonyl}-1H-indazol-5-yl)carbamate

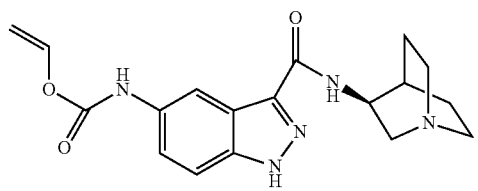 [SMILES: C=COC(=O)Nc1ccc2[nH]nc(C(=O)N[C@@H]3CN4CCC3CC4)c2c1]

Prepared using Procedure Y in 50% yield. LC/MS (EI) t$_R$ 3.30, m/z 356 (M$^+$+1).

Example 284

Isopropyl{3-{[(3R)-1-azabicyclo[2.2.2]oct-3-ylamino]carbonyl}-1H-indazol-5-yl}carbamate hydroformate

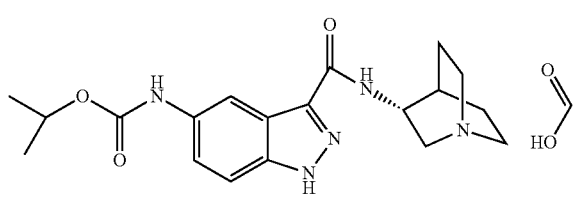

Prepared using Procedure Y in 36% yield. LC/MS (EI) t$_R$ 2.90, m/z 372 (M$^+$+1).

Example 285

Isopropyl{3-{[(3R)-1-azabicyclo[2.2.2]oct-3-ylamino]carbonyl}-1-[(isopropylamino)carbonyl]-1H-indazol-5-yl}carbamate hydroformate

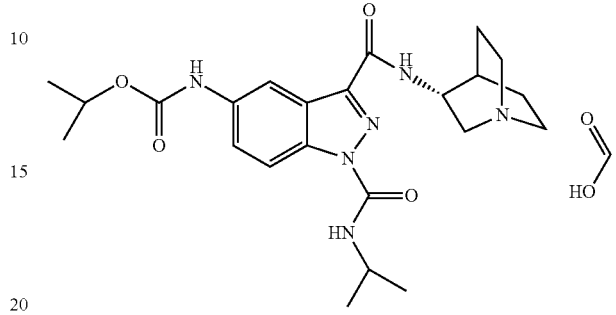

Prepared using Procedure Y in 18% yield. LC/MS (EI) t$_R$ 5.16, m/z 458 (M$^+$+1).

Procedure Z.

Procedure Z provides a method for the oxidation of quinuclidinecarboxamides to form N-oxide derivatives.

A 0° C. solution of m-chloroperbenzoic acid (6.66 mmoL) in dichloromethane (30 mL) was added dropwise to a solution of the quinuclidine amide (4.44 mmol) in dichloromethane (40 mL) and the reaction mixture was maintained for 3 h. The reaction mixture was concentrated and the residue was purified by chromatography on neutral alumina using a gradient of 100/0 to 90/10 dichloromethane/methanol, thus providing the product in 58% yield.

The following compounds were prepared by this method:

Example 286

N-[(3S)-1-Oxido-1-azabicyclo[2.2.2]oct-3-yl]-1H-indazole-3-carboxamide

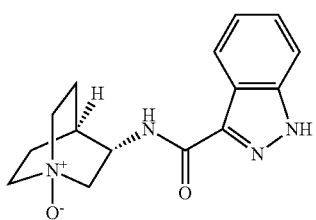

Prepared using Procedure Z in 58% yield. $^1$H NMR (CD$_3$OD, 500 MHz) δ 8.21 (d, J=8.0, 1H), 7.59 (d, J=9.0, 1H), 7.42 (dt, Jt=7.5, Jd=1.0, 1H), 7.26 (dt, Jt=7.5, Jd=1.0, 1H), 4.65 (m, 1H), 3.83 (m, 1H), 3.42 (m, 5H), 2.37 (m, 4H), 2.27 (m, 1H), 2.17 (m, 2H), 2.02 (m, 1H); LC/MS (EI) t$_R$ 12.4 [Analytical HPLC was performed on 4.6 mm×250 mm YMC 0DS-AQ S-5 120 m columns using a gradient of 05/95 to 95/05 acetonitrile (0.05% trifluoroacetic acid)/water (0.05% trifluoroacetic acid) over 35 min], m/z 287 (M$^+$+1).

Procedure AA.

Procedure AA provides a method for the demethylation of methoxy-substituted quinuclidinecarboxamides to form phenol derivatives.

The following compounds were prepared by this method:

Example 287

N-[(3S)-1-Azabicyclo[2.2.2]oct-3-yl]-5-hydroxy-1H-indazole-3-carboxamide hydrobromide.

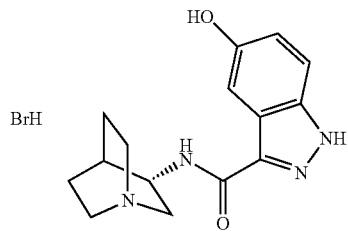 [SMILES: Br ; O=C(N[C@@H]1CN2CCC1CC2)c1n[nH]c2ccc(O)cc12]

Prepared using Procedure AA in 32% yield. $^1$H NMR (Me$_2$SO-d$_6$) δ 13.43 (s, 1H), 9.49 (br s, 1H), 9.35 (s, 1H), 8.62 (d, J=5.9, 1H), 7.46-7.44 (m, 1H), 6.95 (d, J=6.5, 1H), 4.41 (br s, 1H), 3.68-3.63 (m, 1H), 3.33-3.18 (m, 7H), 2.22-2.20 (m, 1H), 2.09-2.08 (m, 1H), 1.94-1.93 (m, 1H), 1.75-1.70 (M, 1H). LC/MS (EI) t$_R$ 10.72, m/z 287 (M$^+$+1).
as follows:

Example 288

N-[(3S)-1-Azabicyclo[2.2.2]oct-3-yl]-6-hydroxy-1H-indazole-3-carboxamide hydrobromide

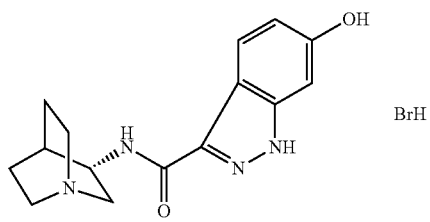 [SMILES: O=C(N[C@@H]1CN2CCC1CC2)c1n[nH]c2cc(O)ccc12 ; Br]

Prepared using Procedure AA in 39% yield. LC/MS (EI) t$_R$ 10.32 [Analytical HPLC was performed on 4.6 mm×250 mm YMC 0DS-AQ S-5 120 m columns using a gradient of 05/95 to 95/05 acetonitrile (0.05% trifluoroacetic acid)/water (0.05% trifluoroacetic acid) over 35 min], m/z 287 (M$^+$+1).
Procedure AB.

Procedure AB provides a method for the preparation of urea derivatives using phosgene equivalents.

The following compounds were prepared by this method:

Example 289

N-[(3S)-1-Azabicyclo[2.2.2]oct-3-yl]-5-{[(diethylamino)carbonyl]amino}-1H-indazole-3-carboxamide hydroformate.

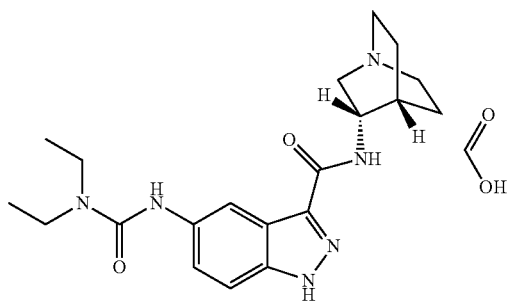

Prepared using Procedure AB in 55% yield. $^1$H NMR (CD$_3$OD) δ 8.40 (s, 1H), 8.10 (s, 1H), 7.51 (s, 1H), 4.52 (m, 1H), 3.83 (t, J=15.0, 1H), 3.37 (t, J=9.0, 4H), 3.36-3.30 (m, 4H), 2.30 (m, 1H), 2.15 (m, 2H), 1.95 (m, 1H), 1.19 (t, J=6.0, 6H). LC/MS (EI) t$_R$ 2.45, m/z 385 (M$^+$+1).

Example 290

N-[(3S)-1-Azabicyclo[2.2.2]oct-3-yl]-5-[(pyrrolidin-1-ylcarbonyl)amino]-1H-indazole-3-carboxamide hydroformate

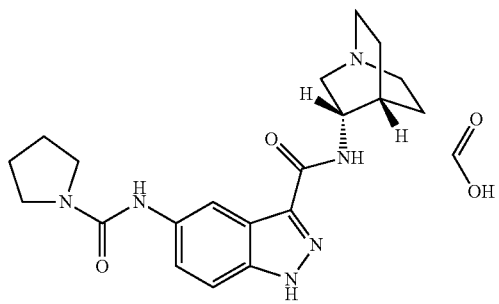

Prepared using Procedure AB in 57% yield. LC/MS (EI) t$_R$ 2.47, m/z 383 (M$^+$+1).

Example 291

N-[(3S)-1-Azabicyclo[2.2.2]oct-3-yl]-6-[(pyrrolidin-1-ylcarbonyl)amino]-1H-indazole-3-carboxamide hydroformate

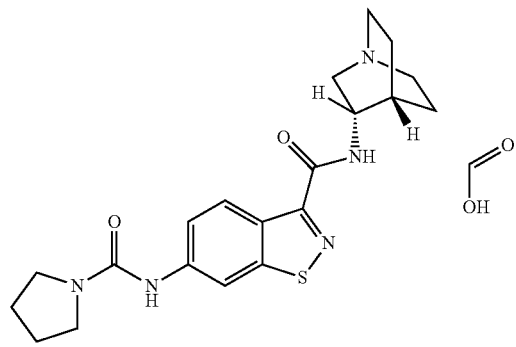

Prepared using Procedure AB in 69% yield. LC/MS (EI) t$_R$ 3.35, m/z 400 (M$^+$+1).
Procedure AC.

Procedure AC provides a method for the preparation of cyclic amide derivatives from the corresponding brominated quinuclidine derivatives.

Palladium (II) acetate (0.09 mmol) was added to a solution of (S)-(−)-2,2'-bis(diphenylphosphino)-1,1'-binaphthyl (0.14 mmol) in toluene (10 mL) and the reaction mixture was maintained until the contents completely dissolved. The resultant yellow solution was transferred to a mixture of N-[(3S)-1-azabicyclo[2.2.2]oct-3-yl]-6-bromo-1,2-benzisothiazole-3-carboxamide (0.33 mmol), cesium carbonate (0.60 mmol) and 2-pyrrolidinone (1.00 mmol) under an atmosphere of nitrogen gas and the reaction mixture was heated at 100° C. for 16 h. The reaction mixture was filtered through Celite and concentrated. The residue was purified by HPLC, thus providing the product in 72% yield.

The following compounds were prepared using this method:

Example 292

N-[(3S)-1-Azabicyclo[2.2.2]oct-3-yl]-6-(2-oxopyrrolidin-1-yl)-1,2-benzisothiazole-3-carboxamide hydroformate

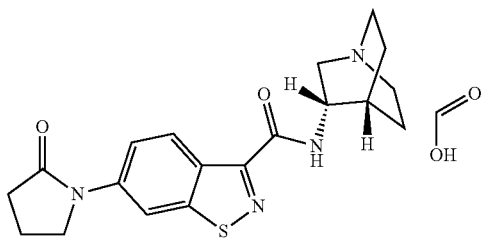

Prepared using Procedure AC in 72% yield. $^1$H NMR (CD$_3$OD) δ 8.78 (d, J=9.0, 1H), 8.53 (broad, 1H), 8.81 (s, 1H), 7.63 (d, J=9.0, 1H), 4.5 (m, 1H), 4.07 (t, J=6.0, 2H), 3.76 (t, J=12.0, 1H), 3.50-3.30 (m, 4H), 2.35 (t, J=6.0, 2H), 2.35 (m, 1H), 2.20 (m, 3H), 2.10 (m, 2H), 1.90 (m, 1H). LC/MS (EI) $t_R$ 2.43, m/z 371 (M$^+$+1).

Example 293

N-[(3S)-1-Azabicyclo[2.2.2]oct-3-yl]-5-(2-oxopyrrolidin-1-yl)-1,2-benzisothiazole-3-carboxamide hydroformate

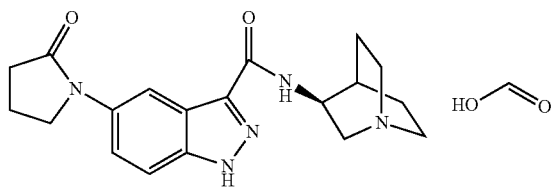

Prepared using Procedure AC in 40% yield. LC/MS (EI) $t_R$ 2.11, m/z 354 (M$^+$+1).

Example 294

N-[(3S)-1-Azabicyclo[2.2.2]oct-3-yl]-6-(2-oxo-4-phenylpyrrolidin-1-yl)-1,2-benzisothiazole-3-carboxamide hydroformate

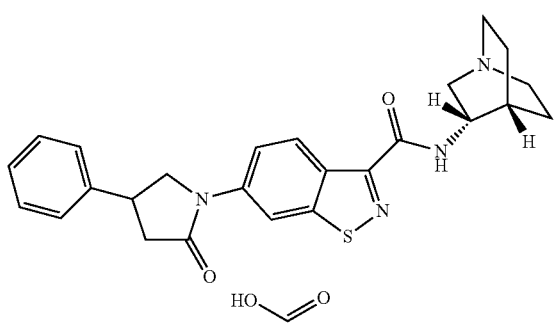

Prepared using Procedure AC in 50% yield. LC/MS (EI) $t_R$ 5.17, m/z 447 (M$^+$+1).

Procedure AD.

Procedure AD provides a method for the preparation of cyclic urea derivatives from the corresponding amino quinuclidine derivatives.

To a solution of 6-amino-N-[(3S)-1-azabicyclo[2.2.2]oct-3-yl]-1,2-benzisothiazole-3-carboxamide (0.400 mmol) in methanol (5 mL) was added tert-butyl N-(2-oxoethyl)carbamate (0.56 mmol), sodium cyanoborohydride (1.00 mmol) and acetic acid (0.4 mL) and the reaction mixture was maintained for 4 h. The reaction mixture was diluted with 3 N hydrochloric acid (5 mL) and the reaction mixture was maintained for 2 h. The reaction mixture was concentrated and the residue was purified by HPLC, thus providing the reduced amine in 63% yield.

To solution of the reduced amine (0.100 mmol) in N,N-dimethylformamide (4 mL) was added N,N-carbonyldiimidazole (0.150 mmol) and the reaction mixture was heated at 100° C. for 3 h. The reaction mixture was concentrated and the residue was purified by HPLC, thus providing the cyclic urea in 60% yield.

The following compounds were prepared using this method:

Example 295

N-[(3S)-1-Azabicyclo[2.2.2]oct-3-yl]-6-(2-oxoimidazolidin-1-yl)-1,2-benzisothiazole-3-carboxamide hydroformate

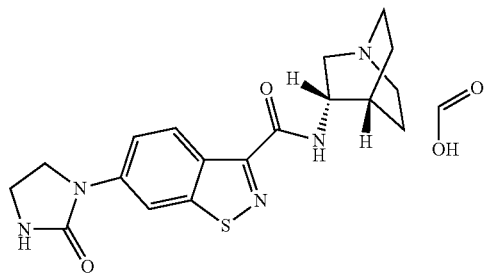

Prepared using Procedure AD in 60% yield. $^1$H NMR (CD$_3$OD) δ 8.67 (d, J=9.0, 1H), 8.51 (broad, 1H), 8.18 (s, 1H), 7.96 (d, J=9.0, 1H), 4.48 (d, 1H), 4.08 (dd, J=6.0, 6.0, 2H), 3.79 (t, J=12.0, 1H), 3.60 (dd, J=6.0, 6.0, 2H), 3.5-3.3 (m, 4H), 2.38 (m, 1H), 2.22 (m, 1H), 2.08 (m, 2H), 1.90 (m, 1H). LC/MS (EI) $t_R$ 2.43, m/z 372 (M$^+$+1).

Example 296

N-[(3S)-1-Azabicyclo[2.2.2]oct-3-yl]-5-(2-oxoimidazolidin-1-yl)-1H-indazole-3-carboxamide hydroformate

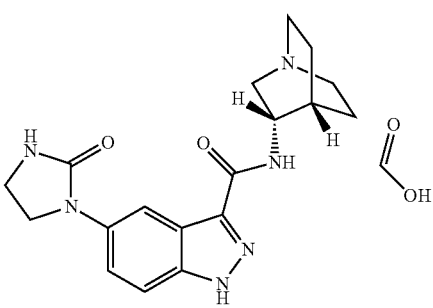

Prepared using Procedure AD in 60% yield. LC/MS (EI) $t_R$ 1.26, m/z 355 (M$^+$+1).

Example 297

N-[(3S)-1-Azabicyclo[2.2.2]oct-3-yl]-5-(2-oxo-3-propylimidazolidin-1-yl)-1H-indazole-3-carboxamide hydroformate

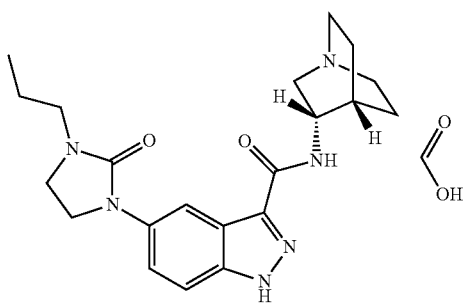

Prepared using Procedure AD in 40% yield. LC/MS (EI) $t_R$ 3.27, m/z 397 (M$^+$+1).

Example 298

N-[(3S)-1-Azabicyclo[2.2.2]oct-3-yl]-6-{[2-(propylamino)ethyl]amino}-1,2-benzisothiazole-3-carboxamide hydroformate

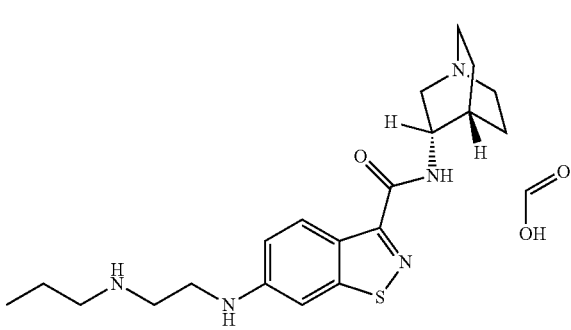

Prepared using Procedure AD in 35% yield. LC/MS (EI) $t_R$ 1.47, m/z 303 (M$^+$+1).

Procedure AE.

Procedure AE provides a method for the preparation of cyclic urea derivatives from the corresponding brominated quinuclidine derivatives.

Palladium (II) acetate (0.09 mmol) was added to a solution of (R)-(+)-2,2'-bis(diphenylphosphino)-1,1'-binaphthyl (0.14 mmol) in toluene (8 mL) and the reaction mixture was maintained until the contents completely dissolved. The resultant yellow solution was transferred to a mixture of N-[(3S)-1-azabicyclo[2.2.2]oct-3-yl]-6-bromo-1,2-benzisothiazole-3-carboxamide (0.33 mmol), cesium carbonate (0.39 mmol) and 1-methyl-2-imidazolidinone 2-pyrrolidinone (0.500 mmol) under an atmosphere of nitrogen gas and the reaction mixture was heated at 100° C. for 16 h. The reaction mixture was filtered through Celite and concentrated. The residue was purified by HPLC, thus providing the product in 70% yield.

The following compounds were prepared using this method:

Example 299

N-[(3S)-1-Azabicyclo[2.2.2]oct-3-yl]-6-(3-methyl-2-oxoimidazolidin-1-yl)-1,2-benzisothiazole-3-carboxamide hydroformate

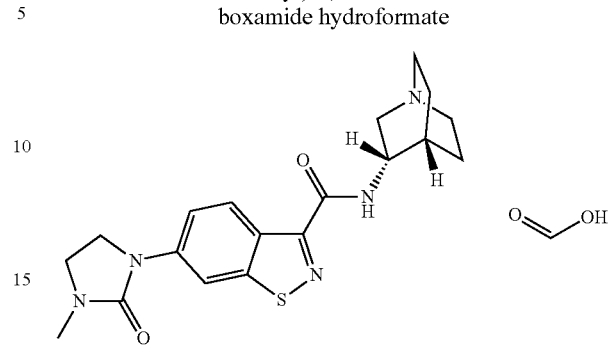

Prepared using Procedure AE in 70% yield. $^1$H NMR (CD$_3$OD) δ 8.64 (d, J=9.0, 1H), 8.55 (s, 1H), 8.18 (d, J=9.0, 1H), 4.20 (m, 1H), 3.95 (dd, J=6.0, 6.0, 2H), 3.51 (dd, J=6.0, 6.0, 2H), 3.35 (s, 3H), 3.45-3.30 (m, 4H), 2.10 (m, 1H), 1.95 (m, 1H), 1.80 (m, 2H), 1.60 (m, 1H). LC/MS (EI) $t_R$ 2.73, m/z 386 (M$^+$+1).

Example 300

N-[(3S)-1-Azabicyclo[2.2.2]oct-3-yl]-6-(3-isopropyl-2-oxoimidazolidin-1-yl)-1,2-benzisothiazole-3-carboxamide hydroformate

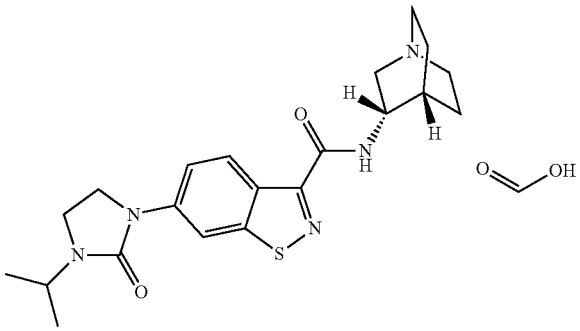

Prepared using Procedure AE in 65% yield. LC/MS (EI) $t_R$ 3.65, m/z 414 (M$^+$+1).

Example 301

N-[(3S)-1-Azabicyclo[2.2.2]oct-3-yl]-6-(3-propyl-2-oxoimidazolidin-1-yl)-1,2-benzisothiazole-3-carboxamide hydroformate

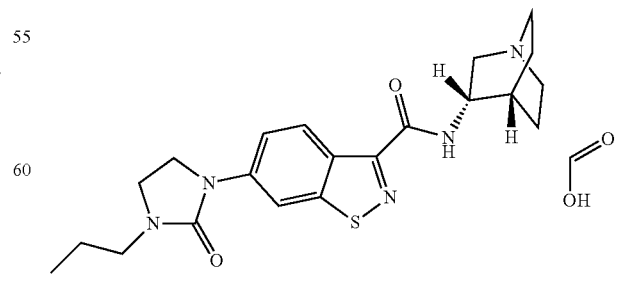

Prepared using Procedure AE in 67% yield. LC/MS (EI) $t_R$ 4.61, m/z 414 (M$^+$+1).

Example 302

N-[(3S)-1-Azabicyclo[2.2.2]oct-3-yl]-5-(3-methyl-2-oxoimidazolidin-1-yl)-1,2-benzisothiazole-3-carboxamide

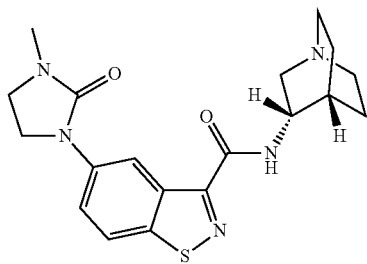

Prepared using Procedure AF in 27% yield. LC/MS (EI) $t_R$ 3.07, m/z 387 (M$^+$+1).

Example 303

N-[(3S)-1-Azabicyclo[2.2.2]oct-3-yl]-5-(3-isopropyl-2-oxoimidazolidin-1-yl)-1,2-benzisothiazole-3-carboxamide

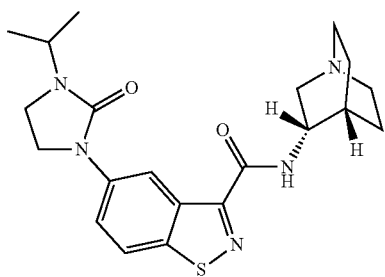

Prepared using Procedure AF in 31% yield. LC/MS (EI) $t_R$ 3.70, m/z 414 (M$^+$+1).

Example 304

N-[(3S)-1-Azabicyclo[2.2.2]oct-3-yl]-5-(3-propyl-2-oxoimidazolidin-1-yl)-1,2-benzisothiazole-3-carboxamide

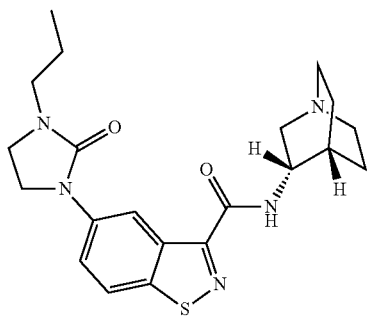

Prepared using Procedure AF in 24% yield. LC/MS (EI) $t_R$ 3.66, m/z 414 (M$^+$+1).

Procedure AF.

Procedure AF provides a method for the preparation of benzisoxazole quinuclidine amides from ethyl benzisoxazole-3-carboxylates.

(S)-3-aminoquinuclidine hydrochloride (3.52 mmol) was dissolved in N,N-diisopropylethylamine (0.5 mL) and ethanol (3 mL) with warming. Ethyl 5-bromo-1,2-benzisoxazole-3-carboxylate (1.86 mmol) was added and the reaction mixture was heated at 85° C. for 72 h. The reaction mixture was diluted with dichloromethane (30 mL) and washed with 10 mL of saturated sodium carbonate. The aqueous layer was extracted with dichloromethane (30 mL) and the combined organic layers were washed with brine and dried (sodium sulfate). The organic layer was loaded on a 10 g SCX column and the column was washed with methanol (50 mL). The crude product was eluted with 2 M ammonia in methanol (60 mL) and concentrated. The residue was purified by chromatography [40/60 to 0/100 ethyl acetate/(70/30/1 ethyl acetate/methanol/ammonium hydroxide)], thus providing the amide in 59% yield as a light yellow oil.

The following compounds were prepared using this method:

Example 305

N-[(3S)-1-Azabicyclo[2.2.2]oct-3-yl]-5-bromo-1,2-benzisoxazole-3-carboxamide

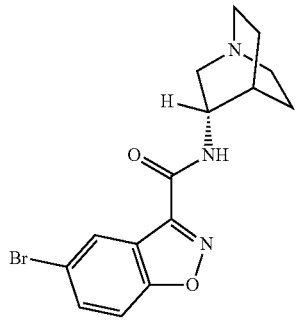 [SMILES: O=C(N[C@@H]1CN2CCC1CC2)c1noc2ccc(Br)cc12]

Prepared using Procedure AF in 59% yield. $^1$H NMR (CD$_3$OD) δ 8.16 (d, J=0.6, 1H), 7.71 (dd, J=8.9, 0.6, 1H), 7.59 (d, J=8.9, 1H), 4.21 (m, 1H), 3.37 (m, 1H), 3.02 (m, 1H), 2.84 (m, 4H), 2.08 (m, 1H), 1.96 (m, 1H), 1.78 (m, 2H), 1.55 (m, 1H); LC/MS (EI) $t_R$ 2.33, m/z 350/352 (M+/M++2).

Example 306

N-[(3S)-1-Azabicyclo[2.2.2]oct-3-yl]-6-bromo-1,2-benzisoxazole-3-carboxamide

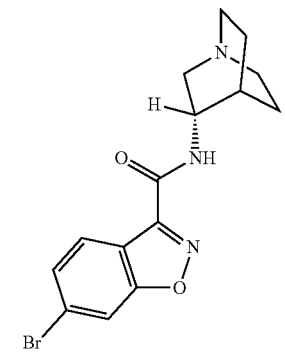 [SMILES: O=C(N[C@@H]1CN2CCC1CC2)c1noc2cc(Br)ccc12]

Prepared using Procedure AF in 63% yield. LC/MS (EI) $t_R$ 2.22, m/z 350/352 (M$^+$+1).

Procedure AG.

Procedure AG provides a method for the preparation of acyclic amide derivatives from the corresponding brominated quinuclidine derivatives.

Palladium (II) acetate (0.040 mmol) was added to a solution of (R)-(+)-2,2'-bis(diphenylphosphino)-1,1'-binaphthyl (0.050 mmol) in toluene (6 mL) and the reaction mixture was maintained until the contents completely dissolved. The resultant yellow solution was transferred to a mixture of N-[(3S)-1-azabicyclo[2.2.2]oct-3-yl]-6-bromo-1,2-benzisothiazole-3-carboxamide (0.30 mmol), cesium carbonate (0.50 mmol) and N-methylacetamide (0.500 mmol) under an atmosphere of nitrogen gas and the reaction mixture was subjected to microwave irradiation at 200° C. for 300 s. The reaction mixture was filtered through Celite and concentrated. The residue was purified by HPLC, thus providing the product in 50% yield.

The following compounds were prepared using this method:

Example 307

6-[Acetylmethyl)amino]-N-[(3S)-1-azabicyclo[2.2.2]oct-3-yl]-1,2-benzisothiazole-3-carboxamide hydroformate

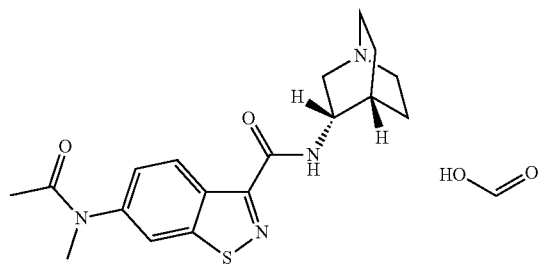

Prepared using Procedure AG in 50% yield. $^1$H NMR (CD$_3$OD) δ 8.85 (d, J=9.0, 2H), 8.40 (broad, 1H), 8.13 (s, 1H), 7.53 (d, J=9.0, 1H), 4.43 (m, 1H), 3.85 (m, 1H), 3.5-3.2 (m, 7H), 2.45 (m, 1H), 2.30 (m, 1H), 2.10 (m, 3H), 1.95 (m, 3H). LC/MS (EI) t$_R$ 2.40, m/z 359 (M$^+$+1).

Example 308

N-[(3S)-1-Azabicyclo[2.2.2]oct-3-yl]-6-[methyl(propionyl)amino]-1,2-benzisothiazole-3-carboxamide hydroformate

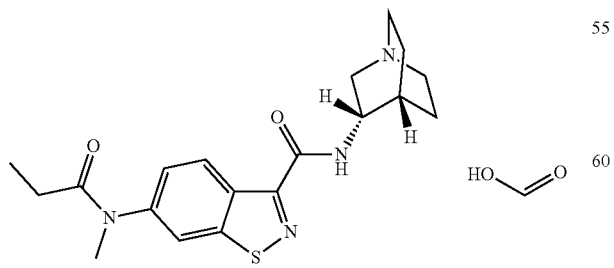

Prepared using Procedure AG in 60% yield. LC/MS (EI) t$_R$ 2.42, m/z 373 (M$^+$+1).

Example 309

N-[(3S)-1-Azabicyclo[2.2.2]oct-3-yl]-1-(cyclopropylmethyl)-6-(1,3-thiazol-2-yl)-1H-indazole-3-carboxamide hydroformate

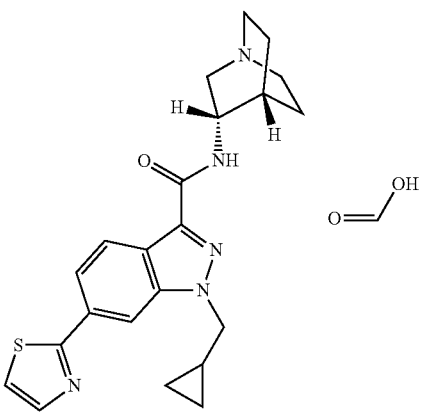

Prepared using Procedure AH in 31% yield. $^1$H NMR (CD$_3$OD) δ 8.43 (s, 1H), 8.28 (d, J=8.4, 1H), 8.27 (s, 1H), 7.94 (d, J=3.3, 1H), 7.85 (d, J=8.3, 1H), 7.68 (d, J=3.3, 1H), 4.55 (m, 1H), 4.46 (d, J=7.0, 2H), 3.84 (m, 1H), 3.6-3.3 (m, 5H), 2.41 (m, 1H), 2.29 (m, 1H), 2.15 (m, 2H), 1.95 (m, 1H), 1.45 (m, 1H), 0.62 (m, 2H), 0.53 (m, 2H); LC/MS (EI) t$_R$ 3.99 min, m/z 408 (M$^+$+1).

Example 310

N-[(3S)-1-Azabicyclo[2.2.2]oct-3-yl]-1-(tetrahydrofuran-3-yl)-6-(1,3-thiazol-2-yl)-1H-indazole-3-carboxamide hydroformate

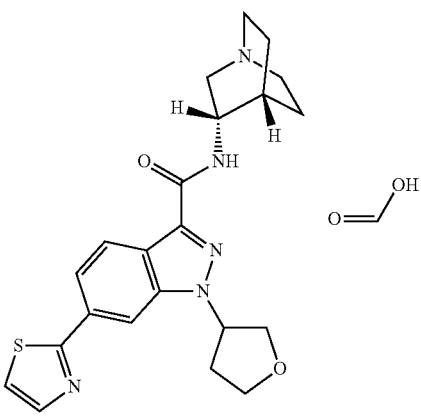

Prepared using Procedure AH in 40% yield. LC/MS (EI) t$_R$ 3.68 min, m/z 424 (M$^+$+1).

Example 311

N-[(3S)-1-Azabicyclo[2.2.2]oct-3-yl]-1-(2-methoxyethyl)-6-(1,3-thiazol-2-yl)-1H-indazole-3-carboxamide hydroformate

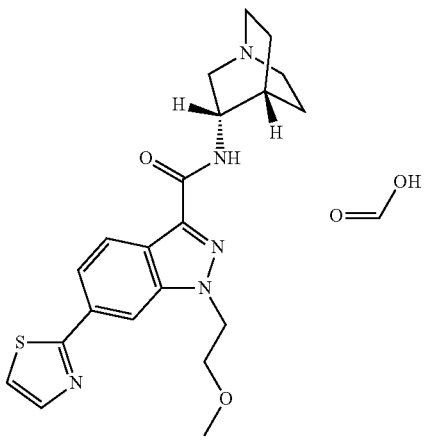

Prepared using Procedure AH in 27% yield. LC/MS (EI) $t_R$ 3.64 min, m/z 412 (M$^+$+1).

Example 312 tert-Butyl 3-[3-{[(3S)-1-azabicyclo[2.2.2]oct-3-ylamino]carbonyl}-6-(1,3-thiazol-2-yl)-1H-indazol-1-yl]pyrrolidine-1-carboxylate hydroformate

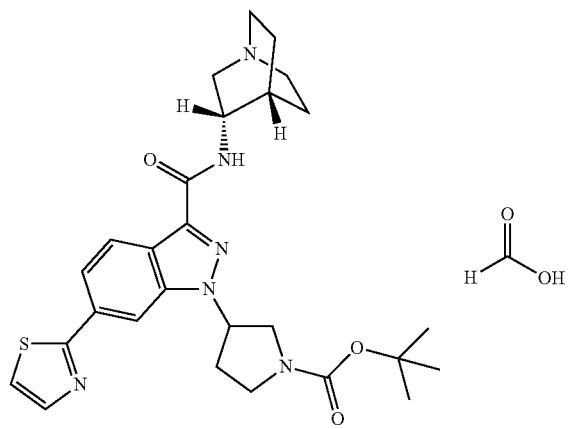

Prepared using Procedure AH in 38% yield. LC/MS (EI) $t_R$ 4.30 min, m/z 523 (M$^+$+1).

Example 313

N-[(3S)-1-Azabicyclo[2.2.2]oct-3-yl]-1-pyrrolidin-3-yl-6-(1,3-thiazol-2-yl)-1H-indazole-3-carboxamide

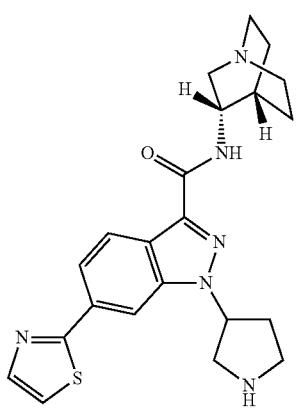

Prepared from Example 312, by exposure to trifluoroacetic acid, in 88% yield. LC/MS (EI) $t_R$ 2.41 min, m/z 423 (M$^+$+1).

Example 314

N-[(3S)-1-Azabicyclo[2.2.2]oct-3-yl]-6-(1,3-thiazol-2-yl)-1-(2-thienylmethyl)-1H-indazole-3-carboxamide hydroformate

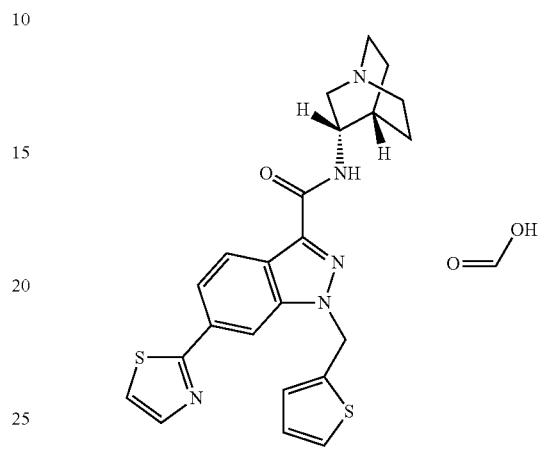

Prepared using Procedure AH in 11% yield. LC/MS (EI) $t_R$ 4.15 min, m/z 450 (M$^+$+1).

Example 315

N-[(3S)-1-Azabicyclo[2.2.2]oct-3-yl]-1-(2-phenoxyethyl)-6-(1,3-thiazol-2-yl)-1H-indazole-3-carboxamide hydroformate

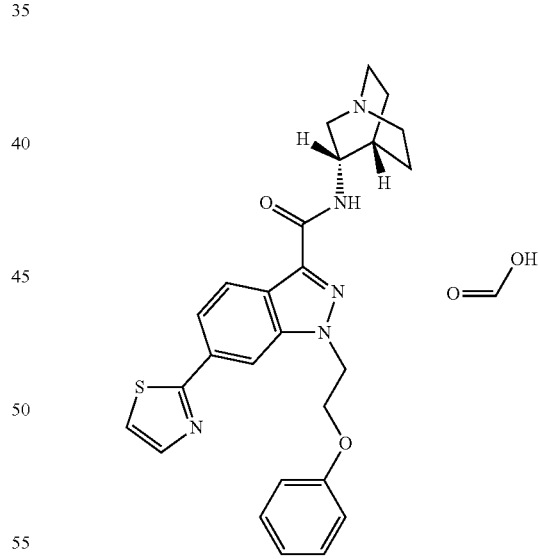

Prepared using Procedure AH in 54% yield. LC/MS (EI) $t_R$ 4.33 min, m/z 474 (M$^+$+1).

Example 316

[$^3$H] MLA Binding

Materials:
Rat Brain: Pel-Freez Biologicals, CAT No. 56004-2
Protease inhibitor cocktail tablet: Roche, CAT No. 1697498

Membrane Preparation

Rat brains in 20 vol (w/v) of ice-cold 0.32 M sucrose with protease inhibitors (one tablet per 50 ml,) were homogenized with a polytron for 10 sec at setting 11, then centrifuged 10 min at 1000 g, 4° C. The supernatant was centrifuged again for 20 min at 20,000 g, 4° C. The pellets were resuspended in binding buffer (200 mM TRIS-HCl, 20 mM HEPES, pH 7.5, 144 mM NaCl, 1.5 mM KCl, 1 mM $MgSO_4$, 2 mM $CaCl_2$, 0.1% (w/v) BSA) and stored membrane prep at −80° C.

For saturation assay, the 200 μl assay mixture in binding buffer contains 200 μg of membrane protein, 0.2 to 44 nM of [$^3$H] MLA. The nonspecific binding was defined using 1 μM MLA. Competition assay was carried out with 2 nM [$^3$H] MLA and a desirable range of compounds. The assay mixture was incubated at 22° C. for 2 hours, then harvested with GF/B filter presoaked with 0.3% PEI in binding buffer using Tomtec harvester. The filter was washed three time with binding buffer and the radioactivity was counted with Trilux.

Binding affinities for the preferred compounds of the invention are 2 nM to 25 μM, especially 2 nM to 2.5 μM.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A method of treating a patient suffering from anxiety, Alzheimer's disease, Parkinson disease, schizophrenia, memory loss, dementia, cognition deficit, attention deficit, Attention Deficit Hyperactive disorder, memory impairment, depression or an inflammatory disease, comprising administering to the patient an effective amount of a compound according to Formula I:

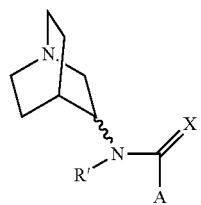

(I)

wherein
A is

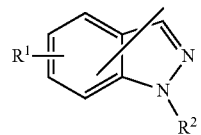

X is O or S;
R' is H;
$R^1$ is OH, CN, nitro, $NH_2$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, alkoxy having 1 to 4 carbon atoms, cycloalkoxy having 3 to 7 carbon atoms, cycloalkylalkoxy having 4 to 7 carbon atoms, fluorinated alkoxy having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, Het, or OAr;

$R^2$ is H, alkyl having 1 to 4 carbon atoms, cycloalkyl having 3 to 7 carbon atoms, or cycloalkylalkyl having 4 to 7 carbon atoms;

Ar is phenyl which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof;

Het is dihydropyranyl, tetrahydropyranyl, tetrahydrofuranyl, thiazolyl, oxazolyl, pyrrolidinyl, piperidinyl, imidazolyl, imidazolidinyl, or morpholinyl, which is unsubstituted or substituted one or more times by alkyl having 1 to 8 C atoms, alkoxy having 1 to 8 C atoms; or a pharmaceutically acceptable salt thereof,
wherein A is attached to the remainder of the compound via its 3 position.

2. A method according to claim 1, wherein said patient is suffering from schizophrenia, anxiety, depression, Parkinson's disease, Alzheimer's disease, memory impairment, memory loss, attention deficit, and/or Attention Deficit Hyperactivity Disorder.

3. A method of treating a patient suffering from dementia and/or memory loss, comprising administering to the patient an effective amount of a compound according to Formula I:

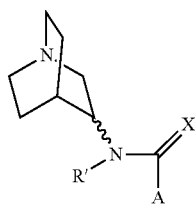

(I)

wherein
A is

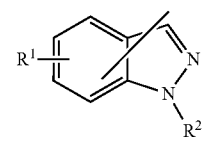

X is O or S;
R' is H;
$R^1$ is OH, CN, nitro, $NH_2$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, alkoxy having 1 to 4 carbon atoms, cycloalkoxy having 3 to 7 carbon atoms, cycloalkylalkoxy having 4 to 7 carbon atoms, fluorinated alkoxy having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, Het, or OAr;

$R^2$ is H, alkyl having 1 to 4 carbon atoms, cycloalkyl having 3 to 7 carbon atoms, or cycloalkylalkyl having 4 to 7 carbon atoms;

Ar is phenyl which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof;

Het is dihydropyranyl, tetrahydropyranyl, tetrahydrofuranyl, thiazolyl, oxazolyl, pyrrolidinyl, piperidinyl, imidazolyl, imidazolidinyl, or morpholinyl, which is unsubstituted or substituted one or more times by alkyl having 1 to 8 C atoms, alkoxy having 1 to 8 C atoms; or a pharmaceutically acceptable salt thereof, wherein A is attached to the remainder of the compound via its 3 position.

4. A method of treating a patient suffering from memory impairment due to Alzheimer's disease, mild cognitive impairment due to aging, schizophrenia, Parkinson's disease, Huntington's disease, and/or depression comprising administering to the patient an effective amount of a compound according to Formula I:

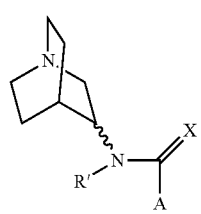

(I)

wherein
A is

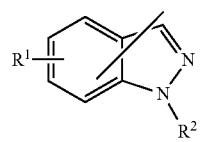

X is O or S;
R' is H;
$R^1$ is OH, CN, nitro, $NH_2$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, alkoxy having 1 to 4 carbon atoms, cycloalkoxy having 3 to 7 carbon atoms, cycloalkylalkoxy having 4 to 7 carbon atoms, fluorinated alkoxy having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, Het, or OAr;

$R^2$ is H, alkyl having 1 to 4 carbon atoms, cycloalkyl having 3 to 7 carbon atoms, or cycloalkylalkyl having 4 to 7 carbon atoms;

Ar is phenyl which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof;

Het is dihydropyranyl, tetrahydropyranyl, tetrahydrofuranyl, thiazolyl, oxazolyl, pyrrolidinyl, piperidinyl, imidazolyl, imidazolidinyl, or morpholinyl, which is unsubstituted or substituted one or more times by alkyl having 1 to 8 C atoms, alkoxy having 1 to 8 C atoms; or a pharmaceutically acceptable salt thereof, wherein A is attached to the remainder of the compound via its 3 position.

5. A method for treating loss of memory comprising administering to a patient in need thereof an effective amount of a compound according to Formula I:

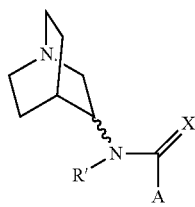

(I)

wherein
A is

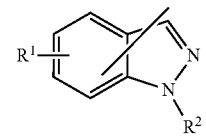

X is O or S;
R' is H;
$R^1$ is OH, CN, nitro, $NH_2$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, alkoxy having 1 to 4 carbon atoms, cycloalkoxy having 3 to 7 carbon atoms, cycloalkylalkoxy having 4 to 7 carbon atoms, fluorinated alkoxy having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, Het, or OAr;

$R^2$ is H, alkyl having 1 to 4 carbon atoms, cycloalkyl having 3 to 7 carbon atoms, or cycloalkylalkyl having 4 to 7 carbon atoms;

Ar is phenyl which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof;

Het is dihydropyranyl, tetrahydropyranyl, tetrahydrofuranyl, thiazolyl, oxazolyl, pyrrolidinyl, piperidinyl, imidazolyl, imidazolidinyl, or morpholinyl, which is unsubstituted or substituted one or more times by alkyl having 1 to 8 C atoms, alkoxy having 1 to 8 C atoms; or a pharmaceutically acceptable salt thereof, wherein A is attached to the remainder of the compound via its 3 position.

6. A method for treating a patient suffering from memory impairment comprising administering to the patient a compound according to Formula I:

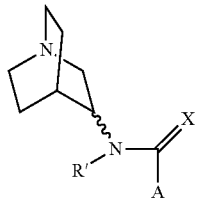

(I)

wherein
A is

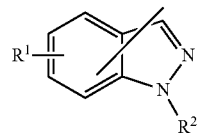

X is O or S;
R' is H;
$R^1$ is OH, CN, nitro, $NH_2$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, alkoxy having 1 to 4 carbon atoms, cycloalkoxy having 3 to 7 carbon atoms, cycloalkylalkoxy having 4 to 7 carbon atoms, fluorinated alkoxy having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, Het, or OAr;

$R^2$ is H, alkyl having 1 to 4 carbon atoms, cycloalkyl having 3 to 7 carbon atoms, or cycloalkylalkyl having 4 to 7 carbon atoms;

Ar is phenyl which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof;

Het is dihydropyranyl, tetrahydropyranyl, tetrahydrofuranyl, thiazolyl, oxazolyl, pyrrolidinyl, piperidinyl, imidazolyl, imidazolidinyl, or morpholinyl, which is unsubstituted or substituted one or more times by alkyl having 1 to 8 C atoms, alkoxy having 1 to 8 C atoms; or a pharmaceutically acceptable salt thereof, wherein A is attached to the remainder of the compound via its 3 position.

7. A method according to claim 6, wherein said memory impairment is due to decreased nicotinic acetylcholine receptor activity.

8. A method of treating a patient suffering from an inflammatory disease comprising administering to the patient an effective amount of a compound according to Formula I:

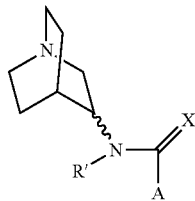

(I)

wherein
A is

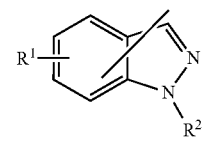

X is O or S;
R' is H;
$R^1$ is OH, CN, nitro, $NH_2$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each unsubstituted or substituted by Ar or Het, alkoxy having 1 to 4 carbon atoms, cycloalkoxy having 3 to 7 carbon atoms, cycloalkylalkoxy having 4 to 7 carbon atoms, fluorinated alkoxy having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, Het, or OAr;

$R^2$ is H, alkyl having 1 to 4 carbon atoms, cycloalkyl having 3 to 7 carbon atoms, or cycloalkylalkyl having 4 to 7 carbon atoms;

Ar is phenyl which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted, aryloxy wherein the aryl portion contains 6 to 10 carbon atoms and is optionally substituted, arylthio wherein the aryl portion contains 6 to 10 carbon atoms and is optionally substituted, cycloalkyloxy wherein the cycloalkyl group has 3 to 7 C atoms and is optionally substituted, sulfo, sulfonylamino, acylamido, acyloxy or combinations thereof;

Het is dihydropyranyl, tetrahydropyranyl, tetrahydrofuranyl, thiazolyl, oxazolyl, pyrrolidinyl, piperidinyl, imidazolyl, imidazolidinyl, or morpholinyl, which is unsubstituted or substituted one or more times by alkyl having 1 to 8 C atoms, alkoxy having 1 to 8 C atoms; or a pharmaceutically acceptable salt thereof, wherein A is attached to the remainder of the compound via its 3 position.

9. A method according to claim 8, wherein said inflammatory disease is rheumatoid arthritis, diabetes or sepsis.

10. A method according to claim 1, wherein said patient is a human.

11. The method according to claim 1, wherein R' is H or $CH_3$.

12. The method according to claim 1, wherein $R^1$ is alkynyl having 2 to 6 carbon atoms, fluorinated hydroxyalkyl having 1 to 4 carbon atoms, or Ar-alkynyl.

13. The method according to claim 1, wherein said compound is of formula I.

14. The method according to claim 13, wherein $R^1$ is $NH_2$, $CF_3$, $OCH_3$, $OC_2H_5$, $OCF_3$, dihydropyranyl, thiazolyl, oxazolyl, pyrrolidinyl, piperidinyl, or morpholinyl.

15. The method according to claim 1, wherein X is O.

16. The method according to claim 1, wherein said compound is selected from:

6-Amino-N-[(3S)-1-azabicyclo[2.2.2]oct-3-yl]-1H-indazole-3-carboxamide,
N-[(3R)-1-Azabicyclo[2.2.2]oct-3-yl]-5-(1,3-oxazol-2-yl)-1H-indazole-3-carboxamide,
N-[(3R)-1-Azabicyclo[2.2.2]oct-3-yl]-5-(1,3-thiazol-2-yl)-1H-indazole-3-carboxamide,
N-[(3R)-1-Azabicyclo[2.2.2]oct-3-yl]-5-(tetrahydro-2H-pyran-4-yl)-1H-indazole-3-carboxamide,
N-[(3R)-1-Azabicyclo[2.2.2]oct-3-yl]-5-(trifluoromethoxy)-1H-indazole-3-carboxamide,
N-[(3R)-1-Azabicyclo[2.2.2]oct-3-yl]-5-cyano-1H-indazole-3-carboxamide,
N-[(3R)-1-Azabicyclo[2.2.2]oct-3-yl]-5-ethynyl-1H-indazole-3-carboxamide,
N-[(3R)-1-azabicyclo[2.2.2]oct-3-yl]-5-hydroxy-1H-indazole-3-carboxamide,
N-[(3R)-1-Azabicyclo[2.2.2]oct-3-yl]-5-methoxy-1H-indazole-3-carboxamide,
N-[(3R)-1-Azabicyclo[2.2.2]oct-3-yl]-5-phenoxy-1H-indazole-3-carboxamide,
N-[(3R)-1-Azabicyclo[2.2.2]oct-3-yl]-5-piperidin-1-yl-1H-indazole-3-carboxamide,
N-[(3R)-1-Azabicyclo[2.2.2]oct-3-yl]-5-pyrrolidin-1-yl-1H-indazole-3-carboxamide,
N-[(3R)-1-Azabicyclo[2.2.2]oct-3-yl]-6-(1,3-oxazol-2-yl)-1H-indazole-3-carboxamide,
N-[(3R)-1-Azabicyclo[2.2.2]oct-3-yl]-6-(1,3-thiazol-2-yl)-1H-indazole-3-carboxamide,
N-[(3R)-1-Azabicyclo[2.2.2]oct-3-yl]-6-(1-methyl-1H-imidazol-2-yl)-1H-indazole-3-carboxamide,
N-[(3R)-1-Azabicyclo[2.2.2]oct-3-yl]-6-(3,6-dihydro-2H-pyran-4-yl)-1H-indazole-3-carboxamide,
N-[(3R)-1-Azabicyclo[2.2.2]oct-3-yl]-6-(pent-1-yn-1-yl)-1H-indazole-3-carboxamide,
N-[(3R)-1-Azabicyclo[2.2.2]oct-3-yl]-6-(phenylethynyl)-1H-indazole-3-carboxamide,
N-[(3R)-1-Azabicyclo[2.2.2]oct-3-yl]-6-cyano-1H-indazole-3-carboxamide,
N-[(3R)-1-Azabicyclo[2.2.2]oct-3-yl]-6-ethynyl-1H-indazole-3-carboxamide,
N-[(3R)-1-Azabicyclo[2.2.2]oct-3-yl]-6-hydroxy-1H-indazole-3-carboxamide,
N-[(3R)-1-Azabicyclo[2.2.2]oct-3-yl]-6-methoxy-1H-indazole-3-carboxamide,
N-[(3R)-1-Azabicyclo[2.2.2]oct-3-yl]-6-morpholin-4-yl-1H-indazole-3-carboxamide,
N-[(3R)-1-Azabicyclo[2.2.2]oct-3-yl]-6-piperidin-1-yl-1H-indazole-3-carboxamide,
N-[(3R)-1-Azabicyclo[2.2.2]oct-3-yl]-6-pyrrolidin-1-yl-1H-indazole-3-carboxamide,
N-[(3S)-1-Azabicyclo[2.2.2]oct-3-yl]-5-(1,3-oxazol-2-yl)-1H-indazole-3-carboxamide,
N-[(3S)-1-Azabicyclo[2.2.2]oct-3-yl]-5-(1,3-thiazol-2-yl)-1H-indazole-3-carboxamide,
N-[(3S)-1-Azabicyclo[2.2.2]oct-3-yl]-5-(tetrahydro-2H-pyran-4-yl)-1H-indazole-3-carboxamide,
N-[(3S)-1-Azabicyclo[2.2.2]oct-3-yl]-5-(trifluoromethoxy)-1H-indazole-3-carboxamide,
N-[(3S)-1-Azabicyclo[2.2.2]oct-3-yl]-5-chloro-1H-indazole-3-carboxamide,
N-[(3S)-1-Azabicyclo[2.2.2]oct-3-yl]-5-cyano-1H-indazole-3-carboxamide,
N-[(3S)-1-Azabicyclo[2.2.2]oct-3-yl]-5-ethynyl-1H-indazole-3-carboxamide,
N-[(3S)-1-Azabicyclo[2.2.2]oct-3-yl]-5-methoxy-1H-indazole-3-carboxamide,
N-[(3S)-1-Azabicyclo[2.2.2]oct-3-yl]-5-nitro-1H-indazole-3-carboxamide,
N-[(3S)-1-Azabicyclo[2.2.2]oct-3-yl]-6-(1,3-oxazol-2-yl)-1H-indazole-3-carboxamide,
N-[(3S)-1-Azabicyclo[2.2.2]oct-3-yl]-6-(1,3-thiazol-2-yl)-1H-indazole-3-carboxamide,
N-[(3S)-1-Azabicyclo[2.2.2]oct-3-yl]-6-(1-methyl-1H-imidazol-2-yl)-1H-indazole-3-carboxamide, N-[(3S)-1-Azabicyclo[2.2.2]oct-3-yl]-6-(3,6-dihydro-2H-pyran-4-yl)-1H-indazole-3-carboxamide,
N-[(3S)-1-Azabicyclo[2.2.2]oct-3-yl]-6-(morpholin-4-yl)-1H-indazole-3-carboxamide,
N-[(3S)-1-Azabicyclo[2.2.2]oct-3-yl]-6-(prop-1-yn-1-yl)-1H-indazole-3-carboxamide,
N-[(3S)-1-Azabicyclo[2.2.2]oct-3-yl]-6-(trifluoromethyl)-1H-indazole-3-carboxamide,
N-[(3S)-1-Azabicyclo[2.2.2]oct-3-yl]-6-[2,2,2-trifluoro-1-hydroxy-1-(trifluoromethyl)ethyl]-1H-indazole-3-carboxamide,
N-[(3S)-1-Azabicyclo[2.2.2]oct-3-yl]-6-cyano-1H-indazole-3-carboxamide,
N-[(3S)-1-Azabicyclo[2.2.2]oct-3-yl]-6-ethynyl-1H-indazole-3-carboxamide,
N-[(3S)-1-Azabicyclo[2.2.2]oct-3-yl]-6-methoxy-1H-indazole-3-carboxamide,
N-[(3S)-1-Azabicyclo[2.2.2]oct-3-yl]-6-nitro-1H-indazole-3-carboxamide,
and pharmaceutically acceptable salts thereof.

17. The method according to claim 16, wherein said compound is selected from:
N-[(3R)-1-Azabicyclo[2.2.2]oct-3-yl]-5-(1,3-oxazol-2-yl)-1H-indazole-3-carboxamide,
N-[(3R)-1-Azabicyclo[2.2.2]oct-3-yl]-5-(1,3-thiazol-2-yl)-1H-indazole-3-carboxamide,
N-[(3R)-1-Azabicyclo[2.2.2]oct-3-yl]-5-(tetrahydro-2H-pyran-4-yl)-1H-indazole-3-carboxamide,
N-[(3R)-1-Azabicyclo[2.2.2]oct-3-yl]-5-(trifluoromethoxy)-1H-indazole-3-carboxamide,
N-[(3R)-1-Azabicyclo[2.2.2]oct-3-yl]-5-cyano-1H-indazole-3-carboxamide,
N-[(3R)-1-Azabicyclo[2.2.2]oct-3-yl]-5-ethynyl-1H-indazole-3-carboxamide,
N-[(3R)-1-azabicyclo[2.2.2]oct-3-yl]-5-hydroxy-1H-indazole-3-carboxamide,
N-[(3R)-1-Azabicyclo[2.2.2]oct-3-yl]-5-methoxy-1H-indazole-3-carboxamide,
N-[(3R)-1-Azabicyclo[2.2.2]oct-3-yl]-5-phenoxy-1H-indazole-3-carboxamide,
N-[(3R)-1-Azabicyclo[2.2.2]oct-3-yl]-5-piperidin-1-yl-1H-indazole-3-carboxamide,
and pharmaceutically acceptable salts thereof.

18. The method according to claim 16, wherein said compound is selected from:
N-[(3R)-1-Azabicyclo[2.2.2]oct-3-yl]-5-pyrrolidin-1-yl-1H-indazole-3-carboxamide,
N-[(3S)-1-Azabicyclo[2.2.2]oct-3-yl]-5-(1,3-oxazol-2-yl)-1H-indazole-3-carboxamide,
N-[(3S)-1-Azabicyclo[2.2.2]oct-3-yl]-5-(1,3-thiazol-2-yl)-1H-indazole-3-carboxamide,
N-[(3S)-1-Azabicyclo[2.2.2]oct-3-yl]-5-(tetrahydro-2H-pyran-4-yl)-1H-indazole-3-carboxamide,
N-[(3S)-1-Azabicyclo[2.2.2]oct-3-yl]-5-(trifluoromethoxy)-1H-indazole-3-carboxamide,
N-[(3S)-1-Azabicyclo[2.2.2]oct-3-yl]-5-chloro-1H-indazole-3-carboxamide,
N-[(3S)-1-Azabicyclo[2.2.2]oct-3-yl]-5-cyano-1H-indazole-3-carboxamide,
N-[(3S)-1-Azabicyclo[2.2.2]oct-3-yl]-5-ethynyl-1H-indazole-3-carboxamide,
N-[(3S)-1-Azabicyclo[2.2.2]oct-3-yl]-5-methoxy-1H-indazole-3-carboxamide,
N-[(3S)-1-Azabicyclo[2.2.2]oct-3-yl]-5-nitro-1H-indazole-3-carboxamide,
and pharmaceutically acceptable salts thereof.

19. The method according to claim 16, wherein said compound is selected from:
6-Amino-N-[(3S)-1-azabicyclo[2.2.2]oct-3-yl]-1H-indazole-3-carboxamide,
N-[(3R)-1-Azabicyclo[2.2.2]oct-3-yl]-6-(1,3-oxazol-2-yl)-1H-indazole-3-carboxamide,
N-[(3R)-1-Azabicyclo[2.2.2]oct-3-yl]-6-(1,3-thiazol-2-yl)-1H-indazole-3-carboxamide,
N-[(3R)-1-Azabicyclo[2.2.2]oct-3-yl]-6-(1-methyl-1H-imidazol-2-yl)-1H-indazole-3-carboxamide,
N-[(3R)-1-Azabicyclo[2.2.2]oct-3-yl]-6-(3,6-dihydro-2H-pyran-4-yl)-1H-indazole-3-carboxamide,
N-[(3R)-1-Azabicyclo[2.2.2]oct-3-yl]-6-(pent-1-yn-1-yl)-1H-indazole-3-carboxamide,
N-[(3R)-1-Azabicyclo[2.2.2]oct-3-yl]-6-(phenylethynyl)-1H-indazole-3-carboxamide,
N-[(3R)-1-Azabicyclo[2.2.2]oct-3-yl]-6-cyano-1H-indazole-3-carboxamide,
N-[(3R)-1-Azabicyclo[2.2.2]oct-3-yl]-6-ethynyl-1H-indazole-3-carboxamide,
N-[(3R)-1-Azabicyclo[2.2.2]oct-3-yl]-6-hydroxy-1H-indazole-3-carboxamide,
N-[(3R)-1-Azabicyclo[2.2.2]oct-3-yl]-6-methoxy-1H-indazole-3-carboxamide,
and pharmaceutically acceptable salts thereof.

20. The method according to claim 16, wherein said compound is selected from:
N-[(3R)-1-Azabicyclo[2.2.2]oct-3-yl]-6-morpholin-4-yl-1H-indazole-3-carboxamide,
N-[(3R)-1-Azabicyclo[2.2.2]oct-3-yl]-6-piperidin-1-yl-1H-indazole-3-carboxamide,
N-[(3R)-1-Azabicyclo[2.2.2]oct-3-yl]-6-pyrrolidin-1-yl-1H-indazole-3-carboxamide,
N-[(3S)-1-Azabicyclo[2.2.2]oct-3-yl]-6-(1,3-oxazol-2-yl)-1H-indazole-3-carboxamide,
N-[(3S)-1-Azabicyclo[2.2.2]oct-3-yl]-6-(1,3-thiazol-2-yl)-1H-indazole-3-carboxamide,
N-[(3S)-1-Azabicyclo[2.2.2]oct-3-yl]-6-(1-methyl-1H-imidazol-2-yl)-1H-indazole-3-carboxamide,
N-[(3S)-1-Azabicyclo[2.2.2]oct-3-yl]-6-(3,6-dihydro-2H-pyran-4-yl)-1H-indazole-3-carboxamide,
N-[(3S)-1-Azabicyclo[2.2.2]oct-3-yl]-6-(morpholin-4-yl)-1H-indazole-3-carboxamide,
N-[(3S)-1-Azabicyclo[2.2.2]oct-3-yl]-6-(prop-1-yn-1-yl)-1H-indazole-3-carboxamide,
N-[(3S)-1-Azabicyclo[2.2.2]oct-3-yl]-6-(trifluoromethyl)-1H-indazole-3-carboxamide,
N-[(3S)-1-Azabicyclo[2.2.2]oct-3-yl]-6-[2,2,2-trifluoro-1-hydroxy-1-(trifluoromethyl)ethyl]-1H-indazole-3-carboxamide,
N-[(3S)-1-Azabicyclo[2.2.2]oct-3-yl]-6-cyano-1H-indazole-3-carboxamide,
N-[(3S)-1-Azabicyclo[2.2.2]oct-3-yl]-6-ethynyl-1H-indazole-3-carboxamide,
N-[(3S)-1-Azabicyclo[2.2.2]oct-3-yl]-6-methoxy-1H-indazole-3-carboxamide,
N-[(3S)-1-Azabicyclo[2.2.2]oct-3-yl]-6-nitro-1H-indazole-3-carboxamide,
and pharmaceutically acceptable salts thereof.

21. The method according to claim 16, wherein said compound is in the form of a hydrochloride, a hydroformate or a hydrotrifluoroacetate salt.

22. The method according to claim 21, wherein said compound is selected from:
N-[(3R)-1-Azabicyclo[2.2.2]oct-3-yl]-5-(1,3-thiazol-2-yl)-1H-indazole-3-carboxamide hydroformate, N-[(3R)-1-Azabicyclo[2.2.2]oct-3-yl]-5-(trifluoromethoxy)-1H-indazole-3-carboxamide hydroformate, N-[(3R)-1-Azabicyclo[2.2.2]oct-3-yl]-5-cyano-1H-indazole-3-carboxamide hydroformate, N-[(3R)-1-Azabicyclo[2.2.2]oct-3-yl]-5-ethynyl-1H-indazole-3-carboxamide hydrochloride, N-[(3R)-1-Azabicyclo[2.2.2]oct-3-yl]-5-ethynyl-1H-indazole-3-carboxamide hydroformate, N-[(3R)-1-azabicyclo[2.2.2]oct-3-yl]-5-hydroxy-1H-indazole-3-carboxamide hydroformate, N-[(3R)-1-Azabicyclo[2.2.2]oct-3-yl]-5-methoxy-1H-indazole-3-carboxamide hydroformate, N-[(3R)-1-Azabicyclo[2.2.2]oct-3-yl]-5-phenoxy-1H-indazole-3-carboxamide hydroformate, and N-[(3R)-1-Azabicyclo[2.2.2]oct-3-yl]-5-piperidin-1-yl-1H-indazole-3-carboxamide hydroformate.

23. The method according to claim 21, wherein said compound is selected from:

N-[(3S)-1-Azabicyclo[2.2.2]oct-3-yl]-5-(1,3-thiazol-2-yl)-1H-indazole-3-carboxamide hydroformate, N-[(3S)-1-Azabicyclo[2.2.2]oct-3-yl]-5-(trifluoromethoxy)-1H-indazole-3-carboxamide hydrochloride, N-[(3S)-1-Azabicyclo[2.2.2]oct-3-yl]-5-(trifluoromethoxy)-1H-indazole-3-carboxamide hydroformate, N-[(3S)-1-Azabicyclo[2.2.2]oct-3-yl]-5-chloro-1H-indazole-3-carboxamide hydroformate, N-[(3S)-1-Azabicyclo[2.2.2]oct-3-yl]-5-cyano-1H-indazole-3-carboxamide hydroformate, N-[(3S)-1-Azabicyclo[2.2.2]oct-3-yl]-5-cyclopentyl-1H-indazole-3-carboxamide, N-[(3S)-1-Azabicyclo[2.2.2]oct-3-yl]-5-ethynyl-1H-indazole-3-carboxamide hydroformate, and N-[(3S)-1-Azabicyclo[2.2.2]oct-3-yl]-5-methoxy-1H-indazole-3-carboxamide hydroformate.

24. The method according to claim 21, wherein said compound is selected from:

N-[(3R)-1-Azabicyclo[2.2.2]oct-3-yl]-6-(1,3-thiazol-2-yl)-1H-indazole-3-carboxamide hydrochloride, N-[(3R)-1-Azabicyclo[2.2.2]oct-3-yl]-6-(1,3-thiazol-2-yl)-1H-indazole-3-carboxamide hydroformate, N-[(3R)-1-Azabicyclo[2.2.2]oct-3-yl]-6-(1-methyl-1H-imidazol-2-yl)-1H-indazole-3-carboxamide hydroformate, N-[(3R)-1-Azabicyclo[2.2.2]oct-3-yl]-6-(3,6-dihydro-2H-pyran-4-yl)-1H-indazole-3-carboxamide hydroformate, N-[(3R)-1-Azabicyclo[2.2.2]oct-3-yl]-6-(pent-1-yn-1-yl)-1H-indazole-3-carboxamide hydroformate, N-[(3R)-1-Azabicyclo[2.2.2]oct-3-yl]-6-(phenylethynyl)-1H-indazole-3-carboxamide hydroformate, N-[(3R)-1-Azabicyclo[2.2.2]oct-3-yl]-6-cyano-1H-indazole-3-carboxamide hydroformate, N-[(3R)-1-Azabicyclo[2.2.2]oct-3-yl]-6-ethynyl-1H-indazole-3-carboxamide hydroformate, N-[(3R)-1-Azabicyclo[2.2.2]oct-3-yl]-6-hydroxy-1H-indazole-3-carboxamide hydroformate, and N-[(3R)-1-Azabicyclo[2.2.2]oct-3-yl]-6-methoxy-1H-indazole-3-carboxamide hydrochloride.

25. The method according to claim 21, wherein said compound is selected from:

N-[(3R)-1-Azabicyclo[2.2.2]oct-3-yl]-6-piperidin-1-yl-1H-indazole-3-carboxamide hydrotrifluoroacetate, N-[(3S)-1-Azabicyclo[2.2.2]oct-3-yl]-6-(1,3-thiazol-2-yl)-1H-indazole-3-carboxamide hydrochloride, N-[(3S)-1-Azabicyclo[2.2.2]oct-3-yl]-6-(1,3-thiazol-2-yl)-1H-indazole-3-carboxamide hydroformate, N-[(3S)-1-Azabicyclo[2.2.2]oct-3-yl]-6-(1-methyl-1H-imidazol-2-yl)-1H-indazole-3-carboxamide hydroformate, N-[(3S)-1-Azabicyclo[2.2.2]oct-3-yl]-6-(3,6-dihydro-2H-pyran-4-yl)-1H-indazole-3-carboxamide hydroformate, N-[(3S)-1-Azabicyclo[2.2.2]oct-3-yl]-6-(prop-1-yn-1-yl)-1H-indazole-3-carboxamide hydroformate, N-[(3S)-1-Azabicyclo[2.2.2]oct-3-yl]-6-cyano-1H-indazole-3-carboxamide hydroformate, and N-[(3S)-1-Azabicyclo[2.2.2]oct-3-yl]-6-ethynyl-1H-indazole-3-carboxamide hydroformate.

26. The method according to claim 16, wherein said compound is N-[1-Azabicyclo[2.2.2]oct-3-yl]-5-(trifluoromethoxy)-1H-indazole-3-carboxamide, N-[(3R)-1-Azabicyclo[2.2.2]oct-3-yl]-5-(trifluoromethoxy)-1H-indazole-3-carboxamide, N-[(3S)-1-Azabicyclo[2.2.2]oct-3-yl]-5-(trifluoromethoxy)-1H-indazole-3-carboxamide, or a pharmaceutically acceptable salt thereof.

27. The method according to claim 26, wherein said compound is N-[(3S)-1-Azabicyclo[2.2.2]oct-3-yl]-5-(trifluoromethoxy)-1H-indazole-3-carboxamide, or a pharmaceutically acceptable salt thereof.

28. The method according to claim 27, wherein said compound is N-[(3S)-1-Azabicyclo[2.2.2]oct-3-yl]-5-(trifluoromethoxy)-1H-indazole-3-carboxamide hydrochloride.

* * * * *